US006306491B1

(12) United States Patent
Kram et al.

(10) Patent No.: US 6,306,491 B1
(45) Date of Patent: Oct. 23, 2001

(54) RESPIRATORY AIDS

(75) Inventors: Brian H. Kram; Stanley L. Mish; Michael J. Muehlbauer; James R. Bain, all of Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 09/282,384

(22) Filed: Mar. 31, 1999

Related U.S. Application Data

(63) Continuation-in-part of application No. 08/994,801, filed on Dec. 19, 1997, now abandoned, which is a continuation-in-part of application No. 08/993,751, filed on Dec. 19, 1997, now abandoned.
(60) Provisional application No. 60/033,562, filed on Dec. 20, 1996.

(51) Int. Cl.[7] .................................. B32B 3/02; B32B 3/10
(52) U.S. Cl. ........................... 428/315.5; 428/305.5; 428/306.6; 428/314.4; 428/316.6; 428/319.1; 428/320.2; 428/322.7; 424/422; 424/423; 424/424; 435/177; 435/180
(58) Field of Search ............................ 428/305.5, 306.6, 428/314.4, 316.6, 319.1, 320.2, 322.7, 315.5; 424/422, 423, 424; 435/177, 180

(56) References Cited

U.S. PATENT DOCUMENTS

| | | | |
|---|---|---|---|
| 3,228,394 | 1/1966 | Ayres | 128/142 |
| 3,890,107 | 6/1975 | White et al. | 29/183 |
| 3,929,971 | 12/1975 | Roy | 423/308 |
| 4,075,092 | 2/1978 | White et al. | 210/22 R |
| 4,190,079 | 2/1980 | White et al. | 137/361 R |
| 4,231,110 | 11/1980 | White et al. | 264/81 |
| 4,749,654 | 6/1988 | Karrer et al. | 435/240.21 |
| 4,792,454 | 12/1988 | Lemonnier | 426/8 |
| 4,861,733 | 8/1989 | White | 501/1 |
| 4,896,664 | 1/1990 | Harayama | 128/200.25 |
| 4,909,989 | 3/1990 | Fukazawa | 422/48 |
| 4,937,196 | 6/1990 | Wrasidlo et al. | 435/313 |
| 5,102,711 | 4/1992 | Keller et al. | 428/71 |
| 5,149,649 | * 9/1992 | Miyamori et al. | 435/240.242 |
| 5,158,881 | 10/1992 | Aebischer et al. | 435/182 |
| 5,173,225 | * 12/1992 | Range et al. | 264/45.5 |
| 5,190,879 | * 3/1993 | Wolfe et al. | 435/287 |
| 5,277,176 | 1/1994 | Habashi | 128/200.24 |
| 5,314,471 | 5/1994 | Brauker et al. | 623/11 |
| 5,322,730 | 6/1994 | Ou | 428/316.6 |
| 5,348,788 | 9/1994 | White | 428/131 |
| 5,411,550 | 5/1995 | Herweck et al. | 623/1 |
| 5,413,925 | 5/1995 | Lemonnier | 435/183 |
| 5,416,022 | 5/1995 | Amiot | 435/284 |
| 5,443,508 | 8/1995 | Giampapa | 623/11 |
| 5,455,100 | 10/1995 | White | 428/131 |
| 5,556,591 | 9/1996 | Jallerat et al. | 264/516 |
| 5,576,211 | 11/1996 | Falkenberg et al. | 435/297.1 |
| 5,650,164 | 7/1997 | Della Valle et al. | 424/422 |
| 5,658,331 | 8/1997 | Della Valle et al. | 623/15 |
| 5,693,537 | 12/1997 | Wilson et al. | 435/401 |
| 5,707,869 | 1/1998 | Wolf et al. | 435/401 |
| 5,714,384 | 2/1998 | Wilson et al. | 435/401 |
| 5,763,279 | 6/1998 | Schwarz et al. | 435/383 |
| 5,766,317 | 6/1998 | Cable et al. | 96/10 |
| 5,798,261 | * 8/1998 | Koontz | 435/283.1 |
| 5,843,069 | * 12/1998 | Butler et al. | 604/891.1 |
| 5,980,889 | * 11/1999 | Butler et al. | 424/93.7 |

FOREIGN PATENT DOCUMENTS

| | | |
|---|---|---|
| 0113328 | 7/1984 | (EP) . |
| 360009 | 3/1990 | (EP) . |
| 1228825 | 4/1971 | (GB) . |
| 1538386 | 1/1979 | (GB) . |
| 62027004 | 2/1987 | (JP) . |
| 01210016 | 8/1989 | (JP) . |
| 03202133 | 9/1991 | (JP) . |
| 3-202133 | * 9/1991 | (JP) . |
| 8606094 | 10/1986 | (WO) . |
| 9613573 | 5/1996 | (WO) . |
| 9712960 | 4/1997 | (WO) . |

OTHER PUBLICATIONS

Evren V, Pisking E. Membrane Oxygenators Embodying Silicone–Cotaed Microporous Membranes. In: *Progress in Artificial Organs*, ed Nose Y, Kjellstrand C, Ivanovich P. Cleveland: ISAO Press 1986.

Heidelberger E, Reeves RB. $O_2$ transfer kinetics in a whole blood unicellular thin layer. J Appl. Physiol. 1990; 68(5): 1854–1864.

Henzler HJ, Kauling DJ. Oxygenation of cell cultures. Bioprocess Engineering 1993; 9:61–75.

Hyder A et al. Variable responses of islet cells of different ages and species to hypoxia. Transplantation Proceedings 1998; 30:578–580.

Kawakami K et al. Immobilization of microbial cells in a mixed matrix of silicone polymer and calcium alginate gel: epoxidation of 1–octene by *nocardia corallina* B–276 in organic media. Biotechnol. Prog. 1990; 6:357–361.

(List continued on next page.)

*Primary Examiner*—Mark Kopec
*Assistant Examiner*—Charles Boyer
(74) *Attorney, Agent, or Firm*—Eric J Sheets

(57) ABSTRACT

The present invention is directed to materials that assist respiration of living cells contained in cell-containing systems. The materials form air-filled conduits or channels through which gases, such as oxygen and carbon dioxide, can readily exchange by diffusional means between regions of different gas partial pressures. When the present invention is placed within an aqueous environment, such as cell-culture media or host tissue, the invention provides aid to cellular respiration in cell-containing systems.

84 Claims, 50 Drawing Sheets

OTHER PUBLICATIONS

Kawakami K et al. Reaction characteristics of microbial cells immobilized in a mixed matrix of silicone polymer and aqueous medium. Physiology of Immobilized Cells, Proceeding of an International Symposium, The Netherlands. Dec. 10–13, 1989.

Mortensen JD and Berry G. Conceptual and design features of a practical, clinically effective intravenous mechanical blood oxygen/carbon dioxide exchange device (Ivox). Intl Jour. Of Artificial Organs 1989; 12(6):384–389.

Oriel P. Anylase production by *Escherichia coli* immobilized in silicone foam. Biotechnology Letters 1988; 10(2):113–116.

Poncelet D et al. Microencapsulation of silicone oils within polyamide–polyethylenimine membranes as oxygen carriers for bioreactor oxygenation. J Chem. Tech. Biotechnol. 1993. 57:253–263.

Schneider M et al. Bubble–free oxygenation by means of hydrophobic porous membranes. Enzyme and microbial Technology 1995; 17:839–847.

Weissman BA et al. Polarographic oxygen permeability measurement of silicone elastomer contact lens material. Jour. Of the American Optometric Assoc. 1991; 64(3):187–190.

Yasuda H, Lamaze CE. Transfer of gas to dissolved oxygen in water via porous and nonporous polymer membranes. J Applied Polymer Sci. 1972; 16:595–601.

Paganelli CV et al. Artificial gills for gas exchange in water. In: *Underwater Physiology*, ed. Lambertsen CJ. Baltimore: Williams & Wilkins Company 1967; 452–481.

\* cited by examiner-

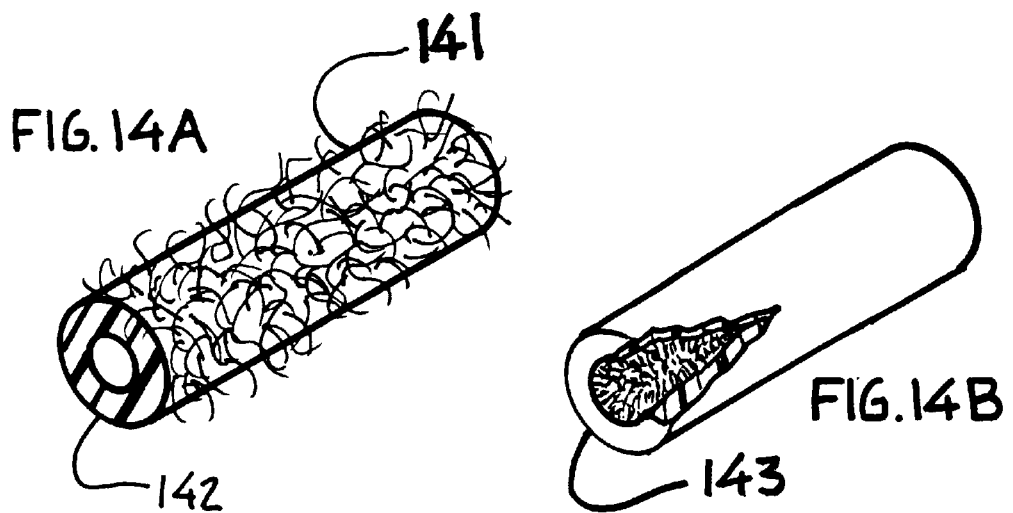
FIG. 14A
FIG. 14B
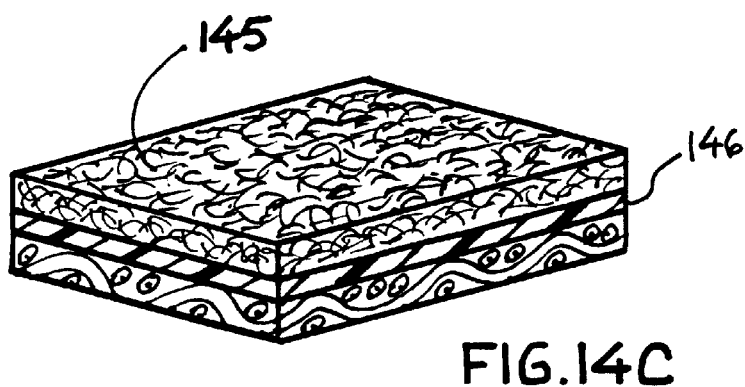
FIG. 14C
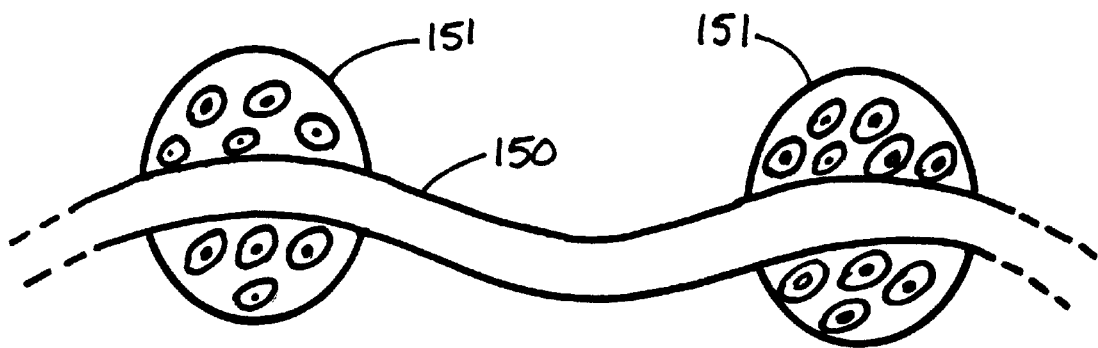
FIG. 15

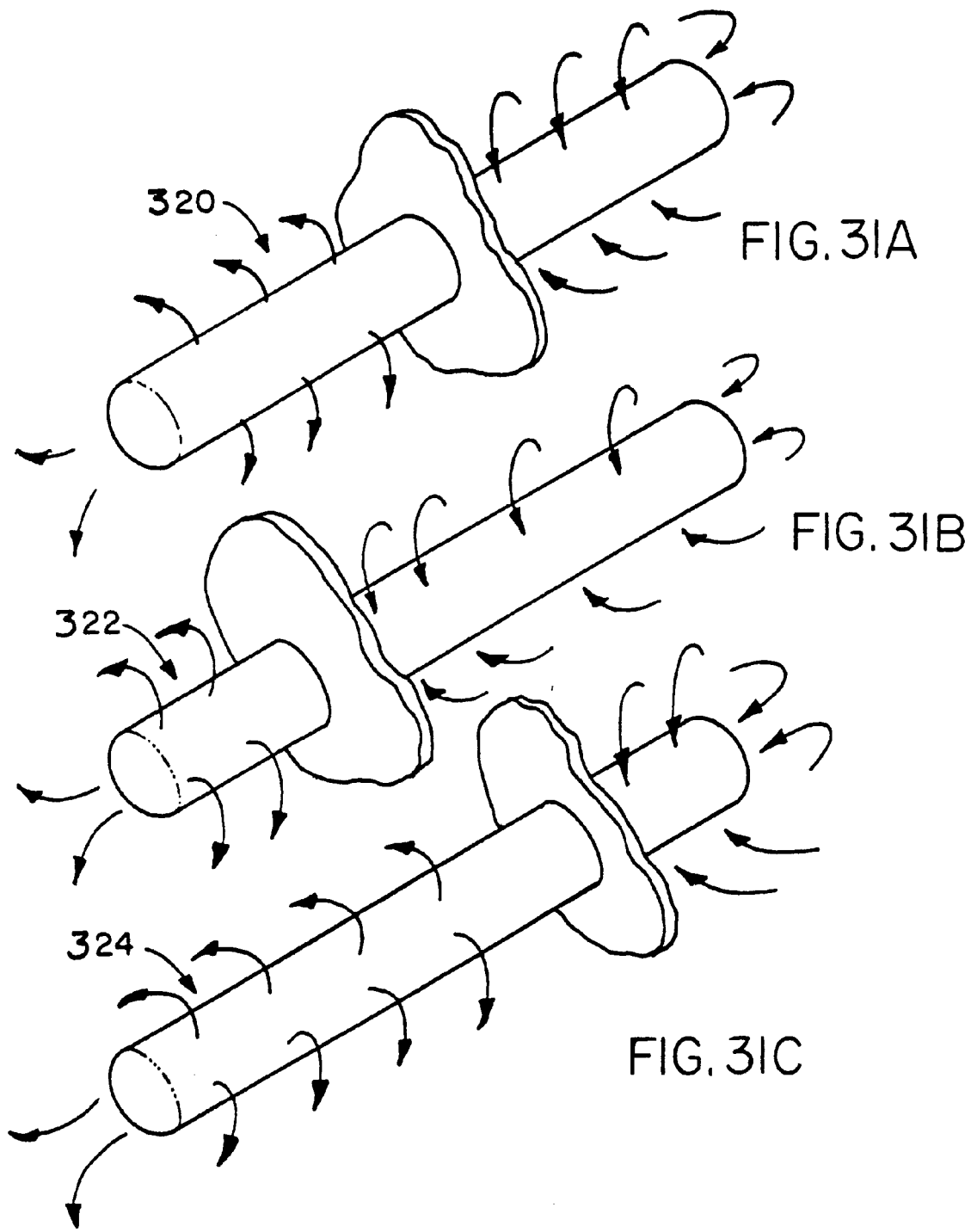

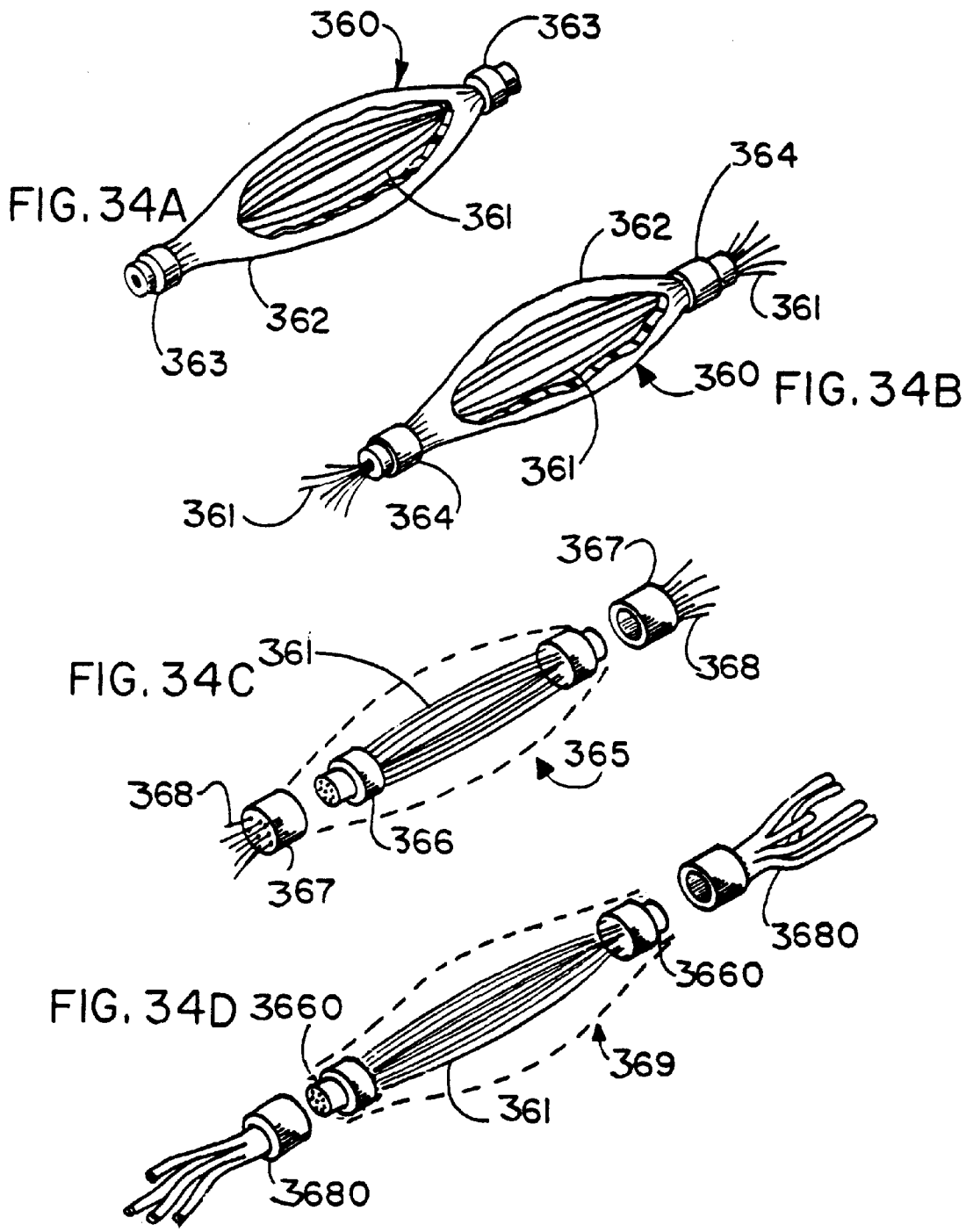

RESPIRATORY AIDS

This application is a continuation-in-part of application Ser. No. 08/994,801, filed Dec. 19, 1997 now abandoned and application Ser. No. 08/993,751, filed Dec. 19, 1997, now abandon both of which are based on provisional application Ser. No. 60/033,562, filed Dec. 20, 1996.

FIELD OF THE INVENTION

This invention generally relates to materials that assist respiration of living cells contained in a cell-containing device. More particularly, the invention relates to materials within which gases are easily acquired, conducted, and/or delivered from a site of higher partial gas pressure to a site of lower partial gas pressure in support of living cells.

BACKGROUND

All biological entities undergoing metabolism consume nutrients and produce waste products to maintain their metabolic processes. Biological entities include organelles, cells, tissues, organs, and organisms. In most instances, exchange of nutrients and waste products occurs continuously between biological entities and an external environment of the entities. For most biological systems, exchange of nutrients and wastes takes place through a particular aqueous medium, such as cytoplasm, intercellular fluid, plasma, lymph, cell-culture media, fresh water, seawater, or blood. Exchange of nutrients and wastes also takes place across structural forms, such as intra-cellular membranes, cell membranes, cell walls, extra-cellular matrix material, alveoli, and capillaries. The rate of exchange of nutrients and wastes is influenced by the particular type of biological entity, the degree of activity of the entity, the composition of the aqueous media and structural forms, as well as the composition of the nutrient or waste material. The nutrients and waste products of most interest with respect to the present invention are the respiratory gases oxygen and carbon dioxide. Exchange of these gases between a metabolically active site of a biological entity and an external environment of the entity is referred to herein as respiration. Respiration of gaseous mass occurs through diffusional means and convective means. The rate of respiration of a particular biological entity is related to the rate of metabolism of the entity.

Metabolism is "the sum of all the physical and chemical processes by which living organized substance is produced and maintained, and also the transformation by which energy is made available for the uses of an organism" (*Dorland's Illustrated Medical Dictionary*, 27$^{th}$ Edition, 1988). In the aerobic metabolism of most human cells, for example, oxygen is consumed and carbon dioxide is produced during generation of such high-energy molecules as adenosine 5'-triphosphate (ATP) by catabolism of the nutrient glucose and other metabolic fuels. In this and other metabolic processes, a localized imbalance of nutrients and wastes occurs with respect to the biological entity and an external environment of the entity. If allowed to persist or increase beyond a certain point, the imbalance leads to a life-threatening buildup of wastes or depletion of nutrients. Metabolic processes can be maintained only if nutrients and wastes are exchanged in an appropriate amount and at an appropriate rate.

Diffusion is a means by which gaseous mass is exchanged between a metabolically active site and an external environmental site. Diffusion is driven by a difference in partial as pressure between the sites. As metabolism depletes oxygen at a metabolically active site, for example, a localized "oxygen sink" is established. If an external environment of the biological entity has oxygen at a higher partial gas pressure than the metabolically active site, oxygen is transferred to the metabolically active site through various media and structures by diffusion. Gaseous wastes, such as carbon dioxide, diffuse according to the same process, but in the opposite direction. Diffusion is most effective in biological entities over small distances ranging from inter-molecular distances to a few millimeters.

In discussing animal physiology, Schmidt-Nielsen, (*Animal Physiology: Adaptation and Environment*, Cambridge University Press, 4$^{th}$ Edition, pages 16–17 (1990)) employed the following equation developed by E. Newton Harvey (1928) to illustrate that dependence on diffusion alone places distinct limitations on the maximum size to which a population of cells or an organism can grow. This in turn gives an indication of the distances over which diffusion through aqueous media can effectively operate in biological systems as a means of respiratory gas exchange.

$$F_{O_2} = \frac{V_{O_2} r^2}{6K}$$

In the equation, $F_{O_2}$ represents the concentration of oxygen at the surface of a spherical organism, expressed in fractions of an atmosphere; $V_{O_2}$ represents the rate of oxygen consumption by the organism as cubic centimeters of oxygen per cubic centimeter of tissue per minute; r is the radius of the spherical cell or organism in centimeters; and K is the diffusion constant in square centimeters per atmosphere of oxygen that will diffuse per minute through an area of one square centimeter when the gradient is one atmosphere per centimeter.

When numbers are used in the equation for a hypothetical organism having a spherical shape and a radius of one centimeter, with an oxygen consumption of 0.001 milliliters per gram oxygen per minute, and a diffusion constant of $11 \times 10^{-6}$ per square centimeter per atmosphere per minute (Ibid.), it is found that the concentration of oxygen at the surface, necessary to supply the entire organism by diffusion alone, is fifteen atmospheres. Since the partial pressure of oxygen in the earth's atmosphere and upper levels of the oceans is about 0.21 atmospheres, an organism of this type is too large to exist using diffusion alone. For a more realistic organism having a radius of about one millimeter, the required oxygen concentration at the surface of the organism is 0.15 atmospheres. Well-aerated water at sea level contains about 0.21 atmospheres of oxygen. Accordingly, an organism with a radius on the order of one millimeter could survive on aqueously dissolved oxygen by diffusion alone. Generally, the reliance of these organisms on diffusion through aqueous media to exchange dissolved respiratory gases places a size limit on the organisms of about a one millimeter radius. Viewed another way, diffusion-based exchange of respiratory gases through aqueous media can support the metabolic activity of this hypothetical biological entity only if the diffusion distances required for the exchange of the respiratory gases do not exceed about one millimeter in length. This maximum distance for diffusion-based exchange of respiratory gases between a biological entity and an external environment defines a "diffusion-delimited boundary."

Respiratory gas exchange within a diffusion-delimited boundary is referred to herein as occurring within an "internal respiratory system." Examples of biological entities that function within an internal respiratory system include mitochondria, chloroplasts, individual cells, single-celled organisms, small multi-cellular organisms, collections of small numbers of cells, and specific anatomic regions of certain aquatic organisms, such as jellyfish. Depending on their actual size and metabolic requirements, the cell walls, cell membranes, or the edges of the cell masses usually represent the diffusion-delimited boundary of these biological entities. These entities survive within a diffusion-delimited boundary because diffusion-based exchange of respiratory gas occurs over distances that are effective in transferring respiratory gases in sufficient amounts and at sufficient rates to support the metabolic activities of the entities.

In many cases, the diffusion-based process of the internal respiratory system may be supplemented by convection-based processes beyond the diffusion-delimited boundary. Respiratory gas exchange beyond a diffusion-delimited boundary is referred to herein as occurring in an "external respiratory system." Gas exchange in external respiratory systems occurs with the aid of convection-based means. Examples of convection-based external respiratory systems include animal vascular systems and pulmonary systems of both aquatic and terrestrial organisms. External respiratory systems are characterized by well defined anatomical structures that maintain convection-based processes in an organism. In contrast to passive diffusion-based internal respiratory systems, all external respiratory systems rely on energy expenditure to function.

Insects represent a solution to respiratory gas exchange that enables diffusion-delimited boundaries to exceed those of organisms restricted to diffusion-based exchange of respiratory gas through aqueous media alone. As Schmidt-Nielsen teaches (Ibid., p. 17):

Insects have a special form of respiratory system. Small openings on an insect's body surface connect to a system of tubes (tracheae) that branch and lead to all parts of the body. In this case the respiratory organ combines a distribution system (the tubes) with the gas-exchange system, for most of the gas passes through the walls of the finest branches of this system and diffuses directly to the cells.

A generalized illustration of an insect tracheal system is shown in FIGS. 1A and 1B. In an insect respiratory system, large air-filled structures, called "tracheae," provide directed transport of respiratory gases to and from an external environment. Gases are conducted within the insect body through increasingly smaller, yet more numerous, air-filled "tracheoles." Beyond the tracheoles are "tracheole termini" where the gases diffuse across the tracheole walls to metabolically active sites. It is noteworthy that the gas-exchange system in an insect is separate from the liquid-exchange system. Insects do not rely on liquids, such as blood, to collect, transfer, and distribute respiratory gases to and from tissues in the animal. Rather, they use the tracheal system. Air in the insect respiratory system is an excellent medium for rapid and directed exchange of respiratory gases between an external environment and metabolic sites deep within the insect's body. This is primarily due to much lower resistances presented to a diffusing gas by a gaseous medium than resistances presented to respiratory gases diffusing through water or an aqueous media.

An open tracheal system (e.g., FIG. 1A) may or may not combine convection-based gas transport processes with diffusion-based processes as a means of exchanging respiratory gases between an external environment and metabolically active sites in an insect. In these systems, convection-based exchange of respiratory gases may occur through trachea in fluid communication with an external environment. The diffusion-based exchange of respiratory gases occurs at the level of the tracheoles or tracheole termini. The boundary between the convection-based processes and the diffusion-based processes may be dynamic, changing with the respiratory rate and physical movement of the animal, for example. Accordingly, convection-based exchange of respiratory gases may not be present at all, as in the case of a goat moth larvae, or convection-based exchange of respiratory gases may represent a significant portion of exchange in insects, such as an active bumble bee.

FIG. 1B illustrates an insect with gas-filled respiratory structures that are closed to the environment outside the insect by a gas-permeable membrane sealing the openings to the trachea. Respiratory gas exchange occurs in this insect type entirely by diffusion without the aid of convection-based means. Accordingly, the entire tracheal system of these insects represents a particular example of an anatomical structure that functions as an aid to internal respiration. This system is successful in these insects because diffusion-based exchange of respiratory gases through air-filled void spaces is an energy efficient means of moving relatively large amounts of respiratory gases to and from metabolically active sites across distances much larger than those possible through water or aqueous media alone. This type of diffusion-based exchange of respiratory gases through discrete gas-filled spaces is central to the present invention.

The efficient collection, conduction, and distribution of respiratory gases through air-filled conduits in insects is largely determined by the geometry of the respiratory structures. Particularly elegant respiratory structures are ones having a ramiform geometry. Such structures are replete in nature (FIG. 2).

Modifications of insect respiratory systems that enhance collection of respiratory gases include structures commonly referred to as "gills." Gills are specialized gas-collecting structures having high surface area-to-volume ratios that are conjoined with numerous highly divided tracheoles in close apposition with the gill surfaces. The high surface area-to-volume ratios enable the gas-collecting structures to serve as a means of improving gas transfer through layers of water that are resistant to diffusion of gas. Stagnant layers of water reside at the immediate boundary between the outer surfaces of these gas-collecting structures and an external aqueous environment.

Tracheoles have properties that permit respiratory gases to be efficiently conducted through structures having very small cross-sectional areas. As the diameter of insect tracheoles is decreased, the number of tracheoles occupying the same volume can be increased. Increased numbers of tracheoles permit ramification throughout the insect's body, thereby providing respiratory structures in close proximity to metabolically active sites in the insect's body. A decreased diameter in the tracheoles also means the surface-area-to-volume ratio of individual tracheoles increase. As the surface-area-to-volume ratio is increased, the number of cells that can be supported increases. The net result is that insect respiratory structures provide efficient collection, conduction, and distribution of respiratory gases from the environment to metabolic sites deep within the insect.

Artificial biological systems, such as cells contained within a cell-containing device, also undergo respiration. Artificial biological systems exchange nutrients and wastes by diffusion-based means. In many applications, convection-based means are employed to assist respiratory gas exchange in cell-containing devices. As with cells in natural diffusion-delimited systems, there are limits to the size and shape that a cell mass can assume in a diffusion-based cell-containing device. A common feature of most cell-encapsulation devices is a permeable membrane that serves to retain a population of cells within the device, while allowing nutrients and wastes to passively exchange across the membrane in support of the metabolic activity of the encapsulated cells. The exchange of nutrients and wastes occurs through aqueous liquid-filled channels established in the membrane during use. Cells within the device cannot be positioned farther from the permeable membrane than diffusion of nutrients and wastes can support. The permeable membrane may represent a diffusion-delimited boundary in cell-containing devices. As can be deduced from the Harvey Equation and examples from nature, a metabolically active cell in a cell-containing device cannot thrive if positioned more than a few hundred microns from a permeable membrane through which nutrients are supplied if the cell is to be supported by diffusion across the membrane through aqueous media alone.

In addition to the constraints imposed on a population of encapsulated cells by the limited mass-transport capacities of aqueous-mediated diffusion, the permeable membrane presents further limitations on the size, shape, and performance of a contained cell mass. A principle limitation to the diffusion of respiratory gases across a permeable membrane in a cell-encapsulation device is the need to use aqueous channels traversing the membrane as media through which the gases are transported across the membrane. Aqueous channels present a limitation to respiratory gas transport because most aqueous media are not particularly good substances for dissolving and transporting respiratory gases. This is the case both in terms of the concentrations of gases that can be dissolved in the aqueous media, as well as the rates of movement of the gases through the aqueous media. As a result, the use of aqueous channels as a means to support exchange of respiratory gases in a cell-encapsulation device is inadequate for cell masses more than a few hundred microns in thickness or more than a few hundred microns removed from a diffusion-delimited boundary.

As with natural systems, cell-encapsulation devices have internal respiratory systems. Some cell-encapsulation devices are designed to incorporate external respiratory systems. Encapsulated cell masses more than a few hundred microns in thickness or more than a few hundred microns removed from a diffusion-delimited boundary usually require an external respiratory system to supplement the processes of diffusion operating in the internal respiratory system. With implantable cell-encapsulation devices, for example, an external respiratory system in the form of implant host capillaries is often induced to grow close to the device (Hunter, et al., "Promotion of neovascularization around hollow fiber bioartificial organs using biologically active substances," *ASAIO Journal*, Vol. 45, pp.37–40, (1999)). A close association of capillaries with a permeable cell-encapsulating membrane is said to result in an increase in the concentration gradient of oxygen on an external surface of the permeable membrane. Another strategy to establish an external respiratory system in association with a cell-encapsulation device is the use of well-perfused tissues as in-vivo implantation sites (Dionne, et al., "Effects of oxygen on isolated pancreatic tissue," *Transactions of the American Society for Artificial Internal Organs*, Vol. 35, pp. 735–741 (1984)). Finally, in an extreme case, some investigators have placed cell-encapsulation devices in direct contact with an external respiratory system in the form of flowing arterial blood (e.g., Monaco, et al., "Transplantation of islet allografts and xenografts in totally pancreatectomized diabetic dogs using the hybrid artificial pancreas," *Annals of Surgery*, Vol. 214, pp. 339–362 (1991)). This technique is usually impractical as it carries a risk of thrombosis and embolism to the implant recipient. All these manipulations of external respiratory systems to enhance oxygen concentrations at the external surfaces of cell-containing membranes have only modest effects on enhancing transport of respiratory gases across the cell-containing permeable membranes. This is due primarily to resistances to transport of respiratory gases inherent in permeable cell-containing membranes that rely on aqueous liquid-filled channels as means through which exchange of respiratory gases occurs. Increasing the performance of an external respiratory system cannot remedy mass-transport limitations in artificial biological systems that are the result of a deficient internal respiratory system design.

With these and other artificial biological systems, materials that improve passive mass transfer of respiratory gases to and from metabolically active sites within the systems would be advantageous. The materials would aid the internal respiration of these artificial biological systems by collecting, conducting, and distributing respiratory gases between a diffusion-delimited boundary of the artificial system and metabolically active sites within the system. The materials would permit cell populations contained within diffusion-based devices to be greater in thickness than a few hundred microns. The materials would also allow cells in diffusion-based devices to be located more than a few hundred microns from their diffusion-delimited boundary. The materials would also provide for greater respiratory gas exchange, and thus greater cellular activity and performance.

SUMMARY OF THE INVENTION

The present invention is directed to materials and methods that aid internal respiratory systems in cell-containing devices. These "respiratory aids" have elements that are inspired by respiratory structures in certain aquatic insects that utilize channels of entrapped gas for passive collection, conduction, and distribution of gases from regions of higher partial gas pressure to regions of lower partial gas pressure. The respiratory aids can be used with cell-containing devices to increase the size and/or performance of a cell population contained in the devices. The respiratory aids may permit cell types that are difficult to encapsulate in a device to be more readily encapsulated. In addition, the present invention can be configured to reflect mass-transport in an insect by providing materials with channels that become aqueous liquid-filled in use and operate much like an insect's open, hemolymph-based vascular system. In such configurations, dissolved nutrients, such as glucose exchange, between the contained cells and an external environment of the cells separately from the respiratory system.

As in the insect model, the present invention can passively exchange respiratory gas over distances much greater than the distances possible with diffusion through aqueous media alone. The rates that respiratory gases can be passively exchanged with the present invention are much greater than those of diffusion through aqueous media alone. These differences are due in principle part to differences in resistances to diffusion through aqueous media encountered by dissolved respiratory gases as compared to resistances to diffusion of respiratory gases encountered when gases move through a gaseous medium. The resistance to diffusion of respiratory gases through a gaseous medium, such as air, is much less than the resistance to diffusion of respiratory gases through aqueous media. For example, the resistance to diffusion of oxygen through a gaseous medium 30 centimeters in length is equivalent to the resistance encountered by oxygen when it diffuses through only one micron of water under standard conditions. In the present invention, advantage is taken of this property by providing devices that operate in parallel with aqueous liquid-filled channels to facilitate exchange of respiratory gases between a contained-cell population and a surrounding environment.

The present invention relies on diffusion-based processes rather than convection-based processes to transport respiratory gases from regions of higher partial gas pressure to regions of lower partial gas pressure. Unlike cell-containing devices that depend on convection-based means to assist gas exchange, the present invention does not require input of mechanical energy or thermal energy for efficient gas exchange. Rather, exchange of respiratory gases occurs by passive, diffusion-based, means in the present invention. When materials of the present invention are intended for use, or placed, within the diffusion-delimited boundary of an internal respiratory system to assist exchange of respiratory gases, the materials are referred to as "internal respiratory aids."

In addition, the present invention can increase a diffusion-delimited boundary beyond its native dimensions. Accordingly, materials of the present invention that extend, expand, or enlarge the diffusion-delimited boundary of an internal respiratory system are also referred to as "internal respiratory aids."

As cells in association with materials of the present invention utilize oxygen, a localized depletion of oxygen develops in the vicinity of the cells. The depletion of oxygen causes oxygen from other locations to diffuse toward the oxygen-consuming cells. As oxygen is consumed by the contained cells, oxygen continuously diffuses into internal respiratory aids of the present invention from locations of higher partial oxygen pressure. The oxygen then rapidly diffuses through gas-transporting regions of the internal respiratory aids to locations in the respiratory aid near an oxygen-depleted site. A difference in partial oxygen pressure between the internal respiratory aids and oxygen-depleted sites among the cells causes oxygen to diffuse out of the present invention to the sites. Gas exchange occurs in the opposite direction through the present invention when concentration gradients of gases such as carbon dioxide drive the removal of such gases from a cell population to locations beyond the cell population.

Efficient diffusion-based gas exchange occurs through the present invention with gas-containing materials that are highly gas-permeable and highly gas-transmissive. In addition, materials of the present invention have a high gas-carrying capacity. In many embodiments, the gas-carrying capacity of the present invention is much greater than conventional oxygen carriers, such as perfluorocarbon-based materials (e.g., perfluorooctyl bromide). In use, the high gas-carrying, highly gas-permeable, highly gas-transmissive materials of the present invention require only a small percentage of the volume of a contained cell-population be allocated to the invention to effect efficient gas exchange. A ramiform geometry consisting of a highly distributed branched network is an example of a preferred configuration for the internal respiratory aids of the present invention. These geometries allow the internal respiratory aids to be distributed throughout a cell population such that each cell is positioned near a gas-exchanging surface of the invention. Internal respiratory aids with ramiform geometries also reduce the uneven gas exchange within a contained cell population often found in conventional diffusion-based cell-containing devices. The higher efficiency of gas exchange with the present invention allows fabrication of smaller devices. When implanted in a recipient, smaller sized cell-containment devices often results in improved comfort for the implant recipient.

Though modeled after respiratory systems of aquatic insects, the present invention is not required to emulate the ramiform geometry of insect respiratory systems. Many natural and artificial structures having high surface area-to-volume ratios suggest suitable geometries for the present invention. Some fundamental forms include, but are not limited to, coral-like forms, foams, networks of very fine fibers, or particulate materials. Materials having these forms can be further configured in a variety of shapes, such as sheets, discs, cylinders, tubes, spheres, and spiral rolls. Examples of those forms are illustrated in FIGS. 14–36C. These and other configurations can be made in any size that is suitable for maintaining a viable cell population. Viable cell populations can be contained and serviced with the present invention in implantable cell-encapsulation devices, in vitro cell-containing devices, extra-corporeal devices, and other devices utilizing living cells.

In the gas-transporting portions of the present invention, a boundary between gas-entrapped regions within the invention and a surrounding environment of the invention is preferably provided to assist in maintaining the integrity of the gas-transporting elements. Preferably, the boundary is made with a coating of a gas-permeable material placed on exterior, or perimeter, surfaces of the gas-entrapping regions of the invention. The gas-transporting portions of the present invention can be scaled, in whole or in part, with a gas-permeable material. Preferably, the gas-permeable coating material provides a liquid-tight seal to prevent ingress of liquids into gas-entrapping void spaces of the invention.

In a preferred embodiment, one end of an internal respiratory aid is configured with a high surface area-to-volume ratio extending into an external environment where it functions as a gill-like oxygen collector. At its opposite end, the respiratory aid passes through a cell-retaining membrane to an array of tracheole-like structures that reach and ramify throughout a contained cell population and distribute oxygen to metabolically active sites in the population. This embodiment provides highly efficient exchange of oxygen and carbon dioxide between an oxygen-rich external environment and a population of contained metabolically active cells.

In other embodiments of the present invention, resistance to gas transport through a single highly diffusion-resistant component of an internal respiratory system is improved by replacing all, or part, of the resistive component with an internal respiratory aid. In one such embodiment, a membrane of a cell-containing device has an internal respiratory aid in the form of gas-entrapped channels, or gas-filled void spaces, that supports high rates of respiratory gas transport therethrough (e.g., FIGS. 17–23 and 24A–24C). The membrane also has channels that fill with water or aqueous fluid during use, providing an "aqueous liquid-fillable" component. The internal respiratory aid provides gas transport through the membrane, while the aqueous liquid-fillable component in the membrane provides means for exchanging aqueous-dissolved nutrients and wastes across the membrane. The internal respiratory aid is isolated from the aqueous liquid-fillable component such that the flux of gases across the material through the internal respiratory aid occurs separate from, yet substantially in parallel with, the flux of water and aqueous solutes across the material through the aqueous liquid-fillable component.

In many embodiments, the internal respiratory aid and the aqueous liquid-fillable component traverse the entire thickness of a particular embodiment of the present invention. In other embodiments, the respective permeable components extend across at least a portion of the thickness of the material. Respiratory gases passively conduct through the internal respiratory aid of the membrane in a much more efficient manner than through the aqueous liquid-fillable component. This embodiment is particularly useful when the membrane portion of the system presents the greatest resistance to gas exchange of the entire internal respiratory system, as is often the case with cell-encapsulation devices.

In addition to oxygen and carbon dioxide, various gases can be collected, conducted, and/or delivered with the present invention. For example, gases such as nitrogen, carbon monoxide, ammonia, hydrogen sulfide, methane, nitric oxides, and certain free radicals can be exchanged with the present invention. In some embodiments, agents can be used in the present invention to render noxious or toxic agents less harmful to cells. Preferred agents for this purpose include metallic catalysts and/or enzymes. In addition, gas-permeable coating materials that are permselective to different gases can be used in the present invention to selectively transport one gas with respect to one or more other gases. Lastly, gas-permeable liquids, such as certain perfluorocarbons, may be optionally placed, in whole or in part, within void spaces of the internal respiratory aid.

In addition to being a conduit for gases, parts of the internal respiratory aid can serve as structural components of a cell-containment device. In most membrane embodiments, a material of the present invention has a plurality of internal respiratory aid elements and aqueous liquid-fillable component elements traversing the thickness of the membrane. The internal respiratory aid and aqueous liquid-fillable component can each be made of porous materials, non-porous materials, or both. In some embodiments of the present invention, the aqueous liquid-fillable component is capable of containing free cells, encapsulated cells (e.g., FIGS. 27 and 27A), immobilized enzymes, immobilized ribosomes, cell scaffolding materials, or inorganic catalysts.

In the present invention, the internal respiratory aid permits greater quantities of gases to be acquired, delivered to, and removed from cells contained or immobilized by a material of the present invention than conventional semi-permeable materials having only aqueous channels for gas exchange. As a result of the increased quantities of gases that can be exchanged with cells retained, contained, or immobilized with a material of the present invention, a population of cells with increased numbers, enhanced viability, and/or function can be sustained using such a material. This is of particular significance when it is desired to contain cells that must be sustained by a relatively high flux of gases. Accordingly, a preferred embodiment of the present invention is a cell-containment device comprising at least one permeable membrane capable of retaining living cells, wherein the permeable membrane forms at least a portion of a chamber for containing living cells, the chamber comprising at least one void volume in which living cells are placed, and an internal respiratory aid in association with the cell-containment device, the internal respiratory aid comprising at least one porous element comprising at least one exterior surface and at least one gas-filled void space in an interior portion of the porous element, wherein the gas-filled void space is in fluid communication with at least a portion of the exterior surface, whereby passage of gas through the internal respiratory aid into the chamber from liquids outside the device and passage of gas out of the chamber through the internal respiratory aid to liquids outside the device occurs by diffusion-based means when the device is containing living cells. In further embodiments, the device also comprises access means through which cells are introduced into the chamber. Various embodiments of these cell-containing devices can be implanted in tissues or in body cavities of a recipient. Tissues include soft tissues, hard tissues, and blood.

An internal respiratory aid of the present invention can be associated with a cell-containment device in a variety of ways. For example, an internal respiratory aid can be configured to improve movement of respiratory gases between metabolically active sites within a cell-containing device (FIGS. 5, 15, 30A–30C, 33A–33C, 34A, 34E, and 36A–36C). Much like insect tracheoles, the present invention can be configured to extend into a cell population from a permeable cell-encapsulating membrane and passively transport and distribute respiratory gases to numerous locations throughout the cell population. The internal respiratory aid can be configured to reside partially or completely within the cell population. Preferably, these internal respiratory aids have high surface area-to-volume ratios. Structures with high surface area-to-volume ratios are better able to distribute oxygen than low surface area-to-volume structures. When driven by a partial pressure gradient, oxygen from the internal respiratory aid diffuses out of the respiratory aid to nearby oxygen-utilizing cells. In this manner, the internal respiratory aid can function as a "gas distributor." This embodiment is particularly useful when transport of gases through a cell-containing portion of an internal respiratory system presents the greatest resistance to gas exchange of the entire internal respiratory system.

An internal respiratory aid can also be associated with a cell-containment device by configuring the internal respiratory aid for use outside a cell-containing device. For example, an internal respiratory aid can reside between a permeable membrane and an external respiratory system (FIGS. 4, and 8–13). In these aspects of the present invention, the internal respiratory aid extends away from a cell-containing device to an external environment and functions much like an insect gill to passively collect respiratory gases from the environment. The internal respiratory aids in these embodiments connect to a permeable cell-retaining or cell-containing membrane. Alternatively, the internal respiratory aids are placed in proximity to a cell-containment device (e.g., within one or two millimeters). Preferably, these internal respiratory aids have structures with high surface area-to-volume ratios. Structures with high surface area-to-volume ratios are better able to collect aqueous-dissolved oxygen than low surface area-to-volume structures. The high surface area of these structures reduces the resistances to respiratory gas transport presented by layers of water that are resistant to diffusion-based movement of gas through the layers. These layers are often found at the external oxygen-collecting surfaces of the invention. In most cases, the gases are collected by this embodiment of the present invention at greater rates and over greater distances than those supported by diffusion through aqueous media alone. In this manner, the internal respiratory aid can function as a "gas collector." This embodiment is particularly useful when transport of gases through the external environment outside of the device presents the greatest resistance to gas exchange of an entire internal respiratory system.

Accordingly, "an internal respiratory aid in association with a cell-containing device" refers to various embodiments of the present invention placed entirely within a cell chamber of a cell-containing device (e.g., FIGS. 5, 34A, and 36B). "Internal respiratory aids in association with a cell-containing device" also refers to embodiments where the aids are placed outside a cell-containing device in proximity to the device and/or in contact with at least a portion of the device (e.g., FIGS. 4, 35A, 35B, and 36D). An internal respiratory aid of the present invention can be "in association with a cell-containing device" by contacting at least a portion of a permeable cell-retaining or cell-containing membrane of the cell-containing device. These internal respiratory aids can contact an inner surface of a permeable membrane (e.g., FIGS. 5 and 14B) or an outer surface of a permeable membrane (e.g., FIGS. 14A, 14C, 35A, and 35B). An internal respiratory aid "in association with a cell-containment device" can also be a component of a cell-retaining or cell-containing material (e.g., FIGS. 7, 16–23, 24B, 24C, and 26A–28B). An internal respiratory aid can also be "in association with a cell-containment device" by combining any and all of the above-summarized configurations (e.g., FIGS. 8–12, 15, 30A, 33A, 34B–34E, 35C, and 36C).

In other embodiments, an internal respiratory aid can also be associated with a cell-containment device by configuring the internal respiratory aid to serve as a conduit for transporting respiratory gases between sites of differing partial pressure. The particular advantage of this embodiment is the ability to maximize the rate of delivery of respiratory gas under the action of the partial pressure difference. As distances between metabolically active sites can be large (i.e., greater than a few millimeters), it is desirable that minimal respiratory gas is lost from the respiratory aid along the transport path. It is also desirable that a substantial resistance to transport is not encountered. An internal respiratory aid in the form of a highly gas-permeable conduit that is insulated on its outer surface from gas transport thereacross in directions perpendicular to the direction of gas transport through the respiratory aid is referred to herein as a "gas conductor." This embodiment is particularly useful in instances where intervening resistances to gas transport from a region of high oxygen availability to a region of oxygen need must be reduced.

The preferred internal respiratory aids of the present invention are made of materials that have a multiplicity of interconnected gas-entrapped, or gas-filled, void spaces coursing through the material that function as the principal means by which gases move through the invention. The present invention is also directed to materials having internal respiratory aids made of highly gas-permeable liquids or solids. Other preferred internal respiratory aids include those that possess high surface areas and function as an efficient means for gases to exchange between the present invention and a surrounding volume of aqueous media. In applications where it is desired to minimize gas exchange with the surrounding aqueous media, low surface area and/or resistive exchange surfaces are preferred.

Waste gases, such as carbon dioxide, can be removed from the cell population through these internal respiratory aids as well. When carbon dioxide is transported with the present invention, the same structures used for oxygen collection function as carbon dioxide distributors. Likewise, structures used for oxygen distribution function as the carbon dioxide collectors. The driving force in each case is an appropriate difference in gas partial pressure. The rates and distances over which either oxygen or waste gas is conducted and distributed by the present invention are greater than those supported by diffusion through aqueous media alone.

As the above embodiments illustrate, the present invention can function across an entire internal respiratory system. Alternatively, it may function solely as an oxygen collector, solely as an oxygen conductor, or solely as an oxygen distributor. Combinations of structures with these functions are also possible with the present invention (FIG. 13). In some embodiments, internal respiratory aids of the present invention are in association with a cell-containment device where two or more aids are attached to one another through connector means (e.g., FIGS. 13, 34C–34E, 35C, and 36C).

BRIEF DESCRIPTION OF THE DRAWINGS

FIG. 14A is a schematic illustration of an embodiment of the present invention (141) placed on outer surfaces of a cell-contacting material (142).

FIG. 14B is a schematic illustration of an embodiment of the present invention (143) placed on inner surfaces of a cell-contacting material (144).

FIG. 14C is a schematic illustration of an embodiment of the present invention (145) placed on outer surfaces of a cell-retaining material (146) and in contact with inner surfaces of the cell-retaining material. Cells (147) are also illustrated.

FIG. 15 is a schematic illustration of an embodiment of the present invention (150) placed within a series of separate cell-encapsulation devices (151).

FIG. 26A is an illustration of an embodiment of the present invention (260), wherein the internal respiratory aid is comprised of fused porous particles (265) and the component comprised of channels that become aqueous liquid-filled during use comprises void spaces (261) there between.

FIG. 31A illustrates an embodiment of the present invention (320) wherein the gas-collecting portion of the invention has available surface area for gas flux equivalent to the gas-delivering portion of the invention. Direction of gas flow through the invention is indicated by the arrows. The gas-collecting portion is shown with arrows pointing into the invention. The gas-delivering, or distributing, portion is shown with arrows pointing away from the invention. The irregular-shaped object separating the gas-collecting portion from the gas-delivering portion indicates a membrane through which the invention transports gas.

FIG. 31B illustrates an embodiment of the present invention (322) wherein the gas-collecting portion of the invention has more available surface area for gas flux than the gas-delivering portion of the invention. The direction of gas flow through the invention is indicated by the arrows. The gas-collecting portion is shown with arrows pointing into the invention. The gas-delivering, or distributing, portion is shown with arrows pointing away from the invention. The irregular shaped object separating the gas-collecting portion from the gas-delivering portion indicates a membrane through which the invention transports gas.

FIG. 31C illustrates an embodiment of the present invention (324) wherein the gas-collecting portion of the invention has less available surface area for gas flux than the gas-delivering portion of the invention. The direction of gas flow through the invention is indicated by the arrows. The gas-collecting portion is shown with arrows pointing into the invention. The gas-delivering, or distributing, portion is shown with arrows pointing away from the invention. The irregular shaped object separating the gas-collecting portion from the gas-delivering portion indicates a membrane through which the invention transports gas.

FIG. 34A illustrates an embodiment of the present invention in the form of a cell-encapsulation device (360) having internal respiratory aid elements (361) inside a permeable membrane (362) that are routed into a sealing means (363).

FIG. 34B illustrates an embodiment of the present invention in the form of a cell-encapsulation device (360) having internal respiratory aid elements (361) inside a permeable membrane (362) that are routed through a sealing means (364) and extend beyond the sealing means to the outside of the device.

FIG. 34C illustrates an embodiment of the present invention in the form of a cell-encapsulation device (365) having internal respiratory aid elements (361) inside a permeable membrane, indicated by dotted lines, that are routed through a sealing means (366). Additional connector means (367) having internal respiratory aid elements (368) are shown at each end of the cell-encapsulation device (365).

FIG. 34D illustrates an embodiment of the present invention in the form of a cell-encapsulation device (369) having internal respiratory aid elements (361) inside a permeable membrane, indicated by dotted lines, that are routed through a sealing means (3660). Additional connector means having internal respiratory aid elements (3680) are shown at each end of the cell-encapsulation device (369).

DETAILED DESCRIPTION OF THE INVENTION

Figure 1A:
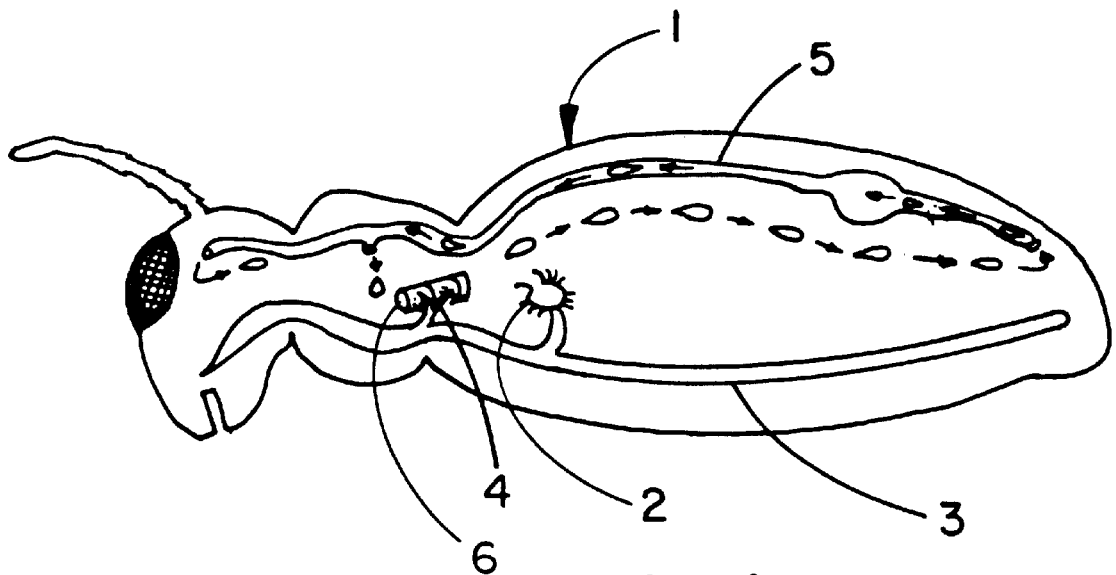
FIG. 1A illustrates a longitudinal cross-section of an insect (1). In this section, a tracheolar system is shown with spiracles open to the atmosphere (2), tracheae (3), tracheoles (4) leading into a muscle fiber (6). In addition, a vascular system (5), separate from the ventilation system, is shown.
Figure 1B:
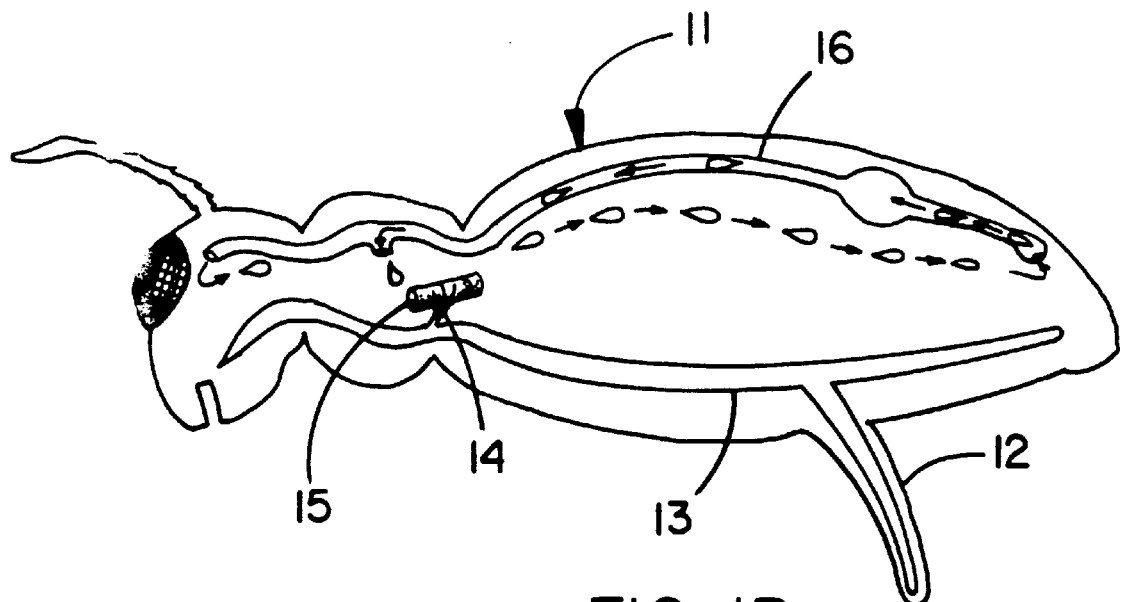
FIG. 1B illustrates a longitudinal cross-section of an insect (11). In this section, a closed tracheolar system is shown with an external gill (12), tracheae (13), tracheoles (14) leading into a muscle fiber (15). In addition, a vascular system (16), separate from the ventilation system, is shown.
Figure 2:
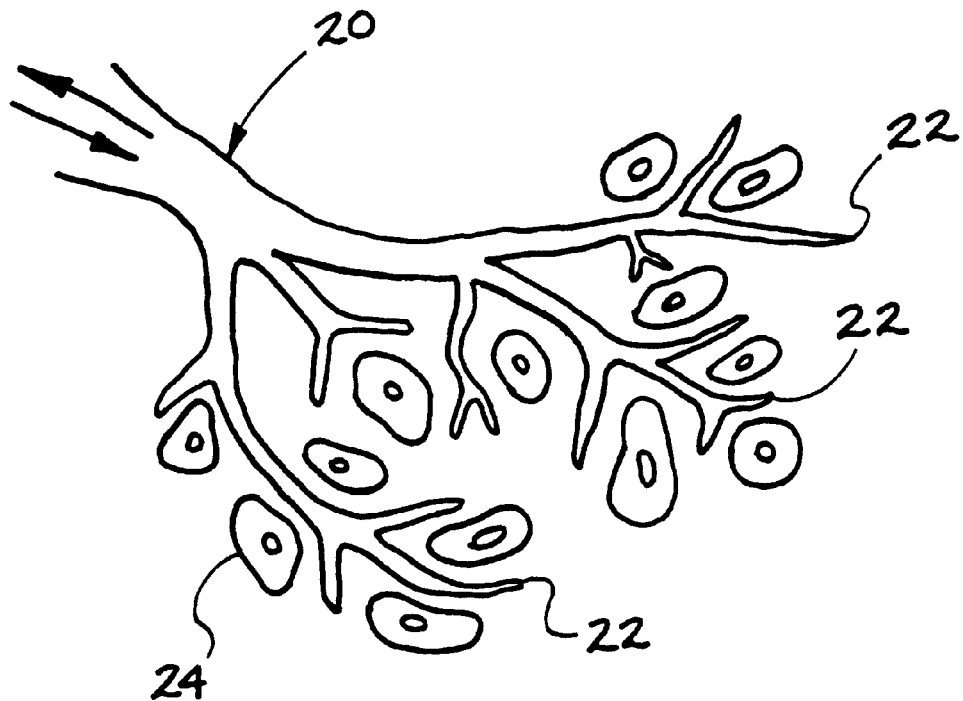
FIG. 2 is a schematic illustration of an insect tracheole (20) and tracheole termini (22) having a ramiform geometry in juxtaposition with insect cells (24). Gas exchange is indicated by the arrows.
Figure 3:
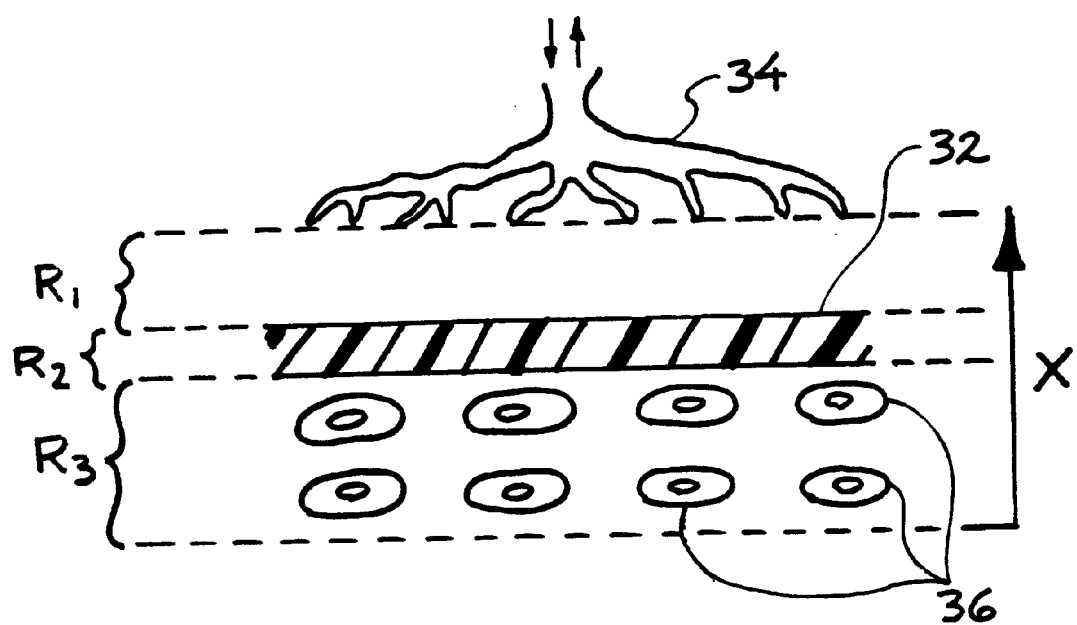
FIG. 3 is a schematic illustration of a conventional cell-containing membrane (32) with a capillary network (34) in the vicinity of the membrane. The principle resistances to gas transport through cell-containing systems are illustrated with the symbols $R_1$, $R_2$, and $R_3$. $R_1$ represents resistances encountered by gases moving between capillaries and the permeable cell-retaining membrane. $R_2$ represents resistances encountered by gases moving through a permeable cell-containing membrane. $R_3$ represents resistances encountered by gases moving through a contained cell mass (36). A diffusion-delimited boundary distance is represented by the symbol "x."
Figure 4:
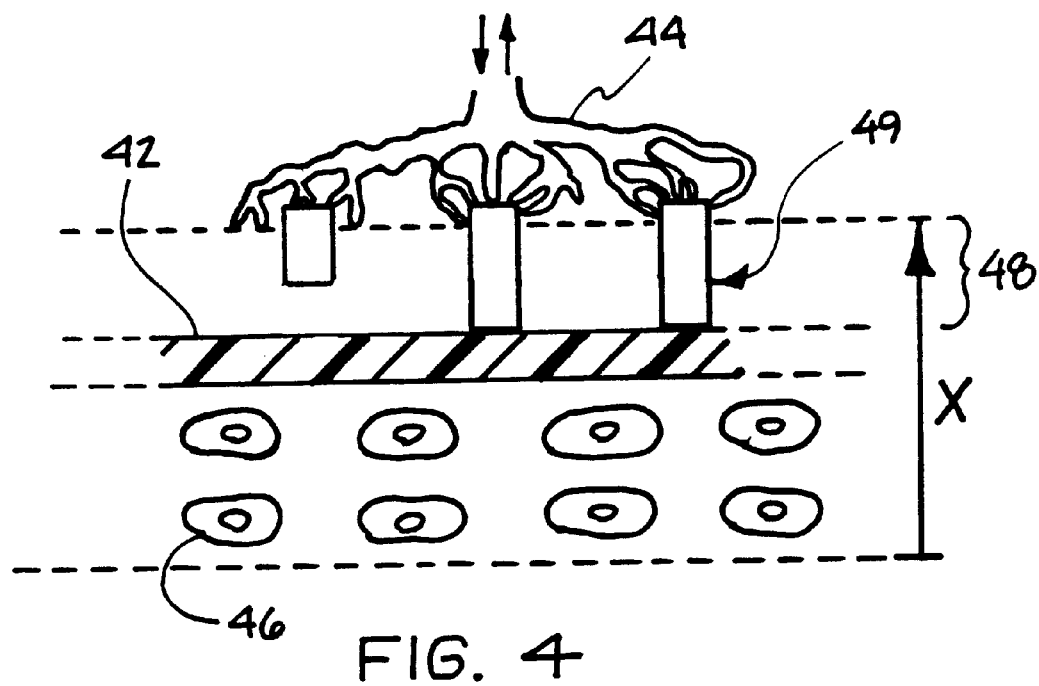
FIG. 4 is a schematic illustration of an embodiment of the present invention (49) in conjunction with a conventional cell-containing membrane (42). In this embodiment, the invention is in close association with the cell-containing membrane and extends beyond the cell-containing membrane to an environment of the cell-containing device (48). A capillary network (44) is illustrated in close association with the invention. Cells (46) are contained by membrane (42). A diffusion-delimited boundary distance is represented by the symbol "x."
Figure 5:
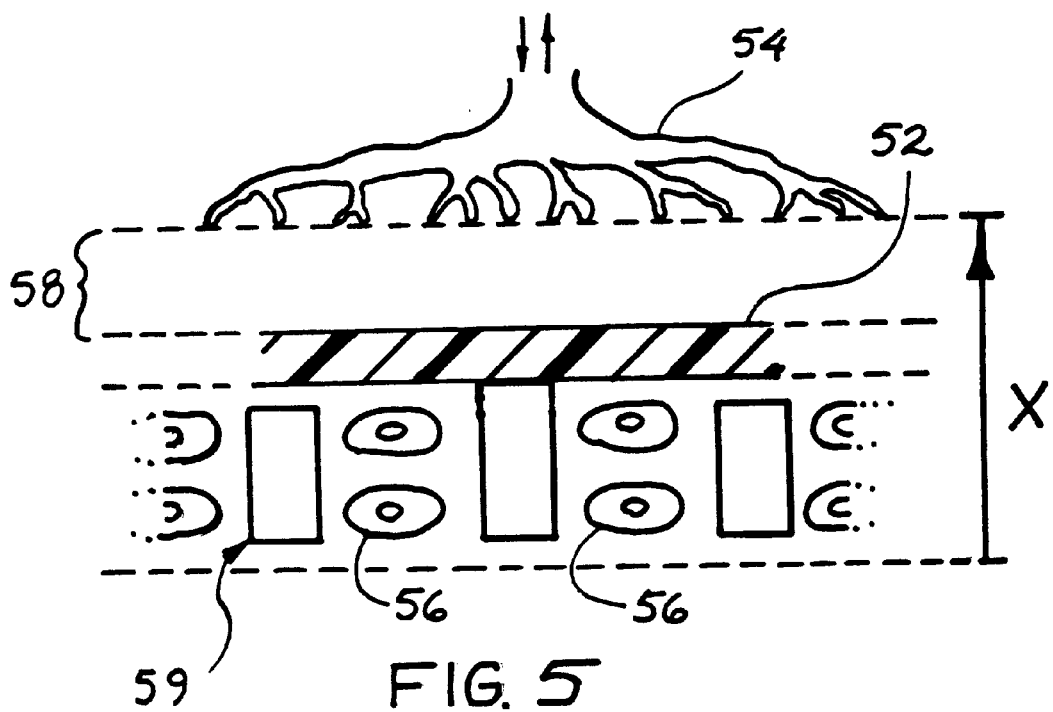
FIG. 5 is a schematic illustration of an embodiment of the present invention (59) in conjunction with a conventional cell-containing membrane (52). In this embodiment, the invention is placed inside the cell-containing membrane among a population of cells (56) in close association with the cell-containing membrane. A capillary network (54) is illustrated in an environment (58) of the conventional cell-containing membrane (52). A diffusion-delimited boundary distance is represented by the symbol "x."
Figure 6:
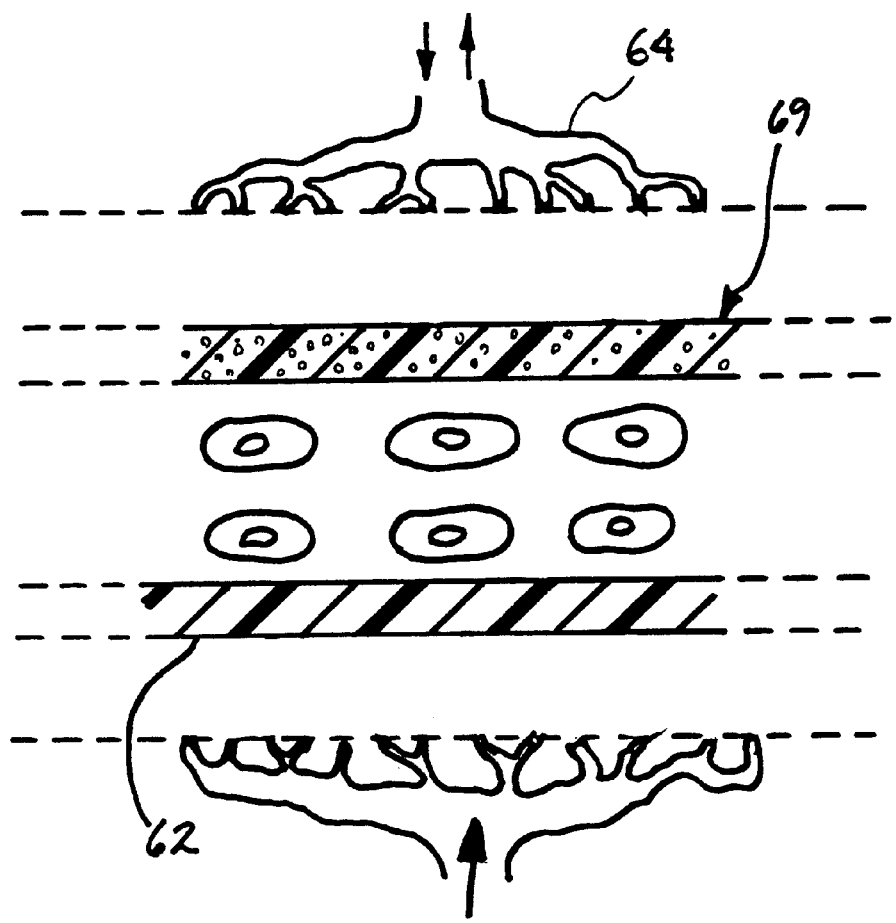
FIG. 6 is a schematic illustration of an embodiment of the present invention (69) having gas-filled void spaces in conjunction with a conventional cell-containing membrane (62). In this embodiment, the invention is configured to form a wall of a cell-containing device. A capillary network (64) is illustrated in close association with the invention for enhanced exchange of respiratory gases. The conventional permeable membrane is also illustrated in close association with a capillary network (64) for exchange of aqueous-dissolved nutrients and wastes. A diffusion-delimited boundary distance is represented by the symbol "x."
Figure 7:
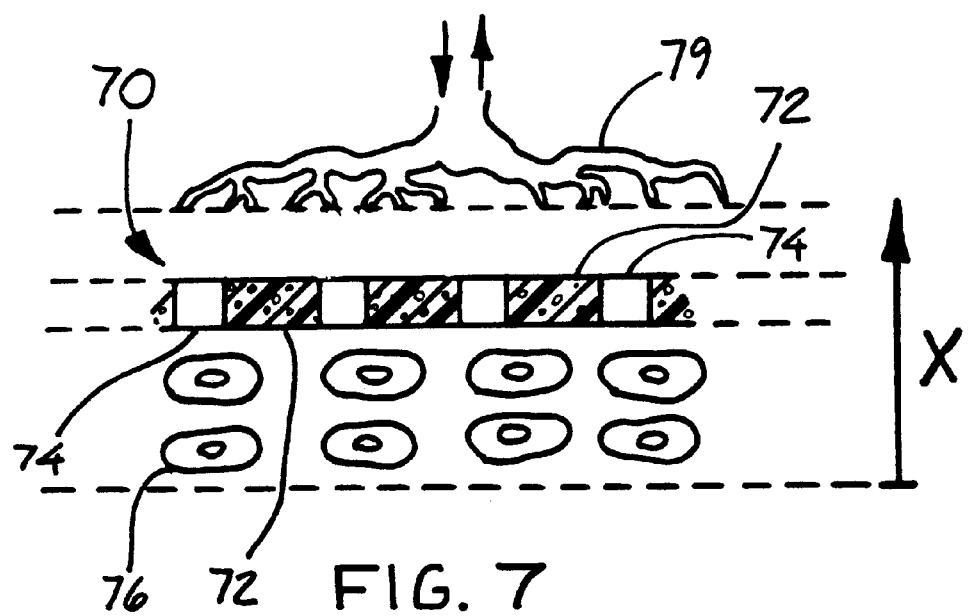
FIG. 7 is a schematic illustration of an embodiment of the present invention (70) that combines in a single material, elements of an internal respiratory aid (72) and channels that become aqueous liquid-filled during use (74). Cells (76) are illustrated in close association with the present invention (70). A capillary network (79) in close association with the present invention (70) is also illustrated. A diffusion-delimited boundary distance is represented by the symbol "x."
Figure 8:
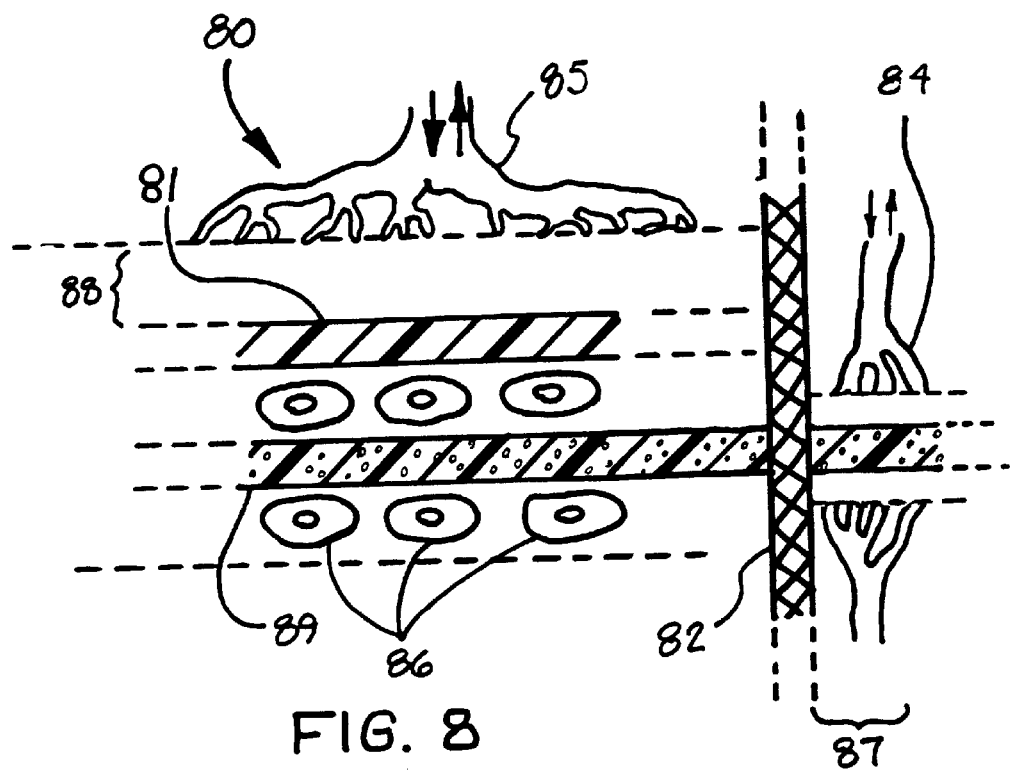
FIG. 8 is a schematic illustration of an embodiment of the present invention (80) in conjunction with a cell-containing device. In this embodiment, the invention has internal respiratory aid elements (89) having gas-filled void spaces that extend from within a contained cell population (86) across a wall of a cell-containing device (82) to an external environment (87). The portion of the invention in the external environment is in close association with a capillary network (84). A conventional cell-retaining membrane (81) is in association with a capillary network (84) in an environment (88). A diffusion-delimited boundary distance is represented by the symbol "x."
Figure 9:
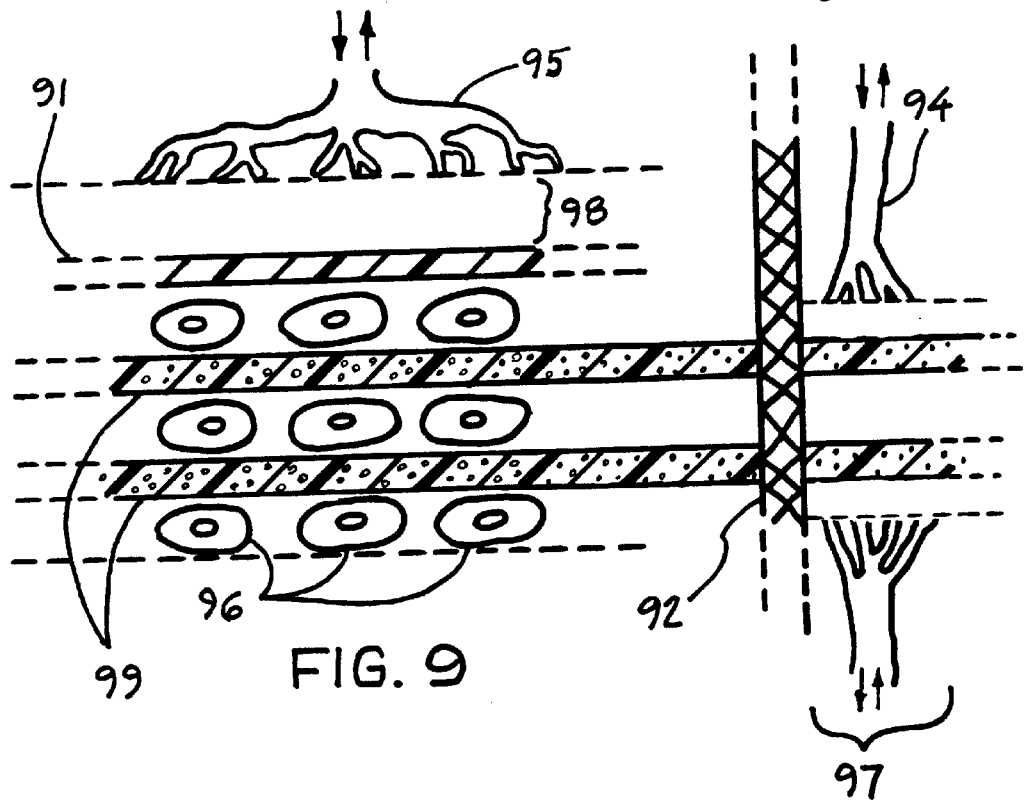
FIG. 9 is a schematic illustration of an embodiment of the present invention (90) in conjunction with a cell-containing device. In this embodiment, the invention has a plurality of internal respiratory aid elements (99) having gas-filled void spaces that extend from within a contained cell population (96) across a wall of a cell-containing device (92) to an external environment (97). The portions of the invention in the external environment are in close association with a capillary network (94). A conventional cell-containing membrane (91) is also closely associated with a capillary network (94) in an environment (98). A diffusion-delimited boundary distance is represented by the symbol "x."
Figure 10:
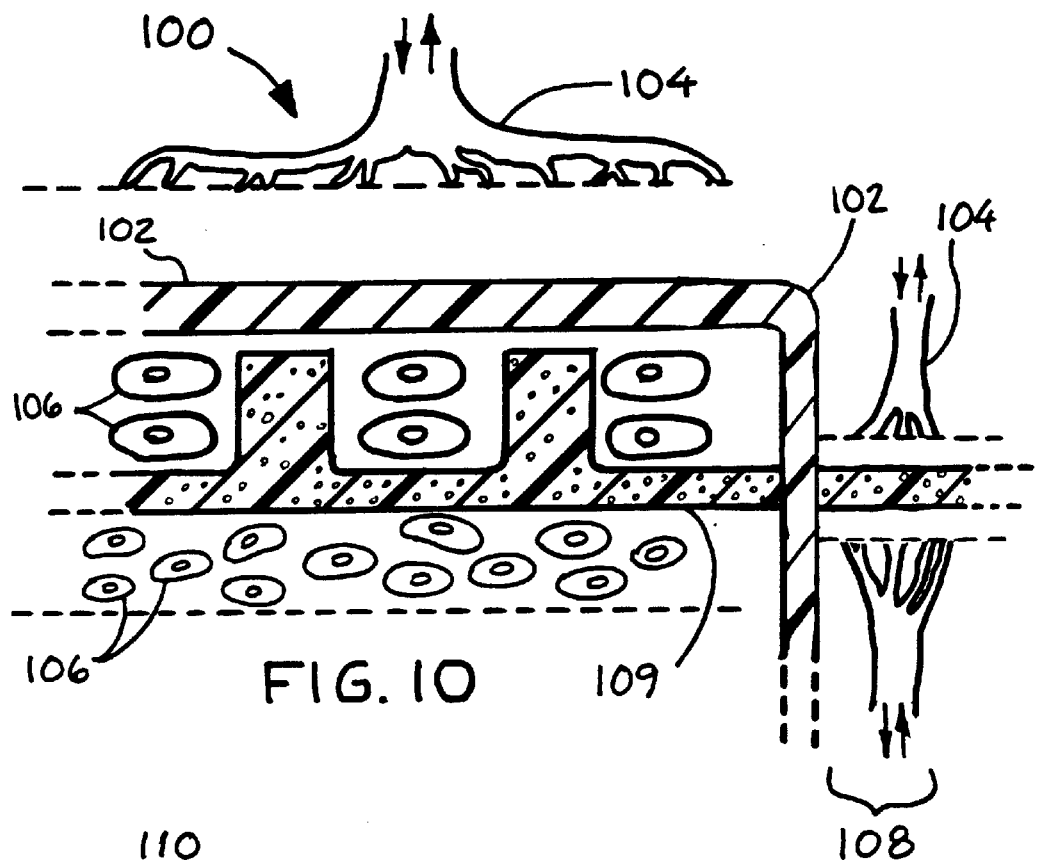
FIG. 10 is a schematic illustration of an embodiment of the present invention (100) in conjunction with a conventional cell-containing membrane (102). In this embodiment, the internal respiratory aid (109) having gas-filled void spaces is in a form that provides a high surface area. Cells (106) are illustrated in close association with membrane (102) and invention (109). Capillary networks (104) are also illustrated in an environment (108) and in association with invention (109). A diffusion-delimited boundary distance is represented by the symbol "x."
Figure 11:
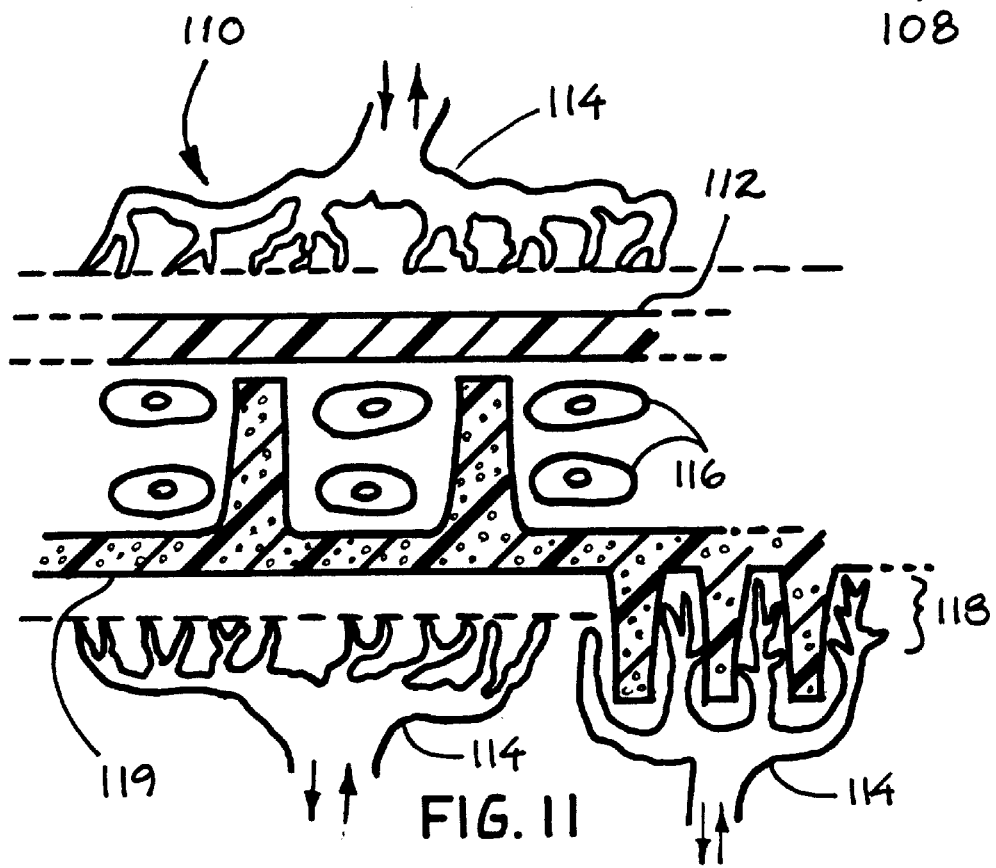
FIG. 11 is a schematic illustration of an embodiment of the present invention (110) in conjunction with a conventional cell-containing membrane (112). In this embodiment, the internal respiratory aid (119) having gas-filled void spaces functions as a cell-containing material in addition to a serving as an improved means for respiratory gas exchange. The internal respiratory aid also projects into a contained cell population (116). In addition, the internal respiratory aid optionally extends beyond the cell-containing portions of the material into an external environment (118) of the invention. Capillary networks (114) are illustrated in close association with both the conventional cell-containing membrane and the present invention. A diffusion-delimited boundary distance is represented by the symbol "x."
Figure 12:
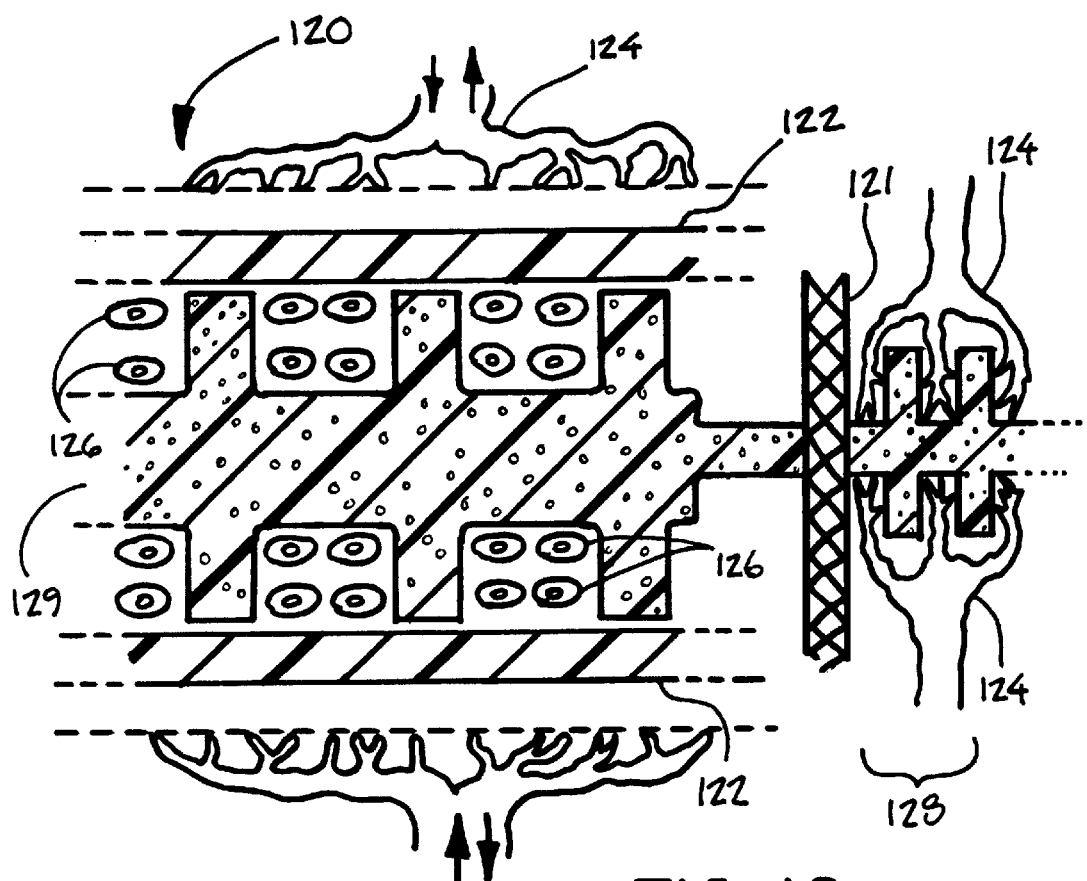
FIG. 12 is a schematic illustration of an embodiment of the present invention (120) in conjunction with a conventional cell-containing membrane (122). In this embodiment, the internal respiratory aid (129) having gas-filled void spaces is placed in a contained cell population (126). The internal respiratory aid positions the contained cells close to the cell-containing membrane for better exchange of aqueous dissolved nutrients and wastes through the membrane. In addition, the internal respiratory aid has a high surface area-to-volume ratio for increasing exchange of respiratory gases. In addition, the internal respiratory aid extends from the contained cell-population through containment means (121) to locations in an external environment (128) beyond the containment means. Capillary networks (124) are illustrated in close association with both the cell-containing membrane and the present invention. A diffusion-delimited boundary distance is represented by the symbol "x."
Figure 13:
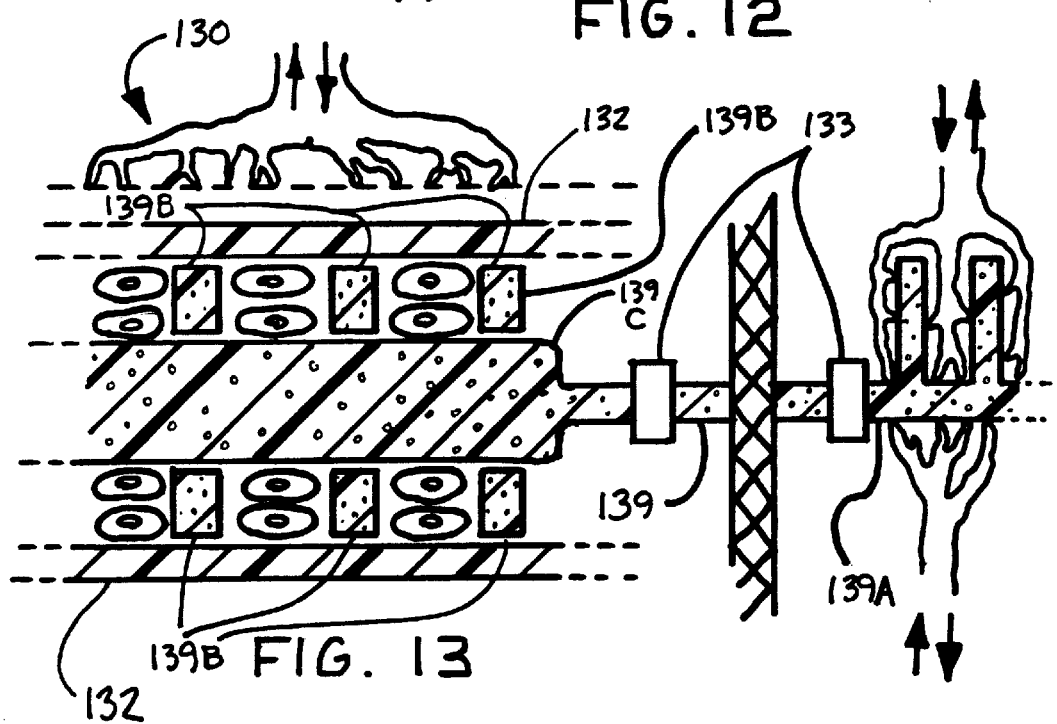
FIG. 13 is a schematic illustration of an embodiment of the present invention (130) in conjunction with a conventional cell-containing membrane (132). In this embodiment, discrete constructs of Internal respiratory aids (139) having gas-filled void spaces are formed and fitted together to make a single combined unit of the internal respiratory aids. The individual constructs comprise a gas collector, a gas conductor, and a gas distributor inside a region of contained cells. Gas-portal means for traversing a barrier are illustrated (137), as are portal means (133) for connecting internal respiratory aid elements.

The present invention can be made from many different materials. The principal characteristic of a suitable material for use in an internal respiratory aid of the present invention is the presence of at least one gas-filled void space in the material that is in fluid communication with at least a portion of the exterior surface of the material. Preferably, there is a plurality of gas-filled void spaces in the material. Most preferably, the gas-filled void spaces are interconnected. The gas-filled void spaces are preferably sealed from loss of entrapped gas and ingress of liquids by covering the void-containing material with a gas-permeable material. In many embodiments, the gas-permeable material is applied to all the exterior surfaces of the material.

Gases found in the void spaces include but are not limited to air, oxygen, nitrogen, carbon dioxide, water vapor, methane, hydrogen sulfide, helium, neon, argon, krypton, xenon, sulfur hexafluoride, gaseous fluorocarbons such as perfluoroethane, decafluorobutane, octafluorocyclobutane, perfluoropentane, and pertluorohexane, and gaseous chlorofluorocarbons, such as chlorodifluoromethane (Freon 22). Most preferably, the present invention comprises voids filled with air, which when implanted in the human body, equilibrates into a mixture of oxygen, nitrogen, carbon dioxide, water vapor, and trace gases such as argon.

In some embodiments, gas-permeable liquids are found in the void spaces of materials of the present invention. Examples of these liquids include but are not limited to bis-(F-butyl)-ethene or $C_4F_9CH=C_4F_9$; chlorofluorocarbon liquids; F-butyltetrahydrofuran; fluorinated silicone oils and other halogenated silicone oils; Forane F66E (Elf Atochem, Lyon, France, $C_6F_{13}$—CH=CH—$C_6F_{13}$); hydrocarbon liquids such as kerosene, hexadecane, n-dodecane, and n-pentadecane; monohydroperfluorooctane; natural oils, such as soybean oil; perfluorodecalin; perfluorodimetlhyladamantane; perfluorodimethylcyclohexane; perfluoroethylcyclohexane; perfluorofluorene; perfluorokerosenes; perfluoromethyladamantane; perfluoromethyldecalin;

perfluoromethyldecaline; perfluoro-N-methyldecahydroisoquinoline or FMIQ; perfluorooctane; perfluorooctyl bromide; perfluoroperhydrophenanthrene; perfluoropolyether liquids such as the K-6 hexamer, Krytox TLF7067, Krytox 6354, and Freon E15; perfluorotributylamine; perfluorotrimethylcyclohexane; perfluorotripropylamine; and silicone oils, including those based on polydimethylsiloxane). Most preferred are perfluorodecalin and perfluorooctyl bromide, which have been widely investigated as oxygen-carrying substitutes in human blood.

Yet further embodiments of the present invention have respiratory pigments in void spaces of materials of the present invention. Examples of such compositions include but are not limited to solutions, viscous solutions, suspensions, emulsions, and gels containing respiratory molecules (e.g., protohemes, hemoglobins, fetal hemoglobins, myoglobils, hemocyaninis, chlorocmorins, hemerythrinis, synthetic and semi-synthetic porphyrins). Such respiratory molecules can be crosslinked or otherwise stabilized, as by conjugation with poly(ethylene glycol), poly(ethylene oxide), dextran, or similar molecules. Such respiratory molecules can be metal-bound (e.g., with cations of iron or copper). Such respiratory molecules can be synthetic, semi-synthetic, recombinant, or natural.

In addition, materials which fill void space in an internal respiratory aid may provide benefits other than facilitating transport of respiratory gases. For example, the filler materials may increase the mechanical properties of the invention. Furthermore, the filler materials may function as scavengers of gaseous free radicals and other reactive compounds.

When an internal respiratory aid is filled with a high gas transport material that is a liquid or a solid, it is especially preferred that the filled void spaces of the internal respiratory aid be interconnected. Otherwise, additional diffusional barriers must be overcome which can lower the overall transmissibility of the internal respiratory aid and the material as a whole.

In many embodiments, the void-containing materials are hydrophobic. Hydrophobic materials have low energy surfaces that are readily wetted by low surface tension fluids, such as low molecular weight hydrocarbons or alcohols, and most low molecular weight organic solvents, such as benzene, acetone, toluene, and dioxane, etc. Hydrophilic surfaces, on the other hand, are high energy surfaces that are readily wetted by high surface tension fluids. Examples of high surface tension fluids include, but are not limited to, liquid water, aqueous salt and protein solutions, dimethyl formamide, dimethyl sulfoxide, glycerol, hexamethyl phosphorictriamide, formamide, and ethylene glycol.

Table 1 lists examples of polymeric materials in order of increasing surface tension, with representative values of the surface tension (dyn/cm) for each material measured at 20° C. (Polymer Handbook, 3rd Edition, J. Brandrup, E. H. Immergont, Eds., John Wiley & Sons, Inc., pp. VI 411–VI 426, 1989). In general, the surface tension of polymeric materials ranges from about 10 to 70 dyn/cm. Many polymers have intermediate surface energies and the wetting behavior of high surface tension fluids on these polymers is dependent on factors such as functional groups, surface roughness, contamination, and surface mobility in addition to the surface tension of the polymer surface.

TABLE 1

| Polymer | Surface Tension (dyn/cm) |
|---|---|
| poly(hexafluoropropylene) | 17 |
| poly(dimethyl siloxane) | 20 |
| poly(tetrafluoroethylene) | 24 |
| poly(trifluoroethylene) | 27 |
| poly(vinylidine fluoride) | 33 |
| poly(vinyl alcohol) | 37 |
| poly(styrene) | 40 |
| poly(methyl methacrylate) | 41 |
| poly(vinyl chloride) | 42 |
| poly(ethylene terephthalate) | 45 |
| poly(hydroxyethyl methacrylate) (40% water) | 69 |

Source: Polymer Handbook, 3rd Edition, J. Brandrup, E. H. Immergut, Eds., John Wiley & Sons, Inc., pp. VI 411–VI 426, 1989. Values were determined at 20° C.

One method to compare the hydrophobicity of a non-porous, solid surface of one material with the non-porous, solid surface of another material is to orient the material horizontally and apply a droplet of distilled water to the surface of the material. The angle which the edge of the water droplet makes with the surface is the advancing contact angle or simply the "contact angle." For most smooth, planar, hydrophobic materials, the contact angle will be above 90°. For example, the contact angle of water on poly(tetrafluoroethylene) is approximately 108° no 110°. For most hydrophilic materials, the contact angle will be below about 30°. For example, the contact angle of water on poly(hydroxyetlhyl methacrylate) is approximately 15°, or less. For the purposes of this invention, solid materials which have been modified with one or more layers of hydrophilic polymers will be considered having been rendered hydrophilic if the contact angle decreases by 10° or more. A preferred result would be a resulting contact angle less than 30°.

For porous materials, a simple test to compare the wettability of one material with another is to position the material horizontally and apply a droplet of distilled water onto the surface of the material. For most hydrophobic, porous materials, the water droplet will remain on the surface. For most hydrophilic, porous materials, the water droplet will immediately penetrate into the pores of the sample. The fibers or polymer strands which form the sides of the pores act as hydrophilic surfaces which the water spreads on. The pores attract the water droplet by capillary action. For the purposes of this invention, porous materials which wet within I second after exposure to a droplet of water are considered hydrophilic. Porous materials which do not spontaneously wet, which require more than 1 second to wet, or which require mechanical agitation to thoroughly wet, are considered hydrophobic.

In many embodiments, the gas-filled void spaces of an internal respiratory aid are in the form of pores. Pore sizes of internal respiratory aids range from about 1,000 microns to about 500 microns, preferably about 500 microns to about 100 microns, more preferably about 100 microns to about 10 microns, yet more preferably about 10 microns to about 1.0 micron, and most preferably from about 1.0 micron to about 0.1 micron. In some embodiments, the pore sizes range from about 0.1 micron to about 0.01 micron. Materials, or portions of materials, with pore sizes in the ranges of about 100 microns or less are considered to be "microporous" materials. In addition to preferring smaller pore sizes in the present invention, it is preferred to have a large number of these small pores in the invention to provide as many exchange points as possible for gases to enter and exit the invention. It is also preferred to use hydrophobic materials comprised of small pores in order to further increase resistance to entry of water into the pores, thereby maintaining the integrity of the gas-filled portions of the internal respiratory aid without a gas-permeable material to seal gas in the void spaces. Suitable porous materials for use in the present invention include, but are not limited to, expanded polytetrafluoroethylenie, porous silicone, porous polyethylene, and porous polypropylene.

For porous expanded polytetrafluoroethylene materials (ePTFE) or similarly fibrillated materials, the pore sizes of the materials is related to the lengths of fibrils within the material and the thickness of the material. Thicker fibrillated materials generally have more tortuous pathways connecting one end of a pore to the other end of the pore.

Fibril length is measured as described in U.S. Pat. No. 4,482,516, issued to Bowman et al., which is incorporated herein by reference. The fibril length of ePTFE that has been expanded in a single direction is defined herein as the average of ten measurements between nodes connected by fibrils in the direction of expansion. Ten measurements are made in the following manner. First, a photomicrograph is made of a representative portion of the sample surface with adequate magnification to show at least five sequential fibrils within the length of the photomicrograph. Two parallel lines are drawn across the length of the photomicrograph so as to divide the image into three equal areas, with the lines being drawn in the direction of expansion and parallel to direction of orientation of the fibrils. Measuring from left to right, five measurements of fibril length are made along the top line in the photomicrograph beginning with the first node to intersect the line near the left edge of the photomicrograph and continuing with consecutive nodes intersecting the line. Five more measurements are made along the other line from right to left beginning with the first node to intersect the line on the right hand side of the photomicrograph. The ten measurements obtained by this method are averaged to obtain the fibril length of the material.

For a porous ePTFE material that has been expanded in more than one direction, the fibril length is estimated by examining a representative photomicrograph of the material surface and comparing fibril lengths as described above in a manner than represents the various directional orientations of the fibrils.

It should be noted that at very small pore sizes, i.e. about 0.1 micron or less and especially below 0.01 micron, gas diffusion through the internal respiratory aids becomes hindered by interactions of the gas molecules with the surfaces of the pores in the internal respiratory aid. This is particularly evident at physiological temperatures of a homeothermic animal and under the partial gas pressures of the tissues of such an organism. Even with such a hindrance to gas flux, gas permeability through such small pores can still be orders of magnitude greater than through a liquid medium, particularly an aqueous medium.

The porosity of the present invention does not have to be particularly high. For example, a porosity of about 10%, 1%, or even 0.1% is often sufficient for high gas transport through the invention due to the vastly greater permeability of gases through the contained gas compared to the permeability of these gases through liquids. Porosity of a particular material (e.g., an internal respiratory aid) is defined as the percentage of void volume with respect to the total material volume.

In addition, there is always a concern regarding the degree to which the porosity of the internal respiratory aid affects the mechanical properties of the material of the present invention. Since the internal respiratory aid can also serve as a structural member of the present invention, numerous small pores are preferred relative to a lesser number of large pores in the internal respiratory aid in order to more evenly distribute the structural properties of the internal respiratory aid.

With various materials suitable for use in the present invention, the contours of the exterior surfaces of the materials is often irregular. For example, a porous expanded polytetrafluoroethylene material is comprised of agglomerations of polytetrafluoroethylene material called "nodes" that are connected together with thin thread-like "fibrils" of polytetrafluoroethylene material. Spaces, or voids, between the nodes and fibrils are referred to as "pores." The microscopic architecture, or "microstructure," of a porous expanded polytetrafluoroethylene material is comprised of these nodes, fibrils, and pores. At a microscopic level, the outer boundaries of a porous expanded polytetrafluoroethylene material follow the contours of nodes, fibrils, and pores located at the perimeter of the material. Collectively, these contours form the exterior surfaces of the porous expanded polytetrafluoroethylene material. In many embodiments, a gas-permeable material is applied to a porous expanded polytetrafluoroethylene materials so as to coat, cover, enclose, or seal the contours comprising the exterior surfaces of the porous expanded polytetrafluoroethylene material. Preferably, the gas-permeable material covers the nodes and fibrils at the periphery of the material, as well as spanning the void spaces of the pores to provide a continuous layer of gas-permeable material on the exterior, or peripheral, surfaces of the materials. The covering of gas-permeable material surrounds at least one gas-filled void space (i.e., a pore) in the porous expanded polytetrafluoroethylene material to seal gas in the gas-filled void spaces. In other embodiments, porous materials with more regular exterior surfaces are also covered with a continuous layer of a gas-permeable material to maintain gas in gas-filled void spaces of the porous material. Accordingly, exterior surfaces of porous materials delimit boundaries at the periphery or outer edges of the porous materials beyond which the porous material no longer exists.

Preferably, these embodiments comprise at least one porous element comprising at least one exterior surface and at least one gas-filled void space in an interior portion of the porous element, wherein the gas-filled void space is in fluid communication with at least a portion of the exterior surfaces, and a hydrophobic material surrounding the exterior surface of the porous element, wherein the material is permeable to gases and has a transmissibility to oxygen of at least $5 \times 10^{-4}$ centimeters per second, and wherein the hydrophobic material maintains gas in the gas-filled void space and prevents ingress of liquids into the gas-filled void space, whereby passage of gas into and out of the device occurs through diffusion-based means.

Figure 25A:
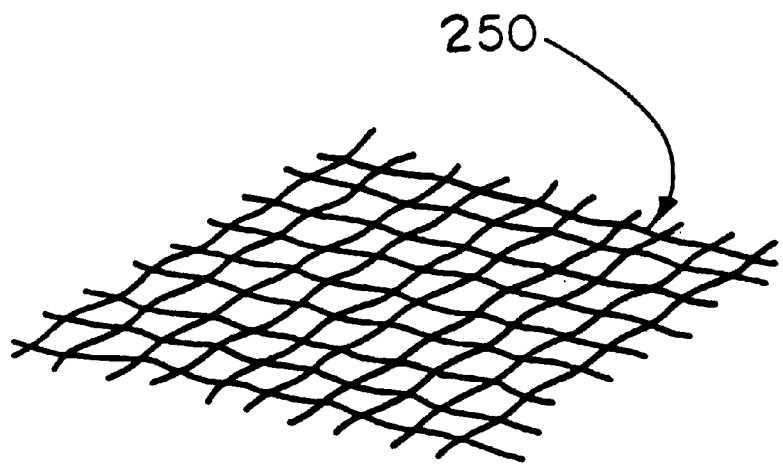
FIG. 25A is an illustration of an embodiment of the present invention (250), wherein the selectively permeable porous material is a weave of a porous fiber material.
Figure 25B:
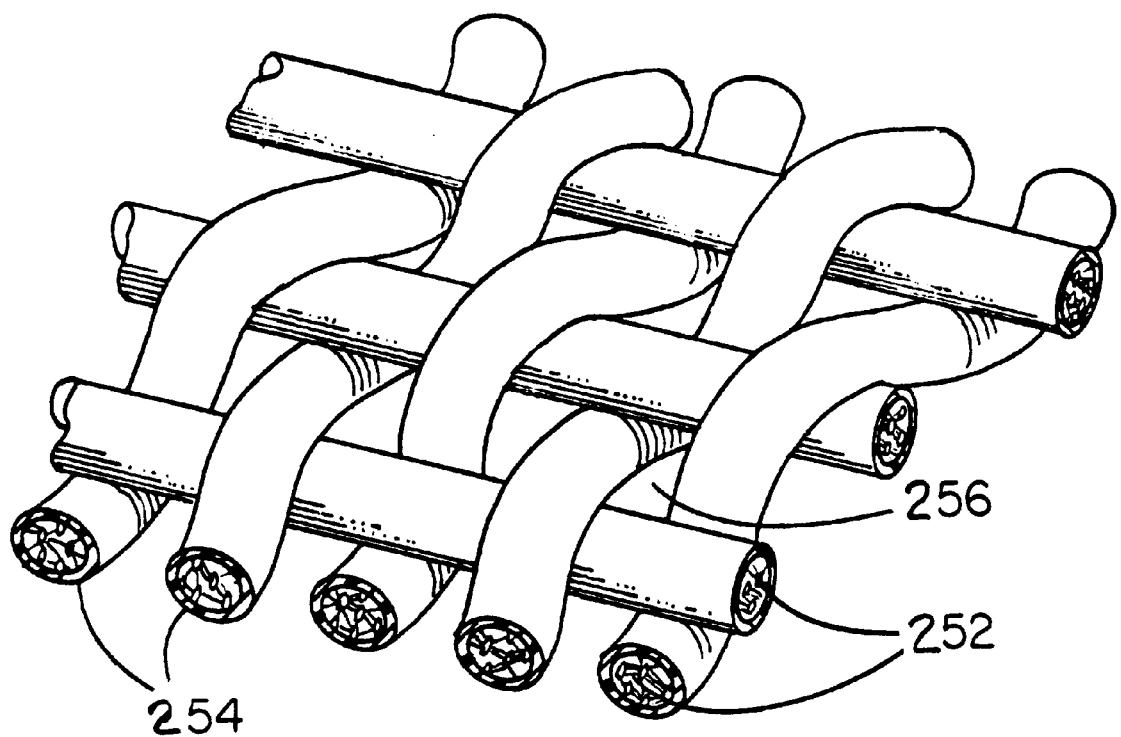
FIG. 25B is an enlargement of the illustration of FIG. 25A, wherein the internal respiratory aid is comprised of porous fibers (252) that are coated with a material (254) that is permeable to gases prior to weaving the porous fibers together. Material (254) may be treated to be hydrophilic. The component comprised of channels that become aqueous liquid-filled during use comprises the spaces (256) in between the porous fibers of the woven material.
Figure 25C:
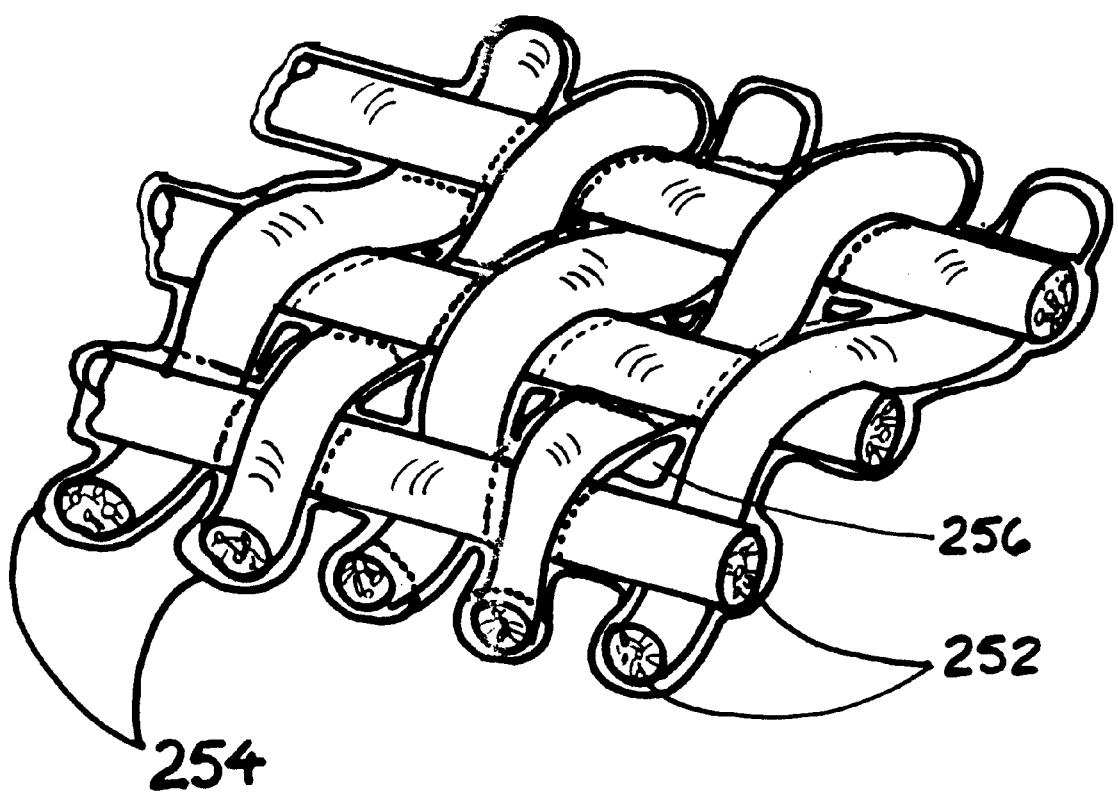
FIG. 25C is an illustration of an internal respiratory aid comprised of woven porous fibers (252) having a coating of a gas-permeable material (254) applied to the porous fibers after the fibers are woven together. The component comprised of channels that become aqueous liquid-filled during use comprises the spaces (256) in between the porous fibers of the woven material.
Figure 25D:
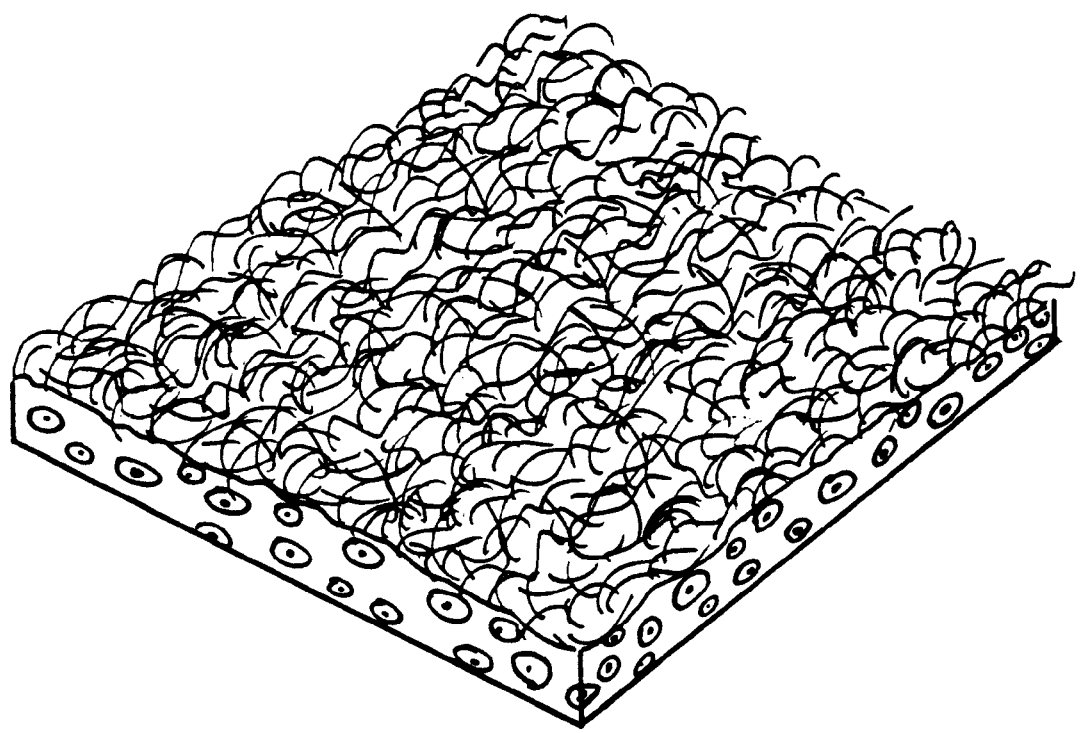
FIG. 25D is an illustration of an embodiment of the present invention (251) wherein the internal respiratory aid is comprised of loosely oriented fibers and the component comprised of channels that become aqueous liquid-filled during use comprises the spaces between the fibers. Cells (253) are also illustrated.

In some embodiments, an internal respiratory aid in the form of a network is constructed. In these networks, the internal respiratory aid comprises a collection of gas-filled elements that exhibit some degree of interconnectivity (FIGS. 25A and 25B) and preferably in fluid communication between one another (FIG. 25C). Where gas-filled elements cross one another, transport of gases from one gas-filled element to another is possible. Woven or matted materials of the present invention are particularly useful in effecting uniform exchange of gases throughout a particular medium. To augment gas transport among the elements of such internal respiratory aids, the elements are fused at crossover points in some embodiments. Preferably, this embodiment comprises a multiplicity of porous elements in the form of a network, the porous elements each comprising at least one exterior surface and at least one gas-filled void space in an interior region of each porous element, wherein the gas-filled void space is in fluid communication with at least a portion of the exterior surface of the porous element, wherein the network has locations at which the porous elements contact one another, a material covering the exterior surface of the porous elements, except the exterior surface at the locations where the porous elements contact one another, wherein the material maintains gas in the gas-filled void space and resists ingress of liquids into the gas-filled void space, while permitting fluid communication between the porous elements at the locations where the porous elements contact one another, and wherein the material is permeable to gases and has a transmissibility to oxygen of at least $5 \times 10^{-4}$ centimeters per second, whereby passage of gas into and out of the device occurs through diffusion-based means.

Figure 34E:
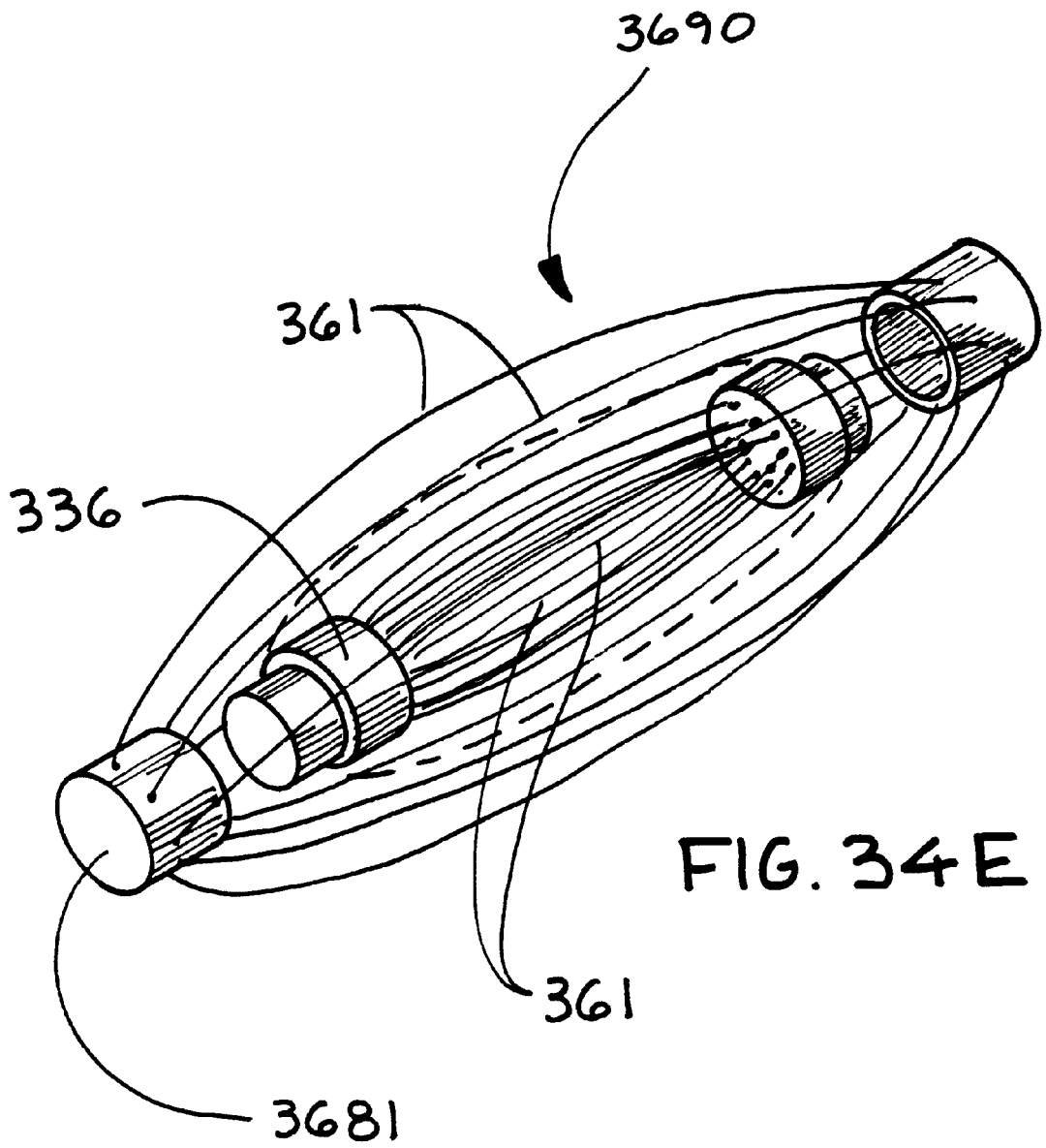
FIG. 34E illustrates an embodiment of the present invention in the form of a cell-encapsulation device (3690) having internal respiratory aid element (361) inside a permeable membrane, indicated by dotted lines, that are routed through a sealing means (336). Additional connector means (3681) having internal respiratory aid elements (361) are shown at each end of the cell-encapsulation device (3690). A permeable cell-retaining membrane is shown as a dotted line.
Figure 35A:
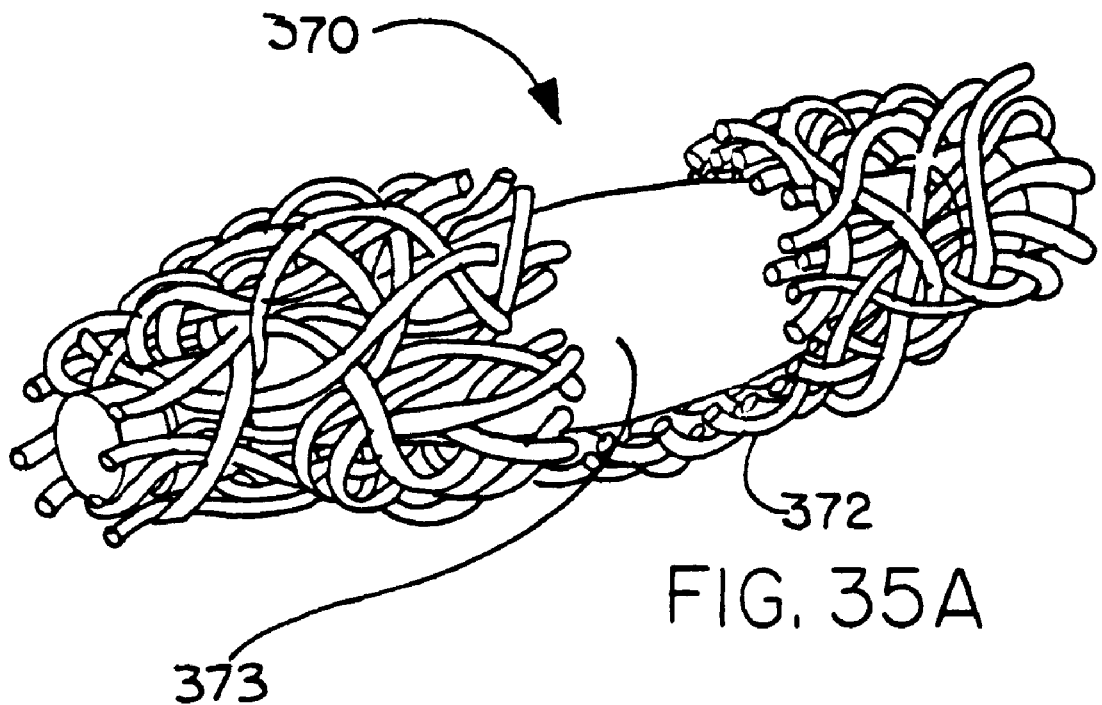
FIG. 35A is a view of an embodiment of the present invention illustrating a cell-encapsulation device (370) with a mat of internal respiratory aid elements (372) surrounding the device in proximity to a cell-retaining membrane (373) and in contact with the membrane. A portion of the internal respiratory aid is shown cut away to illustrate the cell-retaining membrane.
Figure 35B:
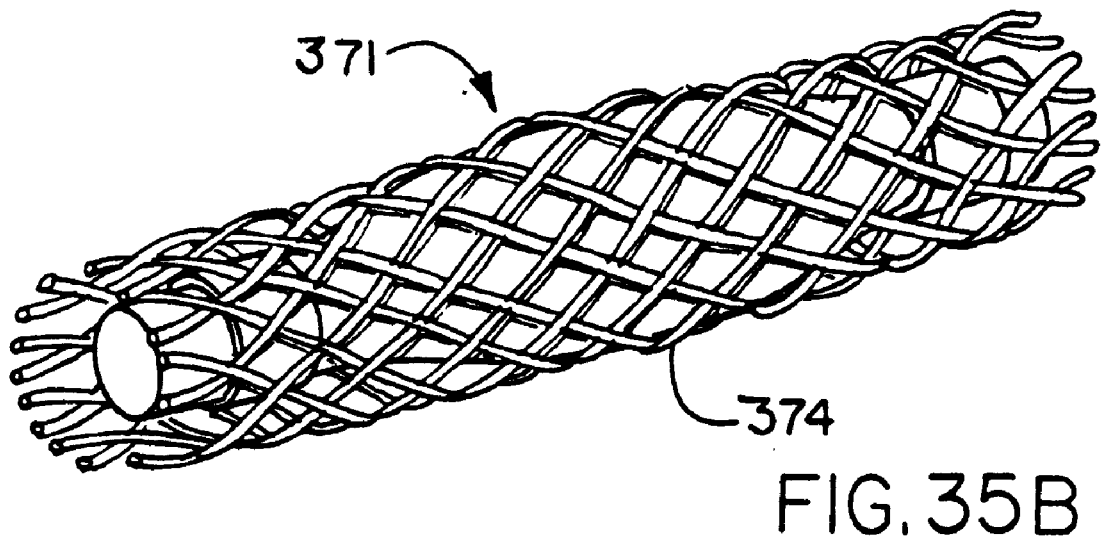
FIG. 35B is a view of an embodiment of the present invention illustrating a cell-encapsulation device (371) with an ordered network of internal respiratory aid elements (374) surrounding the device.
Figure 35C:
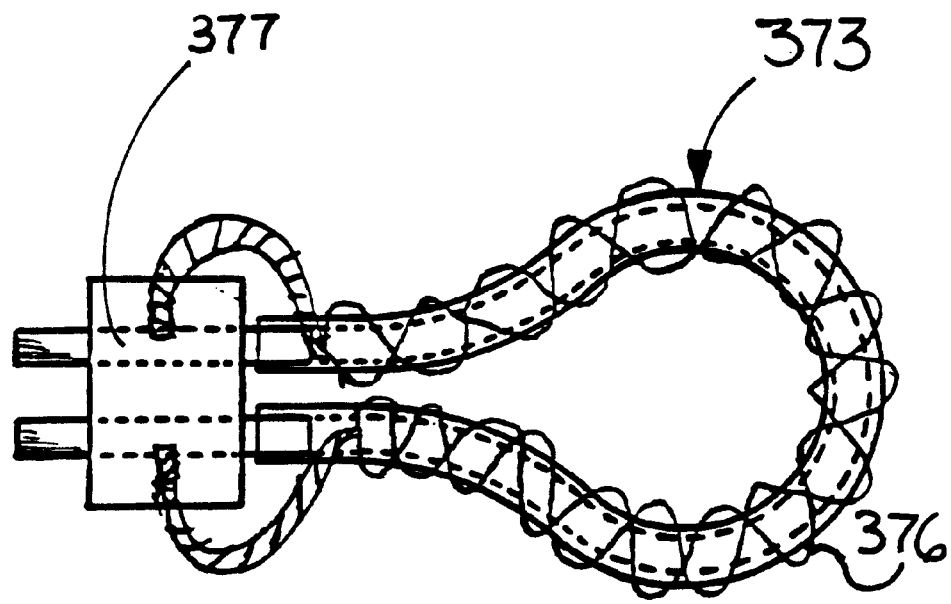
FIG. 35C is a view of an embodiment of the present invention illustrating a containment apparatus for a cell-encapsulation device (373) with a network of internal respiratory aid elements (376) surrounding the device. In this embodiment, the internal respiratory aid is connected to the lumen of the containment apparatus (377).
Figure 35D:
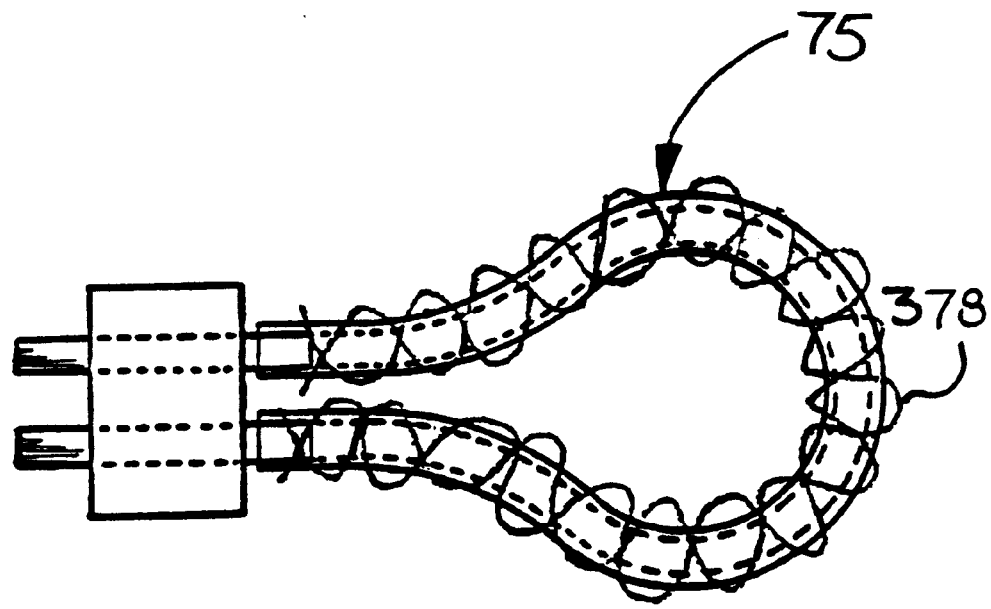
FIG. 35D is a view of an embodiment of the present invention illustrating a containment apparatus for a cell-encapsulation device (375) with a network of internal respiratory aid elements (378) surrounding the device.
Figure 36A:
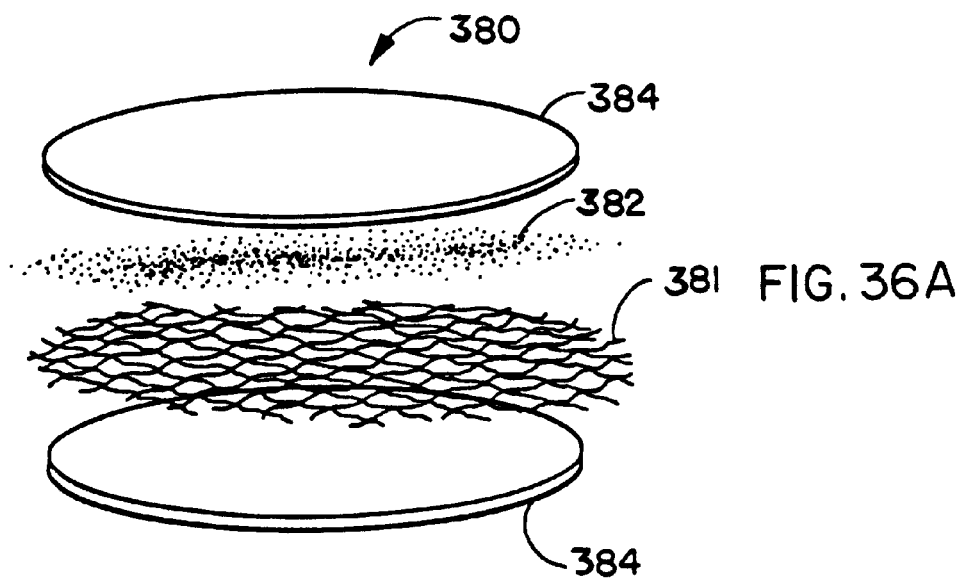
FIG. 36A is an exploded view of an embodiment of the present invention (380) in a planar form having internal respiratory aid elements (381) and cells (382) positioned between permeable membranes (384).
Figure 36B:
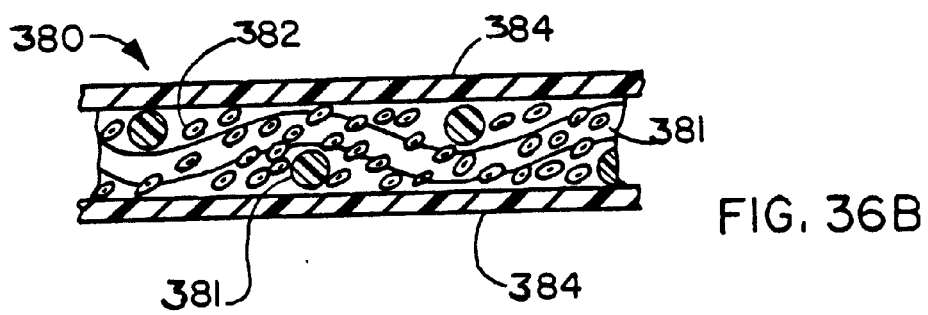
FIG. 36B is a cross-sectional view of the device of FIG. 36A in a finished form. The present invention (380) has permeable membranes (384) enclosing internal respiratory aid elements (381) and cells (382).
Figure 36C:
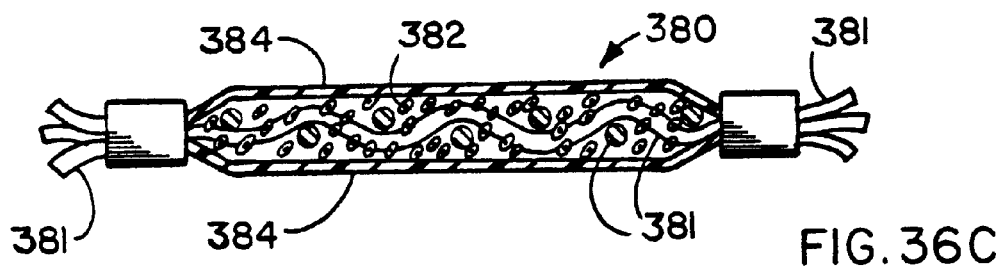
FIG. 36C is a cross-sectional view of the device of FIG. 36A in a finished form. The present invention (380) has permeable membranes (384) enclosing cells (382) and internal respiratory aid elements (381) that extend beyond the permeable membranes (384).
Figure 36D:
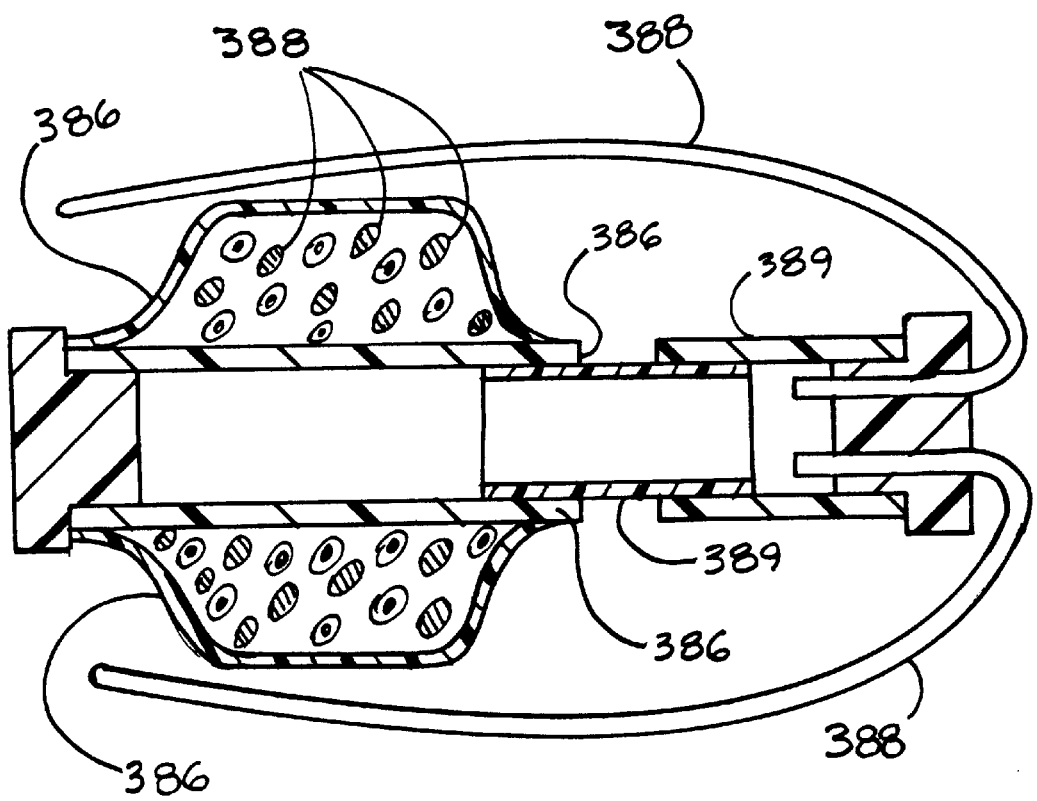
FIG. 36D is a cross-sectional view of a cell-retaining membrane (386) in combination with internal respiratory aids (388). Gas-conducting means (389) are also illustrated.

Another aspect of the present invention involves the use of internal respiratory aids with connector means to attach two or more internal respiratory aids or internal respiratory aid-containing devices together. Referring to FIGS. 34C–34E, for example, devices having internal respiratory aids with connector means are illustrated. The internal respiratory aid portion of each device can be in many forms and geometries. Similarly, a wide variety of connector means can be fashioned for the internal respiratory aids.

FIGS. 34C–34E illustrate another embodiment of the present invention in the form of cell-containment devices. All or part of a semi-permeable membrane containing cells is removed in the illustration to show internal respiratory aids coursing through the space that is occupied by cells when the devices are in use. At both ends of the devices are pluralities of internal respiratory aids with connector means that attach to the cell-containment devices and establish fluid communication between the internal respiratory aids in the connector means with the internal respiratory aids inside the cell-containment devices, as well as the internal respiratory aids in the connector at the opposite end of the cell-containment devices. This non-limiting example is representative of the many types of connections and connectors that can be used to couple internal respiratory aids of the present invention together.

In the non-limiting embodiment illustrated in FIGS. 34C–34E, a plurality of internal respiratory aids are potted into connectors that are adapted to attach to a mated connector on a particular device, such as a cell-containment device. Suitable materials in which to pot, or imbed, internal respiratory aids include, but are not limited to, highly-gas-permeable adhesives, such as silicones, other organosilicon polymers, certain fluoropolyimides, certain amorphous fluoropolymers, and certain polyurethanes, or less-gas-permeable adhesives, fluorinated poly(ethylene-co-propylene), poly(ethylene vinyl acetate), polyacrylates, polyepoxies, polyesters, polyolefins, and cyanoacrylates. The important feature of any connector device is that fluid communication is permitted between internal respiratory aids across, or through, the connection. Accordingly, it is preferred that no sealing layer is introduced between the connected elements with a connector. Rather, it is preferred that there is direct fluid communication, or gas-to-gas communication, between the internal respiratory aids through the connector means.

When it is necessary to prevent the ingress of liquids into the area of the connection between internal respiratory aids, the connector means is sealed with a material that isolates the gas-filled passageways in the connector means between the internal respiratory aids from the potentially contaminating liquids of the local environment. In sealing connector means, at least a portion of the interface between internal respiratory aids in the connector means allows fluid communication between the connected internal respiratory aids. Preferably, the sealed connector means is devoid of gas impermeable or resistive coatings or layers in the portion of the connector means that is in fluid communication with the internal respiratory aids being connected by the connector means.

There are numerous ways in which these connector means can be constructed and applied in the present invention. For example, a coated internal respiratory aid of the present invention is cut, exposing the gas passageways internal to the aid. To re-connect or connect two cut ends, the ends are directly opposed to one another and a bonding material applied that serves to physically connect and hold both ends together. This sealing material also serves to prevent the ingress of liquids into the interface. The bonding, or sealing, material can be permeable or impermeable to gases. Suitable bonding materials include, but are not limited to, highly-gas-permeable adhesives, such as silicones, other organosilicon polymers, certain fluoropolyimides, certain amorphous fluoropolymers, and certain polyurethanes, or less-gas-permeable adhesives, fluorinated poly(ethylene-co-propylene), poly(ethylene vinyl acetate), polyacrylates, polyepoxies, polyesters, polyolefins, and cyanoacrylates.

Connector means in the present invention include, but are not limited to, couplers that attach to each other via threading, swage fitting, or fittings of the type used to couple pressurized hoses together. These connector means often include internal gas spaces within the means to permit the gas spaces of the individual elements to be in fluid communication. Connector means also includes one or more hollow tubes, or needles, attached to an internal respiratory aid-containing device that pierce a septum-like component on a second internal respiratory aid-containing device. Suitable materials for this type of connector include, but are not limited to, polymers, metals, ceramics, glasses, carbons, and composites thereof. Depending on the material, the connector means can be molded, machined, cast, or manufactured by other methods.

Multiple internal respiratory aids of the present invention can be placed in fluid communication with one another with the above-described connector means. Indeed, networks of internal respiratory aids can be interconnected with connector means. Interconnecting internal respiratory aids with connector means can traverse various boundaries and/or media. For example, a network of internal respiratory aids can be assembled and placed in a cell-containing device to provide oases throughout a contained cell population. This interior network of internal respiratory aids can in turn be connected to internal respiratory aids outside the cell-containment device through connector means placed in the wall, or membrane, of the device. The internal respiratory aids outside the cell-containing device can be further interconnected with connector means to form a network of internal respiratory aids around the device. The network of internal respiratory aids outside the cell-containment device collect gas from media surrounding the device, including tissue, and transport the gas across the wall or membrane of the device to a cell population contained in the device. Waste gas is removed from the cell population by the reverse route.

In addition to the wide variety of embodiments of the present invention that connector means provide, this modular approach to constructing the present invention has advantages in manufacturing ease and cost.

Another preferred embodiment of the present invention is in the form of a planar material, such as a membrane. In these materials, gas-filled void spaces provide means through which gases traverse the material. Optionally, neighboring elements of the internal respiratory aid are interconnected in order to transport gases through the material in many directions. Substantially in parallel with these gas-transporting elements are aqueous liquid-fillable void spaces, or channels, in fluid communication with two or more surfaces of the planer material. Neighboring aqueous liquid-fillable channels can be interconnected to facilitate transport of aqueous species through the material in many directions.

Figure 16:
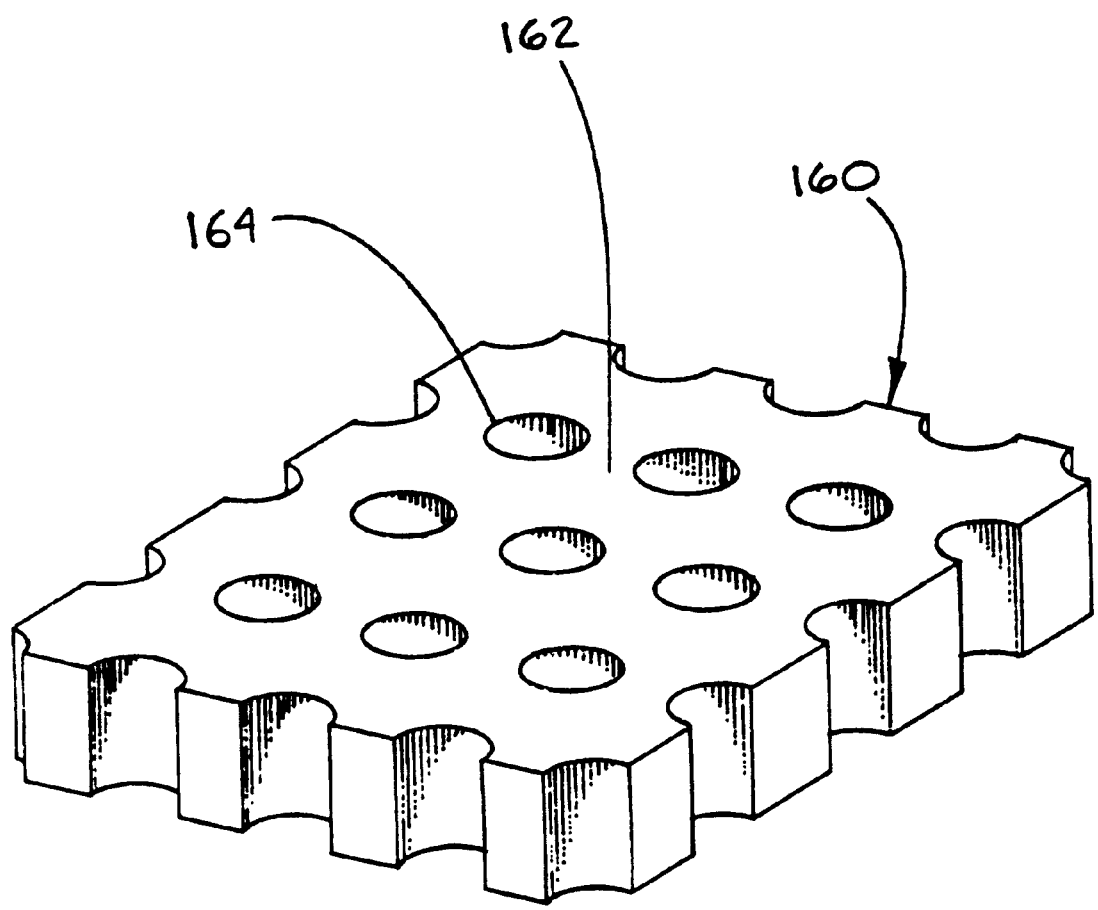
FIG. 16 illustrates an embodiment of the present invention (160) wherein the internal respiratory aid is a gas-permeable material (162) and the channels that become aqueous liquid-filled (164) is comprised of macroscopic holes traversing the thickness of the present invention.
Figure 18:
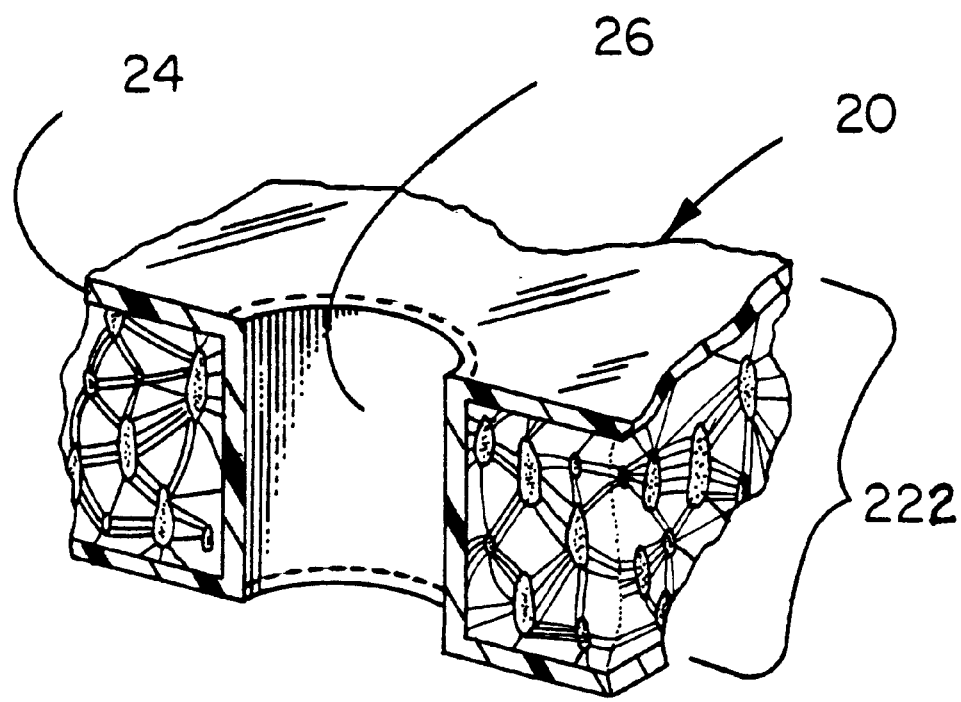
FIG. 18 is a cutaway illustration of an embodiment of the present invention (220), wherein the internal respiratory aid is a microporous material (222) that is coated on its perimeter surfaces with a material (224) that is permeable to gases. The component comprised of channels that become aqueous liquid-filled during use (226) is represented as a section of a cylindrical pore. The internal respiratory aid and the component comprised of channels that become aqueous liquid-filled during use are physically isolated from each other by the coating material. The coating material limits or prevents many non-gaseous species and water from freely diffusing from the macroscopic holes (226) into the internal respiratory aid, thereby maintaining the integrity of the gas-filled spaces of the internal respiratory aid.
Figure 17:
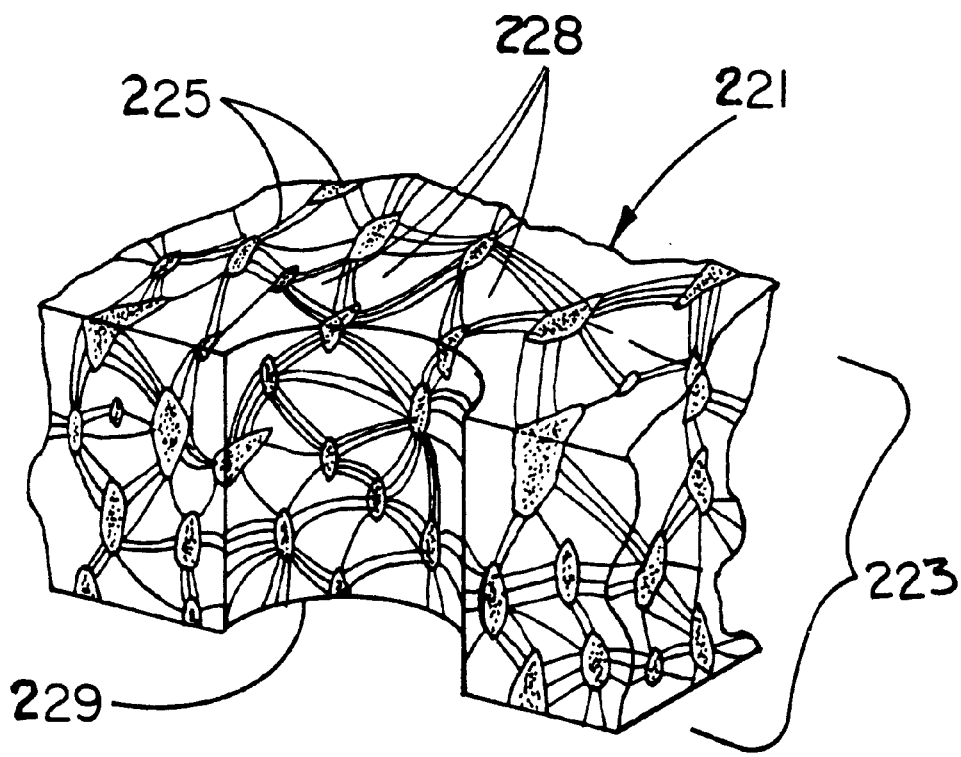
FIG. 17 is a cutaway illustration of an embodiment of the present invention (221), in the form of a microporous material (223) comprised of a series of porous node and fibril structures (225). The pores (228) formed by the nodes and fibrils are gas-filled, highly permeable to gases, and thus function as an internal respiratory aid. When used in an aqueous environment, the internal respiratory aids of the microporous material are either hydrophobic or provided with an oleophobic surface treatment to enable the gas-filled portions to resist becoming wet out with liquid water or aqueous solutions for the environment. An aqueous-liquid fillable component (229) is provided in the material. The surfaces of the macroscopic holes (229) may be further treated with a hydrophilic material or wetting agent to allow the macroscopic holes to wet out more easily.
Figure 17A:
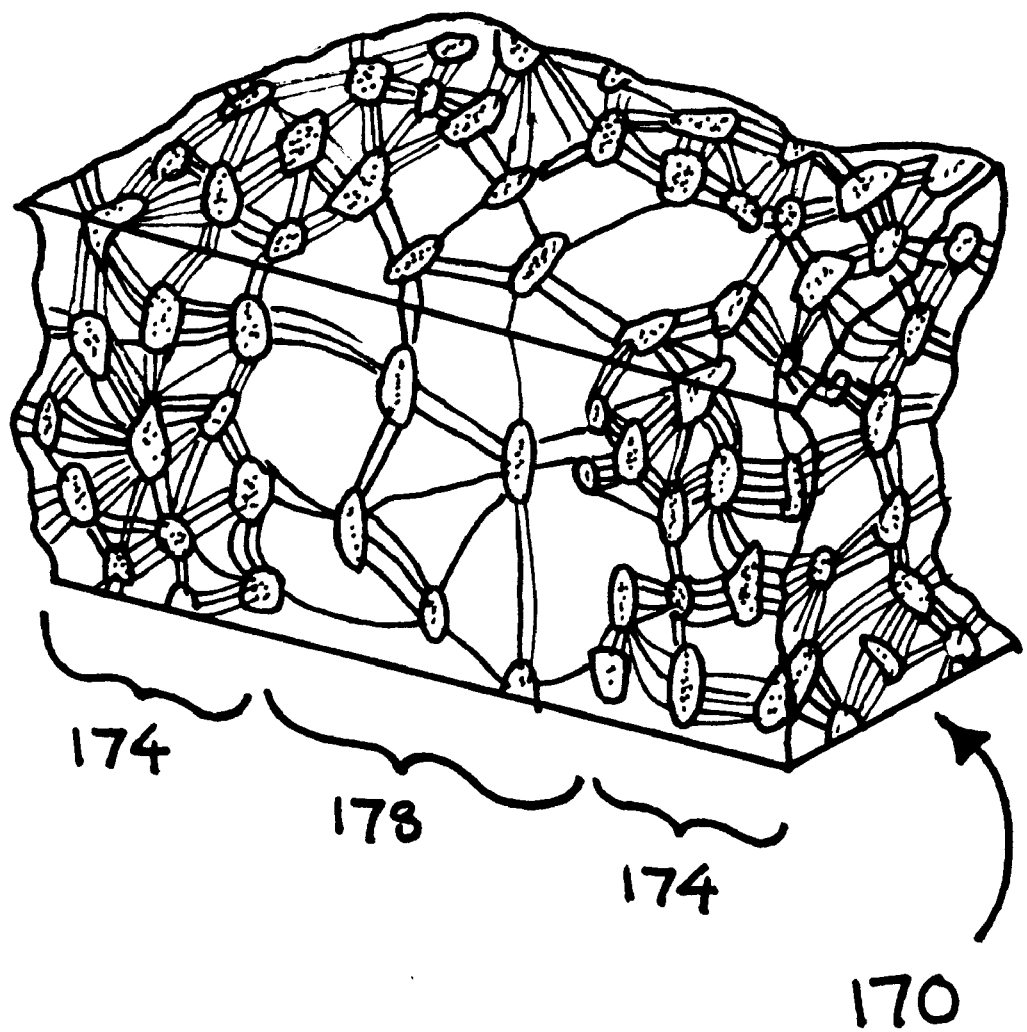
FIG. 17A is a cross-sectional illustration of an embodiment of the present invention (170) is the form of a microporous material (172) having varying interilodal distances that form internal respiratory aids of the present invention in regions of the material with shorter internodal distances (174) and aqueous-liquid fillable portions in regions of the material with longer internodal distances (178).
Figure 19:
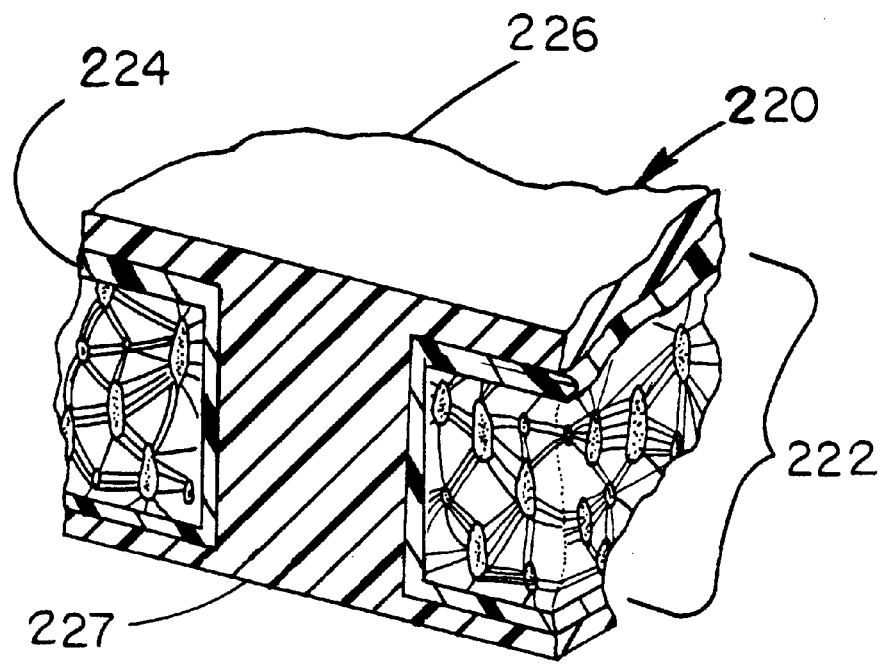
FIG. 19 is an illustration of a water permeable material (227) placed in the component comprised of channels that become aqueous liquid-filled during use (226 of FIG. 18) and on the exposed outer surfaces of the material.
Figure 20:
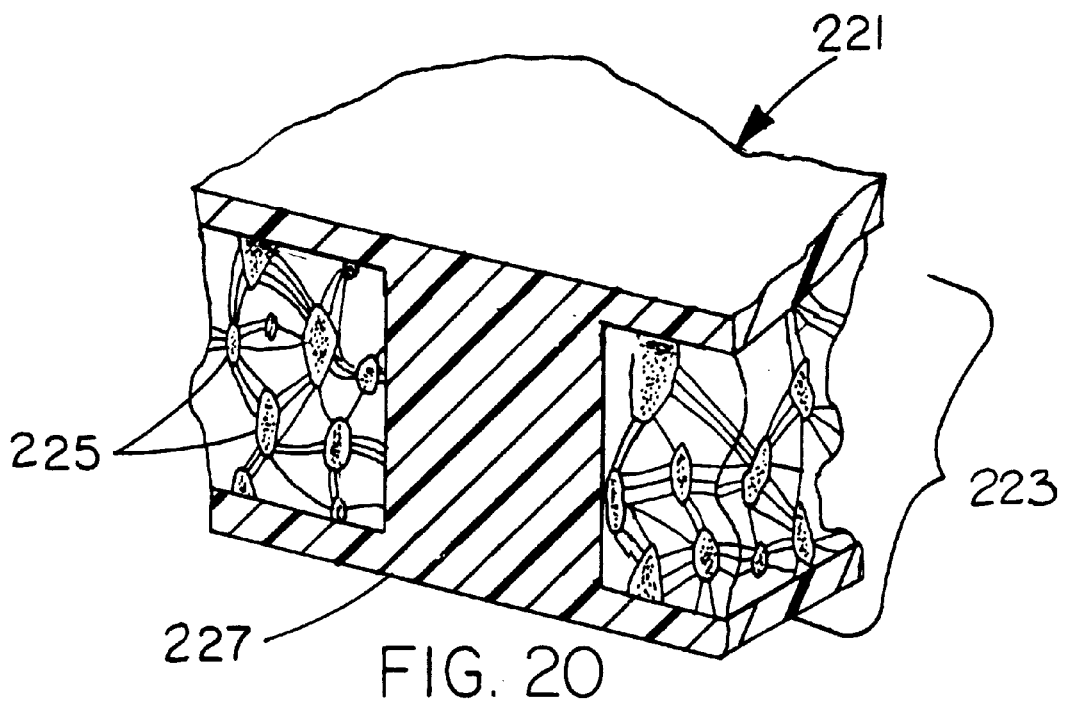
FIG. 20 is an illustration of a water permeable material (227) placed in the component comprised of channels that become aqueous liquid-filled during use (229 of FIG. 17) and on the exposed outer surfaces of the material.

In some embodiments, the aqueous liquid-fillable component comprises void spaces bounded by material that is wettable with water or certain polar solvents (FIG. 17A). Other embodiments have an aqueous liquid-fillable component comprising material that is permeable to water and aqueous solutes (FIG. 20). Further embodiments combine bounded void spaces with water-permeable materials (FIG. 19). The aqueous liquid-fillable component is preferably bounded by material of the internal respiratory aid. This is not a requirement, however, since inert, or non-gas-permeable, material can be present between the internal respiratory aid and the aqueous liquid-fillable component. Preferred embodiments of the present invention have a plurality of internal respiratory aid elements and the aqueous liquid-fillable component elements interspersed with one another. For example, the elements of the internal respiratory aid and the aqueous liquid-fillable component of the present invention can be located adjacent to one another in a material. In this arrangement, the elements of the internal respiratory aid and the aqueous liquid-fillable component can be distributed in an orderly pattern in the material or randomly distributed throughout the material (FIG. 16). Alternatively, a series of elements of the internal respiratory aid can be combined with a series of elements of the aqueous liquid-fillable component.

In a preferred embodiment, the present invention comprises a first material having surfaces and a thickness, the first material comprising at least one gas-filled void space in an interior region of the first material, wherein the gas-filled void space is in fluid communication with at least a portion of the surfaces, a second material enclosing the gas-filled void space, wherein the second material is permeable to gases and has a transmissibility to oxygen of at least $5 \times 10_{-4}$ centimeters per second, wherein the second material maintains gas in the gas-filled void space and restricts ingress of liquids into the gas-filled void space, whereby passage of gas into and out of the device occurs by diffusion-based means, and at least one aqueous liquid-fillable portion traversing the thickness of the first material.

Porous materials in various forms can be used to make these embodiments of the present invention. The porous materials described herein are only illustrative, however, as there are many types of porous materials from which a material of the present invention can be made. In addition to these porous materials, materials that are not initially porous can be made porous by inducing porosity in the materials in various ways. These methods include, but are not limited to, stretching of a material, phase separation, temperature-induced phase separation, porogenl leaching, mechanical hole punching, laser drilling, and foam processing. Accordingly, the present invention is not limited to only those porous materials discussed herein. The only requirement for a given porous starting material in these embodiments is that at least one internal respiratory aid and at least one aqueous liquid-fillable component can be constructed in the porous material. Porous materials such as foams, sponges, drilled polymers, expanded or stretched polymers, and fibrous mats and weaves are non-limiting examples of preferred starting materials for use in the present invention. The materials can be in many forms such as sheets, tubes, rods, cylinders, spheres, cones, ovoids, stellates, discs, regular and irregular geometric shapes, and combinations thereof.

Figure 24A:
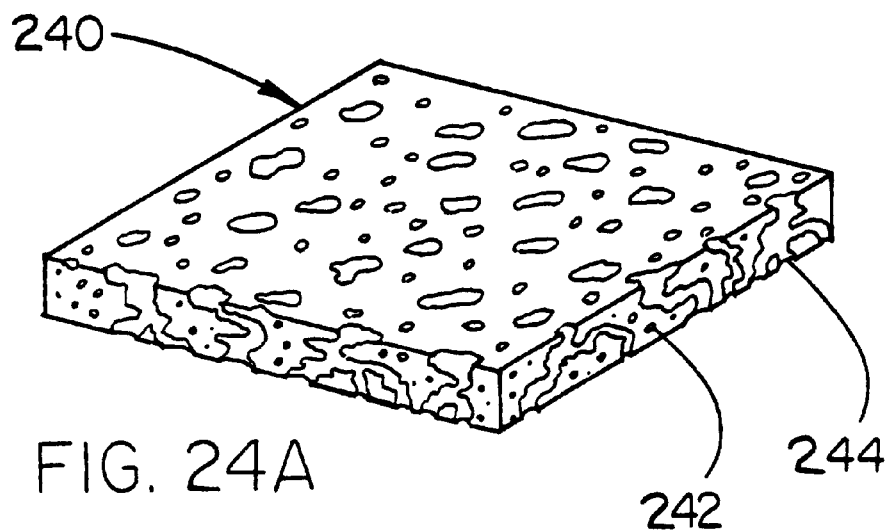
FIG. 24A is an illustration of an embodiment of the present invention (240), wherein the selectively-permeable porous material is a porous foam, or sponge-like material, having a first series of interconnected void spaces, or pores, (242) that are interspersed among a second series of interconnected void spaces, or pores (244).

When both the internal respiratory aid and the aqueous liquid-fillable component are porous (see, e.g., FIGS. 17 and 24A), advantage is often taken of a relative difference in pore size between the portion of the material that will comprise the internal respiratory aid in the product and the portion of the material that will comprise the aqueous liquid-fillable component in the product. In a material comprised of porous portions that differ greatly in pore size, the portions with the smallest pore size are usually made into the internal respiratory aid of the invention. Consequently, the portions of the material that have the largest pore size are usually made into the aqueous liquid-fillable component of the invention (FIG. 17A).

Generally speaking, porous starting materials having a relative difference in pore size of about one or more orders of magnitude are suitable candidates for use in the present invention. In operating principle, however, the pore size of the internal respiratory aid and the aqueous liquid-fillable component do not need to be different. As long as an internal respiratory aid can be fashioned in an appropriate starting material that is physically separate and distinct from the aqueous liquid-fillable component, there is no need to utilize a material comprised of porous portions that differ in pore size. As discussed in greater detail below, however, manufacturing conditions often dictate that portions of the microscopic architecture, or microstructure, of the porous starting material be substantially different in pore size in order to readily form the internal respiratory aid and the aqueous liquid-fillable component therein.

Figure 24B:
FIG. 24B is an enlargement of the illustration of FIG. 24A, wherein the internal respiratory aid is comprised of the first series of void spaces (242). Many of the void spaces of the internal respiratory aid are interconnected. The component comprised of channels that become aqueous liquid-filled during use is made from the second series of interconnected void spaces (244) that are coated with a material (246) that is permeable to gases. The internal respiratory aid and the component comprised of channels that become aqueous liquid-filled during use are physically isolated from each other by the coating material (246). The surfaces of the component comprised of channels that become aqueous liquid-filled during use may be further treated with a hydrophilic material or wetting agent to allow the component to wet out more easily.
Figure 24C:
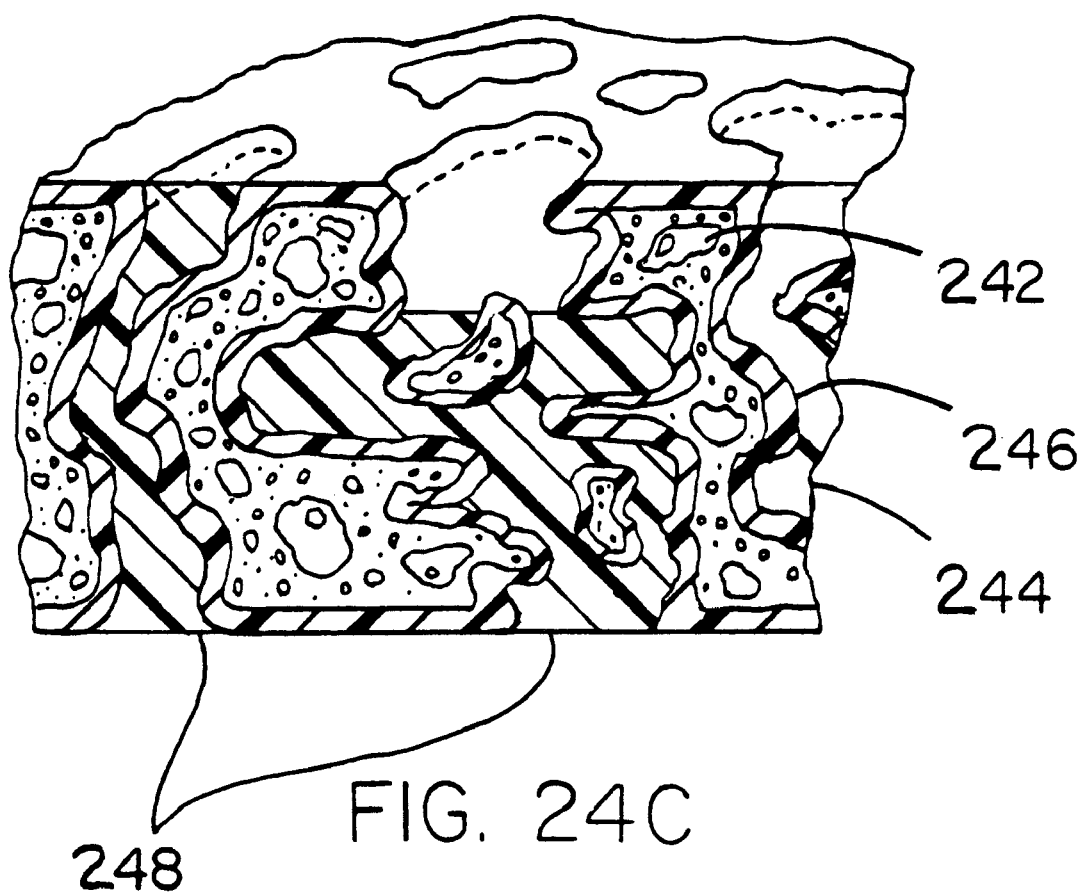
FIG. 24C is an illustration of a water-permeable material (248) placed in all or part of the components comprised of channels that become aqueous liquid-filled during use of FIG. 24B.

Regardless of the degree to which the starting material of the present invention possesses a range in pore sizes, it is preferred that neighboring void spaces comprising pores of the internal respiratory aid are substantially interconnected with one another. It is also preferred that neighboring void spaces comprising pores of the aqueous liquid-fillable component are substantially interconnected with one another (see e.g., FIG. 24B). When the void spaces of the internal respiratory aid are interconnected, exchange of physiological gases between the void spaces is permitted and can occur through the material in many directions. This is a valuable feature since, as with the tracheal system of the insect, gas can enter an internal respiratory aid at one point and distribute through the interconnected void spaces and be delivered to multiple sites distant from the point of entry where the gas is needed.

While gas transport through the present invention occurs with least resistance between neighboring gas-filled void spaces within the internal respiratory aid, gas is free to exit the internal respiratory aid and enter the aqueous portion of a neighboring aqueous liquid-fillable component and visa versa. This gas exchange between internal respiratory aid and the aqueous liquid-fillable component allows the aqueous liquid-fillable component to mediate gas exchange between elements or portions of elements of the internal respiratory aid, and visa versa. In addition, gas exchange between the internal respiratory aid and the aqueous liquid-fillable component is particularly advantageous when a cell population is contained by the present invention. In addition, when pores within the aqueous liquid-fillable component are interconnected, exchange and distribution of aqueous solutions through the aqueous liquid-fillable component is enhanced.

As previously indicated, the starting material need not have a large (i.e., one or more orders of magnitude) difference in pore size. However, a pore size distribution of one or more orders of magnitude may be preferred for manufacturing reasons. A key manufacturing reason for selecting such a material in the present invention is the degree of wettability each porous portion possesses with respect to one another. Generally speaking, wettability in a porous material is a function of the pore sizes, the chemical nature of the material, and the chemical nature of any applied wetting agent. For example, when porous hydrophobic materials are immersed in liquids (such as water or aqueous solutions, including biological fluids containing such surface-active wetting agents as proteins, or certain polar solvents) portions of the material having small pore sizes generally are less wettable by the liquid than portions of the material having large pore sizes (FIG. 17A). This is because smaller pores are more resistant to liquid-filling than larger pores and consequently wet out last, or not at all. Advantage can be taken of this difference in wettability between porous portions of a starting material to manufacture the present invention. As a result, in one embodiment of the present invention, a plurality of aqueous liquid-fillable component elements are formed in the hydrophobic material by preferential wetting out the large pores of the material with water or other polar solutions which leaves the small pores of the material unwetted. The unwetted portions form a plurality of internal respiratory aid elements.

In some instances, macroscopic holes can be cut into a porous material to provide the aqueous liquid-fillable component. The remaining microporous portions of the material form the internal respiratory aid. Macroscopic holes of the aqueous liquid-fillable component range in diameter from about 1,000 microns to about 1.0 micron, preferably about 200 microns to about 20 microns, and most preferably, about 10 microns to about 1.0 micron. Optionally, the macroscopic holes can have a water-permeable material, such as a hydrogel, placed in all or part of the holes to form the aqueous liquid-fillable component (see FIGS. 19 and 20).

Figure 21:
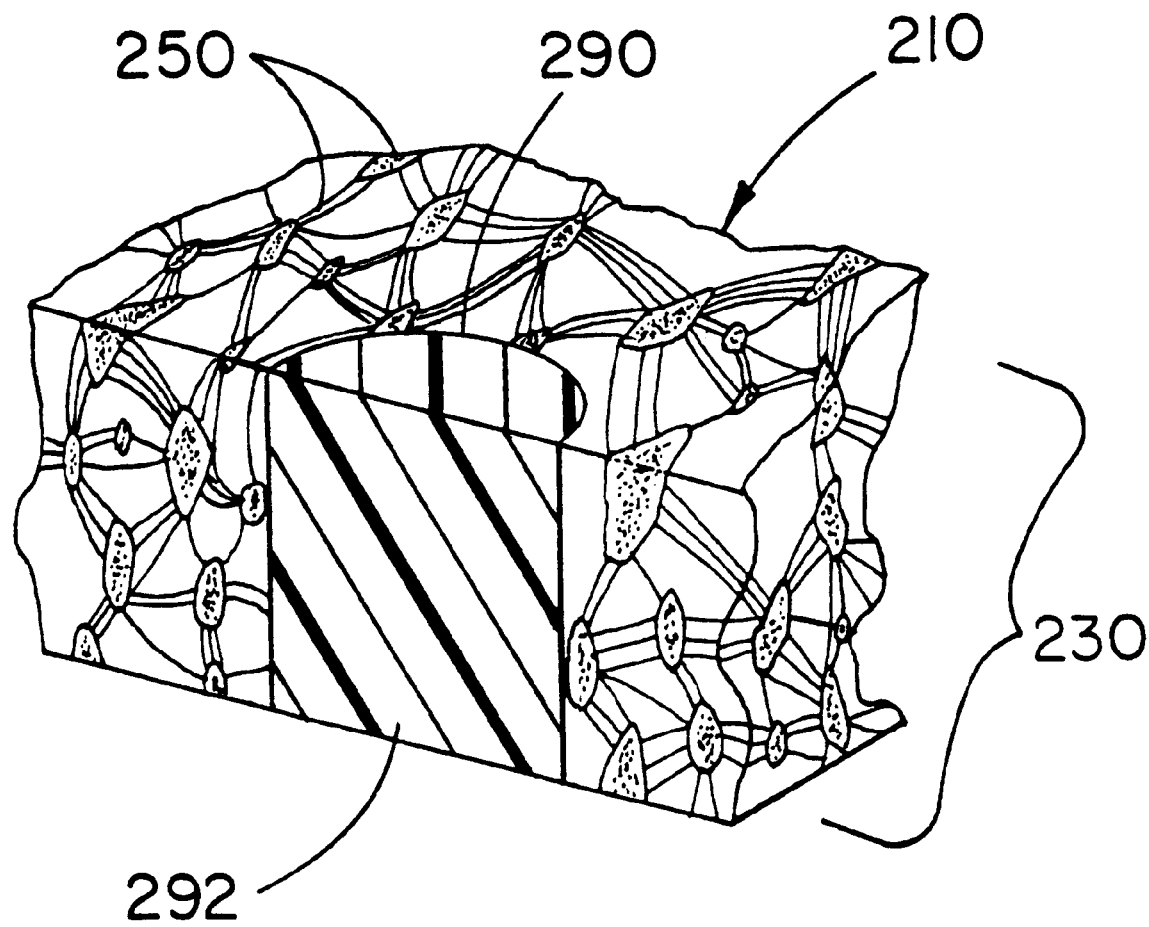
FIG. 21 is a cutaway illustration of an embodiment of the present invention (210), wherein the aqueous-liquid fillable component is a microporous material (230) comprised of a series of porous node and fibril structures (250) that become liquid-filled during use. The liquid-filled portions of the microporous material are either hydrophillic or provided with a hydrophilic surface treatment to enable the liquid-filled portions to become wet out with liquid water or aqueous solution during use. The internal respiratory aid (290) comprises macroscopic holes traversing the thickness of the microporous material, wherein a single hole is represented as a cut-away view as the semi-cylindrical structure of the Figure. The space in the macroscopic hole is filled with a material that is permeable to gases (292) to form an internal respiratory aid therein.
Figure 22:
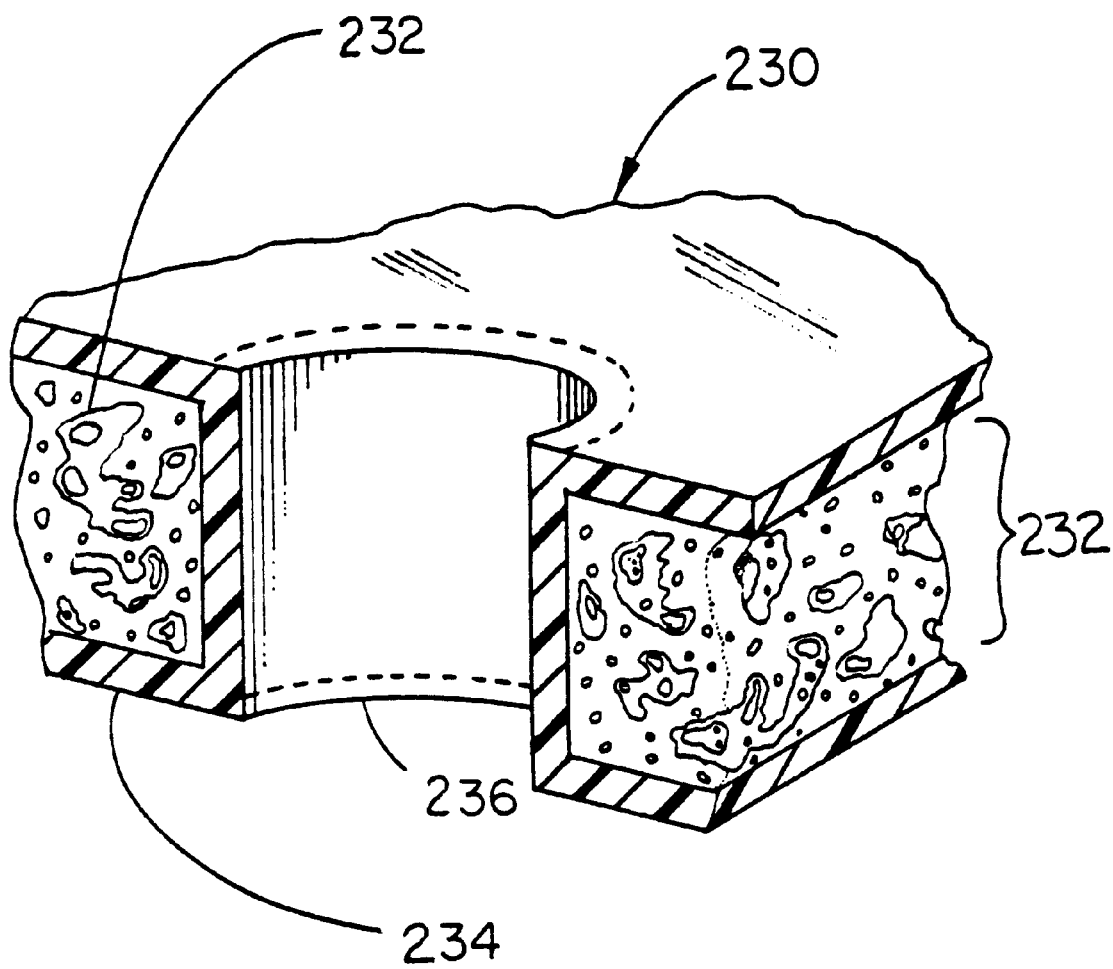
FIG. 22 is a cutaway illustration of an embodiment of the present invention (230), wherein the internal respiratory aid is a microporous material (232) that is coated on its perimeter surfaces with a material (234) that is permeable to gases. Many of the void spaces of the internal respiratory aid are interconnected. The component comprised of channels that become aqueous liquid-filled during use (236) is represented as a semi-cylinder. The surfaces of the component comprised of channels that become aqueous liquid-filled during use may be further treated with a hydrophilic material or wetting agent to allow the component to wet out more easily.
Figure 23:
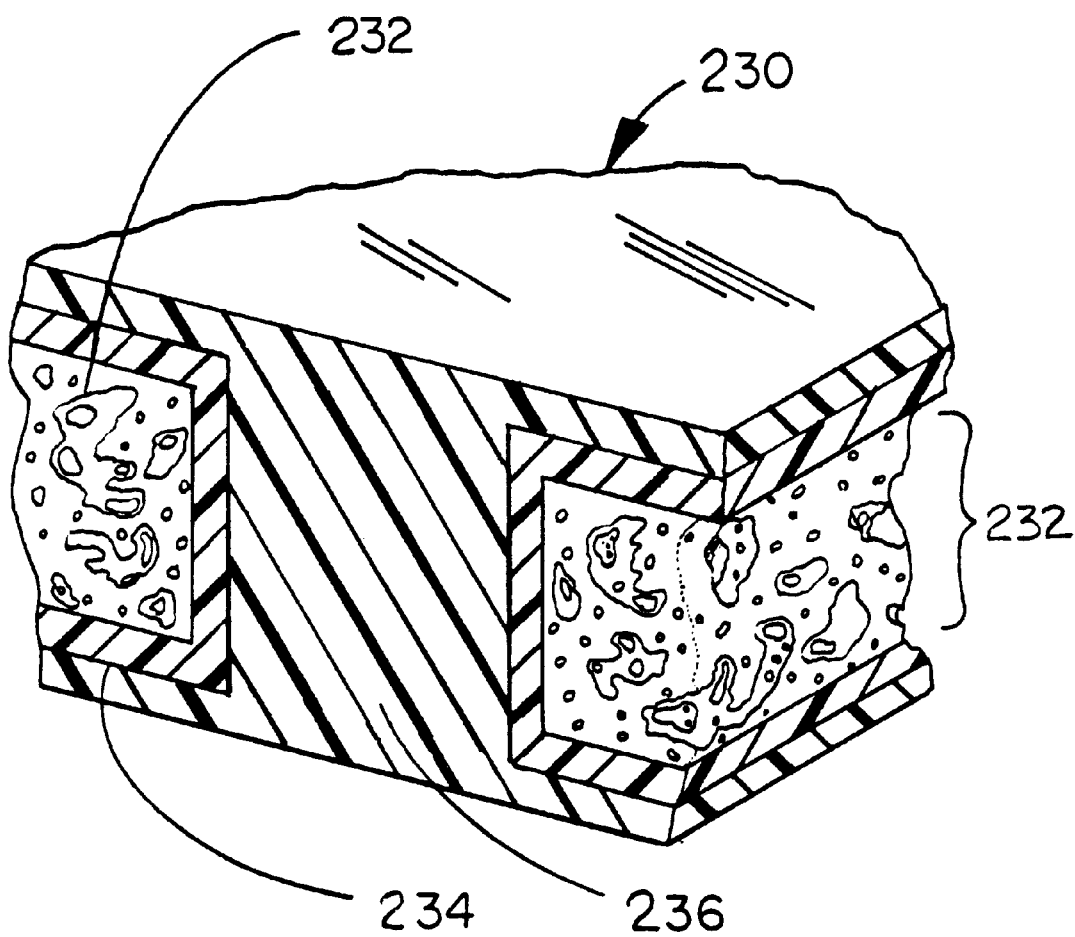
FIG. 23 is an illustration of a liquid water-permeable material (236) placed in the component comprised of channels that become aqueous liquid-filled during use and on the exposed outer surfaces of the material.

Conversely, if the macroscopic holes are filled with a material that is highly permeable to gases, such as silicone, the filled macroscopic holes then comprise the internal respiratory aid of the present invention. If necessary, the remaining microporous portions of the material are rendered water-wettable with a suitable surface treatment or wetting agent to form the aqueous liquid-fillable component (see FIG. 21, for example).

With some embodiments, the air or gas that fills the internal respiratory aid may, over time, dissolve in, or be displaced by, the aqueous fluid of the aqueous liquid-fillable component. For example, as oxygen is consumed by cells in association with the invention, the concentration of oxygen in the internal respiratory aid decreases relative to the concentration of other constituent gases. At the same time, the concentration of nitrogen increases with respect to a surrounding environment, resulting in a loss of nitrogen through diffusion. Those processes, in turn, result in a decrease in total gas pressure in the internal respiratory aid that can render the aid susceptible to wetting out. In some applications, even a partial wetting of the internal respiratory aid can impose an unacceptable resistance to gas transport across the perimeter surface of the aid. To maintain the integrity of the gas volume within the internal respiratory aid, the internal respiratory aid can be rendered more stable by the application of a surface treatment to the aid. For example, the surface treatment imparts a reduced surface energy to the material comprising the porous structure of the internal respiratory aid, thereby resisting the entry of both aqueous solutions and non-polar oils and lipids into the internal respiratory aid. Such a surface treatment also acts to inhibit the attachment of amphiphilic components, such as proteins and lipids, to the surfaces of the internal respiratory aid, thereby retaining the non-wettable character of the internal respiratory aid in resisting the entry of aqueous solutions. Representative examples of surface treatments suitable for use in the present invention are taught in the following U.S. Pat. No. 5,116,650, issued to Bowser; U.S. Pat. Nos. 5,286,279; 5,385,694; 5,539,047; 5,242,747; and 5,539,072, all issued to Wu, each of which is incorporated herein by reference. These and other treatments of the internal respiratory aid described herein are particularly useful in counteracting the tendency of a gas-filled internal respiratory aid to wet out.

In another embodiment, the internal respiratory aid may be rendered more stable by physically isolating the internal respiratory aid from the aqueous liquid-fillable component with a barrier layer or coating layer. For gas exchange between the internal respiratory aid and the aqueous liquid-fillable component, the layer or coating interposed between the two phases must be permeable to gases. Gas transport in this material is a function of the permeability divided by the thickness, defiled as the transmissibility, of the layer or coating material. Embodiments incorporating such coatings are preferred (see FIGS. 18, 22, 24B, 25B, and 26B).

Suitable gas-permeable materials for use in the present invention have a transmissibility to oxygen of at least $5 \times 10^{-4}$ centimeters per second, preferably at least $5 \times 10^{-3}$ centimeters per second, more preferably at least $5 \times 10^{-2}$ centimeters per second, yet more preferably at least $5 \times 10^{-1}$ centimeters per second, and most preferably at least 5 centimeters per second.

Examples of suitable gas-permeable materials include but are not limited to polysiloxanes or silicones, whether linear, branched, crosslinked, or silica-filled, including fluorinated silicones (e.g., fluorosilicone RD542 from Bausch and Lomb, Inc., Rochester, N.Y., and trifluoropropylmethylsiloxanes), other halogenated silicones, and polydimethylsiloxane or PDMS; silicone acrylates and their copolymers, including copolymers of methyl methacrylate or MMA and the silicone acrylate, methacryloylpropyl tris(trimethylsiloxy silane), or TRIS, together with MMA-TRIS systems that include surface-wetting agents (e.g., methacrylic acid), and crosslinking agents (e.g., ethylene glycol dimethacrylate); other silicone copolymers, such as poly (methylvinyl siloxane-(o-dimethyl siloxane), fluorosilicone-acrylates, fluorosilicone-fluoroacrylates, silicone-polysulfones, and polyurethanes with silicone soft segments; amorphous copolymers of tetrafluoroethylene and 2,2-bistrifluoromethyl-4,5-difluoro-1,3-dioxole (e.g., Teflon AF 1600 and Teflon AF 2400, from DuPont, Wilmington, Del.); aromatic polyamides with disrupted molecular packing or nanometer-scale pores ("nanoporosity"); aromatic polyimides with disrupted molecular packing or nanoporosity; aromatic polysulfones with disrupted molecular packing or nanoporosity; block copolymers of aromatic polyamides and PDMS; fluorinated polyethers; fluorinated polyimides such as those based on 2,2'-bis (3,4-dicarboxyphenyl) hexafluoropropane dianhydride (6FDA) and bis[4-(4-aminophenoxy) phenyl]sulfone (APPS), those based on 6FDA and 2,2'-bis (4-aminophenyl) hexafluoropropane (6FAP), those based on 6FDA and diaminophenyl sulfone (DDS), and those containing siloxanes; nanoporous polytetrafluoroethylene; nanoporous, perfluorinated poly (tetrafluoroethylene-co-propylene) (e.g., Teflon FEP, DuPont, Wilmington, Del.); natural rubbers, including polyisoprenes substantially free of antigenic polypeptides, such as hevein; perfluorinated poly(methyl vinyl ether) and its copolymers, including those containing tetrafluoroethylene residues; poly(4-methyl-1-pentene); poly (tert-butylstyrene) and its copolymers; poly(vinyl trimethylsilane); polycarbonates with disrupted molecular packing or nanoporosity; polyorganophosphazenes, including poly (trifluoroethoxy phosphazene) and poly (n-butyl phosphazene); polypyrrolones with disrupted molecular packing or nanoporosity; polysulfones with disrupted molecular packing or nanoporosity; porous polypropylenes or polyethylenes, including those developed for use in blood oxygenators; and silicon-containing polyacetylenes, including poly (1-trimethylsilyl-1-propyne) or PTMSP, fluorinated PTMSPs and other halogenated PTMSPs, PTMSPs modified with hexafluorobutyl methacrylate, irradiated PTMSPs, and other PTMSP variants, such as those described by Chen et al. (J. Membrane Sci., 82:99–115, 1993).

Of the above-listed gas-permeable materials, organosilicon polymers are preferred, including polysiloxanes (silicones) and silicon-bearing polyacetylenes (SiPAs). Representative polysiloxanes include poly(methylvinyl siloxane-co-dimethyl siloxane), fluorinated silicones such as trifluoropropylmethylsiloxanes, and polydimethylsiloxane or PDMS. Representative SiPAs include poly (1-trimethylsilyl-1-propyne) or PTMSP, together with fluorine-containing analogs thereof. Most preferred are the polysiloxanes and fluorinated polysiloxanes.

In a preferred embodiment of the present invention, a porous hydrophobic starting material in the form of a membrane, such as porous expanded polytetrafluoroethylene (ePTFE), is chosen and laser-drilled to make macroscopic holes of about 200 microns in diameter. The resultant material is a porous ePTFE material having a distribution of pore sizes. Porous expanded polytetrafluoroethylenie is made according to the teachings of U.S. Pat. Nos. 3,953,566 and 4,187,390, both issued to Gore, each of which is incorporated herein by reference. Alternatively, ePTFE materials can be purchased from W. L. Gore & Associates, Inc., Flagstaff, Ariz., for example, under the tradename Preclude™ Dura Substitute. In one form, this membrane is 0.3 mm in thickness with pore sizes ranging from 0.5 microns to 10 microns. The microporous portions of the ePTFE material are formed as interconnected elements of the internal respiratory aid. The macroscopic laser-drilled holes are formed into a plurality of discrete elements of the aqueous liquid-fillable component.

The internal respiratory aid and aqueous liquid-fillable component are isolated from one another with a coating material. The surfaces of the laser-drilled holes and the top and bottom surfaces of the ePTFE membrane are selectively and superficially wet out with a solution or suspension of a coating material to preferentially coat the walls of the non-wet out portion of the porous starting material. A preferred coating or suspension for this purpose is a water-based emulsion of medical-grade silicone. In the coating process, the wettable porous portions become filled with bulk coating. Once the coating has been applied, the bulk of the coating material is removed from the wet-out porous portion. The result is a coating of silicone material that covers and separates the pores in the non-wet out portions of the porous material from the pores of the wet-out portions (see FIG. 18, for example).

The most preferred coating material for forming the internal respiratory aid and aqueous liquid-fillable component in a porous substrate material is a silica-filled silicone composition. The composition is used in combination with a thinning organic solvating agent. When applied to a porous substrate material, the composition is removed from the thinning agent as the thinning agent travels through the substrate material. Once sufficient silicone material has been applied to the porous material, the thinning agent is permitted to evaporate from the material. As the thinning agent evaporates from the pores, the silicone composition coats the substrate material delimiting the pores. Preferably, a thin coating of the silicone composition is applied to the material such that the void volume of the pores is not significantly decreased.

Optionally, the surfaces of the silicone coating delimiting the aqueous liquid-fillable component can be treated, or further coated, with a hydrophilic material or wetting agent. This process leaves the aqueous liquid-fillable component easily wettable by water and aqueous solutions. The resulting construction has elements of the internal respiratory aid delimited from neighboring elements of the aqueous liquid-fillable component by the silicone coating material, with the aqueous liquid-fillable component having an optional hydrophilic coating applied thereon.

Alternatively, a solution or suspension of high gas-permeable material can be forced under pressure through the more wettable porous portion of a porous polymeric material. By this process, the high gas-permeable material forms a coating over the less wettable porous portion of the material, thereby forming the less wettable portion into a plurality of internal respiratory aid elements.

The coating material may also provide permselective properties, such as preferentially transporting oxygen through the invention compared to nitrogen, for example. The coating material may also include reactive catalysts that act on gaseous species in various ways, such as reducing gas free radicals or providing elements that favor beneficial cell-surface interactions.

The aqueous liquid-fillable component is not usually enclosed with a coating material. Rather, the coating material bounds or delimits the aqueous liquid-fillable component. A material sealing a liquid in the aqueous liquid-fillable component is within the scope of the present invention, however. In some embodiments, the aqueous liquid-fillable component is partially or completely filled with a water-permeable material, such as a hydrogel (see FIGS. 19, 20, 23, and 24C, for example).

Figure 27:
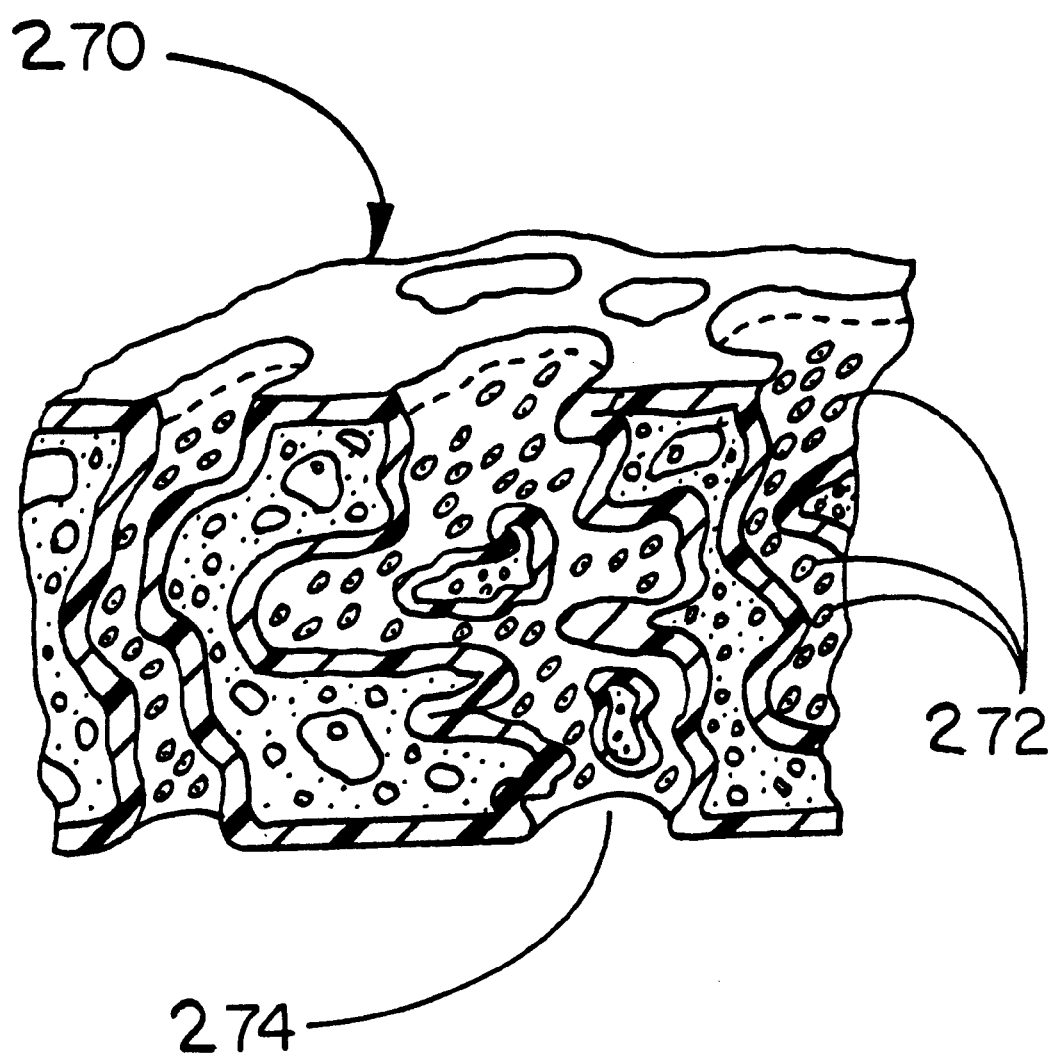
FIG. 27 is an illustration of an embodiment to the present invention (270), wherein cells (272) are residing in the component comprised of channels that become aqueous liquid-filled during use (274).
Figure 27A:
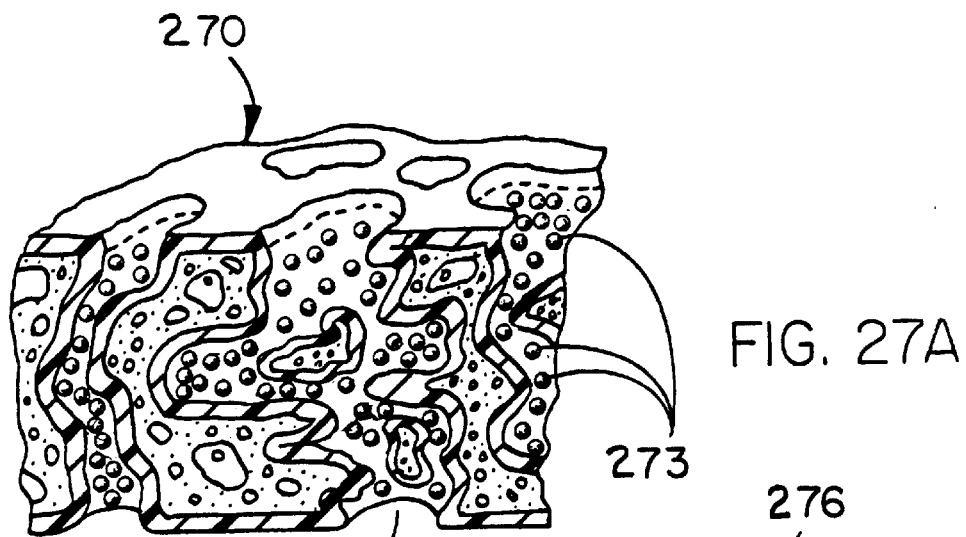
FIG. 27A is an illustration of an embodiment of the present invention (270) wherein cell-containing microcapsules (273) are residing in the component comprised of channels that become aqueous liquid-filled during use (274).

It is important to note that the aqueous liquid-fillable component can be sufficiently large to contain cells therein. The cells can be encapsulated or non-encapsulated (see e.g., FIGS. 27 and 27A). In this aspect, the present invention can serve as a cell-containment device or a portion of a cell-containment device. For some cell types it may be desirable to provide an aqueous liquid-fillable component of the present invention having pore sizes that are just slightly larger than the diameter of the cell being placed in the aqueous liquid-fillable component. To contain most prokaryotic cells in the aqueous liquid-fillable component, the average diameter, measured orthogonally to the longitudinal axis of the aqueous liquid-fillable component, is about 0.3 microns or greater. To contain most eukaryotic cells, the average diameter, measured orthogonally to the longitudinal axis of the aqueous liquid-fillable component, is about 3 microns or greater. In many embodiments in which cells are placed in the aqueous liquid-fillable component, pore sizes ranging from about 1,000 microns to about 1.0 micron are used for the aqueous liquid-fillable component. Pore sizes of less than 100 microns are preferred, with pore sizes less than 50 microns being more preferred, and pore sizes less than 10 microns being most preferred. For many aerobic cell types, it is often desirable to place the cells in the aqueous liquid-fillable component in close proximity to the internal respiratory aid. This minimizes the diffusional distance, and therefore the diffusional resistance, respiratory gases must traverse from the internal respiratory aid to the cells contained in the aqueous liquid-fillable component. In this embodiment, the cells contained in the aqueous liquid-fillable component are supplied with respiratory gases from the aqueous media diffusing through the component as well as with respiratory gases supplied through the walls of the internal respiratory aid that are in close proximity to the cells (see FIGS. 27 and 27A, for example).

Figure 27B:
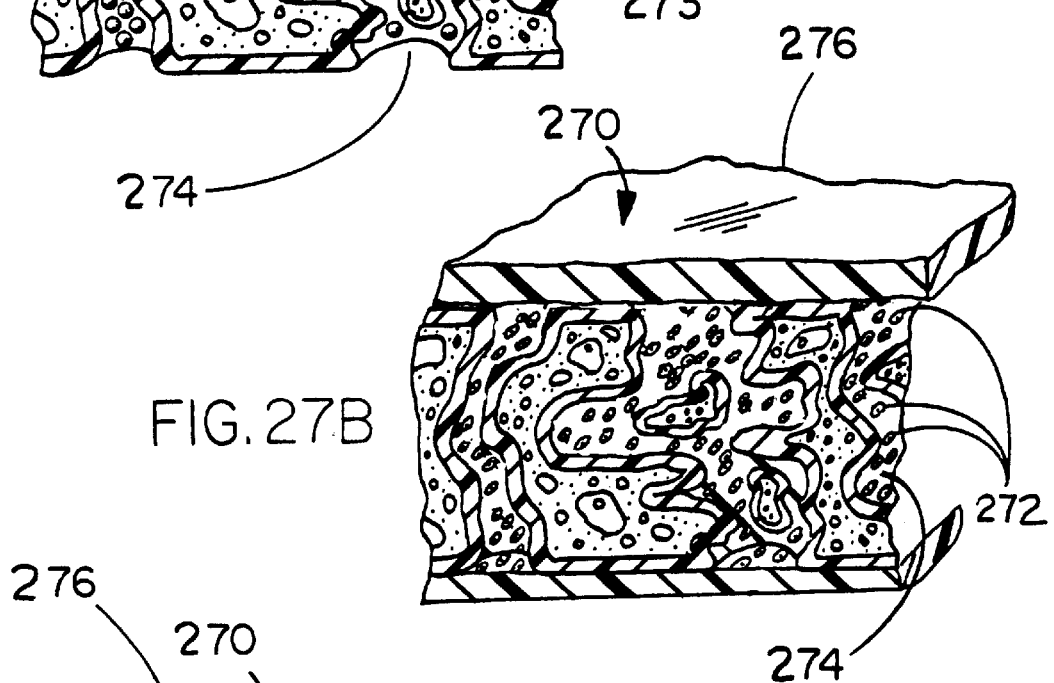
FIG. 27B is a further illustration of the embodiment of FIG. 27 wherein a layer of additional material (276) encloses the cells (272) in the component comprised of channels that become aqueous liquid-filed during use (274).
Figure 27C:
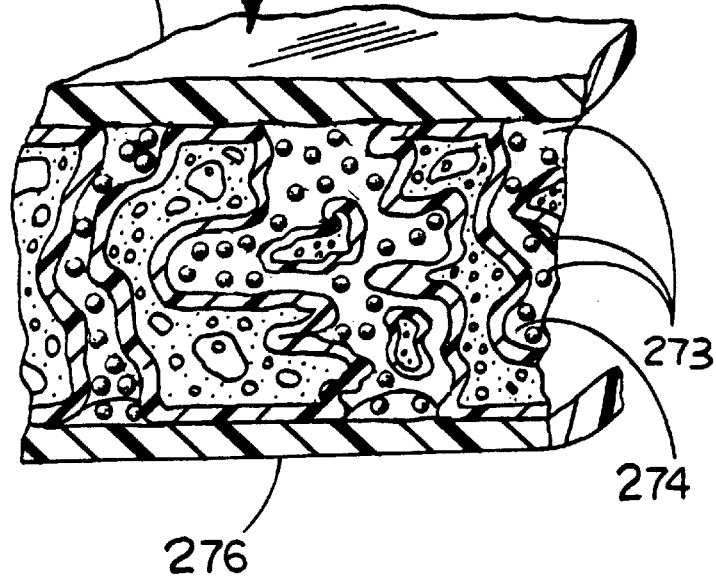
FIG. 27C is a further illustration of the embodiment of FIG. 27A wherein a layer of additional material (276) encloses the microcapsules (273) in the component comprised of channels that become aqueous liquid-filled during use (274).

Once cells and/or cell-containing microcapsules are ensconced in the aqueous liquid-fillable component, one or more additional layers of gas-permeable and/or water-permeable material can overlay or be attached to the present invention to enclose the cells and/or microcapsules inside the component (see FIGS. 27B and 27C, for example). Suitable materials for enclosing cells inside a aqueous liquid-fillable component include, but are not limited to, selectively permeable porous polymeric materials, such as porous expanded polytetrafluoroethylene, porous silicone, porous polyethylene, porous polypropylene, hydrophilic polymers, such as cross-linked forms of the following: poly(vinyl alcohol), alginate, partially hydrolyzed polyacrylonitrile, agarose, chitosan, gelatin, collagen, dextran, poly(vinyl chloride-co-acrylonitrile), poly(2-hydroxyethylmethacrylate), poly(N-vinyl 2-pyrrolidone), poly(oxyethylenes), and cellulosics.

In addition, so-called "asymmetric" membranes are also suitable in the present invention. For example, a common artifact of plastics, such as thermoplastics or thermosets, is the formation of a "skin," or less gas-transmissive outer layer, on extruded or molded materials. Advantage can be taken of these artifacts in the present invention to limit migration of either or both the internal respiratory aid and the aqueous liquid-fillable component at the boundary of the article. In the present invention, a preferred asymmetric material results when a foam is made that also has a thin skin on the outer surface of the material which prevents cells from escaping. In some embodiments, the skin requires some modifications. For example, an impermeable skin can be rendered permeable to liquid exchange by perforating the skin in this application to allow for aqueous channels to communicate between an outside environment and the inner aqueous liquid-fillable component.

The surface area of an internal respiratory aid of the present invention can be increased to enhance the exchange of gases between the invention and a local environment of the invention (see e.g., FIG. 24A, 25A, 26A, and 29A). These configurations include, but are not limited to, protrusions, intrusions, convolutions, evaginations, invaginations, and combinations thereof.

Definitions and Principles

It is useful to discuss aspects of the present invention in physiochemical terms that describe the invention mathematically. In applying the present invention to a wide variety of applications, the following mathematical models are useful tools that describe internal respiratory aids based on the fundamental mass transfer processes. The following terms are reviewed to assist in describing the operation of various internal respiratory aids of the present invention The molarflow rate Q is defined as the number of molecules (or moles) of a material arriving or departing per unit time across an internal respiratory system boundary area A. Transfer can also be referenced on a molecules per unit time per unit area basis, in which case a molar flux J is described. For gaseous substances, the molar flow rate (and the molar flux) is driven by a partial pressure difference $\Delta p$ of the substance across a material or fluid medium. The ability of the material or medium to transfer the substance under the action of $\Delta p$ is characterized by a mass transfer coefficient k. For a gaseous substance, the mass transfer coefficient relates the molar flow rate to the partial pressure difference $\Delta p$ of the substance across the material or medium, such that $Q=kA\Delta p$. Likewise, molar flux $J=k\Delta p$.

In general, the mass transfer coefficient describes the ability of a material or medium to exchange substances, independent of specific mass transfer mechanisms. For instance, the mass transfer coefficient can describe the transfer of a gaseous substance by a convective mechanism (such as in an external respiratory system) or the mass transfer coefficient can describe a diffusive process (such as in an internal respiratory system). In the discussion that follows, the mass transfer coefficient is described with respect to diffusional processes only.

Several factors influence the mass transfer coefficient, but in general it can be defined as the permeability P of the material or medium to a particular substance divided by a diffusional distance $\delta$, such that $k=P/\delta$. Here, the permeability characterizes the ability of a material or fluid medium to transfer substances under the influence of a partial pressure difference $\Delta p$, and the diffusional distance is the distance over which $\Delta p$ exists.

For a material, the diffusional distance is generally described by a thickness dimension in the direction of $\Delta p$. The mass transfer coefficient for a material is also referred to as the transibility T of the material.

The diffusional distance also may be defined in terms of the thickness of a fluid boundary layer, over which $\Delta p$ exists, for a fluid medium. The boundary layer is a thin layer of fluid, typically associated adjacent to a material surface, with a thickness dependent on the fluid properties and the geometry and flow conditions of the system.

The permeability P of a material or fluid medium to a particular substance is the product of the solubility and diffusivity. For gaseous substances, the solubility S of a material or medium is defined as the ratio of concentration c of the substance within the material or medium versus the partial pressure p of the substance in a gaseous phase that is in equilibrium. The diffusivity D is a constant that relates the mass transfer flux of a particular substance within a material or medium to the concentration gradient ($\Delta c/\delta$) of the substance within the material or medium. In one dimension and under steady-state conditions, the molar flux $J=D(\Delta c/\delta)$, where $\Delta c$ is the concentration difference of the substance across a material or medium with thickness $\delta$. Since $c=Sp$ (assuming solubility is constant throughout the material or medium), $J=P(\Delta p/\delta)$. Rearranging, we again observe that $J=k\Delta p$, where the mass transfer coefficient $k=(P/\delta)$.

The permeability of a material or medium may be reduced as a consequence of the inclusion of a non-permeable material fraction. The permeability of this heterogeneous material is determined as $P=\gamma P_m(\epsilon/\tau)$. Here $P_m$ is the permeability of the permeable material or medium; $\epsilon$ is the porosity or volume fraction of permeable material or medium; τ is the tortuosity of the diffusional path for the permeable material or medium; and γ is a hindrance factor that accounts for effects of interaction between solutes in the permeable material or medium and the non-permeable material or medium. For example, water-filled expanded polytetrafluoroethylene (ePTFE) offers a pathway to diffusion through its aqueous channels alone. As an alternate example, gas-filled expanded polytetrafluoroethylene (ePTFE) offers a pathway to diffusion through its gas-filled channels alone. The PTFE in the heterogenous material in both examples is essentially a non-gas-permeable component, so the permeability of the whole article is that of the gas or fluid medium adjusted for content, tortuosity, and the hindrance of the PTFE material.

The permeability ratio P' is the ratio of the permeability of a material with respect to the permeability $P_{aq}$ of pure distilled water, such that $P'=P/P_{aq}$. For example, a particular silicone material may be ten times (10×) more permeable to oxygen than water, such that P'=10. Following the previous discussion, the value for P' for water-filled ePTFE may be determined as $\gamma(\epsilon/\tau)$, a value generally less than one.

Conductance C is generally used to represent the product of the surface area and the mass transfer coefficient for a material or medium, such that C=kA. One observes that the mass transfer coefficient k, defined earlier, can also be described as the conductance per unit area. In terms of conductance, the molar flow rate Q=CΔp. Alternately, the molar flow rate can be described by the resistance R of the material or medium, defined as the inverse of conductance, such that Q=(1/R)Δp.

In determining molar flow rates through a combination of materials or media, one observes that electrical analogies apply. Thus, conductances in parallel across a common partial pressure difference Δp are additive in determining the total system conductance. In this case, the most conductive component controls the overall system conductance. Likewise, resistances in series spanning a region with partial pressure difference Δp are additive. In this case, the least conductive component in the system controls the system conductance, regardless of high conductance levels of other components in the system. Improving the conductance of the other components will not significantly improve the system conductance until the least conductive component is improved.

The exchange of respiratory materials in an internal respiratory system often entails crossing two or more component regions within the system, particularly if the internal respiratory system is heterogeneous in composition. The component regions of an internal respiratory system are typically aqueous in nature, for example as represented by volumes of fluid media, fluid boundary layers, or material consisting of matrices filled with aqueous fluid. The component regions may also contain metabolically active tissue that consumes or produces respiratory gases within the aqueous media. In general, the permeability of the component regions in an internal respiratory system is either comparable to that of water, or somewhat less than water because of matrix effects or the presence of aqueous solutes.

Transport modulating articles are constructs, either homogeneous or heterogeneous in composition, that are imposed into an internal respiratory system to render the system more or less capable of exchanging respiratory gases. The modulating article can have either an obstructing or facilitating influence on respiratory gas transport, resulting in effect from the modulating article replacing either all or a portion of the aqueous diffusive transport path through an internal respiratory system. As a means of characterizing the influence of the modulating article, the coductance ratio C' is defined as the ratio of the conductance of the modulating article versus the conductance of the component region in the internal respiratory system that the modulating article replaces. In the case of a homogeneous article, composed of only one material, the conductance ratio is equivalent to the permeability ratio of the material. In the case of a composite article, for example a coated article, the conductance ratio is determined from the permeability ratios of the combined components. Using the definition of conductance ratio, we classify modulating articles as either obstructing or facilitating. Obstructing articles have a conductance ratio less than one, and therefore diminish gas exchange through an internal respiratory system. Facilitating articles have a conductance ratio greater than one, and therefore enhance gas exchange through an internal respiratory system. A conductance ratio greater than one is also termed a conductance gain. Internal respiratory aids, as described in this invention, are facilitating articles, and have a conductance ratio greater than one.

In determining the conductance ratio of a modulating article, one must determine both the conductance of the actual modulating article and the conductance of the component region in the internal respiratory system that the modulating article replaces. The latter conductance is evaluated as that of an article with the same geometry as the modulating article, but with a permeability equivalent to that of the component region which the modulating article replaces. The permeability of the component region can be difficult to assess, as it is often composed not only of water, but also of aqueous solutes, matrix material, and biological tissue. Herein, we generally estimate the permeability of the component region as being equivalent to pure water. This generally produces an overestimate of the replaced conductance of the component region, but as such results in a conservatively low estimate of the resultant value of conductance ratio for the modulating article.

The effect on respiratory gas transport of incorporating a modulating article into an internal respiratory system is characterized by the flux ratio. The flux ratio is defined as the ratio of respiratory gas flux in an internal respiratory system with the modulating article versus the flux without the modulating article. A flux ratio greater than one is also termed a flux gain, and generally results from the application of facilitating articles, or internal respiratory aids, with a conductance gain of one or greater. Often the internal respiratory aid will replace only a portion of the internal respiratory system within which it is placed. Specifically, the transport area of the internal respiratory aid may encompass some reduced fraction Y of the total transport area of the internal respiratory system. This fraction Y, termed the fractional transport area, ranges from 0 to 1.0 (or 0% to 100%) of the total transport area of the internal respiratory system. Often the value of Y is less than 1.0, to accommodate, for example, aqueous regions for cells to occupy or within which solutes other than respiratory gases can diffuse in an aqueous phase.

In the examples that follow, we illustrate the dependence of flux ratio on the conductance ratio of the internal respiratory aid, as well as the dimensions of the internal respiratory aid, and environmental influences within the internal respiratory system, such as the presence of fluid boundary layers and respiratory cell zones. As will become apparent, a flux ratio greater than one is possible only with the application of an internal respiratory aid, for which the conductance ratio is greater than one.

Planar Structures as Internal Respiratory Aids

As discussed above, the permeability of a material is generally defined as the product of its diffusivity D and solubility S for the gas of interest. The solubility for the gas of interest relates the equilibrium ratio of its molar concentration in the material to its partial pressure in a gas medium. Permeability to a gas is typically reported in units of barrer, where $$1 \text{ barrer} = 10^{-10} \frac{\text{cm}^3(\text{STP}) \cdot \text{cm}}{\text{cm}^2 \cdot \text{sec} \cdot (\text{cm Hg})}$$

Often water is the medium through which gas transport must occur in a material. The diffusivity of oxygen in water at 25° C. is $2.4 \times 10^{-5}$ cm²/sec (Incropera, F. P. and DeWitt, D. P., *Fundamentals of Heat Transfer*, Wiley, N.Y., 1981, p. 785). The solubility (evaluated as the inverse of Henry's Law coefficient) at 25° C. is $1.3 \times 10^{-6}$ (mol/ml)/atm (Ibid, p. 786). The permeability of oxygen is water $P_{aq}$ is evaluated as the product of these two parameters, converted to barrer units as follows:

$$P_{aq} = \left(2.4 \times 10^{-5} \frac{\text{cm}^2}{\text{sec}}\right)\left(1.3 \times 10^{-6} \frac{\text{mol}}{\text{cm}^3 \cdot \text{atm}}\right)$$
$$\left(\frac{22{,}400 \text{ cm}^3(\text{STP})}{\text{mol}}\right)\left(\frac{\text{atm}}{76 \text{ cm Hg}}\right)$$
$$= 9.2 \times 10^{-9} \frac{\text{cm}^3(\text{STP}) \cdot \text{cm}}{\text{cm}^2 \cdot \text{sec} \cdot (\text{cm Hg})}, \text{ or 92 barrer}$$

For practical materials, the water is generally supported within a porous matrix, forming a composite. Typically the matrix material is not permeable to gases, the net effect being a reduction in permeability of the composite relative to that of water. The reduction is described in terms of three dimensionless parameters, defined earlier: the porosity $\epsilon$ that accounts for the reduction in effective area for transport; the tortuosity $\tau$ that describes the increase in effective diffusional path length that gases must follow to navigate around the matrix material; and the hindrance factor $\gamma$ that describes the reduction in transport effected by interaction of the diffusing substance with the structural material within the pores of the matrix. The permeability of the material becomes $P = P_{aq}(\gamma \epsilon / \tau)$. An example of one such matrix is a particular water-filled ePTFE construct possessing a porosity of 0.5 and a tortuosity of 1.5. Pore hindrance is assumed minimal, such that $\gamma=1$. The permeability of this material is therefore reduced three-fold relative to that of water, such that P=31 barrer. Equivalently, we state that the permeability ratio P' is 1/3.

Alternately, nonporous materials with high intrinsic gas permeabilities are chosen to enhance gas transport. One such material is polydimethylsiloxane, which has a permeability to oxygen of about 930 barrer (*Membrane Handbook*, Ho, W. S. W, and Sirkar, K. K. eds., Van Nostrand Reinhold, N.Y., 1992). Permeability ratio P' for this material is roughly 10.

Preferred embodiments of the present invention use air as the gas-transporting medium in an internal respiratory aid. Air has a diffusivity to oxygen at 25° C. of 0.21 cm²/sec (Incropera and DeWitt, Ibid, p. 785). The solubility S is defined as the ratio of the molar concentration of oxygen in air to the partial pressure of oxygen. From the ideal gas law, $S=1/R\theta$, where R is the universal gas constant, and $\theta$ is the absolute temperature. The permeability of air at 25° C. is thus evaluated as:

$$P_{air} = \frac{\left(0.21 \frac{\text{cm}^2}{\text{sec}}\right) \cdot \left(\frac{22{,}400 \text{ cm}^3(\text{STP})}{\text{mol}}\right) \cdot \left(\frac{\text{atm}}{76 \text{ cm Hg}}\right)}{\left(\frac{82.05 \text{ cm}^3 \text{ atm}}{\text{mol K}}\right) \cdot (298 \text{ K})}$$
$$= 2.5 \times 10^{-3} \frac{\text{cm}^3(\text{STP}) \cdot \text{cm}}{\text{cm}^2 \cdot \text{sec} \cdot (\text{cm Hg})}$$
$$= 2.5 \times 10^7 \text{ barrer}$$

Air is thus about $3 \times 10^5$ times more permeable than water to oxygen. Consider the case of the porous ePTFE material described above, now filled with air instead of water. As before, the overall permeability is reduced by the presence of the matrix (with $\epsilon=0.5$, $\tau=1.5$, and $\gamma=1$) by a factor of 3, to value of $8.3 \times 10^6$ barrer. Nonetheless, the air-filled material has a permeability ratio P' of about $10^5$. The conductance ratio C' of the material is also $10^5$. An article composed of this material would therefore function as an internal respiratory aid.

It is often desirable to enclose an air-filled matrix material in a liquid-impermeable coating on the surfaces of the material that interface with liquid water and other aqueous solutions. Such a coating prevents the ingress of water and aqueous liquids into the matrix, thereby retaining the high gas-transporting characteristics of the internal respiratory aid. With coatings on the upper and lower surfaces, the material acquires a total resistance R composed of three resistances in series, described as:

$$R = R_{Matrix} + 2R_{Coat}$$

where $R_{Matrix}$ is the resistance of the air-filled matrix material, and $R_{Coat}$ is the resistance of each individual coating layer. The total conductance equals the inverse of the total resistance, and is evaluated by substituting the appropriate expressions for each of the component resistances:

$$\frac{1}{C} = \frac{\delta_{Matrix}}{AP_{Matrix}} + \frac{2\delta_{Coat}}{AP_{Coat}}$$

As an internal respiratory aid, the material replaces a component region of an internal respiratory system with diffusional distance $\delta = \delta_{Matrix} + 2\delta_{Coat}$. The conductance ratio C' for the material is therefore:

$$C' = \frac{1}{\frac{(\delta_{Matrix}/\delta)}{P'_{Matrix}} + \frac{2(\delta_{Coat}/\delta)}{P'_{Coat}}}$$

As an example, consider polydimethylsiloxane as the coating for the article. Polydimethylsiloxane is liquid-impermeable, yet retains a high degree of oxygen permeability. The air-filled ePTFE matrix material described earlier (P'=$10^5$) has a thickness of 1 mm. The polydimethylsiloxane coating (P'=10) is 15 $\mu$m on either side. The diffusional distance is therefore 1.03 mm. The conductance ratio is thus calculated as 340. This article can also function as an internal respiratory aid. In this example, the combined resistance of the two polydimethylsiloxane coatings represents the controlling resistance to gas transport through the composite material. The combined resistance of the coatings is two orders of magnitude more resistant than the air-filled matrix material, even though the combined coating thickness is 33-fold less. As is often the case for series-composite materials such as these, the resistance of the air-filled matrix is negligible such that the total material resistance is controlled largely by the gas-permeable coating material.

One preferred embodiment of the present invention relates to materials in which there are present dual pathways for transport of respiratory gases and aqueous nutrients. These separate pathways function in parallel and comprise both an internal respiratory aid and channels that fill with aqueous liquids during use, comprising an aqueous liquid-fillable component. In addition to the internal respiratory aid, the aqueous liquid-fillable component also provides pathways through which dissolved respiratory gases can be transported, though to a much lesser extent than the internal respiratory aid. With a fractional transport area of the internal respiratory aid equal to Y, the remaining fraction (1−Y) encompasses the aqueous liquid-fillable component. Thus the flux ratio is evaluated:

$$\text{Flux Ratio} = YC'_{IRA} + (1-Y)C'_{aq}$$

Here, $C'_{IRA}$ represents the conductance gain of the IRA, and $C'_{aq}$ represents the conductance ratio of the aqueous liquid-fillable component. For example, consider the ePTFE polydimethylsiloxane-coated material described above, formed into a composite with parallel aqueous liquid-fillable channels of ePTFF. As previously determined, $C'_{IRA}=340$ and $C'_{aq}=1/3$. Assuming Y=0.5, the flux ratio of the composite is calculated to be 170. In this example, virtually all of the conductance to gas for the composite is provided by the internal respiratory aid. Without the internal respiratory aid, the flux ratio of the system is equivalent to the conductance ratio of the aqueous liquid-fillable component alone, ie. 1/3. Inclusion of the aid therefore represents a 510-fold increase in flux for the system for a given partial pressure difference Δp. The aqueous liquid-fillable component in the composite may be necessary, however, for the transport of aqueous dissolved solutes that would otherwise be unable to permeate the air-filled matrix.

It is also observed that even if the fraction Y of the internal respiratory aid is reduced by one or two orders of magnitude, the internal respiratory aid still provides virtually all of the oxygen transport through the invention. Accordingly, the more gas-permeable the internal respiratory aid, the smaller the fraction Y required to provide the desired levels of gas transport through the internal respiratory system.

In the discussion above for thin materials, it was shown that respiratory gas transport can be substantially enhanced by the incorporation of an internal respiratory aid. The mass transfer coefficient associated with a thin, high gas-permeable material is often much larger than the mass transfer coefficients associated with liquids in boundary layer contact on either side of the material. As such, the mass transfer resistance of the material can often be neglected in comparison to the resistance of the liquid boundary layers, with the latter controlling the overall respiratory gas transport through the material. In order to further enhance transport through these materials, measures can be taken to reduce the resistance to gas transport associated with the liquid boundary layers, as for example by increasing the flow adjacent to the material surfaces.

High gas-permeable materials offer another means of reducing the transport resistance of liquid boundary layers by expanding the surface area associated with these resistances. For example, consider a material covering an opening with area $A_1$, with liquid layers above the material and within the opening below. If a partial pressure difference Δp is imposed between the two liquid layers, across the material, transfer of gas occurs at mass flow rate Q=Δp/R, where R is the total resistance of the composite, including the material and the two liquid boundary layers. If the material is substantially resistant to gas transport, its contribution to the overall resistance will be comparable to or greater than the contributions of the liquid boundary layers. In following the least resistant path through the material, the gas will transfer straight through the material, thereby limiting the transfer area to that of the opening $A_1$. For a high gas-permeable material however, the resistance of the material is negligible relative to that of the liquid boundary layers. The gas can follow any particular path through the material in this case. For example, gas can enter from a relatively remote location into the material, and with little resistance can diffuse over a large distance through the material to the opening. The upper surface area $A_2$ through which gas effectively enters is larger than $A_1$ in this case. If the mass transfer coefficient associated with the upper liquid boundary layer is $k_{B2}$ and the mass transfer coefficient associated with the liquid boundary layer in the opening is $k_{B1}$, the total resistance (neglecting that associated with the high-permeability material) is evaluated:

$$R = \frac{1}{k_{B1}A_1} + \frac{1}{k_{B2}A_2}$$

It is observed that with the increase in upper surface area $A_2$, the overall transport resistance is reduced, thereby increasing the mass flow rate Q through the opening.

Elongated Structures as Internal Respiratory Aids

In other embodiments of the present invention, internal respiratory aids can be constructed in which the diffusional distance is greatly extended beyond the relative thickness of a flat sheet or membrane, as were described in the previous section. Internal respiratory aids with increased diffusional distances are usually employed to transport gases over substantially greater distance through an internal respiratory system. They have a high permeability, enabling them to transport gases over much larger distances across a given partial pressure difference Δp than would be possible through the less permeable aqueous component regions of the internal respiratory system. For instance, the internal respiratory aid may be employed to deliver oxygen to a region with encapsulated cells at one boundary of the internal respiratory aid, from a region with host capillaries at another boundary positioned a considerable distance away.

Preferred embodiments of the internal respiratory aid with increased diffusional distances have air as a high gas-permeable component. As earlier described, air has a permeability for oxygen that is approximately $3\times10^5$ times the permeability of oxygen through water at 25° C. As a result, oxygen can be transported through 3 meters of the present invention before it encounters the equivalent transport resistance presented by only ten microns of water. The permeability is reduced somewhat if the air is entrapped within a structural material or matrix that is impermeable to oxygen. In this case, the permeability is reduced by a factor equal to γε/τ as earlier described, where ε is the material porosity, τ its tortuosity, and γ the hindrance factor. In the example given earlier for air-filled ePTFE, the permeability is reduced three-fold, but the permeability still remains $10^5$ times that of water. This very large difference in permeabilities between materials of internal respiratory aids of the present invention and water, described in terms of the permeability ratio $P'=P/P_{aq}$, illustrates some of the most important advantages provided by the invention.

In one embodiment, an internal respiratory aid in the form of a cylindrical fiber is constructed wherein gas transport through the internal respiratory aid occurs along the length of the aid. In this model, gas is constrained to enter and exit the internal respiratory aid through surfaces at the ends of the internal respiratory aid only. Accordingly, there is no gas flux through the sides comprising the circumferential surfaces of the internal respiratory aid. To assure no gas flux occurs through the circumferential surfaces of the internal respiratory aid, a gas-impermeable coating, or cladding, is applied to the axial, or side, surfaces of the cylindrical fiber portion of the internal respiratory aid to seal out gases and liquids. As a result, gas exchange in the internal respiratory aid occurs only through the uncoated surfaces at the ends of the aid. This construct is analogous to an insulated wire wherein the insulation prevents leakage of heat or electrical current between the wire and the surrounding external environment. This article was previously defined as an internal respiratory aid conductor.

If the physical distance between differing regions of partial gas pressure is less than the length of an internal respiratory aid, the internal respiratory aid can be physically bent or routed in different directions between the regions. This is analogous to electricity flowing along a wire from a point of higher electrical potential to a point of lower electrical potential. Current flows through the wire, even though the wire courses in various directions, as long as a connection is maintained between the two locales of differing electrical potential. Accordingly, while the general direction of gas transport through a medium may not coincide with the specific direction of gas transport through an internal respiratory aid at particular points, the overall direction of gas transport through the internal respiratory aid is driven by the partial pressure difference $\Delta p$ between the ends of the aid. As a result, the present invention can be bent and shaped as desired as long as the invention is placed between regions of different partial pressures.

The length of an internal respiratory aid can be increased many-fold before the resistance of the aid becomes comparable to that of the liquid boundary layers at either end. For example, the internal respiratory aid may be centimeters or meters long in the direction of gas transport before the above condition occurs. For purposes of modeling, a limiting length of the internal respiratory aid $\delta_{limit}$ can be defined at which the resistance of the aid is equivalent to the sum of the resistances of the external liquid boundary layers:

$$R_{IRA}=R_{B1}+R_{B2}$$

At greater lengths beyond this limit, the resistance of the internal respiratory aid becomes the dominant resistance.

To illustrate, consider a fiber article as described earlier, composed of an air-filled ePTFE matrix circumferentially sealed with an impermeable cladding. To determine limiting length of the article, we equate the resistance of the internal respiratory aid to the sum of the resistances of the external liquid boundary layers:

$$\frac{\delta_m}{AP_m} = \frac{\delta_{B1}}{AP_{aq}} + \frac{\delta_{B2}}{AP_{aq}}$$

Here, A is the cross-sectional area of the fiber, $P_m$ the permeability of the air-filled matrix of the fiber, $\delta_m$ the length of the fiber, $P_{aq}$ the permeability of water, and $\delta_{B1}$ and $\delta_{B2}$ the respective thicknesses for the boundary layers at the two ends of the fiber. The permeability ratio of the air-filled matrix of the internal respiratory aid is $P'_m=P_m/P_{aq}$. The limiting length of the internal respiratory aid (equivalent to $\delta_m$) is determined:

$$\delta_{limit}=P'_m(\delta_{B1}+\delta_{B2})$$

With $P'_m=10^5$ for the air-filled ePTFE matrix, and assuming boundary layers 10 microns thick, we find the limiting length at which the resistance of the internal respiratory aid becomes dominant to be 200 cm. The conductance ratio at the limiting length for this internal respiratory aid is equivalent to the permeability ratio of the ePTFE fiber, i.e. $10^5$.

In an alternate construction of the internal respiratory aid, the ends of an ePTFF air-filled fiber are coated with a gas-permeable material, such as polydimethylsiloxane, so as to prevent the ingress of liquid water into the ends. In this case, equating the resistance of the internal respiratory aid to the sum of the resistances of the liquid boundary layers, we obtain:

$$\frac{\delta_m}{AP_m} + \frac{2\delta_{Coat}}{AP_{Coat}} = \frac{\delta_{B1}}{AP_{aq}} + \frac{\delta_{B2}}{AP_{aq}}$$

where $P_{coat}$ is the permeability of the gas-permeable coating, and $\delta_{coat}$ the thickness of the coating at either end of the fiber. With $P'_{coat}$ representing the permeability ratio of the coating, the limiting thickness of the internal respiratory aid is determined:

$$\delta_{limit} = \delta_m + 2\delta_{coat} = P'_m(\delta_{B1} + \delta_{B2}) - 2\left(\frac{P'_m}{P'_{coat}} - 1\right)\delta_{Coat}$$

With $P'_{coat}=10$ for a polydimethylsiloxane coating, with a thickness of 15 microns, we find the limiting length at which the resistance of this internal respiratory aid becomes dominant to be 170 cm. The thin polydimethylsiloxane coating therefore reduces the limiting length of the internal respiratory aid, but not substantially. The conductance ratio at the limiting length for this internal respiratory aid is $8.5\times10^4$.

The examples above illustrate the importance of considering external liquid boundary layers with regards to the limiting length that an internal respiratory aid can span without significantly altering the total transport resistance. The limiting length, determined as 200 and 170 cm respectively in the two preceding examples, represents the length of the internal respiratory aid at which the resistance of the aid matches the sum of the resistances of the external liquid boundary layers. By shortening the length of the internal respiratory aid below this limiting length, one can effect a reduction in the overall resistance and an increase in the rate of oxygen transport through the system, by at most a factor of two. As the internal respiratory aid is made exceedingly small in length, the total resistance approaches a value equivalent to the sum of the resistances of the liquid boundary layers, a factor of only two reduction in total resistance. Constructing the internal respiratory aid with a length up to the limiting length therefore produces a much increased diffusional distance for the internal respiratory aid, at the expense of only a two-fold reduction in mass transfer flux for an equivalent partial pressure difference Ap. This is important in the case of internal respiratory aid conductors for which gases must be transported over large distances.

The enhanced diffusional distance of the internal respiratory aid, as characterized by the limiting length, follows as a result of the increased conductance ratio of the internal respiratory aid. Note by contrast that an internal respiratory aid consisting of a fiber composed completely of polydimethylsiloxane (P'=10) has a conductance ratio of only 10. The limiting length of the internal respiratory aid composed of polydimethylsiloxane is only 200 microns.

The boundary layer resistance for a liquid medium adjacent to a material can be a substantial component in the overall resistance to gas transport. In the present invention, an important approach to significantly reducing the resistance associated with liquid boundary layers is to increase the available surface area over which gas is transported across the boundary layers. As an effect of the increased surface area and in response to an applied partial pressure difference, mass flow of gas through the boundary layer is increased. With subsequent transport into a material that interfaces with the boundary layer, the gas can be efficiently channeled and redirected into a region of reduced transport area if the material is sufficiently highly gas-permeable. The effectiveness of an internal respiratory aid in reducing the resistance associated with liquid boundary layers therefore relies on the high conductance ratio of the internal respiratory aid, combined with a high surface area for media contact. In the present invention, the preferred means of providing a high conductance ratio in an internal respiratory aid is by constructing the aid with interconnected passageways of entrapped gas as a component.

Figure 49:
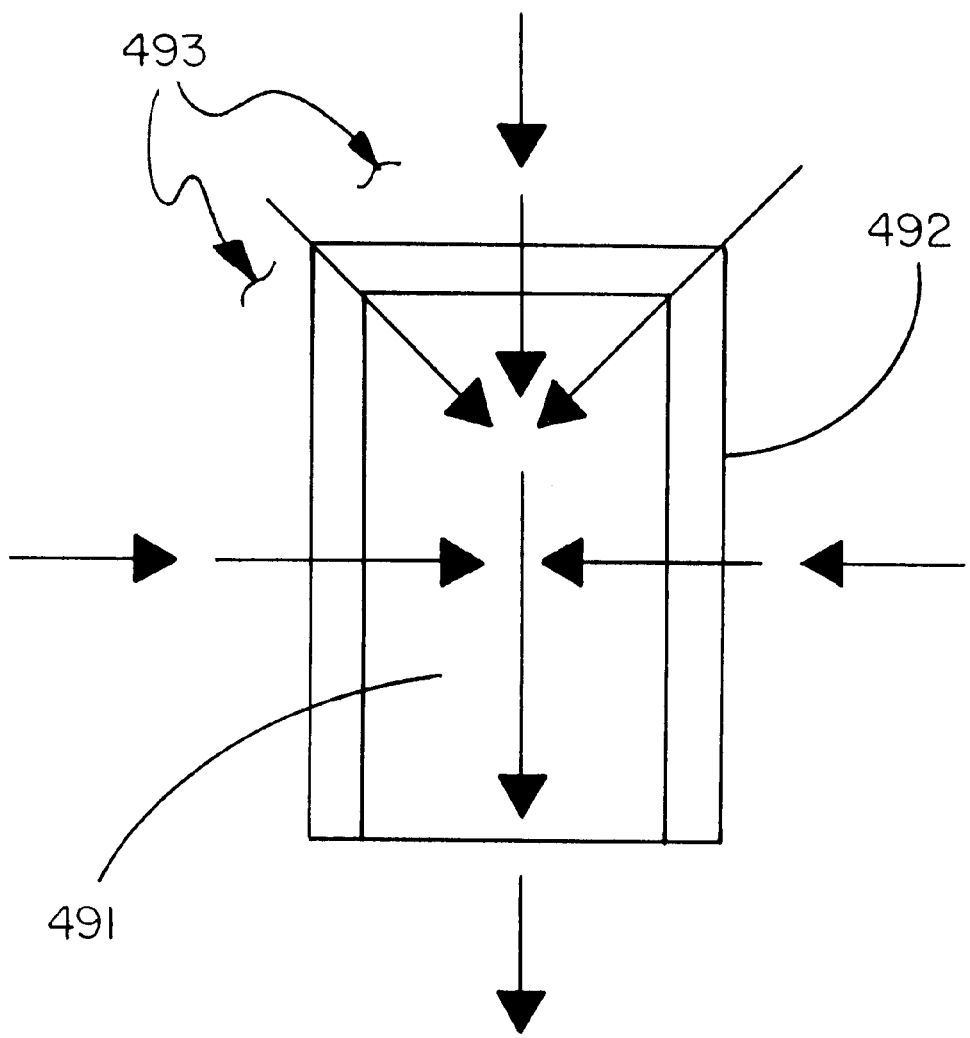
FIG. 49 illustrates an internal respiratory aid collector. The arrows indicate movement of gas into, through, and out of the respiratory aid.

As an example of an internal respiratory aid with an increased boundary layer surface, consider the air-filled ePTFE fiber 491, as illustrated in FIG. 49. As an internal respiratory aid positioned within a liquid media, the fiber functions to deliver oxygen, under the action of an applied partial pressure difference, across both the upper end and the circumferential surface of the fiber, through the high gas-permeable interior of the air-filled ePTFE, and into the reduced area at the lower end of the fiber. The upper end and circumferential surface may be optionally coated with a thin gas-permeable material 492, such as polydimethylsiloxane, to prevent the ingress of liquids into the gas-filled passageways of the internal respiratory aid, while still allowing the exchange of gases.

The article of FIG. 49 illustrates an internal respiratory aid collector, wherein gas collected over a large surface area of the aid in contact with the surrounding medium is delivered into a reduced cross-sectional area A. The gas transport can just as readily be modeled moving in the opposite direction, as in the case where gas is delivered from cross-sectional area A for distribution over a larger surface area into the surrounding medium. This latter type of article is defined as an internal respiratory aid distributor. For a distributor, the direction of the flux arrows in the above illustration are reversed.

Internal respiratory aids acting as collectors or distributors increase the area of contact with the surrounding medium. In the absence of the internal respiratory aid, all gas entering or exiting through an area A must cross the liquid boundary layer through that area alone. With the internal respiratory aid, an increased area of exchange is provided for gas to cross the boundary layer 493, thereby reducing the boundary layer resistance. For example, a fiber with radius r and length L covers a cross-sectional area of $\pi r^2$, whereas the collection or distribution area (neglecting the end) is $2\pi rL$. The increase in surface area across which gas crosses the liquid boundary layer is thus a factor of $2L/r$. For a fiber with a radius of 100 microns and a length of 1 cm, the increase in surface area is 200-fold.

For this increase in surface area to be effective in increasing the overall rate of gas transport into the cross-sectional area A, it is essential that the fiber be composed of materials with high permeability. In effect, the fiber must have a conductance ratio greater than one. The high permeability within the fiber allows the gas to be rapidly transported at long distances into the area A at the bottom of the fiber. Without high permeability, the fiber presents too great a resistance to mass-transport, and the gas, in following the least resistant path through the fiber, enters the lower circumferential surfaces of the fiber only. The consequence is a reduction in effective surface transport area for the gas through the liquid boundary layer, despite the large surface area that may be available.

The flux ratio, as defined earlier, is the ratio of gas flux in an internal respiratory system with the internal respiratory aid versus the flux without the aid. As an example, consider the ePTFE fiber illustrated in FIG. 49, for which a partial pressure difference $\Delta p = p_2 - p_1$ exists between the medium and the bottom of the fiber. Applying a mass balance across a small cross-sectional element of the internal respiratory aid, we generate the differential equation:

$$\overline{P}(\pi r^2)\frac{d^2 p}{dx^2} = k(2\pi r)(p_2 - p)$$

Here, the gradient in the mass flow rate within the element is equated to mass flow rate entering the element by transport through the boundary layer along the circumference of the aid. In the equation, p is the partial pressure of gas (oxygen, in this example) at a position x within the fiber; r is the fiber radius; $\overline{P}$ is the volume-weighted average permeability of the fiber; $p_2$ is the partial pressure in the media; and k is the mass transfer coefficient of the liquid boundary layer in the media adjacent to the fiber. The volume-weighted average permeability of the fiber is determined from the conductance C of the fiber:

$$\overline{P} = \frac{CL}{\pi r^2}$$

where L is the fiber length.

The equation is solved to obtain the profile of partial pressure within the fiber. As boundary conditions, we let $p = p_1$ at $x = 0$ at the base of the fiber into which the gas is delivered, and we assume the partial pressure gradient $dp/dx$ is zero at the furthermost point at which the fiber extends into the media, where $x = L$, the length of the fiber. The latter condition assumes no mass flow of gas into the end of the fiber, such as if the end were coated with a nonpermeable coating. This results in a conservative estimate of total mass flow collected into the fiber.

Solving for the profile, we then determine the mass flow rate through area $A = \pi r^2$ at $x = 0$ as follows:

$$\text{Mass Flow Rate} = -\overline{P}(\pi r^2)\frac{dp}{dx}\bigg|_{x=0}$$
$$= \sqrt{(2\pi r)(\pi r^2)\overline{P}k}\,(\Delta p)\tanh\!\left(L\sqrt{\frac{2k}{\overline{P}r}}\right)$$

In contrast, without the internal respiratory aid, the mass flow rate through area A is $k(\pi r^2)\Delta p$, as gas flow through the boundary layer (with mass transfer coefficient k) occurs without the benefit of the extended surface area of the aid. The flux ratio is thus determined as:

$$\text{Flux Ratio} = \sqrt{\frac{2\overline{P}}{kr}}\,\tanh\!\left(L\sqrt{\frac{2k}{\overline{P}r}}\right)$$

An equivalent expression is obtained by representing the mass transfer coefficient k of the liquid boundary layer as $P_{aq}/\delta_B$, where $P_{aq}$ is the permeability of water, and $\delta_B$ is the boundary layer thickness. Since the conductance ratio C' equals the permeability ratio $\overline{P}/P_{H2O}$ in this example, the flux ratio is found to be:

$$\text{Flux Ratio} = \sqrt{2(\delta_B/r)C'} \tanh\left(L\sqrt{\frac{2}{C'\delta_B r}}\right)$$

The equation illustrates that the flux ratio increases with the circumferential surface area of the internal respiratory aid, reflected by the length of the aid L. As L increases, the flux ratio approaches a maximum value given by $\sqrt{2(\delta_B/r)C'}$. The flux ratio approaches 99% of this maximum value at a length L equal to $1.87\sqrt{C'\delta_B r}$. As indicated in the equation above, the internal respiratory aid enhances flux (relative to a system without the aid) with increases in the boundary layer resistance (as represented by an increase in $\delta_B$), the conductance ratio C', and the surface-to-volume ratio (represented by 2/r) of the internal respiratory aid.

Figure 38:
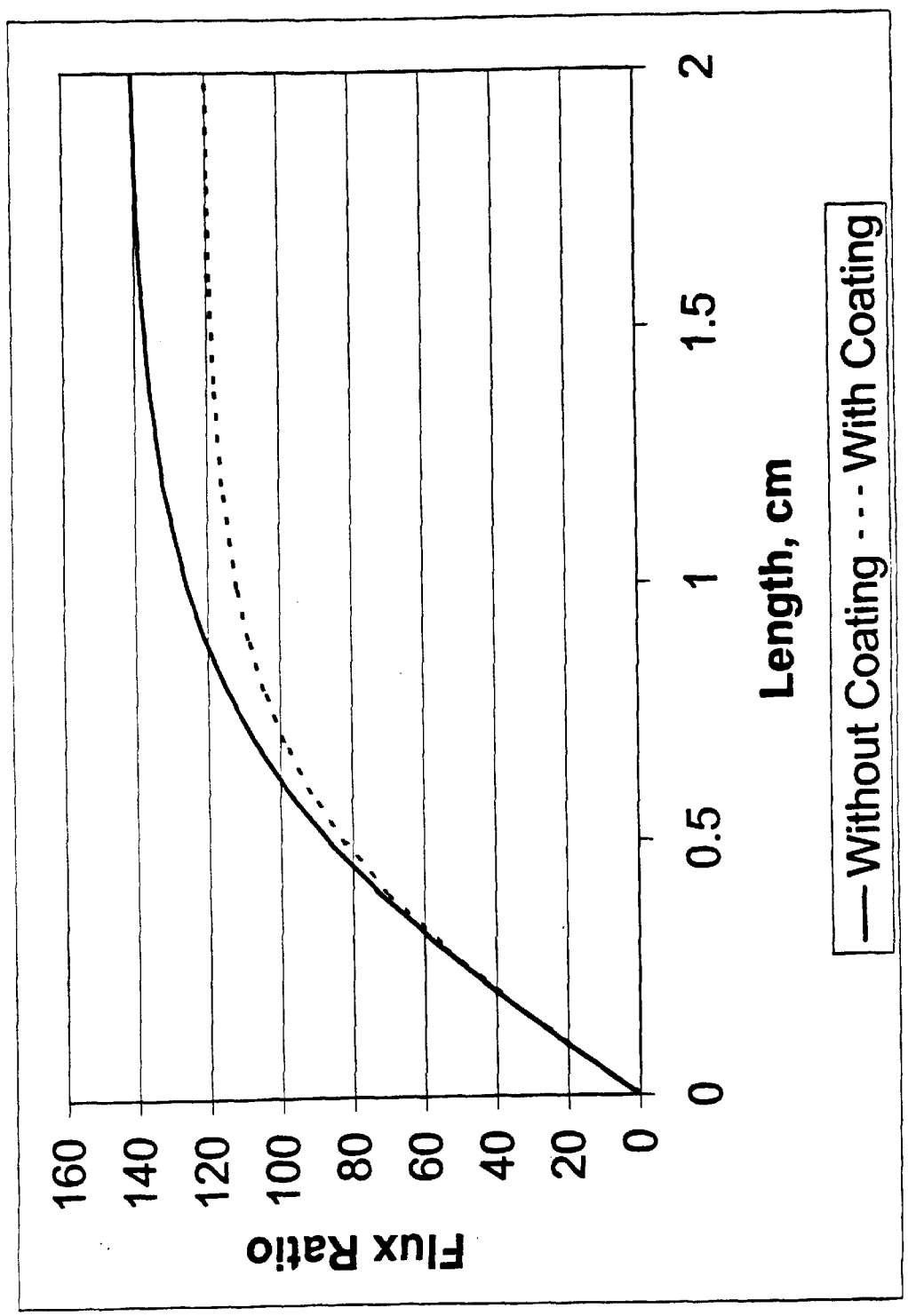
FIG. 38 is a graph illustrating the effect of length on flux ratio for two internal respiratory aid collectors with $C'=10^5$ and $C'=7.2\times10^4$, respectively.

In FIG. 38 is illustrated a plot of flux ratio versus length for two fibers, each 100 μm in radius. The first fiber is composed entirely of air-filled ePTFE without a coating, with conductance ratio $C'=10^5$. The second fiber is also composed of air-filled ePTFE at its center, with an outer 15-μm thickness of polydimethylsiloxane coating, so that $C'=7.2\times10^4$. In the illustration, the liquid boundary layer thickness $\delta_B$ is 10 μm. The maximum flux ratio is 141 and 120 for the uncoated fiber and coated fiber, respectively, occuring at respective lengths of 1.87 and 1.58 cm. The coating diminishes the flux ratio somewhat. In contrast, an internal respiratory aid with 100 μm radius, composed entirely of polydimethylsiloxane (C'=10) has a maximum flux ratio of only 1.4, occuring at a length of only 187 μm.

To further enhance the benefits of increased surface area, an increased number of internal respiratory aid elements may be employed together. For example, a number of smaller diameter fibers can be combined into a network to increase the surface area per unit volume of the present invention. In preferred embodiments, a network of small diameter fibers is constructed and used with cell-containing devices. These embodiments are particularly useful, as it is known in the field of mammalian biology that cellular tissue is generally no farther than about one hundred microns from an oxygen source. With these embodiments, internal respiratory aids for use with cell-containing devices are constructed such that spacing between the gas delivery portion of the internal respiratory aid is no more than about one hundred microns from a given set of cells in a cell population. In this manner, an array of internal respiratory aids of the present invention are assembled together in a cell-containing device to provide gas exchange generally analogous to the tracheole system of an insect. If the internal respiratory aids are highly gas-permeable in these embodiments, the volume occupied by the internal respiratory aid in the cell-containing device is preferably low, so as to leave a large volume available for cells and other components.

Alternatively, internal respiratory aids having high surface area other than cylindrical forms are also preferred embodiments of the present invention. Examples include such forms that emulate marine corals and branching networks, as found in nature.

The surface area of an internal respiratory aid can be categorized as a gas-collecting portion and a gas-delivering portion, each with different associated surface areas (FIGS. 31A–31C). In addition, internal respiratory aids of the present invention may pass between one or more regions where the functions of collection and delivery are separated and/or compartmentalized (FIGS. 8–13). As the internal respiratory aid extends into regions where oxygen is to be either collected or distributed, the surface area of the internal respiratory aid is preferably increased to counter the negative effects of boundary layers in those regions.

For regions between gas-collecting portions and gas delivering portions, the internal respiratory aid functions to conduct gases, preferably without loss to a surrounding environment. This is analogous to a wire conducting heat or electricity between sites at different potentials wherein it is beneficial to use an insulating material to prevent heat or electrical loss to a surrounding environment. In the present invention, this type of internal respiratory aid or portion of an internal respiratory aid was previously defined as a conductor. It is preferred that transporting gases do not 'leak out' or exchange between the walls of a conductor and the surrounding environment. Leakage can be minimized by minimizing the surface area of a conductor. Leakage can also be minimized by reducing the transmissibility of the conductor surfaces through wall thickening and/or through the use of low gas-permeable materials in or on the walls of the conductor. Such means can effectively 'insulate' the conductor from the leakage of gaseous materials.

As with an insect tracheole system, gas-exchange through internal respiratory aids of the present invention can occur in either, or both, directions through the invention. The driving force in determining which direction a particular gas will travel through the internal respiratory aid is the diffusion gradient of the gas, as represented by a partial pressure difference. In this way, the present invention functions to passively collect gas from a particular medium at one locale, passively conduct the gas through the invention to another locale, and passively deliver the gas to another medium at another locale, such as at metabolically active sites. A reverse collection, transport, and delivery of gas is also possible in the same material of the present invention, provided a gas diffusion gradient is appropriately established in the environment surrounding the material. For example, when the present invention is used in biological systems, oxygen is transported from an external respiratory system to living cells and carbon dioxide is transported away from the cells concurrently. Accordingly, the present invention can provide gas transport in more than one direction under appropriate differences in partial gas pressures.

Model for Internal Respiratory Aids in Cell-Containing Systems

A model describing the effect of an internal respiratory aid within a cell-containing system is represented as an arrangement of alternating plates of acellular and cellular material. The acellular plates represent the respiratory aid itself, each plate having a width 2r and permeability P. The cellular plates represent regions of a functional cell zone within a cell-containing system. These zones are loaded with cells at such a density to consume oxygen at a constant rate $\Re$ per unit volume. Each of the plates comprising regions of the cell zone has a width 2s, with transport properties essentially defined as that of water with permeability $P_{aq}$. All plates, whether of the respiratory aid or cell zone, extend from an ambient interface (x=0) at which the oxygen partial pressure p equals $p_o$, to a depth x=L, generally defined as a line of symmetry where the partial pressure gradient dp/dx becomes zero.

In steady-state operation, oxygen diffuses from the ambient interface into both the cellular and acellular plates, and is consumed within the cellular plates of the cell zone alone. The partial pressure p therefore declines with increasing depth into the plates, and may ultimately approach a value of zero for plates of sufficient depth. The function of the acellular plates as an internal respiratory aid is to supply oxygen to the cellular plates of the cell zone, thereby sustaining higher partial pressures and extending the depth at which the partial pressure approaches zero. However, since the respiratory aid has finite volume, it also reduces the total available space in the cell zone in which cells may reside. The selection of the appropriate materials and geometry of the respiratory aid therefore represents a balance between transport enhancement and space allocation.

The effect of the respiratory aid within a cell-containing system is described in terms of the flux ratio. The flux ratio, as defined earlier, represents the ratio of the oxygen flux for a system containing an internal respiratory aid versus the flux for a system without an aid. As distinct from the systems considered earlier, the system in the present example incorporates the additional effect of a cellular component that acts as a metabolic sink for the diffusing oxygen. Flux ratios greater than one represent enhancement of flux within the cell-containing system, whereas those less than one represent a detriment. A flux ratio equal to one indicates no net gain or loss in flux relative to systems without the internal respiratory aid.

The oxygen flux for a cell-containing system without internal respiratory aid can be determined by solution of the steady-state transport-reaction equation in one dimension:

$$P_{aq} \frac{d^2 p}{dx^2} = \mathcal{R}$$

The solution of this equation, subject to the boundary conditions $p=p_o$ at $x=0$, and $dp/dx=0$ at $x=L$, is:

$$p = \frac{\mathcal{R}}{2P_{aq}} x^2 - \frac{\mathcal{R}L}{P_{aq}} x + p_o$$

If it is assumed that the partial pressure becomes zero at $x=L$, then L representing in this case the depth of the cell zone $L_o$ without an internal respiratory aid, can be determined as:

$$L_o = \sqrt{\frac{2 P_{aq} p_o}{\mathcal{R}}}$$

The oxygen flux at the ambient interface of a cell-containing system is equivalent to the rate of oxygen consumption within the system divided by the interface area. For a system without respiratory aid, the flux is therefore evaluated as:

$$\text{Flux} = -P_{aq} \frac{dp}{dx}\bigg|_{x=0} = \mathcal{R} L_o = \sqrt{2 P_{aq} \mathcal{R} p_o}$$

Consider now the oxygen flux for a cell-containing system that includes an internal respiratory aid. The flux for this system is determined with reference to the equivalent interface area as that of the system without the aid. The interface area therefore encompasses that exposed to the ambient by both the cellular and acellular plates. In this context, a hypothetical system is described that has an equivalent rate of oxygen consumption as the actual system containing the aid, in which the cell zone width remains 2s. The cell zone in the hypothetical system is defined to have an equivalent depth $L_{eq}$ in which all cells consume oxygen at the maximal constant volumetric rate $\mathcal{R}$. Flux in the actual system with the internal respiratory aid is thus described with reference to $L_{eq}$ in the hypothetical system as:

$$(2s + 2r) \cdot \text{Flux} = 2s \cdot L_{eq} \cdot \mathcal{R}$$

$L_{eq}$ is exactly identical to L for systems of minimal depth in which the partial pressure remains above zero throughout the cell zone. $L_{eq}$ is reduced from L if there exists regions within the cell zone within which the partial pressure drops to zero. Ultimately $L_{eq}$ approaches an upper limit as L becomes sufficiently large. At this limit, entire regions at the lower depths of the cell zone have a partial pressure of zero, spanning the entire width of the cell zone 2s. The equivalent depth has a practical use in providing a measure of the average functional depth of the cell zone for a system with an internal respiratory aid.

The flux within the cell-containing system with internal respiratory aid is evaluated:

$$\text{Flux} = \mathcal{R} \cdot L_{eq} \cdot (1 - Y)$$

where Y represents the fractional transport area of the respiratory aid, or in this model $Y=r/(s+r)$. The flux ratio, defined with reference to the system without internal respiratory aid, is thus evaluated as:

$$\text{Flux ratio} = (L_{eq}/L_o)(1-Y)$$

Here the ratio $L_{eq}/L_o$ represents the depth ratio of the cell zone, defined as the equivalent depth of the cell zone in a system with an internal respiratory aid versus the depth of the cell zone in the system without an aid. Note that the flux ratio is readily defined dimensionally, as a balance between the reduction in the cell zone width (represented by 1−Y) versus the increase in average functional cell zone depth (represented by $L_{eq}/L_o$), both of which are effected by the incorporation of the internal respiratory aid, $L_{eq}$, as stated above, is identical to L for sufficiently small values of L, becomes less than L at some point as L increases, and ultimately approaches a maximal value. To determine $L_{eq}$, a mathematical finite element model is employed based on the steady-state transport-reaction equation in two dimensions. In the model, the dimension x describes depth into the system from the ambient surface, and the dimension y describes distance parallel to the surface. The differential equation for transport-reaction within the cell zone appears:

$$\frac{\partial^2 p}{\partial x^2} + \frac{\partial^2 p}{\partial y^2} = \frac{\mathcal{R}}{P_{aq}}$$

where $\mathcal{R}$ and $P_{aq}$ are the constant volumetric rate of reaction and cell zone permeability, respectively, as defined earlier. Within the acellular plates, no consumption occurs, and the corresponding differential equation is simply:

$$\frac{\partial^2 p}{\partial x^2} + \frac{\partial^2 p}{\partial y^2} = 0$$

As before, the boundary condition at $x=0$ is $p=p_o$, and at $x=L$, $dp/dx=0$. Symmetry exists within both the cellular and acellular plates, such that $dp/dy=0$ at the middle of all plates. At the interface between cellular and acellular plates, fluxes in the y-direction are equal, such that:

$$P' \left.\frac{\partial p}{\partial y}\right|_{acellular\ interface} = \left.\frac{\partial p}{\partial y}\right|_{cellular\ interface}$$

where $P'=P/P_{aq}$, the permeability ratio of the material of the internal respiratory aid. For a monolithic material, P' is equivalent to the conductance ratio C' of the internal respiratory aid.

By finite element analysis, a steady-state solution is obtained by reiteration whereby partial pressure is resolved as a function of x-y position within the cellular and acellular plates. As reiteration proceeds, when the partial pressure becomes negative (as is likely to occur for a constant volumetric consumption rate $\Re$, the value of partial pressure is set to zero. $L_{eq}$ is evaluated as the product of L and the fractional non-zero volume of the cellular plates. The fractional non-zero volume is the fractional volume of the cell zone with partial pressure greater than zero, or equivalently the fractional volume with non-zero consumption. Regions within the cell zone with partial pressure equal to zero are assigned zero consumption rates, whereas regions with partial pressure greater than zero consume at rate $\Re$.

In the following, simulations are performed using the model as described above to predict the flux ratio as a function of system geometry and material properties. In the simulations, the permeability $P_{aq}$ of water at 37° C. is 97 barrer. The volumetric rate of reaction $\Re = 4.5 \times 10^{-8}$ mol/sec.cm$^3$, typical for cells loaded at a density of $10^9$/cm$^3$. The ambient oxygen partial pressure 39 mm Hg. These parameters, although held constant in the simulations that follow, are expected to vary in other examples of internal respiratory aids in cell-containing systems that the model simulates, with consequences on the observed performance.

Figure 39:
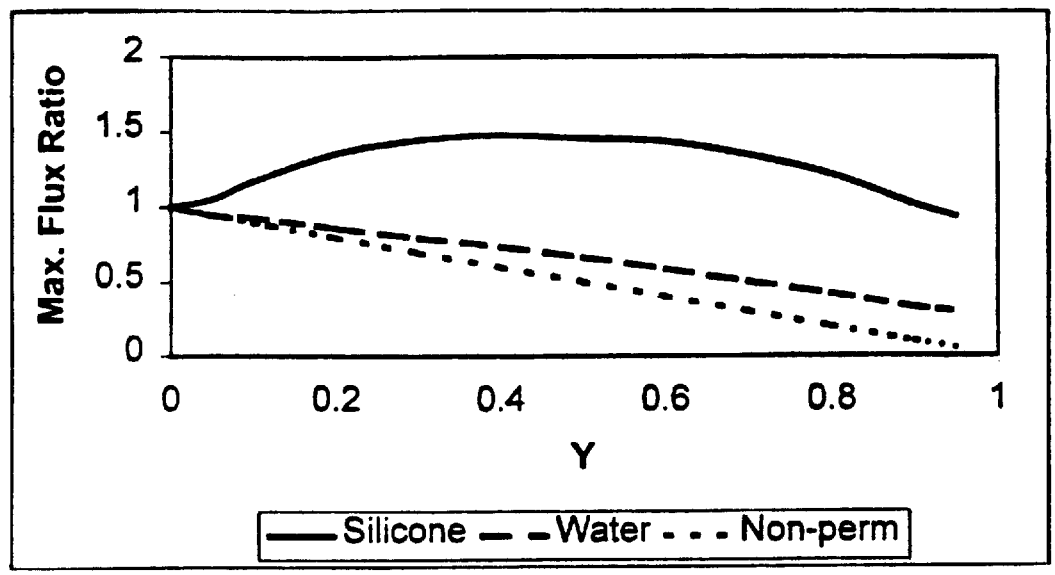
FIG. 39 is a graph illustrating plots of maximum flux ratio for various materials.
Figure 40:
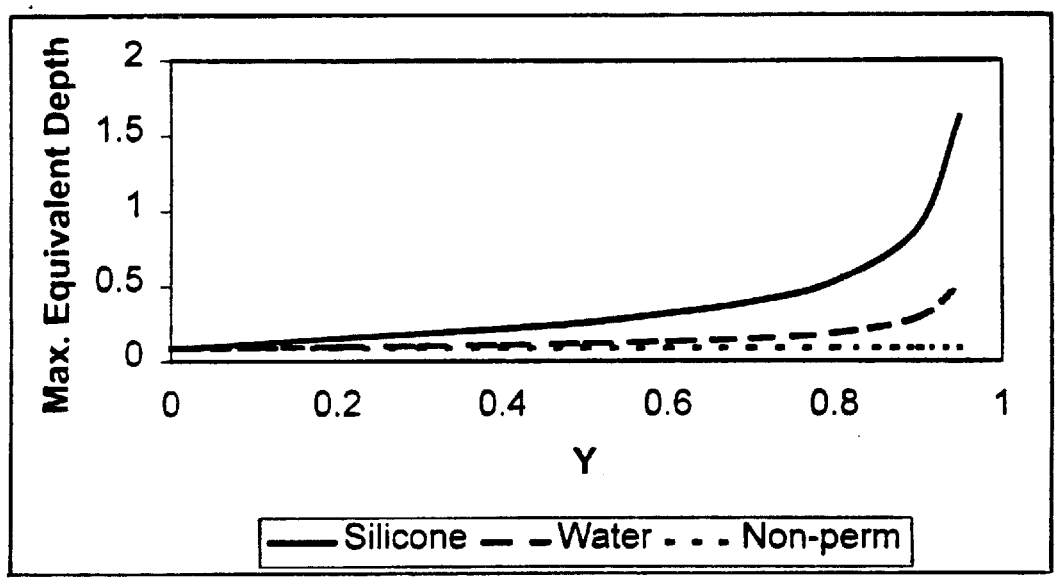
FIG. 40 is a graph illustrating plots of maximum equivalent depth for various materials.

In the simulations illustrated in FIGS. 39 and 40, modulating articles composed of either silicone (with C'=10), water (C'=1), or a non-permeable material (C'=0) are compared. The latter, for example, might be full density PTFE. Plotted as a function of the fractional transport area Y is the maximum equivalent depth $L_{eq}$ for each material, and the associated maximum flux ratio evaluated at maximum $L_{eq}$. The value of (r+s), representing the characteristic interaction scale for the system, equals 50 $\mu$m in all cases. One observes that for silicone, maximum equivalent depth shows a continuous increase with increasing Y. The flux ratio increases slightly with increasing Y to a high value of 1.5 at Y=0.4, and then declines. The interpretation is that silicone, with conductance ratio C'=10, acts marginally as an internal respiratory aid, enhancing oxygen delivery to cells in the cell zone. Oxygen flux for silicone increases with Y because of the increasing capacity of the aid. As Y continues to increase however the volume of the cell zone is diminished, and the flux ratio begins to decline. In contrast, modulating articles composed of water show almost no effect of increasing Y on the equivalent depth. $L_{eq}$ increases only slightly above the value $L_o$ determined for systems without a modulating article (87 $\mu$m), until Y becomes substantially large. On balance, the effect of increasing Y reducing the cell zone dominates, and the flux ratio shows a continuous decline with increasing Y. In the case of a completely nonpermeable modulating article, no effect of increasing Y on equivalent depth is observed. $L_{eq}$ is maintained at 87 $\mu$m, and flux ratio shows a proportional decline with increasing Y. In summary, a flux ratio greater than one is only possible through the application of a modulating article with conductance ratio greater than one, earlier defined as an internal respiratory aid.

Figure 41:
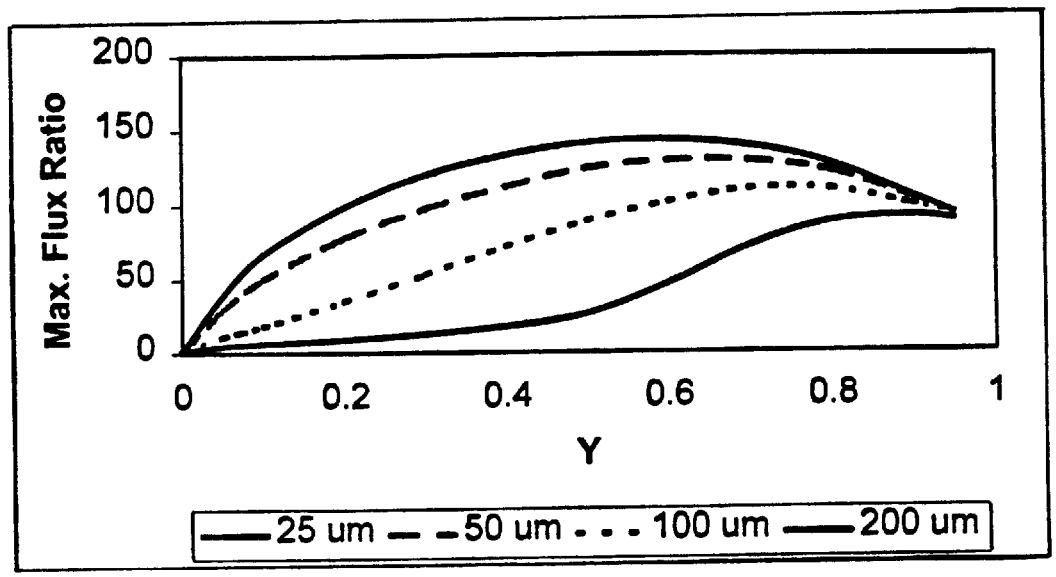
FIG. 41 is a graph illustrating plots of maximum flux ratio for a highly oxygen permeable material.
Figure 42:
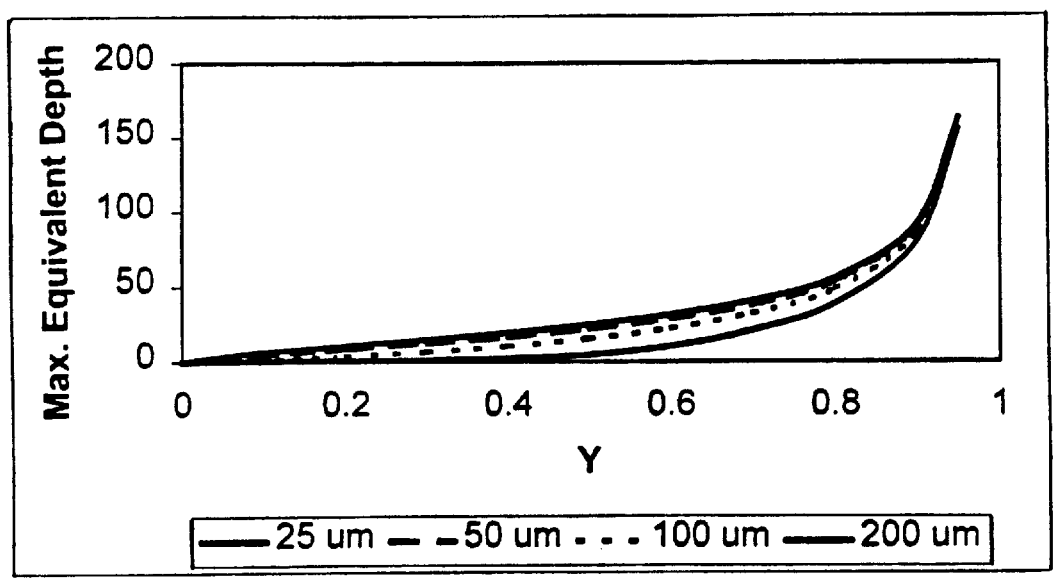
FIG. 42 is a graph illustrating plots of maximum equivalent depth for a highly oxygen permeable material.
Figure 43:
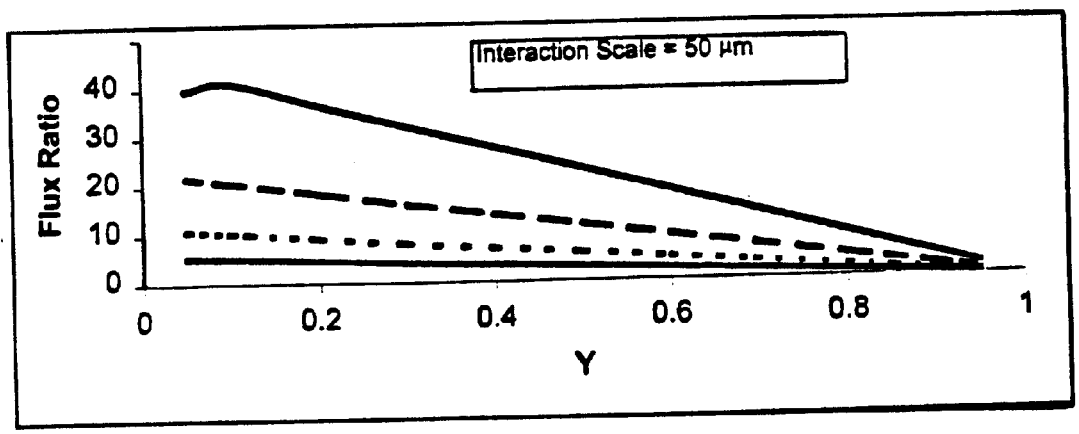
FIG. 43 is a graph illustrating plots of flux ratio for air-filled materials with characteristic interaction scale=50 microns.
Figure 44:
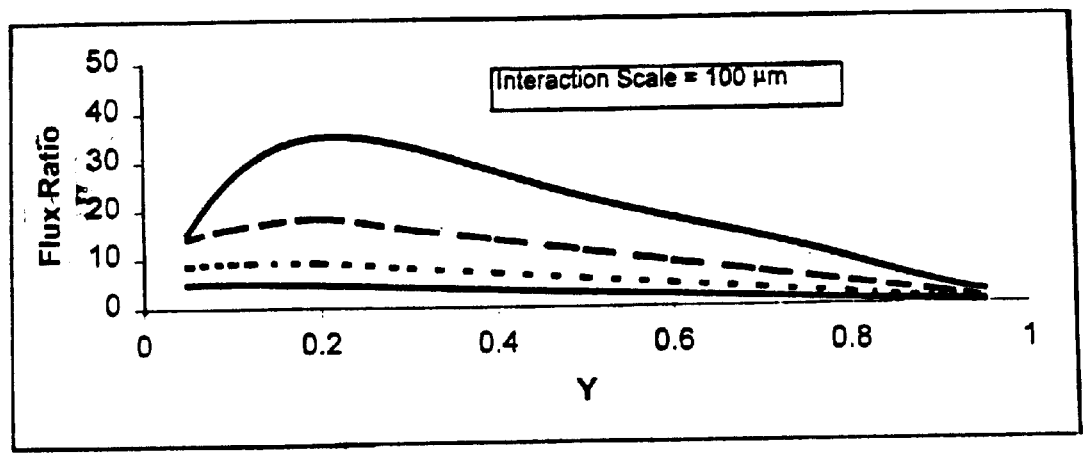
FIG. 44 is a graph illustrating plots of flux ratio for air-filled materials with characteristic interaction scale=100 microns.
Figure 45:
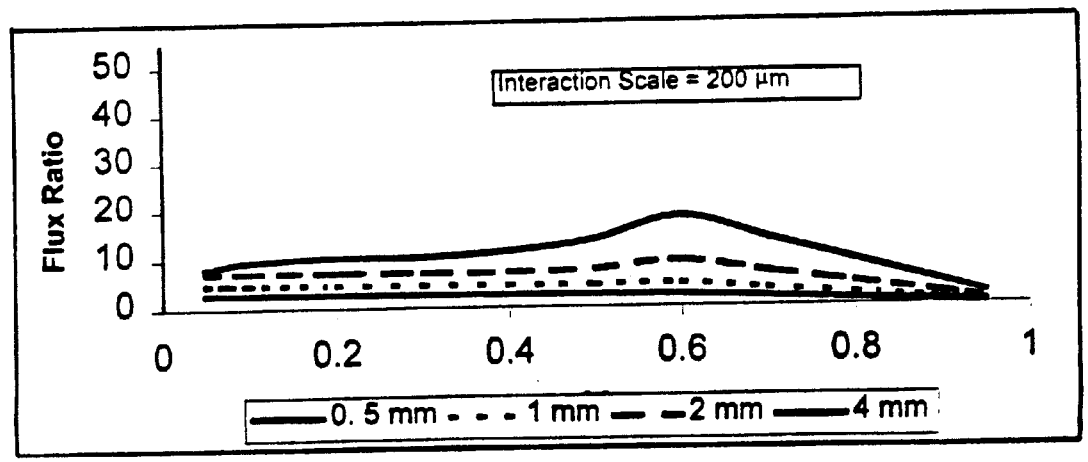
FIG. 45 is a graph illustrating plots of flux ratio for air-filled materials with characteristic interaction scale=200 microns.

Simulations using an extremely high oxygen-permeable material as an internal respiratory aid are next illustrated in FIGS. 41 and 42. Here the material could be expanded PTFE filled with air, with a conductance ratio C' estimated as $10^5$. Permeability $P_{aq}$, volumetric reaction rate $\Re$, and ambient oxygen partial pressure $p_o$ have values as given earlier. In the simulations, values for the characteristic interaction scale (r+s) are varied and the effect on maximum equivalent depth and maximum flux ratio evaluated. The interaction scale provides a measure of the dimensional degree over which the cells in the cell zone and the internal respiratory aid exchange respiratory gases. As the interaction scale is reduced, there is produced a shorter diffusional path length between the cells and the internal respiratory aid supplying oxygen. In effect, a lesser number of larger volume aids are replaced with a larger number of smaller volume aids, with the total volume of aid remaining constant. In essence, the surface-area-to-volume ratio of the internal respiratory aid increases as the interaction scale is reduced, and one expects the supply of oxygen, and thus the flux ratio, to increase as a result.

As before, the maximal value of equivalent depth $L_{eq}$, and also the associated maximal flux ratio, are plotted as a function of the fractional transport area Y. The four curves correspond to four different values for the interaction scale: 25, 50, 100, and 200 $\mu$m. Up to two orders of magnitude increase are noted in both the equivalent depth and the flux ratio in the systems incorporating the air-filled ePTFE as a modulating article, relative to that observed for the previous articles composed of either silicone, water, or non-permeable material. The increase is a direct result of the extremely high conductance ratio of the air-filled article. The presence of an optimal value of Y for the maximization of equivalent depth and flux ratio is again often observed, albeit generally at higher values of Y. This again is a result of the counterbalancing effects of increasing transport capacity and declining cell zone volume as Y increases. Also observed is the effect of the interaction scale (r+s) on both the equivalent depth and the flux ratio. Both show a general increase as the interaction scale is reduced, a direct result of greater contact between the respiratory aid and the cell zone as a result of increasing surface-area-to-volume ratio.

Overall, internal respiratory aids composed of air-filled materials show a greater capacity to support cells in cell-containing systems than other materials, as measured by the maximal equivalent depth and maximum flux ratio. In addition to the conductance ratio of the internal respiratory aid, adjustments in the fractional transport area Y and the interaction scale (r+s) offer important design specifications in selecting an appropriate aid to support a specific cell population. The depth L is an additional parameter that impacts the design of internal respiratory aids in cell-containing systems. In the previous simulations. L was established at a large value so that the equivalent depth $L_{eq}$ became its maximal value for a given value of Y. The instance may occur however in the design of an internal respiratory aid for a cell-containing system where we choose to establish L at a smaller specific dimension that does not maximize $L_{eq}$. As discussed earlier, for sufficiently small values of L, $L_{eq}$ is identical to L. As L increases, $L_{eq}$ becomes less than L, ultimately approaching a maximum as L increases without limit.

Figure 46:
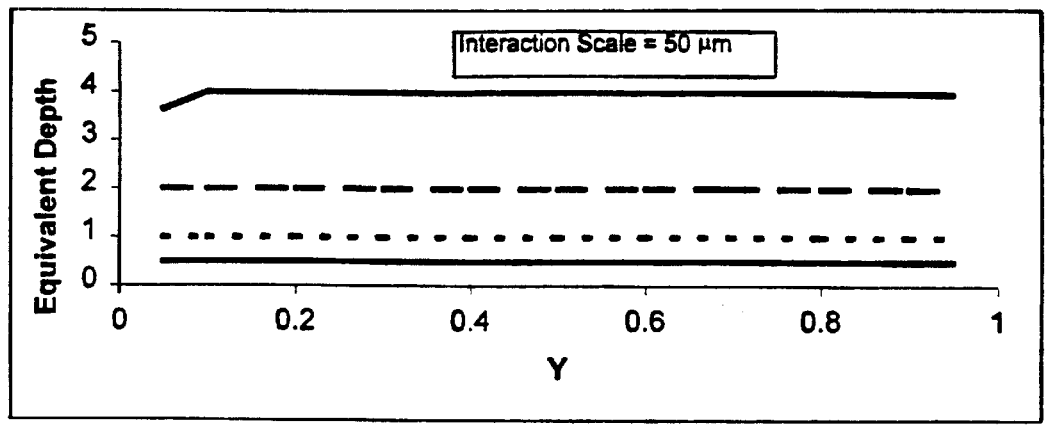
FIG. 46 is a graph illustrating plots of equivalent depth for air-filled materials with characteristic interaction scale=50 microns.
Figure 47:
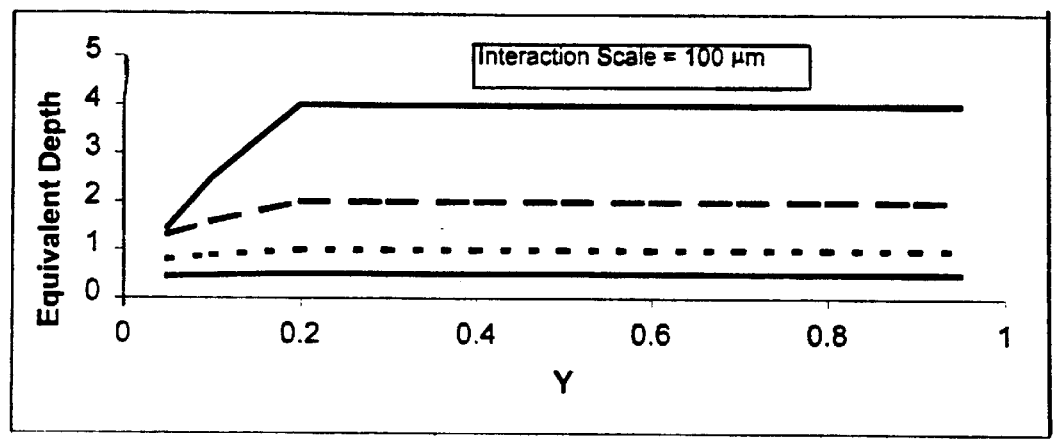
FIG. 47 is a graph illustrating plots of equivalent depth for air-filled materials with characteristic interaction scale=100 microns.
Figure 48:
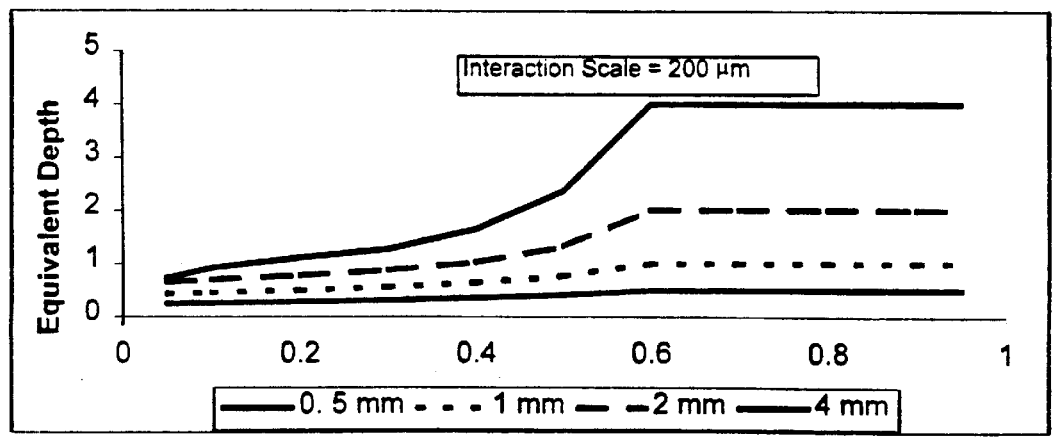
FIG. 48 is a graph illustrating plots of equivalent depth for air-filled materials with characteristic interaction scale=200 microns.

In FIGS. 43–48 are plotted the results of simulations for respiratory aids composed of air-filled materials in which the depth L is maintained at specific values. FIGS. 46–48 display plots of equivalent depth versus Y and FIGS. 43–45 display the corresponding flux ratios versus Y. Each of the figures contains three graphs, corresponding to three different values of the interaction scale (r+s): 50, 100, and 200 $\mu$m; and each graph displays four plots, corresponding to four different values of depth L: 0.5, 1, 2, and 4 mm.

These figures illustrate the effect of different submaximal depths L on respiratory aid performance. The indication is that there exists combinations of sufficiently low values of interaction scale (r+s) combined with specific sufficiently low values of depth L and high values of Y such that the equivalent depth $L_{eq}$ remains identical to L. For the most part, this is the case for (r+s)=50 $\mu$m (except for extremely low values of Y for L=4 mm). As a result, the flux ratio declines proportionally with Y and with L (which is equivalent to $L_{eq}$ in this case). In these instances, there exist no regions of zero partial pressure within the cell zone. The effect of increasing Y is to limit the cell zone volume, and the flux ratio decreases.

As the interaction scale is increased to values of 100 and 200 $\mu$m, a reduction in the equivalent depth $L_{eq}$ relative to L is observed for sufficiently small values of Y. As Y becomes large, $L_{eq}$ again becomes equal to L. An increase in flux ratio is observed with Y in these cases, until roughly the point at which $L_{eq}$=L, at which the flux ratio again declines proportionally with increasing Y. In general, larger values of L and smaller values of interaction scale produce higher values of equivalent depth and flux ratio. It may be the case in the design of an internal respiratory aid for a cell-containing system that one is interested in minimizing the regions at which the oxygen partial pressure falls to zero while still maintaining a cell zone of maximal depth. This may be readily accomplished by setting L at a value such that it remains equivalent to $L_{eq}$, by appropriate adjustment of the interaction scale and Y.

The model suggests useful guidelines for the design of internal respiratory aids based on material properties and system geometry. The model is purposely kept simple in order to allow a more ready interpretation of the key factors that control the performance of internal respiratory aids in cell-containing systems. As a result, in performing simulations using the model, it is possible to clearly distinguish parameters of essential importance—including the conductance ratio P' of the internal respiratory aid, the fraction transport area Y, the interaction scale (r+s), and the depth L—in terms of the effect each has on two characteristic performance parameters: the equivalent depth $L_{eq}$ and the flux ratio. The incorporation of additional complexities in the model may increase the precision of the model in describing a particular article. However the general qualitative insights obtained using the simpler model are expected to be upheld.

Though a simple plate geometry was investigated in the model, it is possible that a different geometry will be used to construct internal respiratory aids for cell-containing systems. For example, an internal respiratory aid in the form of cylindrical fibers positioned within an elongated cylindrical cell zone is utilized with cell-containing devices of the type disclosed by Butler et al. in WO 95/04521, the teachings of which are incorporated herein by reference. A higher precision model can be developed in this case using the appropriate transport-reaction expression in cylindrical coordinates. However, the present model provides approximate solutions for virtually any geometry by appropriate formulation of what has been termed the "characteristic interaction scale." Towards this goal, the characteristic interaction scale may be alternately defined as the inverse of the surface area-to-volume ratio. Here the surface area is defined as the area of contact between an internal respiratory aid and a zone for containing cells wherein the volume is the total volume of the system, including the volume of both the internal respiratory aid and the cell zone. For the plate geometry, this simplifies to (r+s), as previously defined. However, since Y=r/(r+s) for the plate geometry, the interaction scale in this case can also be written as r/Y. For the case of the cylindrical geometry described above, in which n fibers of radius $r_1$ are positioned within a cell zone of radius $r_2$, the interaction scale is determined:

$$\text{Interaction Scale} = \frac{\pi r_2^2 L}{n(2\pi r_1 L)} = \frac{r_2^2}{2nr_1}$$

Since the fraction transport area Y in this case equals $nr_1^2/r_2^2$, the interaction scale becomes $r_1/(2Y)$. For the case of spherically-shaped elements of radius $r_3$ as an internal respiratory aid, it can be shown that the interaction scale is $r_3/(3Y)$. Using the definition of interaction scale as the inverse surface-area-to-volume ratio, approximate predictions of equivalent depth and flux ratio can be made using the planar geometry model as developed.

The model as defined relates to oxygen as the limiting species, whereas under certain conditions, particularly with the application of an internal respiratory aid, other nutrients such as glucose may become limiting. In these cases, the model may be adapted to account for these other species. The model may also be adapted to account for consumption kinetics within the cell zone that are other than zero-order (as characterized by a constant volumetric rate $\Re$. Kinetics such as first order or Michaelis-Menten may, in some cases, may be more representative of the actual consumption for a specific cell type of interest. Also, the boundary condition of a constant ambient oxygen partial pressure may be altered, perhaps to a condition wherein the incoming ambient flux is equated to the flux within the system at the interface.

Oxygen Permeometry Measurement

The oxygen transport capabilities for various embodiments of internal respiratory aids of the present invention are assessed by oxygen permeometry measurements. These measurements, obtained with an electrochemical apparatus, can provide a quantitative evaluation of the transmissibility T of a material to oxygen. Transmissibility was previously defined as P/$\delta$ (with P the permeability to oxygen, and $\delta$ the thickness of the material, respectively), and also as the mass transfer coefficient k for the material, or the unit area conductance of the material. Permeometry measurements are also able to demonstrate, in qualitative tests, the enhanced oxygen collection, conduction, and distribution capabilities of internal respiratory aids of the present invention. Both quantitative and qualitative permeometry measurements will be presented in the Examples Section.

Permeometry measurements for various materials are performed using a Rehder guard ring polarographic cell connected with a Createch 201T Permeometer™; both sold by Rehder Development Company (22472 Queen St., Castro Valley, Calif.). The system (as described in Fatt, I., *Int Contact Lenses Clinic* 1984; 11: 175–183) consists of a 4.00-mm solid gold measuring cathode, surrounded by a silver anode ring (7.00 mm I.D., 15.00 mm O.D.). The particular polarographic cell used in our measurements has a flat electrode surface geometry, with an additional gold guard ring cathode (4.05 mm I.D., 5.5 mm O.D.) positioned between the measuring cathode and the silver anode. Layers of insulation separate the measuring cathode from the guard cathode and the guard cathode from the silver anode. The flat geometry allows the measurement of internal respiratory aids in the form of planar membranes, with the guard cathode designed to reduce edge effects. The system however has also been used in the measurement of other embodiments of internal respiratory aids, such as oxygen collectors in the form of elongated structures, as will be described below.

Reduction of oxygen occurs at the measuring cathode surface according to the half reaction:

$$O_2 + 2H_2O + 4e^- \rightarrow 4OH^-$$

and is monitored by the current read on the Createch apparatus. At steady state, the equilibrium current reflects the amount of oxygen reduced at the cathode surface as limited by the flux of oxygen through the material being measured. Under these transport-limited conditions, the partial pressure at the measuring cathode is zero, and the partial pressure difference Δp across the material is therefore equivalent to the partial pressure of the oxygen in the reservoir. Hence, the transmissibility to oxygen of the material is determined from the steady-state current $I_{ss}$ according to the expression:

$$T = \frac{I_{ss}}{nFAp}$$

Here, n is the number of electrons transferred per molecule of oxygen that is reduced (i.e. 4); F is the Faraday constant 9.65×10⁴ Coloumbs/mol; and A is the surface area of the measuring gold cathode (0.126 Cm²). Transmissibility, according to the above expression, has units appropriate for the oxygen concentration driving force expressed as a partial pressure difference. In the examples, transmissibility is reported in units of centimeters per second, reflecting the oxygen concentration driving force expressed in molar terms. One obtains the latter value of transmissibility from the former by multiplying by Henry's Law coefficient, defined as the equilibrium ratio of partial pressure of oxygen to its molar concentration in water, which at 25 C equals 5.8×10⁸ mm Hg/(mol/cm³).

In Examples 1–10b, below, the oxygen transmissibility of various planar membranes is measured to illustrate the effect of internal respiratory aids in the membrane embodiment. For these measurements, the material to be measured is positioned over a piece of woven polyamide or cigarette paper on top of the electrode assembly, and clamped in place. The reservoir above the assembly is filled with 4.0 mL of 10 mM phosphate buffer, pH 7.2, that is equilibrated with room air of known oxygen partial pressure. The buffer solution is well stirred using a fixed-speed propeller. The current from the electrode is closely monitored, and the reading at steady state is recorded, from which the transmissibility is determined.

In measuring the transmissibility for membranes, we observe that the overall mass transfer resistance is the sum of resistances for the membrane itself and the external fluid layers:

$$R = \frac{1}{T_{meas}A_2} = \frac{1}{TA_2} + \frac{1}{k_1 A_1} + \frac{1}{k_2 A_2}$$

Here, $T_{meas}$ as represents the transmissibility that is measured and is a function of the actual transmissibility T of the membrane, $k_1$ and $k_2$ representing fluid mass transfer coefficients, and $A_1$ and $A_2$, the transport surface areas. The subscripts 1 and 2 correspond to the surfaces above and below the membrane, respectively. In our measurements, we perform a measurement with no membrane, from which the sum of the latter two resistances in the above expression can be determined. This value is used in subsequent membrane measurements to account for the fluid resistances in the determination of the actual value of T. The permeability P of the membrane is then evaluated from P=Tδ, where δ is the membrane thickness. With T in units of cm/sec, permeability is given in the units of diffusivity, i.e. cm²/sec. Likewise, the permeability ratio $P'=P/P_{aq}$ is determined with reference to $P_{aq}$ as the diffusivity of oxygen in water at 25 C, equal to 2.4×10⁻⁵ cm²/sec.

For membranes of sufficient thickness and permeability, the measured value of transmissibility is often larger than the transmissibility measured with no membrane. In these cases, the first term in the above expression, associated with the intrinsic resistance of the membrane, is negligible relative to the sum of resistances associated with the external fluid layers. Under this circumstance, oxygen is allowed to enter the membrane through a larger area $A_1$ than the area $A_2$ on the opposite side from which it emerges and is consumed. The result is a reduction in total resistance, and an increase in the measured transmissibility. The increase in transmissibility is enhanced as membrane thickness increases, a result of a larger increase in $A_1$. Because of these surface area effects, the guard ring in many instances is rendered ineffective, particularly for materials with increased thickness and high permeability that allow oxygen to be funneled from outside the fluid cylinder defined by the guard ring. Also, for these membranes, we are not able to evaluate the true membrane transmissibility T, nor the permeability P or permeability ratio P', although we surmise that each of these values is large.

In other measurements, the permeometer is used to assess the function of internal respiratory aids in the embodiment of oxygen collectors. The internal respiratory aid in these cases generally takes the form of an elongated structure in contact with the electrode at the bottom of the reservoir and extending upward into the reservoir of oxygen-carrying solution. Accordingly, the data obtained in these measurements, while yielding numerical information, is only of a qualitative nature. The reason is that the electrode is 4.00 mm in diameter (0.126 cm² area), while the internal respiratory aids are usually much smaller, leaving most of the electrode surface free to collect oxygen from the surrounding medium as well as from the internal respiratory aid at the electrode interface. For this reason, the guard ring is not utilized in these measurements. For internal respiratory aids in the form of fibers, it is estimated that only approximately 10% of the electrode surface is actually covered by the fibers in most of the experiments described herein.

For some oxygen transmissibility measurements, a modulating article in the form of a fiber material is first secured to a jig that acts as a device for weighting and securing the fiber material in place against the measuring electrode. The fiber material is folded in a radius of approximately 0.5 cm, and depending upon the drape of the particular material, only the apex of the radius may make contact with the electrode, or a segment approximately 0.5 cm may make contact. The rest of the fiber beyond the radius runs vertically up through the reservoir of solution. The length of the jig is approximately 5.5 cm. If the fiber length is less than approximately 12 cm, the fiber material is simply lashed to the body of the jig with a narrow slit length of Parafilm® "M" material (American National Can™, Greenwich, Conn.). If the fiber is longer than 12 cm, the fiber is wrapped around the jig length multiple times and secured with double-sided sticky tape applied at both jig ends between the jig and the fiber material.

To the clamped solution reservoir is pipetted 10.0 ml of 10 mM phosphate buffer, pH 7.2 that is equilibrated with room air of known partial pressure. The altitude (~7000 ft, Flagstaff, Ariz.), temperature, and barometric pressure are noted, since these parameters influence the partial pressure of gases in solution. 10.0 ml is sufficient solution volume to ensure that the fiber-wrapped jig is submerged by 1.0 cm or more below the liquid-air interface. The system may be turned on and a measurement check of the baseline oxygen transmissibility of quiescent solution may be acquired prior to placing the sample into the reservoir.

In these tests, the initial solution is first measured without fiber in a stagnant state for some time to establish a typical baseline profile. Introducing 10.0 ml of solution into the reservoir results in significant mixing, usually taking several minutes after introduction for the solution to become quiescent. Introducing the fiber for measurement also results in mixing of the solution, so the material needs to be measured for some time to establish a profile during a quiescent state. The fiber can then be removed, causing mixing once again, with the quiescent baseline profile again re-establishing over time.

The introduction of the fiber material is observed to either raise the oxygen signal profile, have little or no effect, or depress the profile, thus serving to demonstrate the type of fiber being evaluated. If the fiber is not permeable to gases, as in the case of an obstructing article with conductance ratio equal to zero, the fiber will obscure the electrode, reducing the ability of oxygen from the surrounding quiescent medium to reach some fraction of the 0.126 cm$^2$ surface area electrode. The oxygen signal profile will be depressed in comparison to a quiescent baseline signal profile with no fiber in the reservoir. A fiber made of a material that is permeable to gas, but that is not a facilitating article with conductance ratio greater than one, will not significantly effect the oxygen signal profile. Any oxygen that is supplied to the electrode in the test instrument is that which is present in the fiber at the onset of the test, and not oxygen which has been transported through the fiber to the electrode from remote locations. On the other hand, if the fiber is a facilitating article with conduction ratio greater than one, i.e. is an internal respiratory aid, and additionally possesses high surface area in contact with the medium, the flux at the electrode will be supplemented by oxygen extracted from the medium from locations remote from the electrode surface. This oxygen, collected in the gas-filled passageways of the fiber across a relatively high surface area and transported by the fiber material to the electrode, acts to enhance the oxygen signal profile.

In the test method described above, the surface area of the fiber at the electrode surface is significantly smaller than the surface area of the fiber that is in contact with the media. The method therefore describes the ability of fibers to collect and extract oxygen through a high surface area extended throughout the surrounding medium distant from the measuring electrode. In addition, the method tests the ability of these fibers to transport the collected oxygen from remote locations several centimeters away to the oxygen-consuming electrode. The method also tests the ability of the fiber to distribute oxygen to the electrode over a relative significantly reduced surface area.

EXAMPLES

Examples of Membranes as Internal Respiratory Aids

TABLE 2

| Membrane Description | Thickness | Measured T (cm/sec) | Actual T (cm/sec) | Permeability P (cm$^2$/sec) | Conductance Ratio, C' |
|---|---|---|---|---|---|
| 1 None | 0 | 3.10e−03 | — | — | — |
| 2a FEP | 5 mil | 6.27e−05 | 6.40e−05 | 8.13e−06 | 0.034 |
| 2b PTFE | 2.5 mil | 1.80e−04 | 1.91e−04 | 1.21e−06 | 0.050 |
| 2c PTFE | 10 mil | 2.42e−05 | 2.44e−05 | 6.20e−07 | 0.026 |
| 3a Silicone | 5 mil | 1.88e−03 | 4.78e−03 | 6.07e−05 | 2.53 |
| 3b Silicone | 10 mil | 1.70e−03 | 3.76e−03 | 9.56e−05 | 3.98 |
| 3c Silicone | 15 mil | 1.32e−03 | 2.30e−03 | 8.76e−05 | 3.65 |
| 4a ePTFE-water | 0.1 mm | 7.34e−04 | 9.61e−04 | 9.62e−06 | 0.40 |
| 4b ePTFE-water | 0.3 mm | 3.54e−04 | 4.00e−04 | 1.20e−05 | 0.50 |
| 4c ePTFE-water | 0.7 mm | 1.85e−04 | 1.97e−04 | 1.38e−05 | 0.57 |
| 5a ePTFE-air | 0.1 mm | 3.08e−03 | 4.77e−01 | 4.77e−03 | 199 |
| 5b ePTFE-air | 0.3 mm | 4.01e−03 | ** | ** | ** |
| 5c ePTFE-air | 0.7 mm | 4.03e−03 | ** | ** | ** |
| 6a Si-coated ePTFE | 0.1 mm | 1.92e−03 | 5.04e−03 | 5.04e−05 | 2.10 |
| 6b Si-coated ePTFE | 0.3 mm | 2.11e−03 | 6.61e−03 | 1.98e−04 | 8.26 |
| 6c Si-coated ePTFE | 0.7 mm | 2.75e−03 | 2.44e−02 | 1.70e−03 | 71 |
| 7a Lasered ePTFE-water | 0.1 mm | 8.58e−04 | 1.18e−03 | 1.18e−05 | 0.49 |
| 7b Lasered ePTFE-water | 0.3 mm | 4.22e−04 | 4.88e−04 | 1.46e−05 | 0.61 |
| 7c Lasered ePTFE-water | 0.7 mm | 2.80e−04 | 3.08e−04 | 2.15e−05 | 0.90 |
| 8a Lasered ePTFE-air | 0.1 mm | 3.42e−03 | ** | ** | ** |
| 8b Lasered ePTFE-air | 0.3 mm | 4.34e−03 | ** | ** | ** |
| 8c Lasered ePTFE-air | 0.7 mm | 5.12e−03 | ** | ** | ** |
| 9a Lasered ePTFE-air: Si-coated | 0.1 mm | 2.22e−03 | 7.82e−3 | 7.82e−05 | 3.25 |
| 9b Lasered ePTFE-air: Si-coated | 0.3 mm | 2.21e−03 | 7.70e−03 | 2.31e−04 | 9.62 |
| 9c Lasered ePTFE-air: Si-coated | 0.7 mm | 2.06e−03 | 6.14e−03 | 4.30e−04 | 17.9 |
| 10a UHMW PE: water-filled | 51 mil | 7.40e−05 | 7.58e−05 | 9.82e−06 | 0.41 |
| 10b UHMW PE: air + water-filled | 49 mil | 4.05e−03 | ** | ** | ** |

**For these membranes, the measured transmissibility was greater than that for no membrane, indicating increased surface area transport effects. Actual T, P, and C' could therefore not be estimated.

Table 2 above outlines the results of various measurements as outlined in Examples 1–10b. In the first example, a transmissibility measurement performed with no membrane is used to assess the resistance associated with the external fluids. As earlier described, this first measurement is used in subsequent membrane measurements to determine the actual value of transmissibility T for a particular membrane, from which the permeability P is determined. Transmissibility, in these measurements, is given in units of cm/sec, and thus permeability P has units of diffusivity, i.e. $cm^2/sec$. The conductance ratio C' is equivalent to the permeability ratio $P'=P/P_{aq}$ in these tests. Here, $P_{aq}$ is equivalent to the diffusivity of water at 25 C, equal to $2.4\times10^{-5}$ $cm^2/sec$. In some cases, for membranes of increased thickness and permeability, values for T, P, and C' could not be assessed because of surface area effects, as earlier described. In these instances, the values, though not listed, are expected to be high.

Example 1

In this example, baseline oxygen transmissibility values are established for comparison with the various materials in the following examples by using the permeometer described earlier, with no membrane. The value for this example is listed in Table 2, above.

Example 2a

In this example, a non-porous, poorly gas-permeable material is tested for transmissibility to gaseous oxygen to further establish a basis of comparison with transmissibility tests in subsequent examples.

To perform the test, a sheet of non-porous, fluorinated poly(ethylene-co-propylene) (TEFLON® FEP Fluorocarbon Film) having a thickness of 0.005" (i.e., 125 microns) is obtained (E. I. duPont deNemours & Co., Inc., Wilmington, Del. Catalog no. 37717). There are no visible pores or void spaces in this material. The material is tested for permeability to gaseous oxygen, as described earlier.

As can be seen from Table 2, the transmissibility of this material to gaseous oxygen is low, and the conductance ratio is less than one. It is concluded from the conductance ratio that this material is not suitable for use in the present invention as an internal respiratory aid.

Example 2b

In this example, a non-porous, poorly gas-permeable, material is tested for transmissibility to gaseous oxygen to further establish a basis for comparison with transmissibility tests in subsequent examples.

In the test, a sheet of full density (i.e., 2.21 gm/cc.) non-porous polytetrafluoroethylene (PTFE) having a thickness of 0.0025" (i.e., 62.5 microns) is obtained from Dewal Industries, Inc., 15 Ray Trainor Drive, Saunderstown, R.I. 02874. There are no visible pores or void spaces in this material. The material is tested for transmissibility to gaseous oxygen, as described earlier.

As can be seen from Table 2, the transmissibility of this material to gaseous oxygen is low, and the conductance ratio is less than one. It is concluded from the conductance ratio that this material is not suitable for use in the present invention as an internal respiratory aid.

Example 2c

In this example, a non-porous, poorly-gas-permeable, material is tested for transmissibility to gaseous oxygen to further establish a basis for comparison with transmissibility tests in subsequent examples.

In the test, a sheet of full density (i.e., 2.21 gm/cc.) non-porous polytetrafluoroethylene (PTFE) having a thickness of 0.010" (i.e., 250 microns) is obtained from Dewal Industries, Inc., 15 Ray Trainor Drive, Saunderstown, R.I. 02874. There are no visible pores or void spaces in this material. The material is tested for transmissibility to gaseous oxygen, as described earlier.

As can be seen from Table 2, the transmissibility of this material to gaseous oxygen is low, and the conductance ratio is less than one. It is concluded from the conductance ratio that this material is not suitable for use in the present invention as an internal respiratory aid.

Example 3a

In this example, a silicone material that is highly permeable to oxygen is tested to further establish a basis for comparison with transmissibility tests in subsequent examples.

In this example, a sheet of clear, void-free poly(dimethyl siloxane) is obtained from Applied Silicone Corp. (Ventura, Calif.). The silicone material is 0.005" (i.e., 125 microns) in thickness. There are no visible pores or void spaces in the poly(dimethyl siloxane) material in which a gas or aqueous media could be present.

As can be seen from Table 2, the transmissibility of this material to gaseous oxygen is high, and the conductance ratio is greater than one. It is concluded from the conductance ratio that this silicone material is suitable for use in the present invention to construct an internal respiratory aid.

Example 3b This example is similar to Example 3a,
but with a thicker sheet of silicone. The silicone
sheet in this example is 0.010" (i.e., 250 microns)
in thickness.

As can be seen from Table 2, the transmissibility of this material to gaseous oxygen is high, and the conductance ratio is greater than one. It is concluded from the conductance ratio that this silicone material is suitable for use in the present invention to construct an internal respiratory aid.

Example 3c

This example is similar to Example 3a, but with a yet thicker sheet of silicone. The silicone sheet in this example is 0.015" (i.e., 375 microns) in thickness.

As can be seen from Table 2, the transmissibility of this material to gaseous oxygen is high, and the conductance ratio is greater than one. It is concluded from the conductance ratio that this silicone material is suitable for use in the present invention to construct an internal respiratory aid.

In comparing the data in Table 2 of Examples 3a–c, the negative effect on oxygen transmissibility of increasing the thickness of the silicone material is evident.

Example 4a

This example illustrates the low oxygen transmissibility of a porous material with water-filled channels as a basis to compare the transmissibility of more oxygen-permeable materials, such as silicone, or materials with air-fill ed channels. In this example, a porous expanded PTFE material (ePTFE) sold under the tradename Preclude™ Dura Substitute (W. L. Gore & Associates, Inc. (Flagstaff, Ariz.)) is fully wet out with water and tested for oxygen transmissibility as described above. The thickness of the material is 100 microns. The density of the porous material is 0.73 gm/cc. The material is wet out with water by first wetting out the material with isopropyl alcohol (IPA). The IPA is exchanged with an aqueous 5.0% solution of polyvinyl alcohol (PVA) wetting, agent. The PVA is exchanged with water by rinsing, in de-ionized water. The material is maintained underwater to prevent dewetting, or drying out of the material.

As can be seen from Table 2, the transmissibility of this material to gaseous oxygen is low, and the conductance ratio is less than one. While this material is structurally appropriate for use in the present invention, the material has not been suitably treated to act as an internal respiratory aid, as indicated by the conductance ratio being less than one. The water-filled material is suitable as a membrane for the transport of aqueous solutes, however.

Example 4b

This example illustrates the low oxygen transmissibility of a porous material with water-filled channels as a basis to compare the transmissibility of more oxygen-permeable materials, such as silicone, or materials with air-filled channels. The materials and methods of this example are the same as Example 4a, above, except that the thickness of the ePTFE starting material is 300 microns. The density of the porous material is 0.54 gm/cc.

As can be seen from Table 2, the transmissibility of this material to gaseous oxygen is low, and the conductance ratio is less than one. While this material is structurally appropriate for use in the present invention, the material has not been suitably treated to act as an internal respiratory aid, as indicated by the conductance ratio being less than one. The water-filled material is suitable as a membrane for the transport of aqueous solutes, however.

Example 4c

This example illustrates the low oxygen transmissibility of a porous material with water-filled channels as a basis to compare the transmissibility of more oxygen-permeable materials, such as silicone, or materials with air-filled channels. The materials and methods of this example are the same as Example 4a, above, except that the thickness of the ePTFF starting material is 700 microns. The density of the porous material is 0.43 gm/cc.

As can be seen from Table 2, the transmissibility of this material to gaseous oxygen is low, and the conductance ratio is less than one. While this material is structurally appropriate for use in the present invention, the material has not been suitably treated to act as an internal respiratory aid, as indicated by the conductance ratio being less than one. The water-filled material is suitable as a membrane for the transport of aqueous solutes, however.

In comparing the data in Table 2 of Examples 4a–c, the negative effect on oxygen transmissibility of increasing the thickness of the water-filled material is evident.

Example 5a

This example illustrates the high oxygen transmissibility of a porous material having air-filled channels.

In this example, a porous expanded PTFE material (ePTFE) sold under the tradename Preclude™ Dura Substitute (W. L. Gore & Associates, Inc. (Flagstaff, Ariz.)) that is air-filled is tested for oxygen transmissibility as described above. The thickness of the material is 100 microns. The density of the porous material is 0.73 gm/cc.

As can be seen from Table 2, the transmissibility of this material to gaseous oxygen is high, and the conductance ratio is greater than one. It is concluded from the conductance ratio that this air-filled porous material is suitable for use in the present invention as an internal respiratory aid.

This material has about the same transmissibility value as that measured with no membrane (Example 1). Since oxygen diffuses extremely rapidly through the air-filled spaces of the material, it is believed that the operation of the guard ring in the permeometer is not effective for this type of membrane. It is extremely difficult to control and isolate edge effects in the apparatus where diffusion within and across such a membrane is so rapid. Measurements for this example were thus obtained with the guard ring off on the permeometer.

Example 5b

This example illustrates the high oxygen transmissibility of a porous material having air-filled channels. The materials and methods of this example are the same as Example 5a, above, except that the thickness of the ePTFE starting material is 300 microns. The density of the porous material is 0.54 gm/cc.

As can be seen from Table 2, the transmissibility of this material to gaseous oxygen is high. The value is even higher than the value measured with no membrane in Example 1. These data only make sense when it is recalled that the upper surface area through which oxygen enters the membrane is greater than the 0.126 cm$^2$ area of the electrode surface. In effect, an amplified signal results in which oxygen is collected over a greater surface area than that provided by the bare 4.00-mm diameter electrode surface, as measured in Example 1. Although the conductance ratio cannot be directly assessed, it is concluded from the oxygen transmissibility data that the conductance ratio for this material will be high and that this air-filled porous material is suitable for use in the present invention as an internal respiratory aid.

Example 5c

This example illustrates the high oxygen transmissibility of a porous material having air-filled channels. The materials and methods of this example are the same as Example 5a, above, except that the thickness of the ePTFE starting material is 700 microns. The density of the porous material is 0.43 gm/cc.

As can be seen from Table 2, the transmissibility of this material to gaseous oxygen is high. The value is even higher than the value measured with no membrane in Example 1. Although the conductance ratio cannot be directly assessed, it is concluded from the oxygen transmissibility data that the conductance ratio for this material will be high and that this air-filled porous material is suitable for use in the present invention as an internal respiratory aid.

It is further concluded that the thickness of the porous air-filled materials of Examples 5a–5c is a positive factor in oxygen permeability through the material. This increase in the transmissibility of these samples with increasing thickness is thought to be attributable to increased surface area from the sample edges.

Example 6a

This example illustrates the high oxygen transmissibility of a silicone-coated, porous material.

In this example, a sheet of porous expanded PTFE material (ePTFE) sold under the tradename Preclude™ Dura Substitute (W. L. Gore & Associates, Inc. (Flastaff, Ariz.)) is coated with a layer of silicone and tested for oxygen transmissibility as described above. The thickness of the material is 100 microns. The density of the porous material is 0.73 gm/cc.

A layer of silicone is applied to the exterior surfaces of the ePTFE sheet as a water-based emulsion by dipping the ePTFE material in the silicone emulsion (Shin Etsu, catalog no. KM2002-L1, Akron, Ohio). Excess emulsion is wiped off. The water portion of the emulsion is allowed to dry. The silicone layer is cured on the ePTFE material with heat at 125° C. for at least five minutes. The result is an ePTFE membrane with silicone-scaled portions of the membrane filled with air.

As can be seen from Table 2, the transmissibility of this material to gaseous oxygen is high, and the conductance ratio is greater than one. It is concluded from the conductance ratio that this silicone coated air-filled porous material is suitable for use in the present invention as an internal respiratory aid.

Example 6b

This example illustrates the high oxygen transmissibility of a silicone-coated porous material. The materials and methods of this example are the same as Example 6a, above, except that the thickness of the ePTFE starting material is 300 microns. The density of the porous material is 0.54 gm/cc.

As c an be seen from Table 2, the transmissibility of this material to gaseous oxygen is high, and the conductance ratio is greater than one. It is concluded from the conductance ratio that this silicone coated air-filled porous material is suitable for use in the present invention as an internal respiratory aid.

Example 6c

This example illustrates the high oxygen transmissibility of a silicone-coated porous material. The materials and methods of this example are the same as Example 6a, above, except that the thickness of the ePTFE starting material is 700 microns. The density of the porous material is 0.43 gm/cc.

As can be seen from Table 2, the transmissibility of this material to gaseous oxygen is high, and the conductance ratio is greater than one. It is concluded from the conductance ratio that this silicone coated air-filled porous material is suitable for use in the present invention as an internal respiratory aid.

It is further concluded that the thickness of the porous air-filled materials of Examples 5a–5c is a positive factor in oxygen permeability through the material. This increase in the transmissibility of these samples with increasing thickness is attributable to increased surface area from the sample edges.

Example 7a

This example illustrates low oxygen transmissibility of a wet-out porous material. This example further illustrates the gas transport capability of an aqueous liquid-fillable component formed from a microporous hydrophobic material. The microstructure of a porous expanded polytetrafluoroethylene material (ePTFE) is characterized by an irregular network of nodes connected together by fibrils. The void spaces defined by such a network are referred to in the art as the pores of the material.

To make this embodiment, a porous expanded PTFE material sold under the tradename Preclude™ Dura Substitute (W. L. Gore & Associates, Inc., Flagstaff, Ariz.) is first obtained. The material has an average pore size range of about 1 micron to about 10 microns and a thickness of 0.1 mm. The density of the porous material is 0.73 gm/cc.

In addition, the material is subjected to a carbon dioxide laser-drilling process to create an ordered plurality of holes along the z-axis of the material (i.e., normal to the plane of the material). The holes thus obtained have a diameter of about 200 microns. A hole is present every 400 microns in both the x and y axes of the ePTFE sheeting material. The plurality of holes range over the entire surface area of each sample (FIG. 1c). In this embodiment, the entire porous material, including the laser-drilled macroscopic holes, become wet out.

The material is completely wet out with water and tested for transmissibility to oxygen as described above. The material is wet out with water by first wetting out the material with isopropyl alcohol (IPA). The IPA is exchanged with an aqueous 5.0% solution of polyvinyl alcohol (PVA) wetting agent. The PVA is exchanged with water by rinsing in de-ionized water. The material is maintained underwater to prevent dewetting or drying out of the material.

As can be seen from Table 2, the transmissibility of this material to gaseous oxygen is low, and the conductance ratio is less than one. In its present form, the material is not suitable as all internal respiratory aid. These results are similar to those of Examples 4a.

Example 7b

This example illustrates low oxygen transmissibility of a wet-out porous material. The materials and methods of this example are the same as Example 7a, above, except that the thickness of the ePTFE starting material is 300 microns. The density of the porous material is 0.54 gm/cc.

The material is completely wet out with water and tested for transmissibility to oxygen as described above. The material is wet out with water by first wetting out the material with isopropyl alcohol (IPA). The IPA is exchanged with an aqueous 5.0% solution of polyvinyl alcohol (PVA) wetting agent. The PVA is exchanged with water by rinsing in de-ionized water. The material is maintained underwater to prevent dewetting or drying out of the material.

As can be seen from Table 2, the transmissibility of this material to gaseous oxygen is low, and the conductance ratio is less than one. In its present form, the material is not suitable as an internal respiratory aid. These results are similar to those of Examples 4b.

Example 7c

This example illustrates low oxygen transmissibility of a wet-out porous material. The materials and methods of this example are the same as Example 7a, above, except that the thickness of the ePTFE starting material is 700 microns. The density of the porous material is 0.43 gm/cc.

The material is completely wet out with water and tested for transmissibility to oxygen as described above.

As can be seen from Table 2, the transmissibility of this material to gaseous oxygen is low, and the conductance ratio is less than one. In its present form, the material is not suitable as an internal respiratory aid. These results are similar to those of Examples 4c.

In comparing the data in Table 2 of Examples 7a–c, the negative effect on oxygen transmissibility of increasing the thickness of the water-filled material is evident.

Example 8a

This example illustrates the present invention formed from a microporous hydrophobic material. In this example, a porous expanded polytetrafluoroethylene material acts as an internal respiratory aid. The microstructure of a porous expanded polytetrafluoroethylene material (ePTFE) is characterized by an irregular network of nodes connected together by fibrils. The void spaces defined by such a network are referred to in the art as the pores of the material.

To make this embodiment, a porous expanded PTFE material sold under the tradename Preclude™ Dura Substitute (W. L. Gore & Associates, Inc. (Flagstaff, Ariz.)), is first obtained. The material has an average pore size range of about 1 micron to about 10 microns and a thickness of 0.1 mm. The density of the porous material is 0.73 gm/cc.

To form an aqueous liquid-fillable component in the material, the material is subjected to a carbon dioxide laser-drilling process to create an ordered plurality of holes along the z-axis of the material (i.e., across the plane of the material). The holes thus obtained have a diameter of about 200 microns. A hole is present every 400 microns in both the x and y axes of the ePTFE sheeting material. The plurality of holes range over the entire surface area of each sample (FIG. 16). In this embodiment, only the laser-drilled macroscopic holes become wet out, while the small pores of the non-laser-drilled material are left filled with air. As such, the membrane acts an internal respiratory aid within which is incorporated an aqueous liquid-fillable component for the transport of aqueous solutes.

To selectively wet-out only the laser-drilled macroscopic holes without wetting out the microporous portion of the material, a selective wetting-out process is performed on the material. In the process, de-gassed water containing 5.0% polyvinyl alcohol wetting agent is drawn through the material with a vacuum placed on one side of the material. A reduced pressure in the vacuum chamber causes the PVA solution to flow through the larger laser-drilled holes of the material without wetting out the smaller pores of the ePTFE. The pressure within the chamber is reduced until the air within the larger laser-drilled holes is withdrawn from the material and replaced with the PVA solution. The void spaces, or pores, in the microstructure of the hydrophobic material are much smaller in size than the laser-drilled holes. As a result, water is prevented from entering the void spaces and displacing the air contained therein. Once wetted out, the material is rinsed in de-ionized water and maintained submerged in water to prevent any dewetting or drying out of the laser-drilled holes.

The aqueous liquid-fillable component of the membrane is maintained in a water-filled condition and the material tested for transmissibility to oxygen as described earlier.

As can be seen from Table 2, the transmissibility of this material to gaseous oxygen is high. The value is even higher than the value measured with no membrane in Example 1. Although the conductance ratio cannot be directly assessed, it is concluded from the oxygen transmissibility data that the conductance ratio for this material will be high and that this air-filled porous material is suitable for use in the present invention as an internal respiratory aid.

Example 8b

This example illustrates high oxygen transmissibility of a porous material having air-filled microscopic holes therein. The materials and methods of this example are the same as Example 8a above, except that the thickness of the ePTFE starting material is 300 microns. The density of the porous material is 0.54 gm/cc.

The aqueous liquid-fillable component is maintained in a water-filled condition and the material tested for transmissibility to oxygen as described earlier.

As can be seen from Table 2, the transmissibility of this material to gaseous oxygen is high. The value is even higher than the value measured with no membrane in Example 1. Although the conductance ratio cannot be directly assessed, it is concluded from the oxygen transmissibility data that the conductance ratio for this material will be high and that this air-filled porous material is suitable for use in the present invention as an internal respiratory aid.

Example 8c

This example illustrates high oxygen transmissibility of a porous material having air-filled microscopic holes therein. The materials and methods of this example are the same as Example 8a, above, except that the thickness of the ePTFE starting material is 700 microns. The density of the porous material is 0.43 gm/cc.

The aqueous liquid-fillable component is maintained in a water-filled condition, and the material is tested for transmissibility to oxygen as described earlier.

As can be seen from Table 2, the transmissibility of this material to gaseous oxygen is high. The value is even higher than the value measured with no membrane in Example 1. Although the conductance ratio cannot be directly assessed, it is concluded from the oxygen transmissibility data that the conductance ratio for this material will be high and that this air-filled porous material is suitable for use in the present invention as an internal respiratory aid.

It is further concluded that the thickness of the porous air-filled materials of Examples 8a–8c is a positive factor in oxygen permeability through the material. This increase in the transmissibility of these samples with increasing thickness is thought to be attributable to increased surface area from the sample edges.

Example 9a

This example illustrates the affect of applying a coating of silicone to the porous materials of Example 8a. In this example, an expanded polytetrafluoroethylene material (ePTFE) acting as an internal respiratory aid with an aqueous liquid-fillable component is described. The exposed surfaces of the ePTFE material are coated with a silicone polymer to seal the void spaces, or pores, in the microstructure of the material against intrusion of liquids from the laser-filled holes comprising the aqueous liquid-fillable component of the material and from the environment surrounding the material.

To make this material, a porous expanded PTFE material sold under the tradename Preclude™ Dura Substitute (W. L. Gore & Associates, Inc., Flagstaff, Ariz.) is first obtained. The material has an average pore size range of about 1 micron to about 10 microns and a thickness of 0.1 mm. The density of the porous material is 0.73 gm/cc.

Macroscopic holes are made in the material with a carbon dioxide laser-drilling process to create an ordered plurality of holes across the plane, or thickness, of the material. The holes thus obtained have a diameter of about 200 microns. A hole is present every 400 microns in both the x and y axes of the ePTF sheeting material. The plurality of holes range over the entire surface area of each sample (FIG. 16).

A coating of silicone is then applied to the laser-drilled ePTFE material to coat all of the exposed surfaces of the material. In this procedure, the ePTFE material is placed on a frame to restrain the material in a planar configuration. A vacuum is then applied to one side of the membrane, and a water-based silicone emulsion (Shin Etsu, catalog no.

KM2002-L1, Akron, Ohio) passed through the material. Reduced pressure in the vacuum chamber causes the silicone emulsion to enter and fill the the larger laser-drilled holes of the material. The pressure within the chamber is reduced until air within the larger laser-drilled holes is withdrawn from the material and replaced with the silicone emulsion. The void spaces, or pores, within the microstructure of the ePTFE material are much smaller in size than the laser-drilled holes, and these pores have a high degree of tortuosity. Fine, interstitial pores of the ePTFE are not wetted by the water-based emulsion when it contacts a hydrophobic ePTFE. Rather, the silicone emulsion wets out the exposed surfaces of the material and does not substantially penetrate into the microporous void spaces of the material. As a result, the silicone coating forms a continuous layer over the exposed perimeter surfaces of the of the ePTFE material without coating the interior surfaces of the material defining the pores or void spaces. The silicone coating ensures that the gas phase within the pores or void spaces of the material remains entrapped therein over time.

Reduced pressure continues to draw the silicone emulsion through the larger laser-drilled holes to the opposite side of the material. In this example, the silicone emulsion is applied a total of three times. Any excess emulsion is removed from the opposite side of the material by flowing de-ionized water over the material.

The ePTFE-silicone composite material is then dried and cured at 120° C. for about 5 minutes. The material is then turned over, and the silicone emulsion is applied to the material three more times. The silicone material is tested for pinholes by applying alcohol, such as ethanol, to the material and inspecting the material for any signs of liquid penetrating and/or collecting underneath the silicone coating. If pinholes are discovered in the silicone coating, another coating of silicone is applied to the material, preferably to both sides of the material. The material is then re-tested with alcohol for pinholes.

In this example, the laser-drilled holes are rendered more water-wettable with a coating of the hydrophilic polymer, poly(vinyl alcohol) (PVA). In the process, de-gassed water containing 5.0% PVA wetting agent is drawn through the material with a vacuum placed on one side of the material. The vacuum is increased until the laser-drilled holes are filled with the PVA solution. Bulk PVA material is removed with additional vacuum pressure and rinsing. When wetted out, the material is maintained in an aqueous environment to prevent any dewetting or drying out of the laser-drilled holes.

The material is tested for transmissibility to oxygen, as described earlier. Prior to testing the samples for transmissibility, the samples are rinsed with degassed de-ionized water under pressure to ensure that any possible air bubbles within the laser-drilled holes are replaced with water.

As can be seen from Table 2, the transmissibility of this material to gaseous oxygen is high, and the conductance ratio is greater than one. It is concluded from the conductance ratio that this ePTFE material with a silicone coating is suitable for use in the present invention as an internal respiratory aid.

Example 9b

This example illustrates the affect of applying a coating of silicone to the porous materials of Example 8b. The materials and methods of this example are the same as Example 9a above, except that the thickness of the ePTFE starting material is 0.3 mm. The density of the porous material is 0.54 gm/cc.

The material is tested for transmissibility to oxygen as described earlier. As can be seen from Table 2, the transmissibility of this material to gaseous oxygen is high, and the conductance ratio is greater than one. It is concluded from the conductance ratio that this ePTFE material with a silicone coating is suitable for use in the present invention as an internal respiratory aid. Example 9c This example illustrates the affect of applying a coating of silicone to the porous materials of Example 8c. The materials and methods of this example are the same as Example 9a above, except that the thickness of the ePTFE starting material is 0.7 mm. The density of the porous material is 0.43 gm/cc.

The material is tested for transmissibility to oxygen as described above. As can be seen from Table 2, the transmissibility of this material to gaseous oxygen is high, and the conductance ratio is greater than one. It is concluded from the conductance ratio that this ePTFE material with a silicone coating is suitable for use in the present invention as an internal respiratory aid.

Example 10a

In this example, dual porosity polyethylene materials are made, treated, and tested. Ultra-high-molecular-weight (UHMW) polyethylene polymer (i.e., 3 million molecular weight, Hostalen GUR#4120, from Hoechst Celanese) is blended with mineral oil (Witco's Kaydol 350 white mineral oil) and NaCl salt (sieved to particle size 20 to 70 microns). Upon extraction of the oil and the NaCl, a porous polyethylene material having two ranges of interconnected porosity is formed.

By blending the polyethylene (PE) with the oil at a high temperature, a homogeneous blend is formed. Quenching of the blend in a water bath causes the homogeneous system to phase separate into a PE rich phase (essentially pure PE) and an oil rich phase. When the oil rich phase is extracted, it leaves behind empty spaces that form interconnected micropores in the PE material. This process is described in the literature and used commercially for making microporous materials having pores in the range from 0.1 to 10 microns (e.g., Castro, U.S. Pat. No. 4,247,498; Vitzthum et al., U.S. Pat. No. 4,490,431; and Morzinski, U.S. Pat. No. 4,726,989, each of which is incorporated herein by reference, and Strathmann, H. in: D. R. Lloyd (Ed.), *Materials Science of Synthetic Membranes*, ACS Symposium Series 269, Washington, D.C., 1985).

To form a second set of pores in the PE material, the NaCl salt is removed by dissolution in hot tap water. Large pores are formed in the PE material upon removal of the salt. The resulting material possesses two sets of pores. One set of pores is interconnected with an average size in the 0.1 to 10 micron range. The second set of pores has an average size in the 20 to 70 micron range.

An internal respiratory aid may be constructed from this dual porosity material by leaving the smaller pores filled with air. The larger pores may be filled with water to act as an aqueous liquid-fillable component. Surfactant and water can be aspirated through the material, wetting out the large pores while leaving the small pores air-filled. However, in this example, all air is removed from both sets of pores to collect data from a sample that would not be defined as an internal respiratory aid.

The materials are blended in the following proportions by weight: PE=3%, Oil=17%, Salt=80% in a 42:1 L/D twin screw extruder. Each barrel temperature is set at 175 ° C. with a screw speed set to 100 RPM. All feed streams are at room temperature and the extruded strands are quenched in water. The blend is extruded as 3 millimeter beading.

Once the extrudate has cooled, it is processed into flat sheeting. A beading sample is cut and placed into a press heated to 175° C. Shims are placed in the press to control the final material thickness between 0.060" and 0.075". This sample is allowed to cool.

The processing oil is then extracted by submerging the sample in a container of hexane for several hours. The hexane is then removed and fresh hexane added and the sample extracted for a few more hours. This process is repeated one more time and the sample allowed to dry overnight.

The salt is extracted by submerging the sample in a container of hot tap water which has 0. 1% of the surfactant poly(vinyl alcohol) (PVA) added to it to facilitate wetting of the hydrophobic PE. The water is exchanged two times with fresh hot water having 0.1% PVA. The sample is extracted for about 1 hour in each exchange. The final sample thickness measured about 0.050", indicating some shrinkage of the PE due to the extraction processes.

A one-quarter inch disk is cut from the PE sample using a hole-punch. This article is submerged in isopropyl alcohol and placed under a vacuum for several minutes until the alcohol boils. The purpose of this process is to remove all air from both sets of pores in the PE. Upon removal of vacuum, the sample is first placed in de-ionized water, then placed under vacuum for several minutes, and boiled again. The alcohol is allowed to exchange with the water in this process. Thickness of this article is 0.051".

As can be seen from Table 2, the transmissibility of this material to gaseous oxygen is low, and the conductance ratio is less than one. In its present form, the material is not suitable as an internal respiratory aid.

Example 10b

In this example, the material of Example 10a is made into an embodiment of an internal respiratory aid of the present invention. In this example, air is maintained in the small pores, while the larger pores are filled with water. In order to selectively wet out the larger pores, a 5.0% solution of PVA wetting agent is aspirated through the porous PE material. As the solution is drawn through the material, only the surfaces of the large pores are wet out. Though these larger pores are wet out with PVA during the NaCl extraction, a 5.0% PVA solution is applied to the material to ensure the large pores, comprising an aqueous liquid-fillable component of the material, will readily wet out with water. The sample is then aspirated with de-ionized water to wet out and fill the large pores with water.

The smaller pores of the porous PE material are hydrophobic and will not spontaneously wet out with either the PVA solution treatment step or the subsequent water purge step. When a vacuum is drawn on the sample, these liquids will preferentially flow or 'channel' through the paths of least resistance (i.e., those being the largest pores, thereby leaving the small pores air-filled). A one-quarter inch disk is cut from the sample using a hole-punch and tested for oxygen transmissibility. It measured 0.049" thick.

As can be seen from Table 2, the transmissibility of this material to gaseous oxygen is high. The value is even higher than the value measured with no membrane in Example 1. Although the conductance ratio cannot be directly assessed, it is concluded from the oxygen transmissibility data that the conductance ratio for this material will be high and that this air-filled porous material is suitable for use in the present invention as an internal respiratory aid.

Example 11

In this example, an expanded polytetrafluoroethylene material (ePTFE) acting as an internal respiratory aid with an aqueous liquid-fillable component is described. The aqueous liquid-fillable component comprises laser-drilled holes within the material that are filled with hydrogel (FIG. 20).

To make this material, a porous expanded PTFE material sold under the tradename Preclude™ Dura Substitute (W. L. Gore & Associates, Inc. (Flagstaff, Ariz.)) may be used. The material has an average pore size range of about 1 micron to about 10 microns. It ranges in thickness, examples being materials with a thickness of 0.1 mm (density =0.73 gm/cc), 0.3 mm (density =0.54 gm/cc), or 0.7 mm (density=0.43 gm/cc).

Macroscopic holes are made in the material with a carbon dioxide laser-drilling process to create an ordered plurality of holes across the plane, or thickness, of the material. The holes thus obtained have a diameter of about 200 microns. A hole is present every 400 microns in both the x and y axes of the ePTFE sheeting material. The plurality of holes range over the entire surface area of each sample (FIG. 16).

Hydrogel in the form of partially hydrolyzed polyacrylonitrile is then applied to the laser-drilled ePTFE material to coat and fill essentially all of the exposed surfaces of the material. In this procedure, the ePTFE material is placed on a frame with a vacuum applied to one side of the membrane and a solution of partially hydrolyzed polyacrylonitrile (Kingstone International, Inc., Dayton, N.J.) is passed through the material (10% HN86 in a 55% aqueous NaSCN solution). Reduced pressure in the vacuum chamber causes the partially hydrolyzed polyacrylonitrile solution to controllably enter and fill the larger laser-drilled holes of the material. Pressure within the chamber is reduced until air within the larger laser-drilled holes is withdrawn from the material and replaced with the partially hydrolyzed polyacrylonitrile solution. The void space, or pores, in the microstructure of the material are much smaller in size than the laser-drilled holes. As a result, the hydrogel wets out the exposed surfaces of the membrane, but does not substantially penetrate into the microporous void spaces of the membrane due to the small size and high degree of tortuosity of the microscopic pores in the ePTFE starting material. Rather, the hydrogel forms a continuous layer over the microscopic sized pores of the ePTFE material and fills the macroscopic laser-drilled holes. The hydrogel coating ensures that the air within the void space, or pores, of the material remains entrapped therein over time. Excess hydrogel is knifed or scrapped off of the top and bottom surface, leaving a thin residual hydrogel layer enclosing the ePTIE material. The partially-hydrolyzed polyacrylonitrile must be coagulated in place for it to become stabilized. This hydrogel material is coagulated by rinsing the hydrogel-coated material in de-ionized water.

Example 12a

In this example, a porous silicone material is made into an embodiment of the present invention. To render a silicone material porous, a two-part silicone formulation (Applied Silicone Corp., Ventura, Calif.) is admixed with a filler comprised of silver carbonate ($Ag_2CO_3$) in the form of a fine powder. The silver carbonate is admixed with the silicone solution in a ratio of about 2:1 by volume (silver carbonate to silicone solution). This admixture is then formed into a membrane having a thickness of about 0.010 inches (250 microns) as a sheet of poly(dimethyl siloxane).

The filler is dissolved in a suitable solvent to create a plethora of interconnected microporous void spaces. These void spaces remain filled with air, rendering the material highly permeable to oxygen, allowing it to act as an internal respiratory aid in the present invention. The retained air is not displaced by water when the material is placed into water.

The microporous silicone material thus obtained is laser-drilled according to the process described in Examples 7a–c and 8a–c above, to provide the material with an aqueous liquid-fillable component. The air in the laser-drilled holes is replaced with water according to the methods described in Example 8a.

Example 12b

In this example, samples from Example 12a above are further coated with a silicone barrier to ensure the long-term presence of entrapped air within the microporous void spaces of the material. The same methods utilized in Examples 9a–c above are used to coat the material with silicone. The material acts as an internal respiratory aid in the present invention.

Example 13a

In this example, an embodiment of the present invention is made from a microporous film of polysulfone. To render a film of polysulfone porous, polysulfone melt is admixed with filler comprised of silver carbonate ($Ag_2CO_3$) in the form of a fine powder. The silver carbonate is admixed with the polysulfone melt in a ratio of about 2:1 by volume (silver carbonate to polysulfone). This admixture is then formed into a membrane having a thickness of about 0.010 inches (250 microns).

The filler is dissolved in a suitable solvent to create a plethora of interconnected microporous void spaces. These void spaces remain filled with air, and render the material highly permeable to oxygen, allowing it to act as an internal respiratory aid in the present invention. The retained air is not displaced by water when the material is placed into water.

The microporous silicone material thus obtained is laser-drilled according to the process described in Examples 7a–c and 8a–c above, to provide the material with an aqueous liquid-fillable component. The air in the laser-drilled holes is replaced with water according to the methods described in Example 8a.

Example 13b

In this example, samples from Example 13a above are further coated with a silicone barrier to ensure the long-term presence of entrapped air within the microporous void spaces of the material. The same methods utilized in Examples 9a–c above are used to coat the material with silicone. The material acts as an internal respiratory aid in the present invention.

Example 14

In this example, a material of the present invention is made in the form of a woven fabric. Porous expanded polytetrafluoroethylene is made according to the teachings of U.S. Pat. Nos. 3,953,566 and 4,187,390, both issued to Gore, each of which is incorporated herein by reference. A microporous fiber of expanded polytetrafluoroethylene (ePTFE) of about 50 microns in diameter fiber is woven into a textile having spaces of about 200 microns between adjacent fibers in the weave. This textile construct measures about 0.010" (i.e., 250 microns) in thickness.

The fibers of this woven material are then coated with silicone according to the processes described in Example 21, below. The silicone-coated fibers comprise the internal respiratory aid and the spaces in between the silicone-coated fibers comprise an aqueous liquid-fillable component (FIG. 25B).

Example 15

Figure 26A:
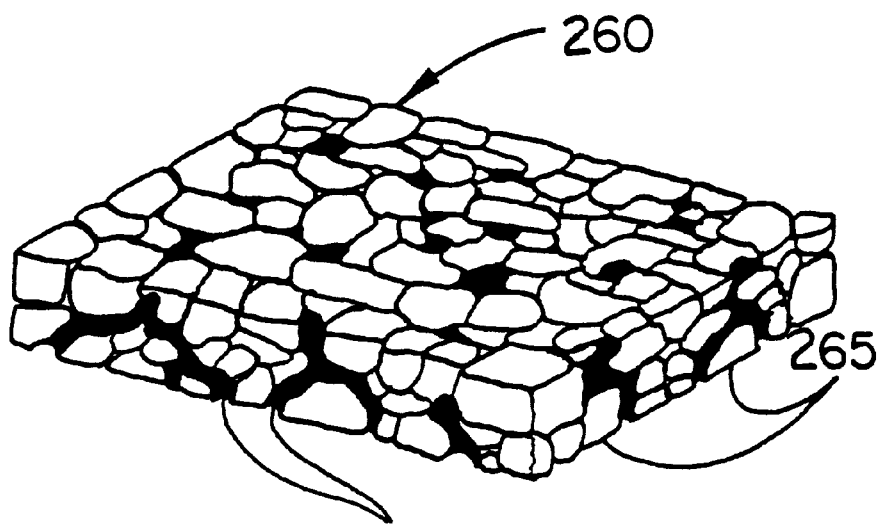
Figure 26B:
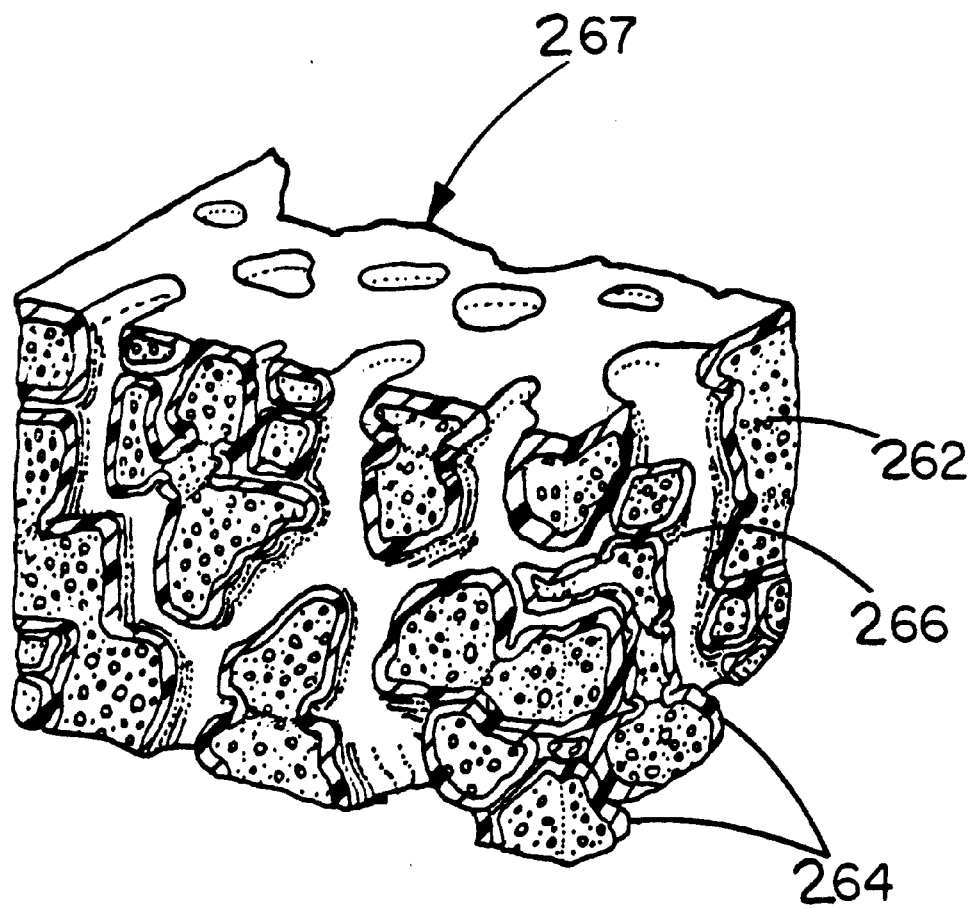
FIG. 26B is an illustration of an embodiment of the present invention (267), wherein the internal respiratory aid is comprised of fused porous particles (262). The component comprised of channels that become aqueous liquid-filled during use comprises the void spaces, or pores, (266) located in between the fused porous particles that have been coated with a material (264) that is permeable to gases.
Figure 26C:
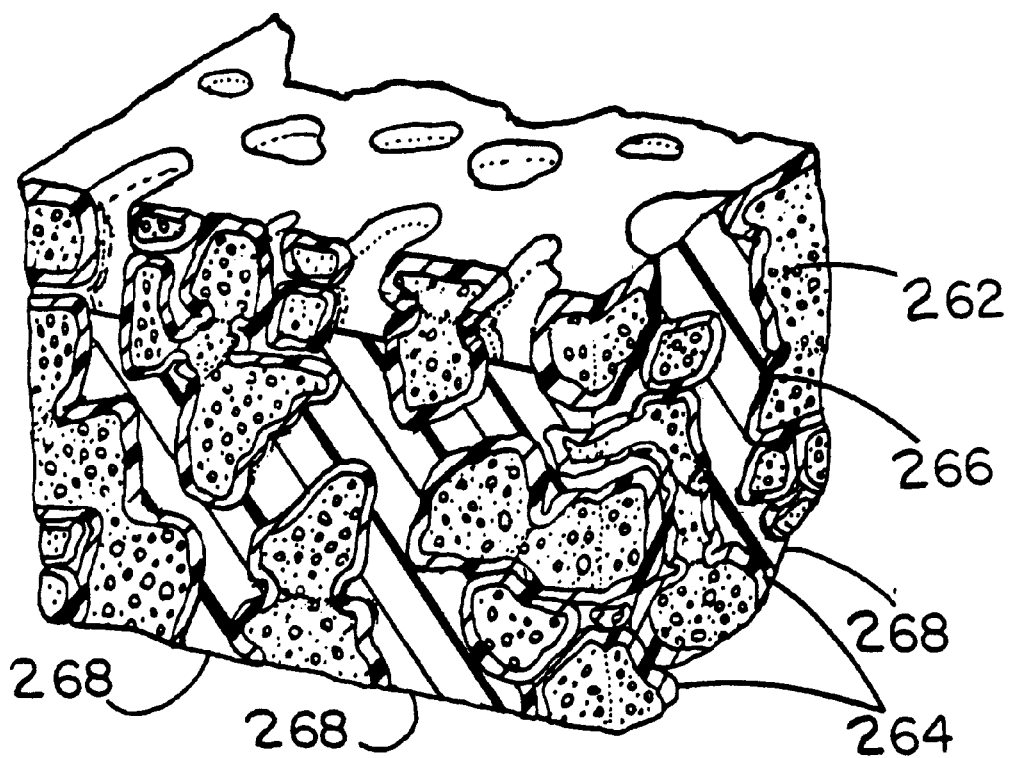
FIG. 26C is an illustration of a water permeable material (268) placed in all or part of the components comprised of channels that become aqueous liquid-filled during use of FIG. 26B.

In this example, a material of the present invention is made from a porous polytetrafluoroethylene material comprised of fused granular particles of polytetrafluoroethylene (PTFE). Granulated particles of PTFE of ~100 microns diameter are suspended in liquid and coated onto a flat smooth plate. These granules contain 50% by weight silica bead filler of 10 microns in diameter. After drying, the PTFE coated plate is baked at 380° C. for thirty minutes and cooled. A membrane results which is removed from the plate and placed in a 25% hydrofluoric acid (HF) solution in isopropanol with 5% (v/v) water to etch out the silica particles. Small pores are created upon the removal of the silica filler that will remain filled with air, rendering the material highly permeable to oxygen, and thereby acting as an internal respiratory aid. Larger pores resulting from the spaces between the granules may be filled with water for transport of aqueous solutes. The membrane may be cut into samples that are then silicone coated according to previously described processing (FIGS. 26A and 26B).

Example 16

In this example, the present invention is in the form of a tube made with a porous expanded polytetrafluoroethylene (ePTFE) starting material. The dimensions of the tubular samples are 0.040" I.D. and 0.060" O.D. (1 mm I.D.; 1.5 mm O.D.) with a length of 3.7 cm. This tubing is made by taking ePTFE film and wrapping it around a length of silver plated copper (SPC) wire of 0.040" diameter (1 mm) followed by a heating, or sintering, step at 380° C. for about five minutes.

Prior to removing the ePTFE tube from the wire, macroporous laser-drilled holes, as described in Example 7a, are placed at regular intervals through the ePTFE material of the tube. The tube thus formed is removed from the SPC wire by pulling on the wire to induce sufficient strain on the wire to cause it to decrease in diameter and release the overlying ePTFE tube.

The tube is then coated with silicone. The resultant tube acts as an internal respiratory aid by virtue of its silicone-sealed air-filled pores defined by the nodes and fibrils of the material. An aqueous liquid-fillable component of the tube is comprised of the macroscopic laser-drilled holes in the silicone coated ePTFE material. This material may be placed into a plasma reactor to chemically render the silicone-coated surfaces of the ePTFE material hydrophilic.

Example 17

In this example, devices composed of an internal respiratory aid with an aqueous liquid-fillable component are made, with cells loaded and contained in the aqueous liquid-fillable component. These devices are then implanted into rats. Histological examination and metabolic performance analysis of devices following the first week in vivo indicate that the cells thrive better in a device made with a material of the present invention than in a control device.

Example 18

This example demonstrates another embodiment of the present invention in which an open-celled foam made from a gas-permeable material acts as an internal respiratory aid of the present invention. The foam serves two functions in this material. The foam provides physical reinforcement to the material, giving it structural integrity and strength. The foam also permits high gas transport via internal air passageways throughout the foam article. Silicone acts to bind the material together and to delimit an aqueous liquid-fillable component. The silicone may also coat the internal air passageways, preventing the ingress of liquids therein.

To make a plurality of internal respiratory aid elements, a few thousand feet of spooled microporous ePTFE fiber 0.0048" outer diameter is obtained from W. L. Gore & Associates, Inc. (Flagstaff, Ariz.). This fiber is processed through a continuous silicone coating machine as follows. The fiber is threaded through an emersion coating machine from a payoff spool, over a series of pulleys such that the fiber is transported through a bath of silicone and then immediately into a curing oven set at 85° C. This is followed by subsequent passes through the silicone bath and oven via multiple pulleys until thirteen coatings of silicone are deposited on the fiber. The oven is 2 feet long and the rate at which the fiber moved through the oven is between 2 and 3 feet per minute. The silicone bath is a solution of 15%, by weight, RTV 863 (available from General Electric Silicones of Waterford, N.Y.) diluted in Isopar-C mineral oil. The coated fiber is then spooled onto a take-up spool. The diameter of the fiber before coating is 0.0048". The coating added 0.0020" to the diameter of the fiber for a final diameter of 0.0068". The silicone fiber is cut into pieces for subsequent use in this example as the elements of an internal respiratory aid.

Figure 28A:
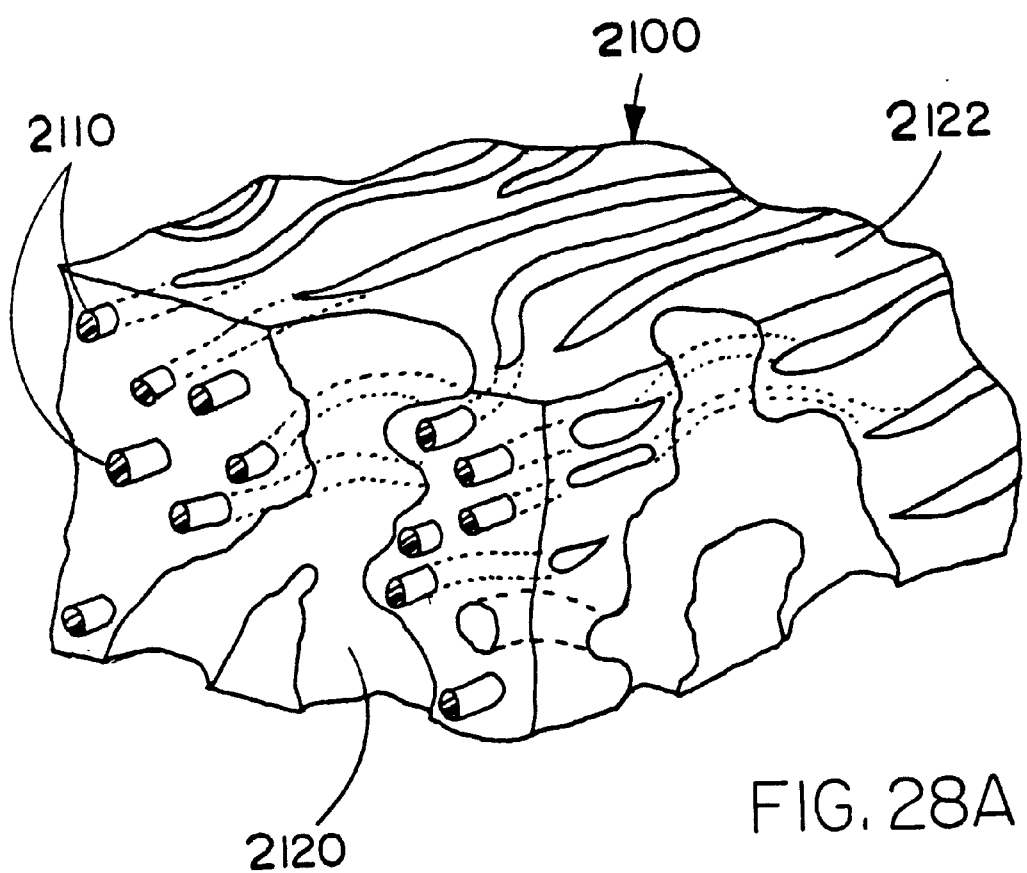
FIG. 28A illustrates an embodiment of the present invention (2100) wherein the internal respiratory aid is comprised of gas conduits (2110). Voids (2120) in a gas-permeable material (2122) comprise the component that becomes aqueous liquid-filled during use.
Figure 29A:
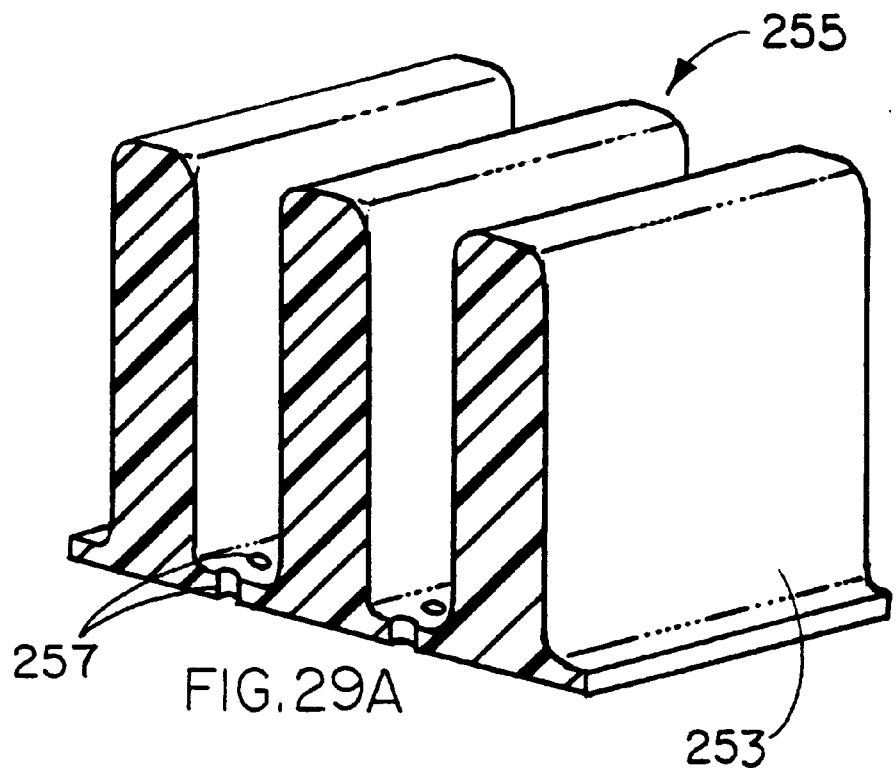
FIG. 29A illustrates an embodiment of the present invention (255) wherein the internal respiratory aid is in the form of fins (253) and wherein the component comprised of channels that become aqueous liquid-filled during use (257) comprise holes in the material.
Figure 29B:
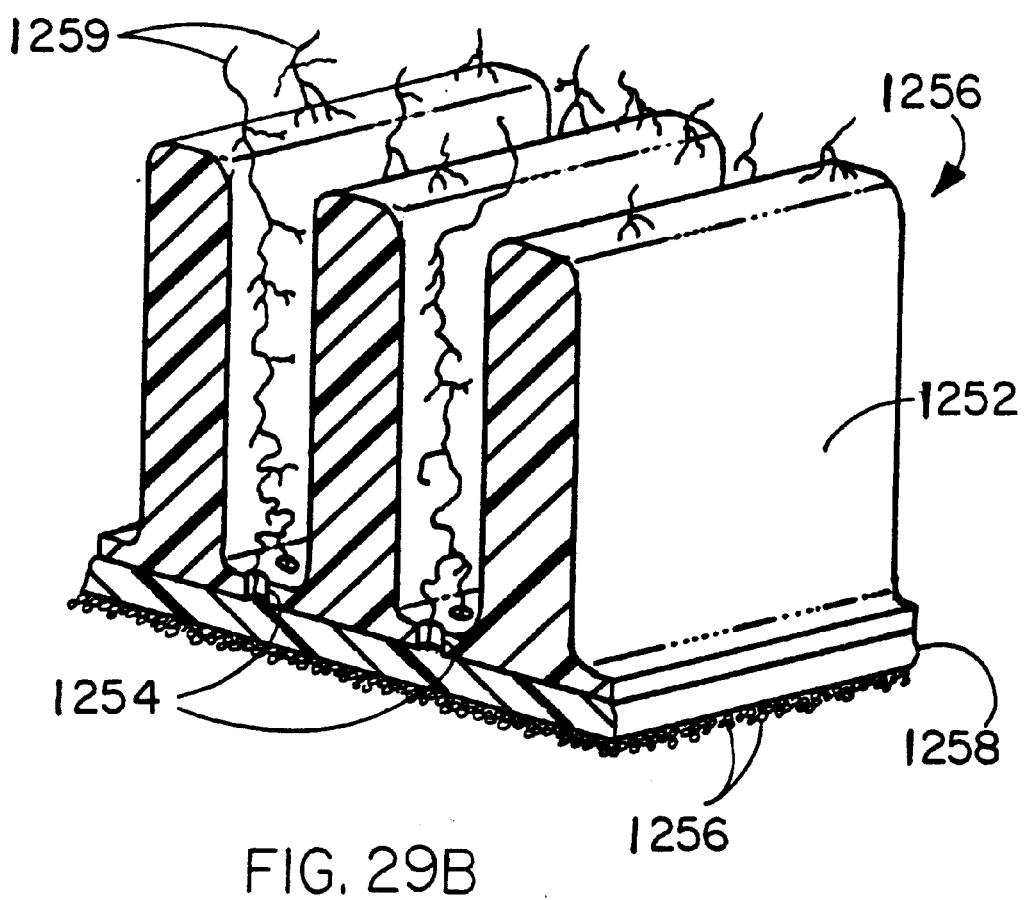
FIG. 29B illustrates an embodiment of the present invention (1256) wherein the internal respiratory aid is in the form of fins (1252) and wherein the component comprised of channels that become aqueous liquid-filled during use (1254) comprise holes in the material. In addition, a cell-impermeable material (1258) is used to separate a population of cells (1256) from migrating into or out of the component comprised of channels that become aqueous liquid-filled during use and is used to separate host tissue, such as capillaries, from migrating across the cell-impermeable material.
Figure 30A:
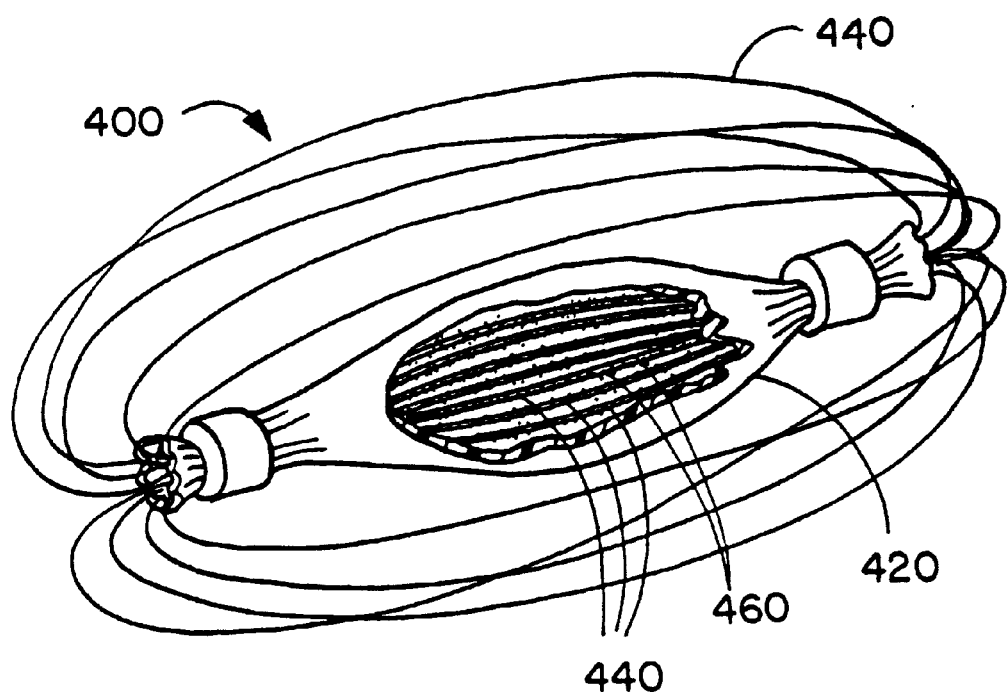
FIG. 30A illustrates an embodiment of the present invention in the form of a cell-containment device (400). The device has a permeable membrane (420) enclosing an internal respiratory aid in the form of gas-conducting fibers (440) and cells (460). The gas-conducting fibers (440) extend from inside of the device to the outside of the device (440).
Figure 30B:
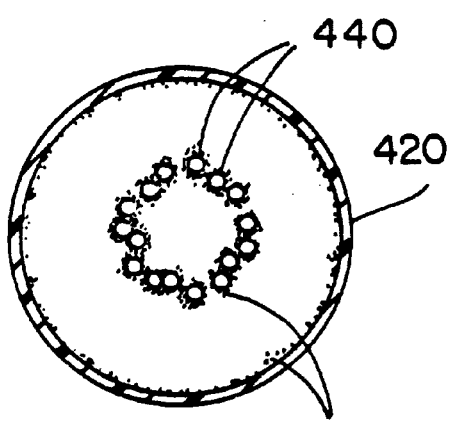
FIG. 30B illustrates a cross-sectional view of the embodiment of FIG. 30A.
Figure 30C:
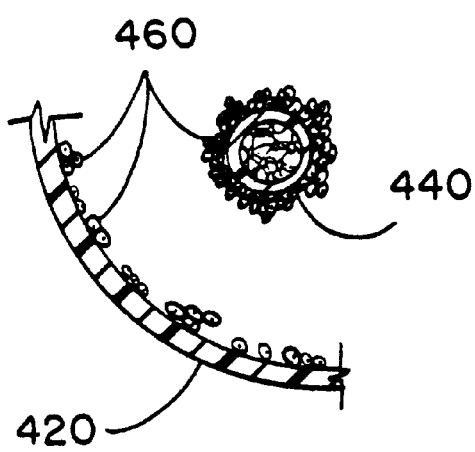
FIG. 30C is an enlarged view of FIG. 30B illustrating cells (460) living in proximity to the permeable membrane (420) and the gas-conducting fibers (440).
Figure 32A:
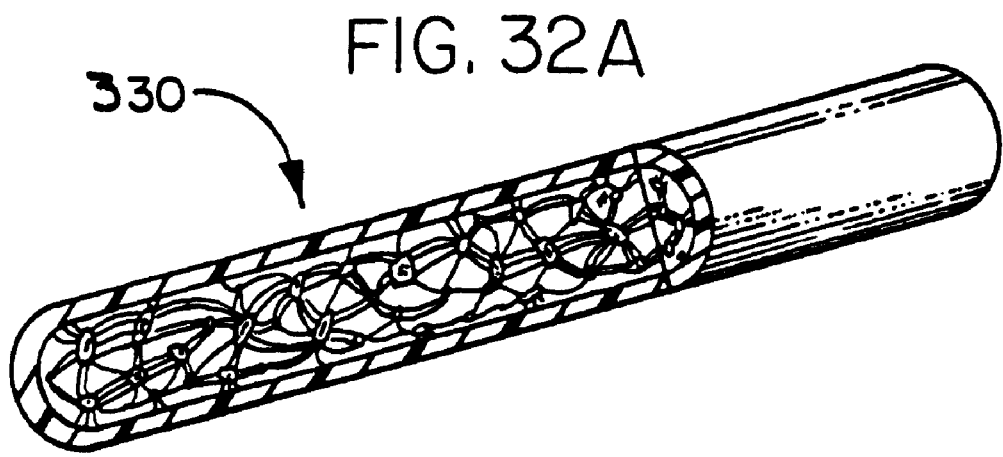
FIG. 32A is a view with a cut away portion illustrating an embodiment of the present invention (330) having interconnected gas-filled passageways that are delimited by a porous material comprised of nodes and fibrils also shows a gas-permeable material on the outer, or perimeter, surfaces of the porous material sealing the gas-filled passageways present inside the invention against liquid intrusion.
Figure 32B:
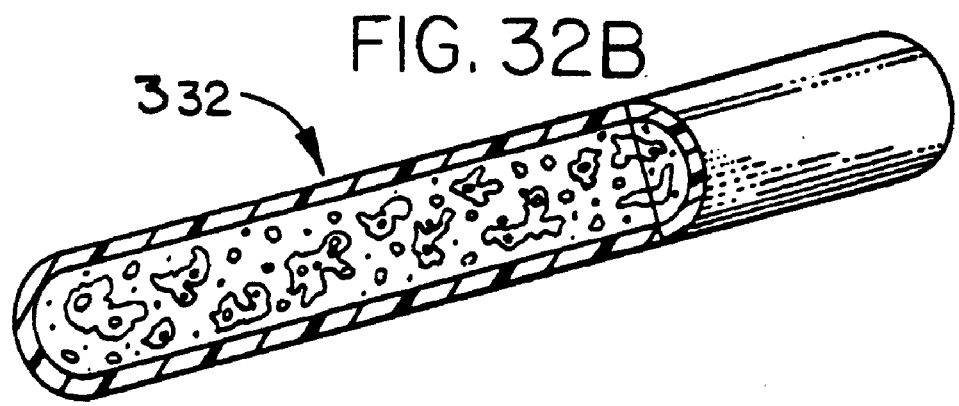
FIG. 32B is a view with a cut away portion illustrating an embodiment of the present invention (332) having interconnected gas-filled passageways that are delimited by a porous material. A gas-permeable material on the outer, or perimeter, surfaces of the porous material sealing the gas-filled passageways present inside the invention against liquid intrusion is also shown.
Figure 32C:
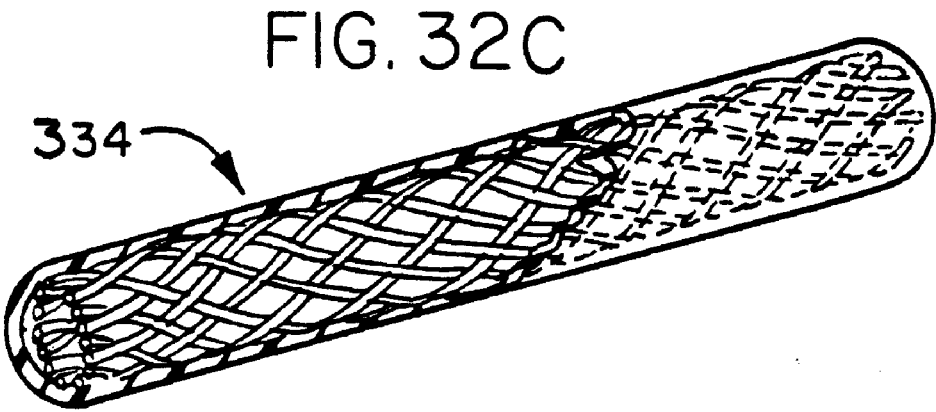
FIG. 32C is a view with a cut away portion illustrating an embodiment of the present invention (334) comprised of a multiplicity of interwoven fibers having interconnected gas-filled passageways therein. A gas-permeable material surrounding the interwoven fibers, sealing the gas-filled passageways present inside the invention against liquid intrusion is also shown.

To make a material of the present invention, a mold is used in which a bed of salt is prepared that incorporates a network of the above-described fibers, or the internal respiratory aid. Fibers are incorporated either in a random or non-random fashion, distributed either uniformly or non-uniformly, throughout the salt bed (FIG. 28A). While NaCl salt is convenient and inexpensive, any appropriate porogen material could be used in the present invention. These agents include, but are not limited to, blowing agents or dissolvable plastics.

Once the fibers are in place in the salt bed, a gas-permeable material, such as liquid silicone, is made to flow into the salt bed by applying a pressure difference across the bed. Once the silicone is made to fill the available void spaces between salt crystals within the bed, the silicone is then cured.

The silicone filled, cured bed of material is removed from the mold and the salt leached out in an appropriate solution, such as hot water. Once the porogen is removed, void spaces are left that are available to be filled with an aqueous phase. These wettable void spaces comprise a plurality of aqueous liquid-fillable component elements of the present invention. Optionally, living cells can be placed within the aqueous liquid-fillable component.

Example 19

An alternative method of making the material of Example 18 is to mix a porogen and silicone together to form a paste-like material. This material is then forced into a network of fibers and then cured. The silicone-filled, cured bed of material is removed from the mold and the salt leached out in an appropriate solution, such as hot water, to form a plurality of aqueous liquid-fillable component elements.

Example 20

An alternative method of making the material of Example 18 is to pre-treat a network of fibers with a flush, or rinse, of silicone material. This is followed by a flush and impregnation of the network with a paste of a porogen-filled silicone material. The silicone material is then cured. The silicone-filled, cured bed of material is removed from the mold and the salt leached out in an appropriate solution, such as hot water, leaving wettable void spaces that comprise a plurality aqueous liquid-fillable component elements. The pre-treatment is helpful in ensuring a continuous silicone coating of the fibers as the internal respiratory aid in the final product.

Example 21

In this example, an expanded polytetrafluoroethylene material (ePTFE) acting as an internal respiratory aid with an aqueous liquid-fillable component is described. The aqueous liquid-fillable component is made in the ePTFE material by selectively treating the material with a hydrophilic polymer to selectively wet out portions of the material. The remaining portions of the ePTFE material that are not selectively-treated to wet out act as an internal respiratory aid by virtue of air-filled void spaces within the ePTFE.

Porous expanded polytetrafluoroethylene is made according to the teachings of U.S. Pat. Nos. 3,953,566 and 4,187,390, both issued to Gore, each of which is incorporated herein by reference. The various thicknesses of the materials made according to these teachings are 127, 254, and 368 microns (i.e., 0.005, 0.01, and 0.0145 inches, respectively). The densities of these materials are 0.706 gm/cc, 0.789 gm/cc, and 0.769 gm/cc, respectively. The density of non-porous polytetrafluoroethylene is about 2.2 gm/cc. The internodal distance, or spacing, for the 127 micron and 254 micron thick materials is about 0.5 microns to about 5.0 microns. The membrane having a thickness of 368 microns, the internodal distance, or spacing, is about 2 to about 10 microns.

The hydrophilic polymer poly(vinyl alcohol) (PVA) is used to selectively treat portions of the material, which become wet out with water when the material is placed in an aqueous environment. These selectively treated portions of the ePTFE material serve as an aqueous liquid-fillable component of the final product. The remaining untreated portions of the material do not wet out, and render the material highly permeable to oxygen to act as an internal respiratory aid.

For use in the construction of these selectively treated ePTFE materials, a stamp was made by laser-etching a block of solid PTFE to have a regular surface pattern of approximately 25% raised squares with 0.5-mm sides. The ePTFE material was placed over the stamp, and a solution of 70% ethyl alcohol was poured on top. The ethyl alcohol was selectively forced into the material overlying the raised portions of the stamp surface only by application of manual pressure. The material was then submerged in 1% USP grade PVA at 80° C. for 45 minutes, effecting exchange of the alcohol with PVA. The material was rinsed twice in deionized water, five minutes each, and then placed in a solution of 5% EM grade glutaraldehyde with 1% USP grade hydrochloric acid for 30 min at 80° C., to effect cross-linking of the PVA. The material was then rinsed twice in deionized water, once in acetone, and air-dried. The resulting material, in this example, has approximately 25% of its ePTFE surface area selectively coated with the PVA, in the pattern transferred from the stamp. These selectively coated areas alone wet out and fill with water when the material is submerged, and thus serve as an aqueous liquid-fillable component. The portions of the ePTFE material surrounding each PVA coated area do not wet out with water, and thus render the material highly permeable to gases to act as an internal respiratory aid.

For comparison against these selectively-treated ePTFE materials, untreated and fully-treated ePTFE materials are used. The latter is prepared by first submerging untreated material in 100% ethyl alcohol and then following the procedures described above for exchanging the alcohol with PVA, and cross-linking with glutaraldehyde. The fully treated material fully wets out when placed in water, and thus will not function as an internal respiratory aid. The untreated material remains completely air-filled when placed in water, and thus is an internal respiratory aid that does not contains an aqueous liquid-fillable component.

Using the oxygen transmissibility apparatus described earlier, measurements were performed to determine the oxygen transmissibility of all materials described above, as a function of thickness. The data are reported in Table 2.1 below.

TABLE 2.1

| Material Thickness ($\square$m) | Fully-treated Transmissibility (cm/sec) | Untreated Transmissibility (cm/sec) | Selectively-treated Transmissibility (cm/sec) |
|---|---|---|---|
| 127 | $2.4 \times 10^{-4}$ | $4.0 \times 10^{-4}$ | $4.8 \times 10^{-4}$ |
| 254 | $1.1 \times 10^{-4}$ | $4.3 \times 10^{-4}$ | $3.0 \times 10^{-4}$ |
| 368 | $8.8 \times 10^{-5}$ | $4.3 \times 10^{-4}$ | $4.3 \times 10^{-4}$ |

The transmissibility to oxygen for the fully treated material decreases as its thickness increases. This is as expected, since by increasing the material thickness, one essentially imposes a larger film of static water across which oxygen must transfer in these fully water-filled materials. The slope of the inverse transmissibility versus thickness represents the reciprocal of the permeability for the material, from which the permeability of the material is evaluated as approximately $3.35 \times 10^{-6}$ cm$^2$/sec. The conductance ratio of the material (equivalent to the permeability ratio in this example) is 0.14. The value appears reasonable considering that the material is essentially filled with water, with its porosity and tortuosity tending to reduce the overall permeability relative to that of water. Extrapolating the plot of inverse transmissibility back to zero thickness, one obtains an intercept the inverse of which is representative of the mass transfer coefficients associated with the fluid boundary layers above and beneath the material on the measurement apparatus, a value of $1.2 \times 10^{-3}$ cm/sec.

Considering the data for the untreated materials, one observes no significant change in the transmissibility to oxygen as a function of material thickness. This material is air-filled, presenting minimal resistance to oxygen transport such that any effect of increasing material thickness is undetectable in the measurement apparatus.

The selectively-treated material behaves similarly to the untreated material in that there is no significant effect of material thickness on oxygen transmissibility. The average value for transmissibility in this material is $4.0 \times 10^{-4}$ cm/sec, comparable to that for the untreated material, $4.2 \times 10^{-4}$ cm/sec. Each average value is again representative of the mass transfer coefficient associated with the fluid boundary layers in the apparatus. In this case, thin cigarette paper is used to restrain the sample membrane to the electrode. This paper increases the resistance somewhat and explains the difference from the value of $1.2 \times 10^{-3}$ cm/sec, listed previously.

The indication from this example is that by incorporating regions within materials that are selectively water-filled, as by selective treatment with PVA, one does not affect the overall transmissibility of the material to oxygen. In effect, the overall mass transfer resistance is controlled by that of the surrounding fluid boundary layers, and shows no effect of increasing material thickness, much like the untreated wholly air-filled material. Unlike the untreated material however, the selectively-treated material has available an aqueous liquid-fillable component, providing, essential transport of aqueous solutes.

Examples of Elongated Structures as Internal Respiratory Aids

TABLE 3

| Article | Type | Coat | Length (cm) | Effect | Curve |
|---|---|---|---|---|---|
| 22 | None | N/A | N/A | 0 | 1 |
| 23a | Wire | N/A | 5.5 | – | 2 |
| 23b | Wire | Silastic Tubing (170 µm wall) | 5.5 | 0 | 3 |
| 23c | Monofilament PP: Ethicon 4-0 | N/A | 75 | – | 4 |
| 23d | Ultex6 | N/A | 75 | – | 5 |
| 23e | Silicone–imbibed 40 denier Dupont multifilament yarn | Silicone–imbibed | 75 | 0 | 6 |
| 24 | ePTFE Suture: CV-0 | N/A | 12 | + | 7 |
| 25a | ePTFE Suture: CV-0 | Silastic Tubing (170 µm wall) | 4.5 | + | 8 |
| 25b | ePTFE Suture: CV-0 | Silicone coat | 5.8 | + | 9 |
| 26 | ePTFE fiber: 0.0048" diameter | Silicone coat | 37.5 | + | 10 |
| 27 | Deknatel White Braided 3-0 Suture | Silicone coat | 10.5 | + | 11 |
| 28a | ePTFE Suture: CV-0 | Hypan HN86 | 5.3 | 0 | 12 |
| 28b | ePTFE Suture: CV-0 | Hypan HN86 with coat exposed at Electrode | 5.3 | + | 13 |
| 29 | ePTFE Suture: CV-0 | Silicone coat | 5.8 | + | 14 |
| 30 | ePTFE Suture: CV-0 | Silicone coat | Various | + | 15–18 |

Table 3 above outlines the results of measurements as outlined in Examples 22–30, illustrating the effect of various articles with elongated structures to collect oxygen from the surrounding medium. Permeometry measurements are qualitative, but demonstrate how different materials are characterized as either obstructing (negative effect in Table 3), facilitating (positive effect), or having no effect. In the first example, a transmissibility measurement is performed with no membrane to act as a control against which to compare the subsequent articles. Construction of each articles is described in the examples, and the results of permeometry are illustrated in the indicated curves, as displayed in the text.

Example 22

Data from this example establishes a baseline, or reference point, for use as a control in subsequent examples. The data are obtained with the Createch 201T Permeometer described above. No membrane or fiber is used in this example. The data are presented in the graph below and summarized in Table 3, above.

To perform the test, 10.0 ml of 10 mM phosphate buffer, pH 7.2, that is equilibrated with room air is added to the reservoir portion of the polarographic cell. Since introduction of fluid causes undesirable mixing of the test solution, the solution is allowed to stand for approximately 5 minutes prior to measurement for the liquid to come to rest.

Figure 50:
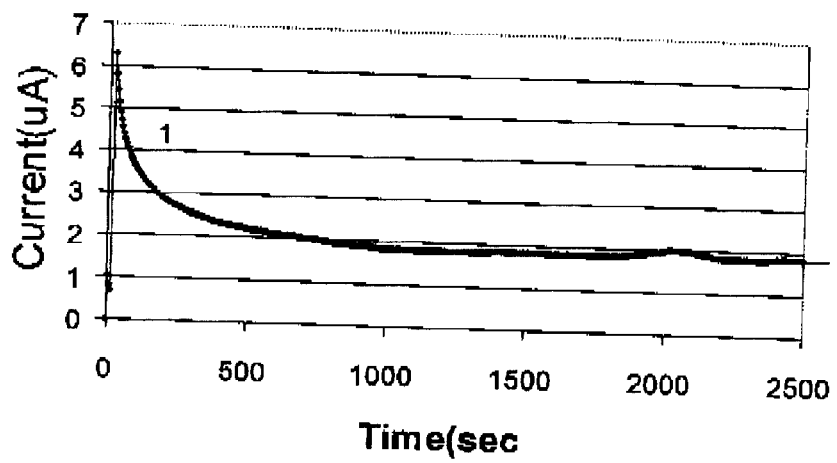
FIG. 50 is a graph illustrating data from Example 22.

The test system is then turned on and the measuring electrode activated. The oxygen signal is observed over approximately 2500 seconds. The oxygen signal reflects the transmissibility of the oxygen through the surrounding quiescent solution to the measuring electrode. This signal profile is indicated as Curve One in FIG. 50. Curve One is also used as a reference in subsequent examples.

As oxygen is depleted from the solution immediately surrounding the measuring electrode, the signal profile asymptotically decays. Given enough time, a steady-state transmission would be obtained. Since the time to steady state in this system is considerable, a quasi-steady-state is approximated after the rate of signal decay becomes small. The asymptotic value in this example is approximately 1.80 microampere (uA) current that corresponds to an oxygen transmissibility of $1.8 \times 10^{-3}$ cm/sec. This transmissibility is equivalent to a layer of water 1330 microns in thickness. The guard ring is left turned off. As a result, oxygen could diffuse in from the edges or sides of the measuring electrode surface, thereby lowering the effective boundary layer resistance. If these edge effects could be reliably isolated, it is expected that the resistance would measure higher than 1330 microns of water. Placing material onto the measuring electrode will either depress or raise the oxygen signal profile dependent upon the gas-collecting and transport properties of the test material.

Example 23a

This example demonstrates the effect of a non-gas-conducting material in the above-described test system.

To perform the test, 10.0 ml of 10 mM phosphate buffer, pH 7.2, equilibrated with room air, is added to the reservoir portion of the polarographic cell. Since introduction of fluid causes undesirable mixing of the test solution, the solution is allowed to stand for approximately 5 minutes prior to measurement for the liquid to come to rest.

Figure 37:
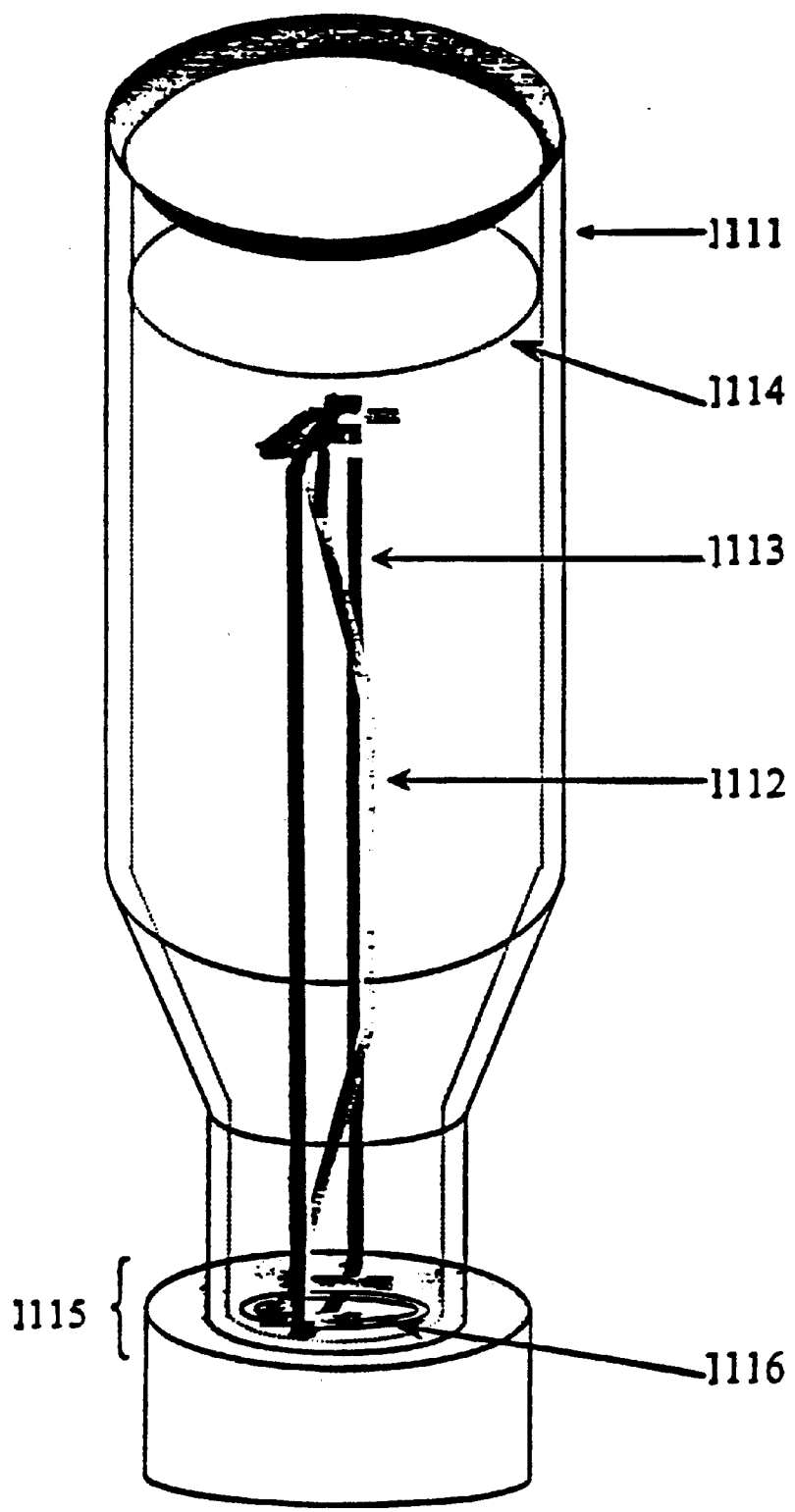
FIG. 37 illustrates a portion of the permeometer test instrument. Reservoir (1111) contains jig (1112) on which is retained a test sample in the form of a fiber (1113). Buffer solution (1114) is shown in the reservoir immersing the jig and fiber. An oxygen consuming electrode (1115) with guard ring (1116) is also shown.

A 5.5 cm length of 0.034" silver plated copper wire is lashed to a jig and placed in the buffer-filled reservoir portion of the polarographic cell as depicted in FIG. 37. A small spot of Room Temperature Vulcanizing (RTV) silicone is applied at the apex of this wire to prevent direct contact between the metal of the wire and the metal of the measuring electrode.

Figure 51:
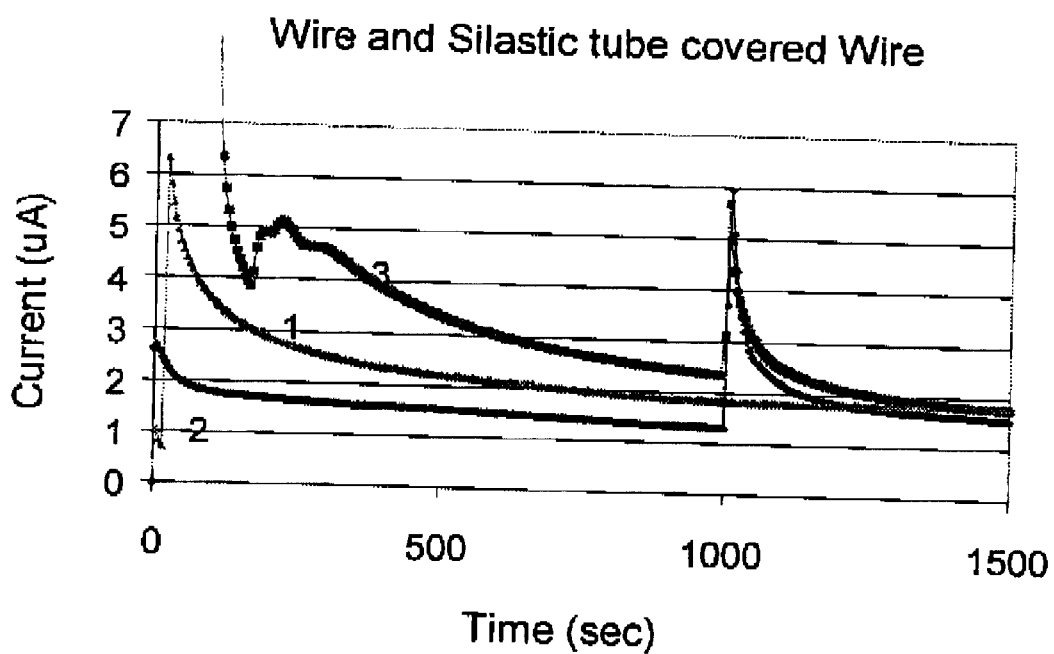
FIG. 51 is a graph illustrating data from Example 23a and 23b.

After a signal is acquired for some length of time, the metal wire is removed from the test apparatus and a quiescent baseline re-established for the buffer solution without the presence of the wire. As shown by Curve Two in FIG. 51, the effect of the wire is to depress the oxygen signal profile. It blocks a portion of the measuring electrode, thereby inhibiting the overall flux of oxygen to this surface. All curves return to the Curve One level after removal of the test element.

Example 23b

This example demonstrates that a coating of a highly gas permeable material on a non-gas conducting material does not itself provide much gas transport. As will be seen in subsequent examples, it is the air-filled interconnected void spaces of the various portions of the present invention that are primarily responsible for high gas flux in the invention.

In this example, a metal wire is sheathed with a silicone rubber tube. The wire serves as a negative control for comparison against material with air-filled interconnected void spaces as described in the present invention. The silicone rubber tubing enclosing the wire is expected to be quite permeable to gases compared to water. Curve Three in FIG. 51 indicates a small contribution to oxygen flux by the silastic tubing enclosing the negative control.

To perform the test, 10.0 ml of 10 mM phosphate buffer, pH 7.2, equilibrated with room air, is added to the reservoir portion of the polarographic cell. Since introduction of fluid causes undesirable mixing of the test solution, the solution is allowed to stand for approximately 5 minutes prior to measurement for the liquid to come to rest.

A 10 cm length of 0.034" silver-plated copper wire is covered with a 5.5 cm length of medical/pharmaceutical grade silicone rubber tubing 0.020" internal diameter and 0.037" outer diameter (VWRbrand Select™, VWR Scientific Products). The silicone rubber tubing is stretched radially and released over the center portion of the wire. This construct is then lashed to a jig and placed in the buffer-filled reservoir portion of the polarographic cell as depicted in FIG. 37.

After a signal is acquired for some length of time, the jig is removed and quiescent baseline re-established for the buffer solution without the test article. As shown by Curve Three in FIG. 51, the effect of the silicone-sheathed wire is to slightly increase the oxygen signal early on, but that the signal rapidly decays and appears to closely approach the baseline oxygen level. Since common silicon-filled PDMS (polydimethylsiloxane) is generally known to have permeability approximately six times of that of water, it is reasonable to expect that the oxygen flux at the electrode initially might be slightly enhanced. But as the oxygen content of the silicone material in the immediate proximity of the measuring electrode is consumed, it is not so readily supplemented by oxygen from more remote locations, for example, from several centimeters distance. This is because there are no highly gas permeable passageways to shuttle oxygen between remote locations and the electrode. In addition, the gas permeable properties of the small cross section of the PDMS coating is not sufficiently improved over that of the surrounding aqueous fluid to afford a substantial improvement in gas transport.

Example 23c

This example demonstrates that a polymeric material having essentially no air-filled void spaces does not provide any gas transport. In this example, a 75 cm length of 4-0 Prolene® blue monofilament polypropylene suture (Ethicon, Inc., Sommerville, N.J.) is selected for testing. As will be seen in subsequent examples, it is the air-filled void spaces of the various portions of the present invention that are primarily responsible for gas transport in the invention.

To perform the test, 10.0 ml of 10 mM phosphate buffer, pH 7.2, equilibrated with room air, is added to the reservoir portion of the polarographic cell. Since introduction of fluid causes undesirable mixing of the test solution, the solution is allowed to stand for approximately 5 minutes prior to measurement for the liquid to come to rest.

The monofilament polypropylene fiber is wrapped six times around a jig and placed in the buffer-filled reservoir portion of the polarographic cell as depicted in FIG. 37.

The fiber is then removed and quiescent baseline re-established for the buffer solution without the fiber. As shown by Curve Four in FIG. 52, the effect of the fiber is to depress the oxygen signal profile. It blocks a portion of the measuring electrode thereby inhibiting the overall flux of oxygen to this surface.

Example 23d

This example demonstrates that a polymeric material having essentially no air-filled interconnected void spaces does not provide any gas transport. In this example, a 75 cm length of Ultex 6-0 ePTFE nonabsorbable monofilament surgical suture (W. L. Gore & Associates, Inc., Flagstaff, Ariz.) is tested. As will be seen in subsequent examples, it is the air-filled interconnected void spaces of the various portions of the present invention that are primarily responsible for gas transport in the invention. This particular type of ePTFE material has no discernible interconnected void spaces.

To perform the test, 10.0 ml of 10 mM phosphate buffer, pH 7.2, equilibrated with room air, is added to the reservoir portion of the polarographic cell. Since introduction of fluid causes undesirable mixing of the test solution, the solution is allowed to stand for approximately 5 minutes prior to measurement for the liquid to come to rest.

The monofilament is wrapped six times around a jig and placed in the buffer-filled reservoir portion of the polarographic cell as depicted in FIG. 37.

Figure 52:
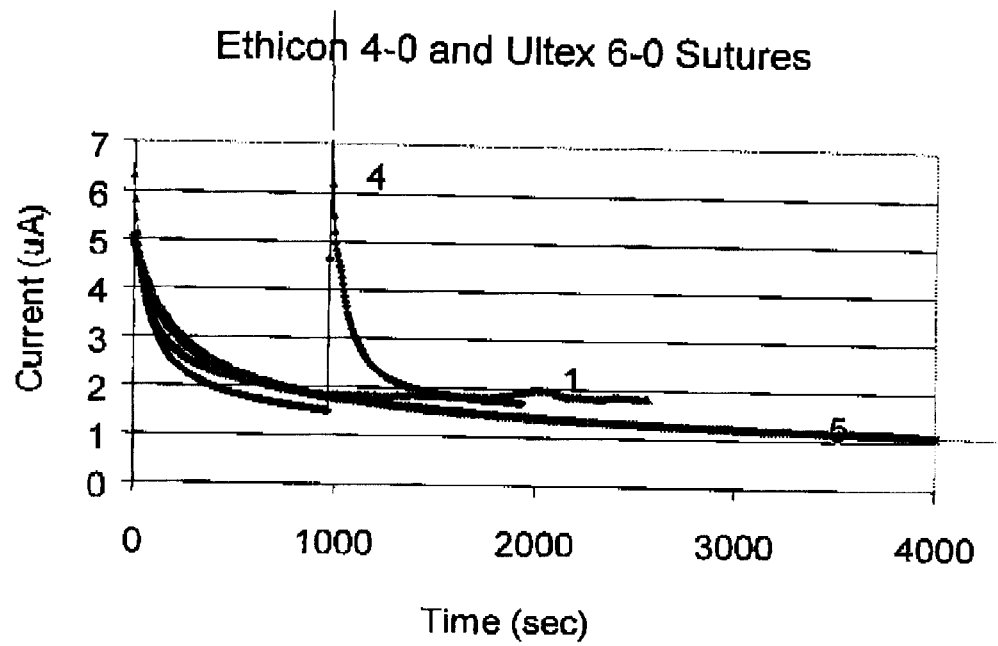
FIG. 52 is a graph illustrating data from Example 23c.

As shown by Curve Five in FIG. 52, the effect of the fiber is to depress the oxygen signal profile. It blocks a portion of the measuring electrode thereby inhibiting the overall flux of oxygen to this surface.

Example 23e

This example demonstrates that a polyamide yarn imbibed with a silicone material does not have high gas transport properties.

To construct the material of this example, a spool of 40 denier yellow multi-filament polyamide yarn is obtained. (E. I. duPont deNemours & Co., Inc., Wilmington, Del.). This yarn is processed through a continuous silicone-coating machine as follows. The yarn is threaded through an emersion coating machine from a payoff spool, over a series of pulleys such that the yarn is moved through a bath of silicone and then immediately into a curing oven set at 85 degrees C. This is followed by subsequent passes through the silicone bath and oven via multiple pulleys until thirteen coatings of silicone are deposited on the yarn. The oven is 2 feet long and the rate at which the yarn moved through the over is between 2 and 3 feet per minute. The silicone bath is a solution of 15%, by weight, RTV 863 (available from General Electric Silicones of Waterford, N.Y.) diluted in Isopar-C mineral oil. The coated yarn is then spooled onto a take up spool. The diameter of the yarn before and after silicone application is 0.0034 inch. The lack of an increase in the diameter of the yarn after a silicone coating is applied thereto indicates that the deposited silicone resides inside the multi-filament yarn between strands and not as a coating that encloses the yarn as a whole. The presence of silicone in between the yarn filaments, rather than as a coating, is also indicated by the inability to scrape silicone off of the yarn with a sharp knife.

Absence of internal interconnected air spaces in the silicone coated yarn is further assessed by cutting a piece of the coated yarn and placing one end into a dye consisting of isopropyl alcohol and Crystal Violet solution (Accustain®, by Sigma Diagnostics, St. Louis, Mo.). The wicking of dye up into the fiber through the cut end would suggest the presence of internal air spaces. No wicking of dye into the coated yarn is observed.

Figure 53:
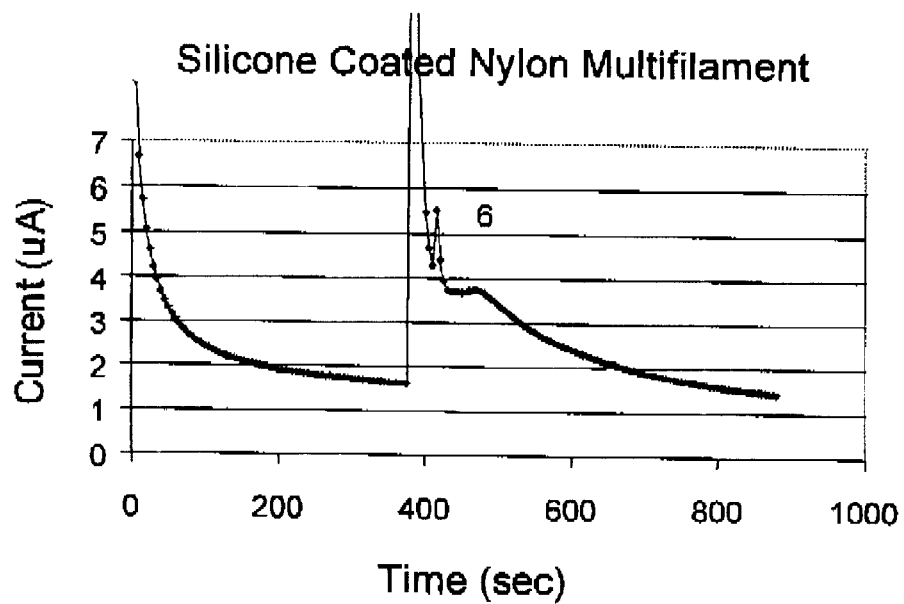
FIG. 53 is a graph illustrating data from Example 23e.

The silicone-impregnated yarn is also tested for oxygen content and transport according to the methods described above. In the test, a 75 cm length of the silicone-imbibed yarn is wrapped six times around a jig. Prior to testing the silicone-imbibed fiber, a signal is established without the jig and yarn for some length of time. Next, the jig with the yarn is added to the reservoir and an oxygen signal acquired for a period of time. As shown by Curve Six in FIG. 53, a slight increase in the oxygen signal is seen early on, but then the signal rapidly decays and appears to closely approach the baseline oxygen level.

Polydimethylsiloxane (PDMS) silica-filled silicone rubber is known to have as permeabilities ranging, from that of water to as high as approximately ten times that of water. Therefore, it is reasonable to expect that the oxygen flux at the electrode initially might be slightly enhanced. But as the oxygen content of the silicone material in the immediate proximity of the measuring electrode is consumed, the oxygen is not readily supplemented. This is because there are no high-gas-transporting, interconnected air passageways in the test material to conduct oxygen from a remote location (i.e., up to several centimeters) through the material to the oxygen-consuming electrode of the test apparatus. In addition, the gas permeable properties of the small cross section of the PDMS coating is not sufficiently improved over that for the surrounding aqueous fluid to afford a substantial improvement in gas transport.

Example 24

This example demonstrates that a porous polymer having air-filled interconnected void spaces is a blood collector, conductor, and distributor of gas. In the test, a 12 cm length of GORE-TEX® CV-0 ePTFE nonabsorbable monofilament suture (W. L. Gore & Associates, Inc., Flagstaff, Ariz.) is wrapped one time around the above-described jig for measurement.

To perform the test, 10.0 ml of 10 mM phosphate buffer, pH 7.2, equilibrated with room air, is added to the reservoir portion of the polarographic cell. Since introduction of fluid causes undesirable mixing of the test solution, the solution is allowed to stand for approximately 5 minutes prior to measurement for the liquid to come to rest.

After a signal was acquired without the fiber for some length of time, the jig and the filament are added to the buffer-filled reservoir portion of the polarographic cell as depicted in FIG. 37 and an oxygen signal acquired for a period of time. The jig and filament are then removed and a quiescent baseline re-established for the buffer solution without the fiber.

Figure 54:
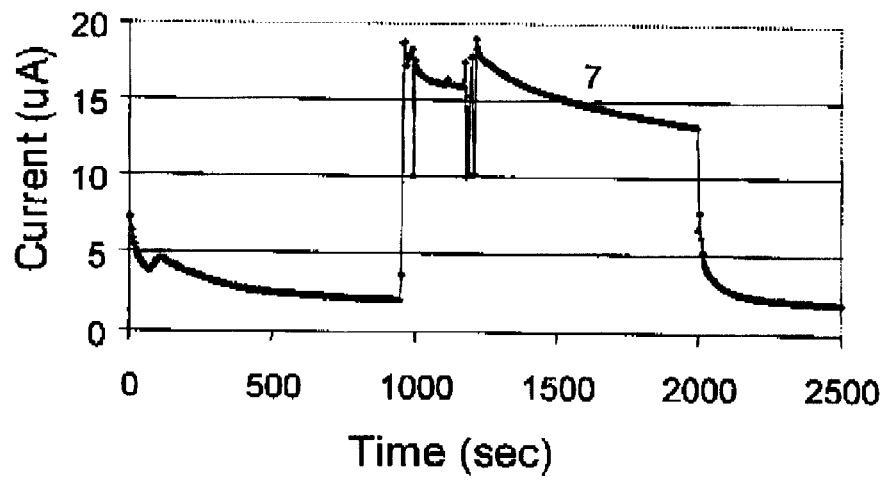
FIG. 54 is a graph illustrating data from Example 24.

As shown by Curve Seven in FIG. 54, the effect of the filament is to dramatically increase the oxygen flux signal, even though only approximately 10% of the measurement electrode is covered by the filament material. Upon removal of the filament, the oxygen signal is observed to fall back to a low baseline.

During the course of this experiment, the jig is jostled as indicated by the perturbations of the signal during the early part of the run. An air bubble is observed, and the apparatus is disturbed in the process of removing the air bubble. Note that the filament signal asymptotically decays with time, but that the signal remains quite high over the time course of the experiment.

Air is known to have permeability to oxygen on the order of $3 \times 10^5$ that of water (supra). As oxygen is consumed at the measurement electrode, a partial-pressure gradient is set up between the filament located at the electrode and the rest of the filament. Communication of oxygen is permitted between remote locations within the filament on the order of several centimeters due to the extremely high permeability of the air contained within the filament. The surface area of the filament remote from the measuring electrode in relation to the surface area in the immediate vicinity of the electrode is on the order of a few orders of magnitude different. Thus, oxygen can be extracted from the surrounding medium over a relatively large surface area of the filament, collected into the gas-filled passageways of the fiber, and channeled the length of the filament to the measuring electrode where an enhanced oxygen flux is detected. The asymptotic decay may be reflecting the initial depletion of the latent oxygen content of the fiber. The signal decay may also indicate a developing boundary layer associated with the fiber collecting surfaces.

Example 25a

This example demonstrates that a porous polymer having air-filled void spaces with perimeter surfaces of the porous polymer sealed in a silicone material is a good collector, conductor, and distributor of gas.

In the test, a 4.5 cm length of GORE-TEX® CV-0 ePTFE noniabsorbable monofilament suture (W. L. Gore & Associates, Inc., Flagstaff, Ariz.) is obtained.

The ePTFE material is covered with a length of Medical/Pharmaceutical grade silastic tubing 0.020" internal diameter and 0.037" outer diameter (VWR brand Select™, VWR Scientific Products). The silicone tubing is stretched radially and released over the center portion of the filament. The filament is then cut where the silicone tubing cover ended. The cut ends are then covered with a drop of RTV silicone to seal off the air passageways within the filament element from the outside environment. The article is then cured at about 100 degrees C. for about 1 hour. This construct is lashed to the above-described jig for measurement.

To perform the test, 10.0 ml of 10 mM phosphate buffer, pH 7.2, equilibrated with room air, is added to the reservoir portion of the polarographic cell. Since introduction of fluid causes undesirable mixing of the test solution, the solution is allowed to stand for approximately 5 minutes prior to measurement for the liquid to come to rest.

After a signal was acquired without the filament for some length of time, the jig and the filament are added to the buffer-filled reservoir portion of the polarographic cell as depicted in FIG. 37 and an oxygen signal acquired for a period of time. The jig and filament are then removed and a quiescent baseline re-established for the buffer solution without the filament.

Figure 55:
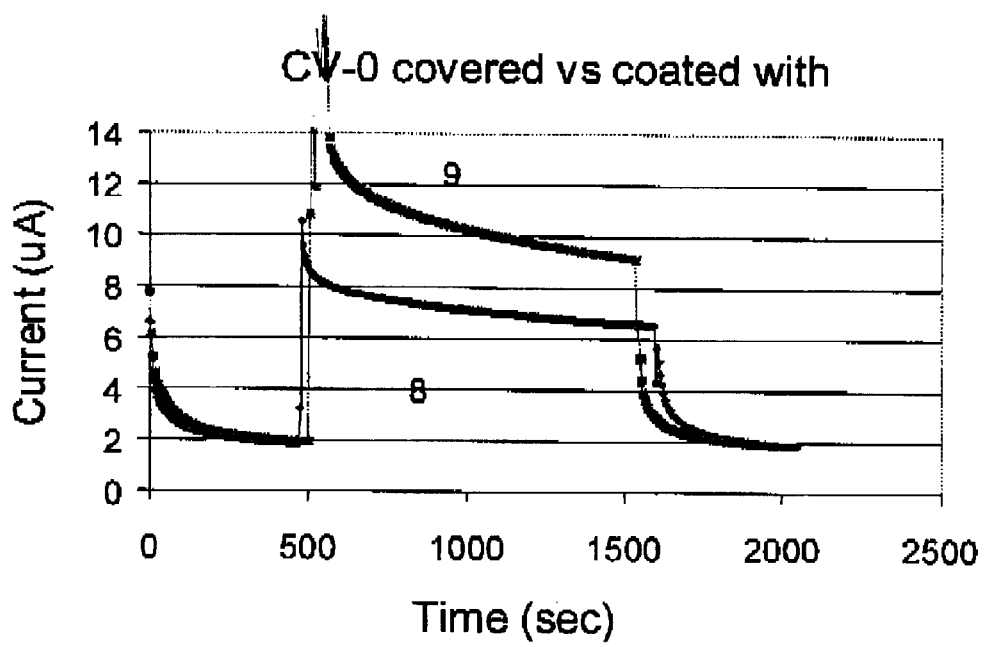
FIG. 55 is a graph illustrating data from Example 25a and 25b.

As shown by Curve Eight in FIG. 55, the effect of the filament is to dramatically increase the oxygen flux signal, even though only approximately 10% of the measurement electrode is covered by the filament material. Upon removal of the filament, the oxygen signal is observed to fall back to a low baseline, Note that the filament signal asymptotically decays with time, but that the signal remains quite high over the time course of the experiment. The effect of adding a silicone covering did not impact the essential performance of the test material. The overall signal may be somewhat lower than if no covering was added. This decrease can be attributed to the addition of an additional resistance layer through which oxygen must diffuse from the surrounding medium into the filament air passageway, and then back out through the silicone layer before it is consumed at the electrode. Since the surface area of the collecting surfaces of this fiber is relatively high, the effect on the total resistance of adding the silicone covering is not thought to be limiting at the collecting surfaces, However, the total resistance may be affected by addition of the silicone layer between the fiber and the measuring electrode.

Example 25b

This example demonstrates that a porous polymer having air-filled void spaces with perimeter surfaces of the porous polymer sealed in a silicone material is a good collector, conductor, and distributor of gas. In the test, a length of GORE-TEX® CV-0 ePTFE nonabsorbable monofilament suture (W. L. Gore & Associates, Inc., Flagstaff, Ariz.) obtained.

The ePTFE material is coated with a two part liquid silicone rubber LSR 40-10:1 part number 40082 (Applied Silicone Corporation Ventura, Calif.). To coat the filament, a small amount of the silicone is applied to a gloved finger and the filament is pulled through the small pool of silicone between two fingers. Excess silicone is carefully wiped off by pulling the coated filament between two fingers of a clean glove. The coated filament is then cured at approximately 1 10 degrees C. for several minutes. Once the filament is coated, it is cut to 5.8 cm and silicone is applied to the cut ends and cured to seal off the air spaces within the filament from the outside environment. To test for continuity of the coat, the sample is dipped in a solution of a dye consisting of isopropyl alcohol and Crystal Violet solution (Accustain (®, by Sigma Diagnostics, St. Louis, Mo.). The wicking of dye up into the filament at any location would indicate that the coating was not complete. Wicking of the dye into the test material is not observed. Once the continuity of the silicone coating is determined, the construct is lashed to the above-described jig for measurement To perform the test, 10.0 ml of 10 mM phosphate buffer, pH 7.2, equilibrated with room air, is added to the reservoir portion of the polarographic cell. Since introduction of fluid causes undesirable mixing of the test solution, the solution is allowed to stand for approximately 5 minutes prior to measurement for the liquid to come to rest.

After a signal was acquired without the filament for some length of time, the jig and the filament are added to the buffer-filled reservoir portion of the polarographic cell as depicted in FIG. 37 and an oxygen signal acquired for a period of time. The jig and filament are then removed and a quiescent baseline re-established for the buffer solution without the filament, As shown by Curve Nine in FIG. 55, the effect of the filament is to dramatically increase the oxygen flux signal, even though only approximately 10% of the measurement electrode is covered by the filament material. Upon removal of the filament, the oxygen signal is observed to fall back to a low baseline. Note that the filament signal asymptotically decays with time, but that the signal remains quite high over the time course of the experiment. The effect of adding a silicone coating did not significantly impact the high performance of the test material. The overall signal may be somewhat lower than if no coating is applied. This decrease can be attributed to a silicone resistance layer for oxygen to diffuse through from the surrounding medium into the filament air passageway, and then back out through the silicone layer before it is consumed at the electrode.

Example 26

This example demonstrates that a porous polymer having air-filled void spaces with perimeter surfaces of the porous polymer sealed in a silicone material is a good collector, conductor, and distributor of gas. In the test, a few thousand feet of spooled microporous ePTFE fiber 0.0048" outer diameter is obtained from W. L. Gore & Associates, Inc. (Medical Products Division, Flagstaff, Ariz.). Porous expanded polytetrafluoroethylene is made according to the teachings of U.S. Pat. Nos. 3,953,566 and 4,187,390, both issued to Gore, each of which is incorporated herein by reference.

This porous fiber is processed through a continuous silicone coating machine as follows. The fiber is threaded through an emersion coating machine from a payoff spool, over a series of pulleys such that the fiber is transported through a bath of silicone and then immediately into a curing oven set at 85 degrees C. This is followed by subsequent passes through the silicone bath and oven via multiple pulleys until thirteen coatings of silicone are deposited on the fiber. The oven is 2 feet long. and the rate at which the fiber moved through the over is between 2 and 3 feet per minute. The silicone bath is a solution of 15%, by weight, RTV 863 (available from General Electric Silicones of Waterford, N.Y.) diluted in Isopar-C mineral oil. The coated fiber is then spooled onto a take up spool. The diameter of the fiber before coating is 0.0048". The coating added 0.0020" to the diameter of the fiber for a final diameter of 0.0068".

The fiber is tested at several locations along its length for continuity of the silicone coating. The material of this example is found to be completely pin-hole-free. To test for continuity of the silicone coating, a sample of the coated fiber is dipped into dye consisting of isopropyl alcohol and Crystal Violet solution (Accustain®, by Sigma Diagnostics, St. Louis, Mo.). The wicking of dye up into the fiber at any location would indicate that the coating was not complete. No wicking of dye into the test material is observed.

A 37.5 cm length of this coated fiber is cut from the finished product and the ends sealed liquid-tight with silicone. The coated fiber is wrapped three times around the above-described jig for measurement of oxygen transport therethrough.

To perform the test, 10.0 ml of 10 mM phosphate buffer, pH 7.2, equilibrated with room air, is added to the reservoir portion of the paloroaphic cell. Since introduction of fluid causes undesirable mixing of the test solution, the solution is allowed to stand for approximately 5 minutes prior to measurement for the liquid to come to rest.

After a signal was acquired without the fiber for some length of time, the jig and the fiber are added to the buffer-filled reservoir portion of the polarographic cell as depicted in FIG. 37 and an oxygen signal acquired for a period of time. The jig and fiber are then removed and a quiescent baseline re-established for the buffer solution without the fiber.

Figure 56:
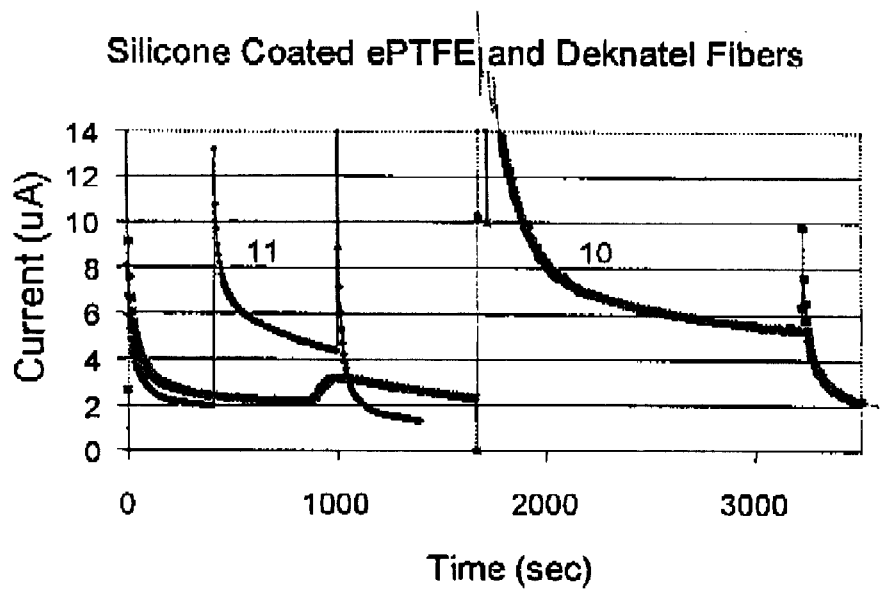
FIG. 56 is a graph illustrating data from Example 26.

As shown by Curve Ten in FIG. 56, the effect of the fiber is to dramatically increase the oxygen flux signal, even though only approximately 10% of the measurement electrode is covered by the fiber material. Upon removal of the fiber, the oxygen signal is observed to fall back to a low baseline. Note that the fiber signal asymptotically decays with time, but that the signal remains quite high over the time course of the experiment.

This fiber is used in a cell-encapsulation device described in Example 31 to enhance respiratory gas exchange between the device interior and an aqueous external environment of the device. As described later, cell survival in the device is favorably influenced with the present invention.

Example 27

This example demonstrates that a braided polymer fiber having air-filled interconnected void spaces formed between the polymer portions of the braid by a coating of a highly gas permeable material on the perimeter, or outermost, surfaces of the polymer is a good collector, conductor, and distributor of gas.

In the test, a length of Deknatel Tevdek II white braided polyester 3-0 suture 0.0111" outer diameter is coated with a silicone-in-water emulsion KM2002T (Shin Etsu, Akron, Ohio). A small amount of the silicone is applied to a gloved finger and the suture is pulled through the small pool of silicone. Excess silicone is carefully wiped off by pulling the coated suture over a clean glove. The coated suture is then allowed to dry at approximately 60 degrees C. for approximately 20 minutes. The sample is then fully cured at approximately 120 degrees C. for five minutes. The coated diameter is 0.0163".

Once the suture is coated, it is cut to 10.5 cm and silicone applied to the cut ends and cured to seal off the air spaces within the suture from the outside environment of the invention. To test for continuity of the silicone coating, the sample is dipped in a solution of a dye consisting of isopropyl alcohol and Crystal Violet solution (Accustain®, by Sigma Diagnostics, St. Louis, Mo.). The wicking of dye up into the suture at any location would indicate that the coating was not complete. No wicking of dye into the test material is observed.

This construct is lashed to the above-described jig for measurement. To perform the test, 10.0 ml of 10 mM phosphate buffer, pH 7.2, equilibrated with room air, is added to the reservoir portion of the polarographic cell. Since introduction of fluid causes undesirable mixing of the test solution, the solution is allowed to stand for approximately 5 minutes prior to measurement for the liquid to come to rest.

After a signal was acquired without the suture for some length of time, the jig and the suture are added to the buffer-filled reservoir portion of the polarographic cell as depicted in FIG. 37 and an oxygen signal acquired for a period of time. The jig and suture are then removed and a quiescent baseline re-established for the buffer solution without the suture.

In this example, the guard ring switch is left in the "ON" mode. This serves to drain off some of the overall oxygen flux and to reduce the oxygen signal profile, as is evidenced in an approximate one-half drop in the quiescent baseline values. This does not, however, substantially alter the results of this experiment. It simply means that the overall signals represented here are depressed with respect to what they would be if the guard ring were left off, or inactivated.

As shown by Curve Eleven in FIG. 56, the effect of the suture is to increase the oxygen flux signal, even though only approximately 10% of the measurement electrode is covered by the suture material. Upon removal of the suture, the oxygen signal is observed to fall back to a low baseline. Note that the suture signal asymptotically decays with time, but that the signal remains quite high over the time course of the experiment.

Example 28a

This example demonstrates that a porous polymer having air-filled void spaces with perimeter surfaces of the porous polymer sealed in a relatively thick coating of hydrogel material appears to be a poor collector, conductor, and distributor of gas. In the test, a 5.3 cm length of Gore-Tex® CV-0 ePTFE nonabsorbable monofilament suture (W. L. Gore & Associates, Inc., Flagstaff, Ariz.) is obtained.

The ePTFE material is coated with a hydrogel material. The hydrogel was formulated from HN86, a grade of partially hydrolyzed polyacrylonitrile polymer supplied by Hymedix Corporation (Dayton, N.J.), under the trade name HYPAN®, Structural Hydrogel. This polymer is dissolved in a 55% NaSCN solution at 10% by weight. A small amount of the hydrogel is applied to a gloved finger and the suture fiber pulled through the small pool between two fingers. Excess material is carefully wiped off by pulling the coated fiber between two fingers of a clean glove. The ends of the fiber are also coated so as to seal off the air spaces within the fiber from the outside environment. The hydrogel material coating the fiber is then coagulated by placing the construction into de-ionized water for several minutes.

To test for continuity of the hydrogel coating, the sample is dipped into a specially prepared solution of crystal violet (Accustain® by Sigma Diagnostics, St. Louis, Mo.). The dye is first poured into a container, and the alcohol evaporated. A solution of dye is reconstituted by adding de-ionized water to the dried out dye. In this manner, the dye solution is changed from an alcohol base to a water base. This particular solution can stain a water-filled hydrogel but not a hydrophobic ePTFE material. Since the hydrogel coating takes up dye and turns a dark purple, any discontinuities in the coating show up readily as white ePTFE patches. This is indeed observed in this example, and a total of four coat applications are made before the test material showed a consistent purple coating over the entire surface. The outer diameter of the fiber before coating measured 0.0281". After coating, the test material measured to be 0.0469 inches in diameter.

This construct is lashed to the above-described jig for measurement. To perform the test, 10.0 ml of 10 mM phosphate buffer, pH 7.2, equilibrated with room air, is added to the reservoir portion of the polarographic cell. Since introduction of fluid causes undesirable mixing of the test solution, the solution is allowed to stand for approximately 5 minutes prior to measurement for the liquid to come to rest.

After a signal was acquired without the fiber for some length of time, the jig and the fiber are added to the buffer-filled reservoir portion of the polarographic cell as depicted in FIG. 37 and an oxygen signal acquired for a period of time. The jig and fiber are then removed and a quiescent baseline re-established for the buffer solution without the fiber.

Figure 57:
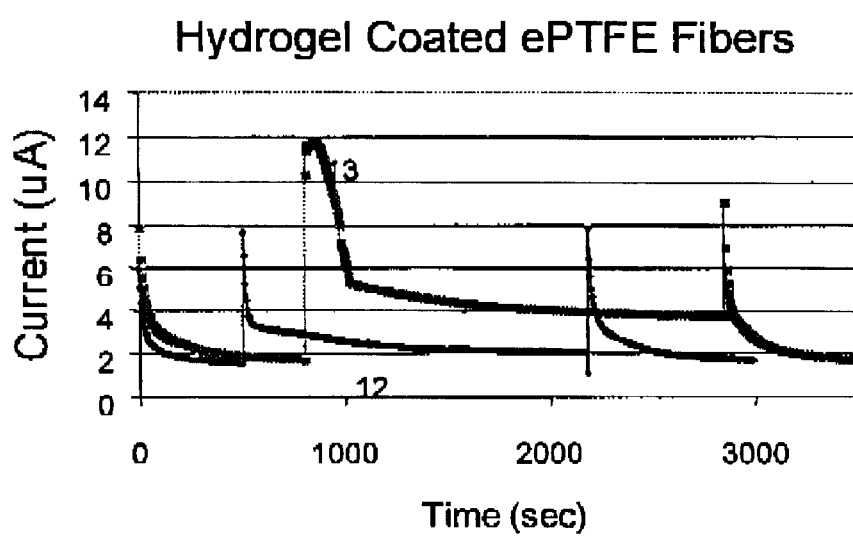
FIG. 57 is a graph illustrating data from Example 28a and 28b.

As shown by Curve Twelve in FIG. 57, the flux from this fiber does not appear to be significant. This signal profile looks much like the silicone-covered wire of Example 23b and the silicone imbibed sample of Example 23e. However, unlike these earlier examples, the sample in this case contains interconnected air-filled passageways for the transport of oxygen as well as a high surface area for collecting oxygen. The significant difference is that the coating material in this case has a much higher relative resistance to flux than any of the coating materials in previous examples. This construct is less permeable to oxygen because of the low gas transmissibility of the hydrogel material and its much greater thickness. The permeability characteristics of hydrogel materials is approximately a factor of 2 less than that of water. While a less-permeable coating will reduce the overall flux of gas, the high area of the collecting surfaces should still be adequate for extracting some additional oxygen from the surrounding medium. However, the oxygen signal is dominated by the thick, fairly resistive coating interposed between the measuring electrode and the fiber.

Example 28b

In this example, the sample from Example 28a was taken and a small area of the test material that makes contact with the measuring electrode during testing is treated to remove the hydrogel coating. The coating is cut off with a sharp knife only at this specific location. This article is lashed to the above-described jig for measurement.

To perform the test, 10.0 ml of 10 mM phosphate buffer, pH 7.2, equilibrated with room air, is added to the reservoir portion of the polarographic cell. Since introduction of fluid causes undesirable mixing of the test solution, the solution is allowed to stand for approximately 5 minutes prior to measurement for the liquid to come to rest.

After a signal was acquired without the fiber for some length of time, the jig and the fiber are added to the buffer-filled reservoir portion of the polarographic cell as depicted in FIG. 37 and an oxygen signal acquired for a period of time. The jig and fiber are then removed and a quiescent baseline re-established for the buffer solution without the fiber.

As shown by Curve Thirteen in FIG. 57, the effect of removing a portion of the hydrogel coating from the fiber is a moderate, yet significant, increase in the oxygen flux signal. This is the case even though only approximately 10% of the measurement electrode is covered by the fiber material. "Moderate" effect in this example is in relation to the above-described results with porous fibers having no coating or those materials having more permeable silicone coatings.

Upon removal of the fiber, the oxygen signal is observed to fall back to a low baseline. Note that the fiber signal asymptotically decays with time, but that the signal remains moderately high over the time course of the experiment.

The shape of the oxygen signal profile immediately upon placement of this material onto the measuring electrode is unusual. The signal does not immediately decay asymptotically, but remains rather high for a short period of time. Since the air within the fiber has direct contact with the measuring electrode through the removed hydrogel material, it is thought that the oxygen content latent within the fiber's air passageways is being rapidly extracted during this time. Since the hydrogel coating at the collecting surfaces has a fairly low transmissibility, there is a bit of a lag time for the oxygen from the surrounding medium to diffuse into the fiber to establish some level of equilibrium. Though the oxygen-collecting surfaces of this article are not as permeable as other articles of the present invention, they still do extract and collect oxygen from the surrounding medium as indicated by this profile via the relatively high surface area of the gas-collecting end of the fiber. The air-filled passageways transport oxygen between remote locations of different partial pressure. These data also suggest that the low surface area of the measuring electrode and the limited fiber area in contact with it can limit the ability to measure the properties of the articles of the present invention. This problem is overcome in this example by removing only a very small piece of the relatively resistive hydrogel coating at the point of contact with the measuring electrode.

Example 29

This example demonstrates the oxygen collection properties via removing most, or all, of the oxygen from a buffer solution and the fiber and then replenishing the solution. In this example, the silicone coated porous polymer having interconnected air-filled void spaces from Example 25b is used in conjunction with buffer solutions that are stripped of oxygen by sparging the system with an inert gas.

The material of Example 25b is lashed to the above-described jig for measurement and placed directly into the apparatus. The reservoir solution, with the fiber in it, is sparged with argon for a few minutes to strip all oxygen content from the liquid and the fiber in the system. Complete stripping of oxygen from the liquid and the fiber is indicated by a near-zero oxygen flux signal. A few milliliters of solution are then removed from the reservoir with care being taken to keep the fiber submerged and not exposed to atmospheric air. A few milliliters of fresh, air-equilibrated solution is added back to the reservoir and mixed with the reservoir solution. This process is repeated several times over the course of several minutes. In this manner, the solution is gradually refreshed with oxygenated solution without exposing the fiber to atmospheric air. After exchange, a signal was acquired for some length of time. The jig and the fiber are then removed and quiescent baseline re-established without the article.

Figure 58:
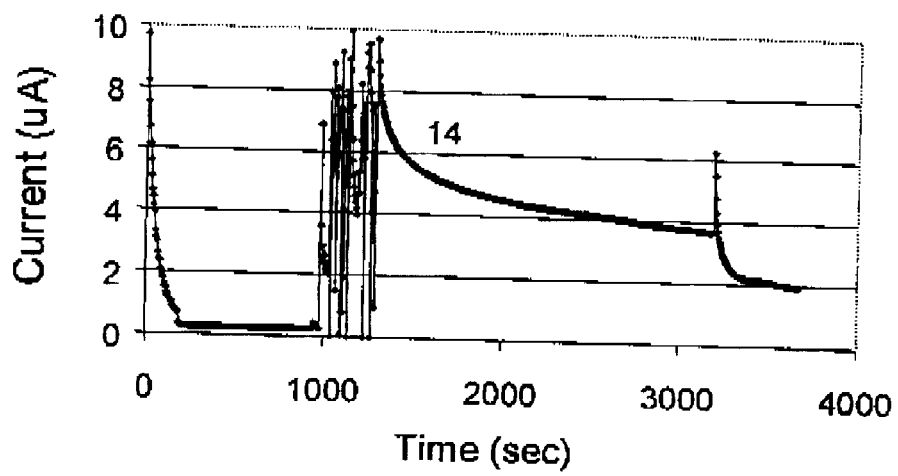
FIG. 58 is a graph illustrating data from Example 29.

As shown by Curve Fourteen in FIG. 58, the effect of depleting oxygen from the liquid and the fiber in the reservoir and replenishing the oxygen depleted liquid with oxygen-containing liquid is to increase the oxygen flux signal through the present invention, even though only approximately 10% of the measurement electrode is covered by the invention.

Upon removal of the fiber, the oxygen signal is observed to fall back to a normal baseline. Note that the fiber signal asymptotically decays with time, but that the signal remains quite high over the time course of the experiment. The signal profile is quite noisy during the solution-exchange period. This is due to highly variable levels of oxygenated solution mixing with the depleted solution, as well as disrupted contact between the fiber sample and the electrode during exchange of liquids.

This example specifically demonstrates the oxygen-collecting attribute of the present invention. In all previous examples, some portion of the oxygen signal measured at the electrode might have simply come from oxygen latent within the fiber, rather than collected from the surrounding liquid medium. Since the latent oxygen content of the fiber in this experiment is removed by argon stripping, any oxygen detected upon solution refreshing must have come from the surrounding liquid medium via the fiber.

Example 30

This example demonstrates the effect of length and associated surface area available for gas collection of fibrous materials of the present invention on oxygen transmissibility through the materials. In this example, the material of Example 25b is obtained in a 5.8 cm length, the ends sealed with RTV silicone, and the material tested for continuity of the silicone coating. A second material having a length of 2.2 cm is similarly prepared. Additional materials are also constructed having lengths of 1.0 cm and 0.5 cm.

For the materials having lengths of 5.8 cm and 2.2 cm, the materials are lashed to the above-described jig for measurement. In the cases of the shorter samples, double-sided sticky tape positioned between the jig and the fiber samples is used to secure the materials to the test instrument.

To perform the test, 10.0 ml of 10 mM phosphate buffer, pH 7.2, equilibrated with room air, is added to the reservoir portion of the polarographic cell. Since introduction of fluid causes undesirable mixing of the test solution, the solution is allowed to stand for approximately 5 minutes prior to measurement for the liquid to come to rest.

After a signal was acquired without the fiber for some length of time, the jig and the fiber are added to the buffer-filled reservoir portion of the polarographic cell as depicted in FIG. 37 and an oxygen signal acquired for a period of time. The jig and fiber are then removed and a quiescent baseline re-established for the buffer solution without the fiber.

In all cases, the guard ring switch is left in the "ON" mode. This serves to drain off some of the overall oxygen flux and to reduce the quiescent baseline values by about one-half. It does not, however, substantially alter the results of this experiment. It simply means that the overall signals represented here are depressed with respect to what they would be if the guard ring was left turned off.

In all cases, that portion of a fiber in contact with the measuring electrode is essentially equivalent. The difference between these cases is the amount of fiber extending up into the buffer solution in the reservoir beyond the immediate vicinity of the measuring electrode.

Figure 59:
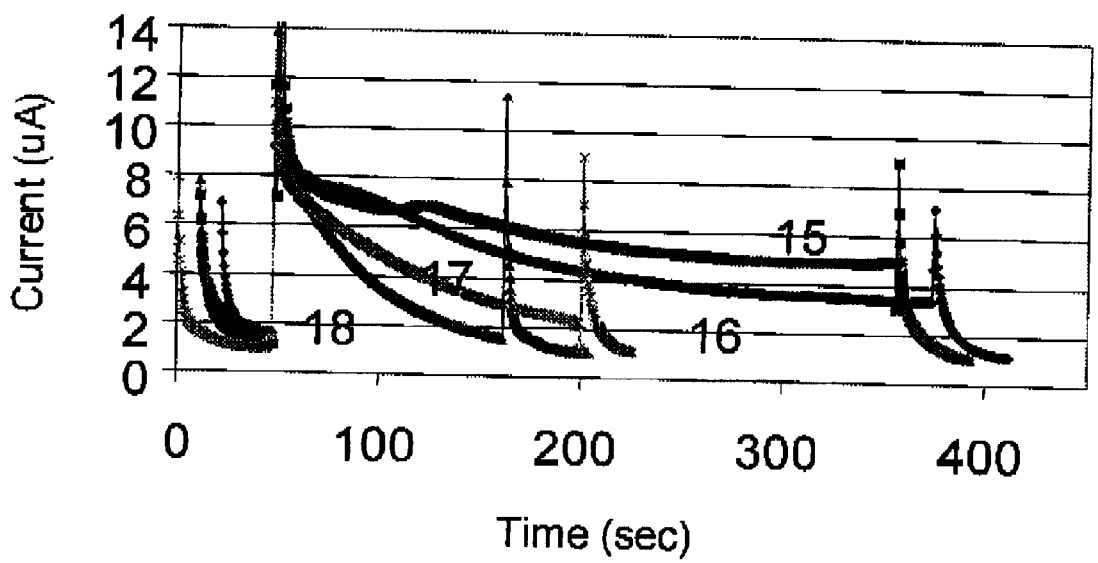
FIG. 59 is a graph illustrating data from Example 30.

As shown in Curves Fifteen to Eighteen in FIG. 59 (i.e., 5.8 cm, 2.2 cm, 1.0 cm, and 0.5 cm lengths, respectively), the effect of fiber length is quite significant even though only approximately 10% of the measurement electrode is covered by the fiber material in any instance. Upon removal of the fiber, the oxygen signal is observed to fall back to a low baseline. Longer fibers have greater collecting capacity for oxygen. They not only possess higher latent contents of oxygen, but they possess higher surface areas for extracting and collecting oxygen from the surrounding liquid medium proportional to their length. Longer fibers possess greater resistance to oxygen flux through longer interconnected air-filled passageways. However, the effect on the total resistance is more than compensated by the reduction of the boundary layer and coating layer resistances at the high surface area collecting surfaces of the longer fibers.

This experiment demonstrates that materials of the present invention having high surface areas via longer lengths favors higher oxygen flux equilibrium between the invention and the surrounding environment of the invention.

Example 31

This example illustrates the construction and in-vitro use of cell-containing devices of the present invention. This embodiment places cells in a space within a semi-permeable membrane through which an internal respiratory aid extends. The internal respiratory aid extends from outside of the semi-permeable membrane containing the cells, through the permeable membrane, to the space where the cells are placed (See FIG. 33A). A water-permeable alginate gel is placed inside the device in association with both the internal respiratory aid and the cells. Once cells are placed in the devices, the cell-loaded devices are cultured under in vitro conditions. In this example, similar devices, but with non-conducting fibers as a sham aid, are used as controls.

In this example, the transgenic rat cell line, RIN 18, which secretes human insulin, is grown in the above-summarized and illustrated cell-containment devices of the present invention. One group has internal respiratory aids of the present invention made of air-filled, silicone-rubber-coated, porous expanded polytetrafluoroethylene (ePTFE) fibers. The fibers of the internal respiratory aids of this example are those described in Example 26, above. As the data from Example 26 show, these internal respiratory aids have high oxygen transmissibility. A second group of cell-containing devices have sham aids fabricated from monofilament polypropylene fibers. As seen in Example 23c, above, monofilament polypropylene fibers do not have high oxygen transmissibility. The second group of devices is used to help evaluate the effect of the internal respiratory aids in the first group of devices and to control for the overall geometry and presence of fibers in contact with the cells.

Both types of devices are loaded with RIN 18 cells suspended in an alginate gel and cultured in vitro for 18 days. Every three days, conditioned media are assayed for glucose consumption and insulin secretion. After 18 days, devices are prepared for histologic evaluation. Results of an in vivo metabolic assay reveal that devices with silicone-ePTFE internal respiratory aids grow to a state of greater glucose consumption and show higher total insulin secretion than devices with polypropylene (sham) aids. Results of histological imaging reveal that in devices with silicone-ePTFE internal respiratory aids, many cells cluster around the fibers comprising the internal respiratory aid deep in the device (FIGS. 33B and 33C), as well as in a superficial position just beneath the hydrophilized ePTFE membrane separating the alginate gel from the culture media. By contrast, cells in devices with polypropylene fibers as a sham aid are almost exclusively superficial (i.e., not clustered around the fibers, but simply located at the periphery of the containment membrane). Air-filled, silicone-ePTFE fibers are useful for nourishing cells encapsulated deep within cell-transplantation devices.

Figure 33A:
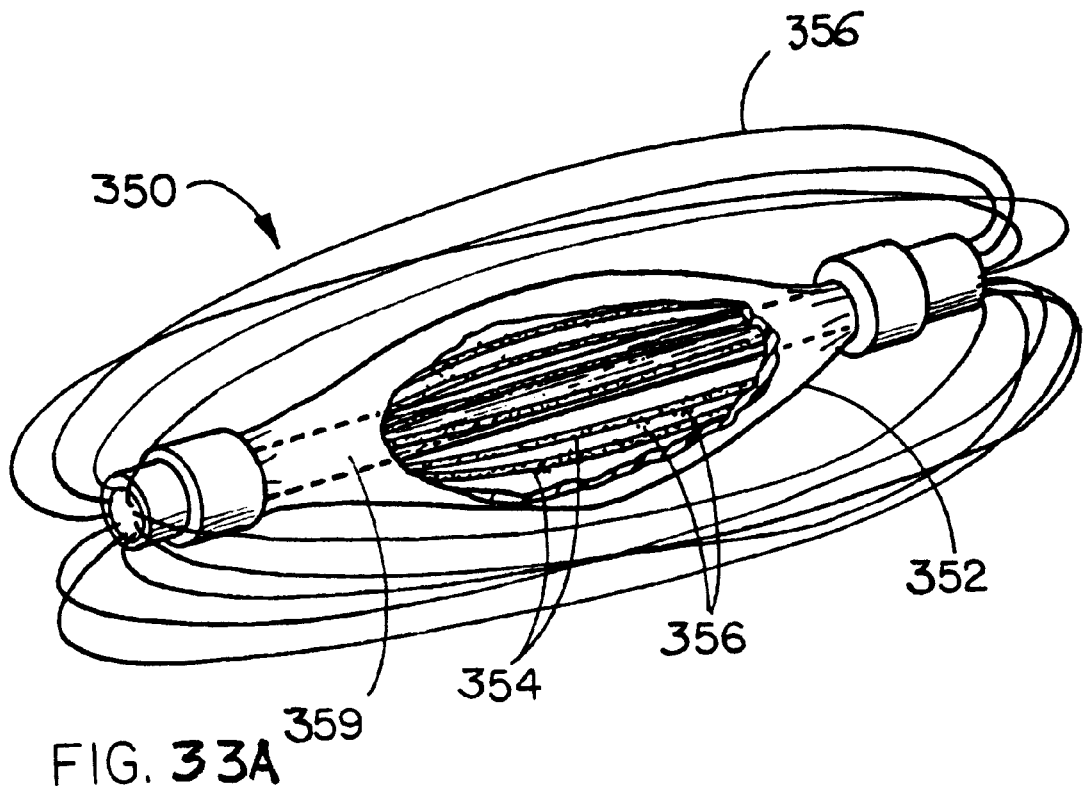
FIG. 33A illustrates an embodiment of the present invention in the form of a cell-containment device (350) with a core. The device has a permeable membrane (352) enclosing an internal respiratory aid in the form of gas-conducting fibers (354) and cells (356). Gas conduits (354) extend from inside of the device to the outside of the device (354). The device also has a cell-displacing core (359) inside the device.

The cell-containing devices illustrated in FIGS. 33A, for example, are constructed as follows. The cylindrical outer sheath is a tube having a microporous polymeric film component comprised of multiple layers of two types of oriented expanded polytetrafluoroethylene (ePTFE) films laminated together in multiple directions, relative to the principal axis of orientation of each ePTFE film layer. The ePTFE film is used to make a laminated tube approximately 3.5 cm in length. The first type of microporous film is made in accordance with U.S. Pat. No. 3,953,566, issued to Gore, and incorporated herein by reference. The second type of film is made according to U.S. Pat. No. 5,476,589, issued to Bacino, and incorporated herein by reference. Each film is used in the following manner and characterized by the following properties.

The first film type is about 0.03 mm in thickness, 40 mm in with, 40 micron fibril length, and about 0.3 gm/cc in density. The density of non-porous polytetrafluoroethylene is about 2.2 gm/cc; consequently this first film type is about 86% porous. The fibril lengths of the porous expanded polytetrafluoroethylene films referred to herein are estimated means values obtained by examining scanning electron photomicrographs of the films.

The second film type is characterized by about two microns in thickness as determined with a laser micrometer. The density of the material is about 1 gm/cc. The average pore size, as measured by SEM, is about 0.2 microns. The porosity of the material, as measured by Bubble Point, is 20–25 psi, with a Frazier number of 4.5–5, and a Ball Burst of 3.2 pounds.

The first type of film is applied to a 0.064 inch mandrel with the fibrils of the film oriented longitudinally with respect to the axis of the composite membrane. The second type of film is wrapped on the first layer of film at an angle with respect to the first layer of film with a slight overlap of about 2 mm occurring between each successive helical wrap. A total of three wraps of the second film type are applied over the first film type. The construction is heat bonded in an air-convection oven set at 370° C. for approximately 8 minutes. The resultant tubular cover is strong in all directions, retained its shape well, and is capable of filtering cells. This cylindrical tube has the following final dimensions: length 3.5 cm, inner diameter 0.064 inches, and wall thickness 18 microns.

Finally, this tube is rendered water-wettable by creation of a thin, aldehyde-cross-linked film of poly(vinyl alcohol).

The polypropylene material used for the sham aid is fabricated from two 36" pieces of 4-0 Prolene® blue monofilament polypropylene suture (Ethicon, Inc., Somerville, N.J.). This fiber has a diameter of 0.0079" or 201 microns. As shown in Example 2c, above, this fiber does not have high oxygen transmissibility.

In this embodiment of the present invention, the internal respiratory aid is one 73 inch-long piece of the fiber specified and characterized in Example 26, above. This fiber has a diameter of 0.0068" or 173 microns.

Both groups of devices are made as follows. The respective fibers are threaded and looped through the 3.5 cm length of the hydrophilized ePTFE tubing, as shown in FIG. 33A. In the first group, 20 passes of ePTFE-silicone fiber are used. In the second group, 14 passes of polypropylene fiber are used. Free ends of fibers are tied and knotted to one another. Thus, either one single or two individual fiber elements are used, rather than several independent elements. In the completed devices, the internal respiratory aid thus traverses the semi-permeable cell-containing membrane and connects the cells in the cell space with the outside of the device, which in use is in contact with cell-culture media.

To provide means to load cells into the cell space from a syringe, a blunt, 16-gauge hypodermic needle for cell infusion is inserted part way into ePTFE tube lumen at one end. Both ends of the devices are sealed by tying a cerclage of 5-0 Prolene suture around each end of the ePTFE tubes. Volume of the cell-containment zone defined by the diameter of the hydrophilized ePTFE tube and the knotted ligatures is estimated to be about 180 microliters (not accounting for fiber element content) or actually about 165 microliters (accounting for fiber element content). In both test groups, about 8% of the cross-sectional area of the hydrophilized ePTFE tube is filled with fibers, leaving about 92% of the space available for cells.

All devices are autoclaved at 121° C. for 20 minutes, then placed into sterile bottles. Cut ends of the silicone-ePTFE fibers are sealed with two-part liquid silicone rubber (part #40082, Applied Silicone Corporation Ventura, Calif.), followed by a cure of 48 hours. Devices with the silicone-ePTFE internal respiratory aid are post-cured in a 90° C. oven for 30 minutes, followed by application of a small volume of 70% isopropanol solution to ensure sterility of the silicone-coated components. The isopropanol is allowed to evaporate prior to loading the device with cells.

The cells used in this example are characterized as follows. The genetically engineered rat insulinoma line, RIN 18 (also known as betaG 18/3E1) is obtained from BetaGene, Inc., Dallas, Tex. RIN 18 is created from cells that were originally isolated from an insulin-secreting adenoma of rats, an insulinoma developed in a New England Deaconess Hospital rat after high-dose X-irradiation. A continuous cell line, RINr, was established from this insulinoma after serial tumor transplants in NEDH rats (A. F. Gazdar, W. L. Chick, H. K. Oie, H. L. Sims, D. L. King, G. C. Weir, and V. Lauris, "Continuous, clonal, insulin- and somatostatin-secreting cell lines established from a transplantable rat islet cell tumor," *Proc. Natl. Acad. Sci. USA*, 77, 3519–3523, (1980)). A RINr clone, RINr1046-38 (J. Philippe, W. L. Chick, and J. F. Habener, "Multipotential phenotypic expression of genes encoding peptide hormones in rat insulinoma cell lines," *J. Clin. Invest.*, 79, 351–358, (1987)), was subjected to iterative genetic engineering to create the RIN 18 cells used in the present study, using the techniques described by Newgard and Clark (C. B. Newgard, "Engineered cells producing insulin in response to glucose," U.S. Pat. No. 5,427,940, (1995); C. B. Newgard, "Regulatory role of glucose transport and phosphorylation in pancreatic islet beta-cells," *Diabetes Rev.*, 4, 191–206, (1996); R. J. Noel and C. B. Newgard, "Prospects for genetic manipulation in diabetes," *Diabetes Ann.*, 10, 65–84, (1996); S. A. Clark, C. Quaade, H. Constandy, P. Hansen, P. Halban, S. Ferber, C. B. Newgard, and K. Normington, "Novel insulinoma cell lines produced by iterative engineering of GLUT2, glucokinase, and human insulin expression," *Diabetes*, 46, 958–967, (1997)). RIN 18 processes human proinsulin to insulin and secretes human insulin in response to common secretagogues. RIN 18 has retained its ability to grow as a solid tumor in both nude and NEDH rats. Prior to use in this study, RIN 18 was shown to be free of contamination with Mycoplasma by the Hoechst bisbenzamide 33258 fluorochrome and by direct Mvcoplasina-specific culture methods (American Type Culture Collection, Rockville, Md.).

The RIN 18 cells are prepared, loaded, and cultured for this example as follows. RIN 18 cells of the fifteenth ($15^{th}$) passage are grown to near confluence in a tissue-culture-polystyrene T-flask. The nearly confluent cell layer is rinsed twice with Hanks' balanced-salt solution without CaCl, $MgCl_2$, $MgSO_4$, or phenol red (HBSS; catalog #14175-020, Gibco BRL, Grand Island, N.Y.), then trypsinized (0.05% trypsin, 0.53 mM tetrasodium salt of ethylene diamine tetraacetic acid, in HBSS, catalog #25300-054, Gibco BRL). Cells thus freed are suspended and centrifuged in the culture medium. Supernatant is aspirated. Cells are re-suspended in culture medium, and counted (Coulter Counter, model ZBI, Coulter Electronics, Inc. Saint Hialeah, Fla.).

Prior to loading this cell population, the cells are suspended in an alginate medium as follows. A two-times (2×) stock solution of high-viscosity alginate (Keltone® part #HVCR, NF-grade sodium alginate, Kelco Corporate Headquarters, San Diego, Calif.) is prepared by mixing 0.6 g sodium alginate with sufficient deionized water to make a total volume of 20 mL. This 2× stock solution (3% sodium alginate) is sterilized on the liquids cycle in an autoclave. Trypsinized RIN 18 cells, rinsed and suspended in the culture medium (supra), are mixed with an equal volume of alginate stock solution, for a final concentration of 1.5% sodium alginate. This gives a suspension in which nearly all cells are singlets, with very few doublets, or higher aggregates. Using aseptic technique, and working in a laminar-flow hood, two million RIN 18 cells, suspended in 165 microliters of this viscous admixture of sodium alginate and culture medium, are injected into each cell-containment device. Needles are removed and discarded. Devices are incubated in 10 mL fresh culture medium for ten minutes, and are then incubated for ten minutes in 10 mL calcium chloride solution (0.1 M $CaCl_2$.2 $H_2O$ in 0.9% NaCl). In this procedure, divalent calcium ions replace monovalent sodium ions, crosslinking the viscous alginate sol into a gel by ionic coacervation, thus entrapping the RIN 18 cells and the internal respiratory aid in static suspension in the lumen of the hydrophilized ePTFE tube. Finally, devices are incubated for ten minutes in 10 mL fresh culture medium to remove excess calcium. This procedure is repeated for the sham devices.

All devices are subsequently cultured in a stagnant state in a humidified incubator at 95% air, 5% $CO_2$, 37° C., upright in T-25 flasks with vented caps (catalog #3056, Costar Corp., Cambridge, Mass.) with 20 mL culture medium. Blunt stirring rods of borosilicate glass, 5 cm in length, are placed gently on the devices to hold them at the bottom of the T flasks throughout the 18-day culture period. Evaporation controls are run in parallel (20 mL culture medium in an upright T-flask). Media are changed every 72 hours, and conditioned media are stored at −20° C. in polypropylene centrifuge tubes until assayed.

At termination of the study, devices are fixed in 10% neutral buffered formalin, gently dehydrated to 70% ethanol by hand, then embedded in paraffin by automated solvent exchange using a conventional histologic tissue processor. While embedded in paraffin, devices are divided transversely, midway along their length, using a sharp instrument. One half is sectioned longitudinally. The other half is sectioned transversely at three points along its length. Sections are cut at a thickness of about 5 microns, mounted on glass slides, stained with hematoxylin and eosin, and cover-slipped.

Conditioned media and media from evaporation controls are subsequently thawed and assayed for glucose consumption using a Ektachem DT60 II® dry-slide analyzer (Johnson and Johnson Clinical Diagnostics, Inc., Rochester, N.Y.). Aliquots of 10 microliters conditioned media are spotted onto dry slides. Reagents in each slide consisted of 0.7 Units of glucose oxidase, with a chromogenic system based on 7 Units peroxidase, 150 micrograms 1,7-dihydroxynaphthalene, and 250 micrograms 4-aminoantipyridine hydrochloride. Radioimmunoassays (RIAs) for human insulin are performed with the Coat-A-Count® (kit from the Diagnostics Products Corporation (Los Angeles, Calif.). This RIA is based on competition between a known quantity of iodine-125-labeled insulin and insulin in the sample for an anti-insulin antibody immobilized on a polypropylene tube. Insulin standards in this kit are traceable to World Health Organization insulin standard 66/304.

Figure 60:
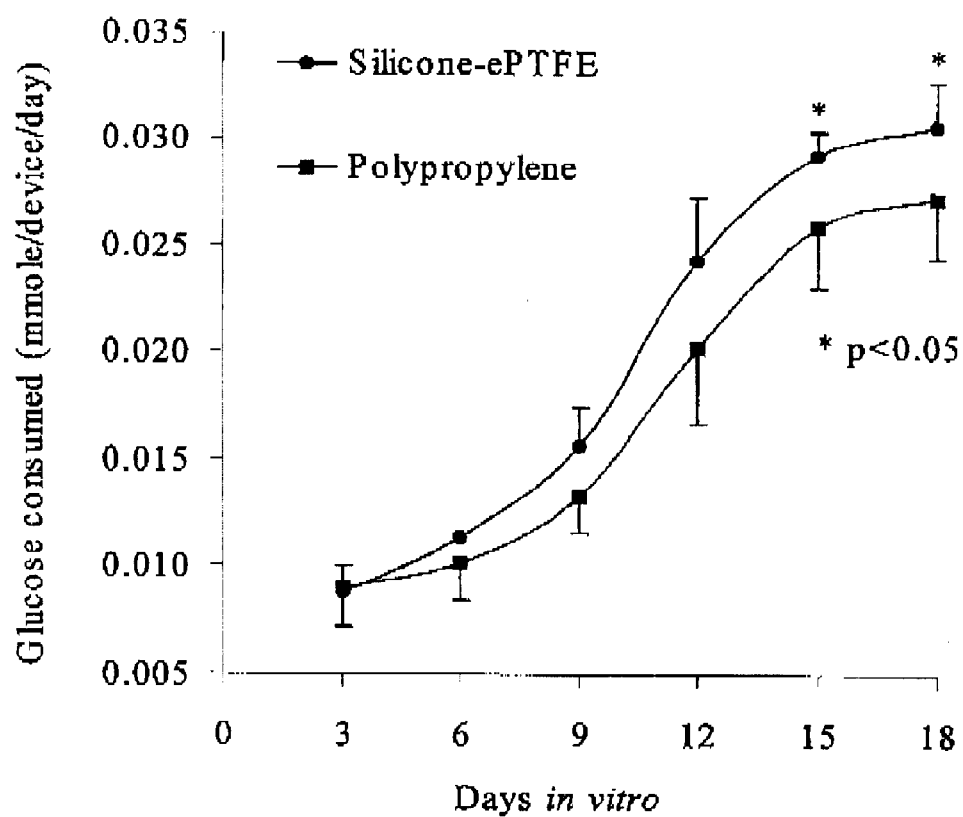
FIG. 60 is a graph illustrating data from Example 31.
Figure 61:
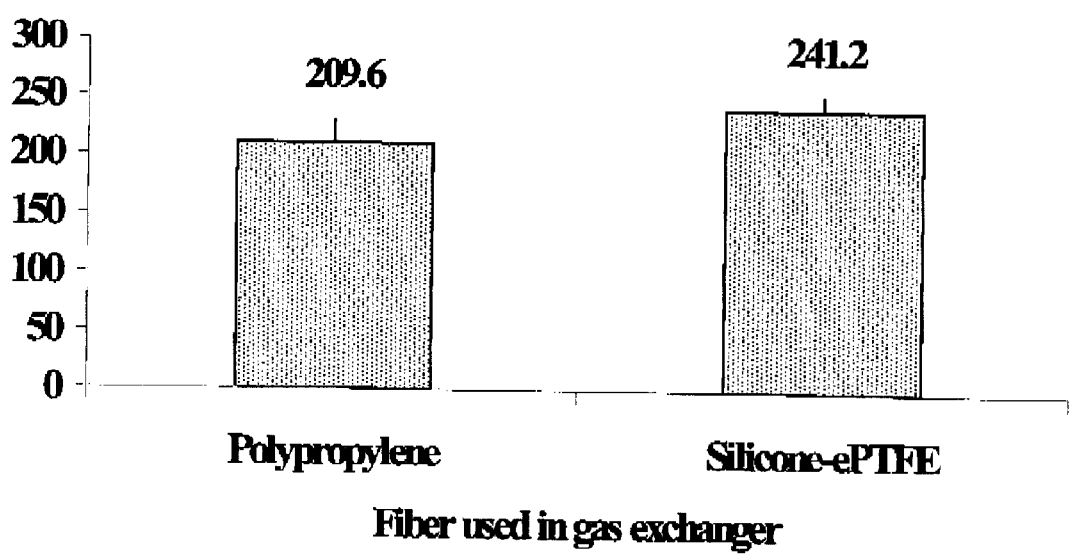
FIG. 61 is a graph illustrating data from Example 31.

The metabolic data from this study are shown in FIG. 60. Initial glucose consumption is equivalent in the two groups, indicating that similar quantities of cells were loaded into all devices. By the eighteenth day of culture, devices with silicone-ePTFE internal respiratory aids grew to a state of greater glucose consumption than devices with polypropylene (sham) aids. In the 72-hour media samples conditioned from days 13 through 15 and days 16 through 18, this difference in glucose consumption is statistically significant ($p<0.05$, as indicated by asterisks); Moreover, as seen in FIG. 61, devices with silicone-ePTFE internal respiratory aids show about 15% higher total insulin secretion than devices with polypropylene (sham) aids. This difference is statistically significant ($p<0.05$):

Histological examination is conducted on the devices as follows. Examination of approximately 50 slides of the devices with polypropylene (sham) aids show extremely rare to no RIN 18 cells around the polypropylene filaments in the lumen of the hydrophilized ePTFE tubing. Virtually all intact cells are superficial (i.e., next, or near, the semi-permeable membrane only). After 18 days of culture, nearly all intact cells are disposed as small clusters or layers, one to four cell diameters in thickness, immediately subjacent to the hydrophilized ePTFE membrane separating the gel-entrapped cells from the culture medium. Deeper than three to four cell diameters away from the limiting membrane, the few RIN 18 cells observed are degenerate or necrotic.

Figure 33B:
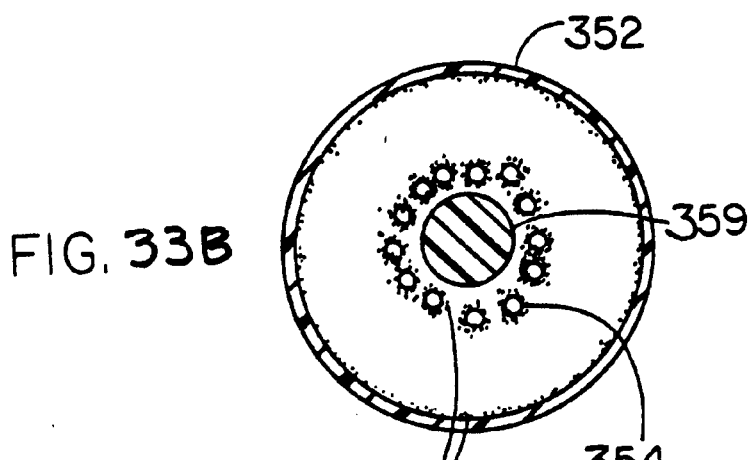
FIG. 33B illustrates a cross-sectional view of the embodiment of FIG. 33A.
Figure 33C:
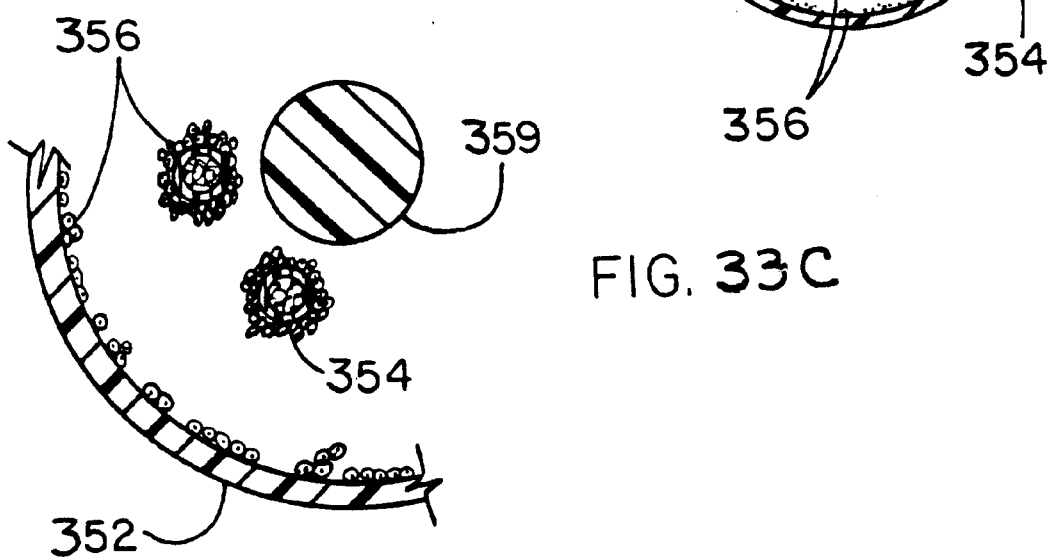
FIG. 33C is an enlarged view of FIG. 33B illustrating cells (356) living in proximity to the permeable membrane (352) and ,as conduits (354).

As in the sham controls, devices with silicone-ePTFE fibers as an internal respiratory aid show peripheral cell clusters and cell layers (FIGS. 33B and 33C), generally no more than four cells thick. But in addition to these superficial cells, devices of this group are inhabited by a second population of RIN 18 clusters, growing deep within the device, closely associated with gas-filled, silicone-ePTFE fibers of the present invention (FIGS. 33B and 33C). In transverse section, this second population of cells appears as continuous rings or discontinuous crescents around the silicone-ePTFE fibers. These crescent- or rind-shaped clusters of cells appear to be most healthy within three to four cell diameters of the filament-contact surface. Beyond this, for one to two cell diameters, RIN 18 cells are degenerate or necrotic. No intact cells are seen between this degenerate marginal layer and the population of cells growing subjacent to the delimiting hydrophilized ePTFE membrane.

Overall, there appear to be more intact cells in devices with the air-filled, silicone-ePTFE internal respiratory aid than in devices with (sham) polypropylene aids. Air-filled, silicone-ePTFE fibers appear to be useful as an internal respiratory aid for nourishing cells encapsulated deep within cell-transplantation devices.

When the present invention is used in a cell-containing device, it is important that the contained cells have ready access to aqueous nutrients, as well as, physiological gases. Accordingly, it may be necessary to include separate water-wettable channels for aqueous transport of nutrients to assure cell survival in the device.

Example 32

In many embodiments of the invention, it is necessary to determine the transmissibility of a layer of material that covers the exterior surfaces of porous gas-filled elements, the entire composite of which functions as an internal respiratory aid. The transmissibility T of the layer of material to oxygen is determined from the equation $T=P/\delta$, where P is the permeability of the material and $\delta$ is the thickness of the material.

The permeability of the material is found through knowledge of the composition of the material. If the composition of the material is not known, it can be determined through analytical techniques such as, for example, solid state NMR, GC/MS, or FTIR. Once the composition of the material is known, the permeability of the material can be found by referencing a materials property handbook. A preferable handbook to reference is *Membrane Handbook*, Ho, W. S. W. and Sirkar, K. K. eds., Van Nostrand Reinhold, N.Y., 1992. Values of permeability are often cited in units of barrer (where 1 barrer=$10^{-10}$ cm$^3$(STP).cm.cm$^{-2}$.sec$^{-1}$.(cm Hg)$^{-1}$). To convert permeability from units of barrer to units typical for diffusivity (cm$^2$/sec), one multiplies by a factor that incorporates the Henry's law coefficient for oxygen in water at the appropriate temperature. For example, in the case of polydimethylsiloxane, P=933 barrer (ibid). Henry's law coefficient for oxygen in water at 25° C. is $7.7\times10^5$ atm/(mol/cm$^3$) (Incropera, F. P. and DeWitt, D. P., *Fundamentals of Heat Transfer*, Wiley, New York, 1981, p. 785). Permeability for polydimethylsiloxane in units of cm$^2$/sec is thus determined:

$$P = \left(933 \times 10^{-10} \frac{cm^3(STP) \cdot cm}{cm^2 \cdot sec \cdot (cm\ Hg)}\right) \cdot \left(\frac{7.7 \times 10^5\ atm}{(mol/cm^3)}\right) \cdot \left(\frac{mol}{22,400\ cm^3(STP)}\right) \cdot \left(\frac{76\ cm\ Hg}{atm}\right)$$

or $P=2.4\times10^{-4}$ cm$^2$/sec.

The thickness of the material as a layer covering the exterior surfaces of porous gas-filled elements in the internal respiratory aid is measurable, for example, by first cutting thin cross sections of the aid, using techniques known in the area of histological sectioning. The thickness of the material visible in the section can then be measured using, for example, scanning electron microscopy. The thickness of the material layer is measured in a direction parallel to that in which gas transport across the material would occur in a functional internal respiratory aid.

The transmissibility of the material layer is then evaluated using the values of permeability and thickness as determined above. For example, for a polydimethylsiloxone layer 10 $\mu$m ($10^{-3}$ cm) thick, transmissibility is determined:

$$T = \frac{2.4 \times 10^{-4}\ cm^2/sec}{10^{-3}\ cm} = 0.24\ cm/sec$$

We claim:
1. A separately gas and liquid permeable material comprising:
   a first surface and a second surface, wherein said material is disposed therebetween;
   at least one liquid-fillable portion traversing said material from said first surface to said second surface;
   at least one gas-permeable portion traversing said material from said first surface to said second surface;
   wherein said gas-permeable portion comprises at least one gas-filled void space in an interior region of said material;
   wherein said gas-filled void space is surrounded with a gas-permeable material;
   wherein said gas-permeable material has a transmissibility to oxygen of at least $5\times10^{-4}$ centimeters per second and prevents ingress of liquid into said gas-filled void space,
   whereby passage of gas from said first surface to said second surface occurs through said gas-permeable portion.
2. The separately gas and liquid permeable material of claim 1 wherein passage of gas through said gas-permeable portion occurs by diffusion-based means.
3. The separately gas and liquid permeable material of claim 1 wherein said material has a multiplicity of gas-permeable portions therein.
4. The separately gas and liquid permeable material of claim 3 wherein said gas-permeable portions have interconnected gas-filled void spaces.
5. The separately gas and liquid permeable material of claim 1 wherein said transmissibility to oxygen is at least $5\times10^{-3}$ centimeters per second.
6. The separately gas and liquid permeable material of claim 1 wherein said transmissibility to oxygen is at least $5\times10^{-2}$ centimeters per second.
7. The separately gas and liquid permeable material of claim 1 wherein said transmissibility to oxygen is at least $5\times10^{-1}$ centimeters per second.
8. The separately gas and liquid permeable material of claim 1 wherein said transmissibility to oxygen is at least 5 centimeters per second.
9. The separately gas and liquid permeable material of claim 1 wherein said material is porous.
10. The separately gas and liquid permeable material of claim 9 wherein said porous material is selected from the group consisting of porous polytetrafluoroethylene, porous polyethylene, and porous polypropylene.
11. The separately gas and liquid permeable material of claim 10 wherein said porous material is a fluoropolymer.
12. The separately gas and liquid permeable material of claim 11 wherein said fluoropolymer is porous polytetrafluoroethylene.
13. The separately gas and liquid permeable material of claim 12 wherein said porous polytetrafluoroethylene is expanded polytetrafluoroethylene.
14. The separately gas and liquid permeable material of claim 1 wherein said gas-permeable material is selected from the group consisting of polysiloxanes and fluorinated polysiloxanes.

15. The separately gas and liquid permeable material claim 1 wherein said gas-permeable material comprises poly(dimethyl)siloxane.

16. The separately gas and liquid permeable material of claim 1 wherein said material is in the form of a membrane.

17. The separately gas and liquid permeable material of claim 1 wherein said material is in the form of a foam.

18. The separately gas and liquid permeable material of claim 1 wherein said material is in the form of a group of sintered microporous polymeric particles.

19. The separately gas and liquid permeable material of claim 1 further comprising living cells in said liquid-fillable portion.

20. The separately gas and liquid permeable material of claim 19 further comprising a polymeric material substantially enclosing said separately gas and liquid permeable material and said living cells;
wherein said polymeric material is permeable to aqueous liquids.

21. The separately gas and liquid permeable material of claim 1 further comprising a hydrogel material in said liquid-fillable portion.

22. The separately gas and liquid permeable material of claim 21 further comprising living cells in said hydrogel material.

23. The separately gas and liquid permeable material of claim 22 further comprising a polymeric material substantially enclosing said separately gas and liquid permeable material and said living cells in said hydrogel material;
wherein said polymeric material is permeable to aqueous liquids.

24. A separately gas and liquid permeable material comprising a multiplicity of porous elements in the form of a network;
wherein substantially all of said porous elements of said network have at least one exterior surface and at least one gas-filled void space in an interior region thereof;
wherein said gas-filled void space is in fluid communication with at least a portion of the exterior surface of said porous element;
wherein said porous elements have locations where said porous elements contact one another for transport of gas therebetween;
wherein said network has spaces between said porous elements;
wherein at least one space in said network comprises a liquid-fillable portion;
a gas permeable material covering said exterior surface of said porous elements, except the exterior surface at the locations where said porous elements contact one another;
wherein said gas permeable material maintains gas in said gas-filled void space and resists ingress of liquid into said gas-filled void space, while permitting fluid communication between said porous elements at the locations where said porous elements contact one another; and
wherein said gas permeable material has a transmissibility to oxygen of at least $5 \times 10^{-4}$ centimeters per second,
whereby passage of gas through said separately gas and liquid permeable material occurs through said gas-filled void spaces.

25. The separately gas and liquid permeable material of claim 24 wherein passage of gas through said gas-filled void spaces occurs by diffusion-based means.

26. The separately gas and liquid permeable material of claim 24 wherein said porous elements each have a multiplicity of gas-filled void spaces therein.

27. The separately gas and liquid permeable material of claim 24 wherein substantially all of said gas-filled void spaces in each porous element are interconnected.

28. The separately gas and liquid permeable material of claim 24 wherein said transmissibility to oxygen is at least $5 \times 10^{-3}$ centimeters per second.

29. The separately gas and liquid permeable material of claim 24 wherein said transmissibility to oxygen is at least $5 \times 10^{-2}$ centimeters per second.

30. The separately gas and liquid permeable material of claim 24 wherein said transmissibility to oxygen is at least $5 \times 10^{-1}$ centimeters per second.

31. The separately gas and liquid permeable material of claim 24 wherein said transmissibility to oxygen is at least 5 centimeters per second.

32. The separately gas and liquid permeable material of claim 24 wherein said porous elements are in the form of hollow fibers.

33. The separately gas and liquid permeable material of claim 24 wherein said porous elements are selected from the group consisting of expanded polytetrafluoroethylene, porous polyethylene, and porous polypropylene.

34. The separately gas and liquid permeable material of claim 24 wherein said porous elements comprise a fluoropolymer.

35. The separately gas and liquid permeable material of claim 34 wherein said fluoropolymer is polytetrafluoroethylene.

36. The separately gas and liquid permeable material of claim 35 wherein said polytetrafluoroethylene is an expanded polytetrafluoroethylene.

37. The separately gas and liquid permeable material of claim 24 wherein said gas-permeable material is selected from the group consisting of polysiloxanes and fluorinated polysiloxanes.

38. The separately gas and liquid permeable material claim 24 wherein said gas-permeable material comprises poly(dimethyl)siloxane.

39. The separately gas and liquid permeable material of claim 24 further comprising living cells in said liquid-fillable portion.

40. The separately gas and liquid permeable material of claim 39 further comprising a polymeric material substantially enclosing said separately gas and liquid permeable material and said living cells;
wherein said polymeric material is permeable to aqueous liquids.

41. The separately gas and liquid permeable material of claim 24 further comprising a hydrogel material in said liquid-fillable portion.

42. The separately gas and liquid permeable material of claim 41 further comprising living cells in said hydrogel material.

43. The separately gas and liquid permeable material of claim 42 further comprising a polymeric material substantially enclosing said separately gas and liquid permeable material and said living cells in said hydrogel material;
wherein said polymeric material is permeable to aqueous liquids.

44. A cell-containment device comprising:
a separately gas and liquid permeable membrane capable of retaining living cells, said membrane comprising a first surface and a second surface, wherein said membrane is disposed therebetween;

at least one liquid-fillable portion traversing said membrane from said first surface to said second surface;

at least one gas-permeable portion traversing said material from said first surface to said second surface;

wherein said gas-permeable portion comprises at least one gas-filled void space in an interior region of said material;

wherein said gas-filled void space is surrounded with a gas-permeable material;

wherein said gas-permeable material has a transmissibility to oxygen of at least $5 \times 10^{-4}$ centimeters per second and prevents ingress of liquid into said gas-filled void space, whereby passage of gas from said first surface to said second surface occurs through said gas-permeable portion, wherein said separately gas and liquid permeable membrane forms at least a portion of a chamber for containing living cells; and wherein said chamber comprises at least one void volume in which living cells are placed.

45. The cell-containment device of claim 44 wherein passage of gas through said gas-permeable portion occurs by diffusion-based means.

46. The cell-containment device of claim 44 wherein said separately gas and liquid permeable membrane has a multiplicity of gas-permeable portions therein.

47. The cell-containment device of claim 46 wherein said gas-permeable portions have interconnected gas-filled void spaces.

48. The cell-containment device of claim 44 wherein said transmissibility to oxygen is at least $5 \times 10^{-3}$ centimeters per second.

49. The cell-containment device of claim 44 wherein said transmissibility to oxygen is at least $5 \times 10^{-2}$ centimeters per second.

50. The cell-containment device of claim 44 wherein said transmissibility to oxygen is at least $5 \times 10^{-1}$ centimeters per second.

51. The cell-containment device of claim 44 wherein said transmissibility to oxygen is at least 5 centimeters per second.

52. The cell-containment device of claim 44 wherein said membrane is porous.

53. The cell-containment device of claim 52 wherein said porous membrane is selected from the group consisting of porous polytetrafluoroethylene, porous polyethylene, and porous polypropylene.

54. The cell-containment device of claim 52 wherein said porous membrane is a fluoropolymer.

55. The cell-containment device of claim 54 wherein said fluoropolymer is porous polytetrafluoroethylene.

56. The cell-containment device of claim 55 wherein said porous polytetrafluoroethylene is expanded polytetrafluoroethylene.

57. The cell-containment device of claim 44 wherein said gas-permeable material is selected from the group consisting of polysiloxanes and fluorinated polysiloxanes.

58. The cell-containment device of claim 44 wherein said gas-permeable material comprises poly(dimethyl)siloxane.

59. The cell-containment device of claim 44 wherein material of said membrane having at least one gas-filled void space therein extends from an interior region of said membrane beyond said first or second surface;

wherein said gas-filled void space is surrounded with a gas-permeable material;

wherein said gas-permeable material has a transmissibility to oxygen of at least $5 \times 10^{-4}$ centimeters per second and prevents ingress of liquid into said gas-filled void space.

60. The cell-containment device of claim 59 wherein passage of gas through said gas-filled void space occurs by diffusion-based means.

61. The cell-containment device of claim 59 wherein said transmissibility to oxygen is at least $5 \times 10^{-3}$ centimeters per second.

62. The cell-containment device of claim 59 wherein said transmissibility to oxygen is at least $6 \times 10^{-2}$ centimeters per second.

63. The cell-containment device of claim 59 wherein said transmissibility to oxygen is at least $5 \times 10^{-1}$ centimeters per second.

64. The cell-containment device of claim 59 wherein said transmissibility to oxygen is at least 5 centimeters per second.

65. A cell-containment device comprising:

at least one permeable membrane capable of retaining living cells;

wherein said membrane forms at least a portion of a chamber for containing living cells;

wherein said chamber comprises at least one void volume in which living cells are placed;

a separately gas and liquid permeable material placed within said chamber;

wherein said separately gas and liquid permeable material comprises a multiplicity of porous elements in the form of a network;

wherein substantially all of said porous elements of said network have at least one exterior surface and at least one gas-filled void space in an interior region thereof;

wherein said gas-filled void space is in fluid communication with at least a portion of said exterior surface of said porous element;

wherein said porous elements have locations where said porous elements contact one another for transport of gas therebetween;

wherein said network has spaces between said porous elements;

wherein at least one space in said network comprises a liquid-fillable portion;

a gas permeable material covering said exterior surface of said porous elements, except the exterior surface at the locations where said porous elements contact one another;

wherein said gas permeable material maintains gas in said gas-filled void space and resists ingress of liquid into said gas-filled void space, while permitting fluid communication between said porous elements at the locations where said porous elements contact one another; and wherein said gas permeable material has a transmissibility to oxygen of at least $5 \times 10^{-4}$ centimeters per second, whereby passage of gas through said separately gas and liquid permeable material occurs through said gas-filled void spaces.

66. The separately gas and liquid permeable material of claim 65 wherein passage of gas through said gas-filled void spaces occurs by diffusion-based means.

67. The separately gas and liquid permeable material of claim 65 wherein said porous elements each have a multiplicity of gas-filled void spaces therein.

68. The separately gas and liquid permeable material of claim 67 wherein substantially all of said gas-filled void spaces in each porous element are interconnected.

69. The separately gas and liquid permeable material of claim 65 wherein said transmissibility to oxygen is at least $5\times10^{-3}$ centimeters per second.

70. The separately gas and liquid permeable material of claim 65 wherein said transmissibility to oxygen is at least $5\times10^{-2}$ centimeters per second.

71. The separately gas and liquid permeable material of claim 65 wherein said transmissibility to oxygen is at least $5\times10^{-1}$ centimeters per second.

72. The separately gas and liquid permeable material of claim 65 wherein said transmissibility to oxygen is at least 5 centimeters per second.

73. The separately gas and liquid permeable material of claim 65 wherein said porous elements are in the form of hollow fibers.

74. The separately gas and liquid permeable material of claim 65 wherein said porous elements are selected from the group consisting of expanded polytetrafluoroethylene, porous polyethylene, and porous polypropylene.

75. The separately gas and liquid permeable material of claim 65 wherein said porous elements comprise a fluoropolymer.

76. The separately gas and liquid permeable material of claim 75 wherein said fluoropolymer is polytetrafluoroethylene.

77. The separately gas and liquid permeable material of claim 76 wherein said polytetrafluoroethylene is an expanded polytetrafluoroethylene.

78. The separately gas and liquid permeable material of claim 65 wherein said gas-permeable material is selected from the group consisting of polysiloxanes and fluorinated polysiloxanes.

79. The separately gas and liquid permeable material claim 65 wherein said gas-permeable material comprises poly(dimethyl)siloxane.

80. The separately gas and liquid permeable material of claim 65 further comprising living cells in said liquid-fillable portion.

81. The separately gas and liquid permeable material of claim 65 further comprising a hydrogel material in said liquid-fillable portion.

82. The separately gas and liquid permeable material of claim 81 further comprising living cells in said hydrogel material.

83. The cell-containment device of claim 65 wherein at least one porous element surrounded by said gas-permeable material extends across said chamber.

84. The cell-containment device of claim 83 wherein said at least one porous element surrounded by said gas-permeable material extends beyond said chamber.

\* \* \* \* \*